US008012482B2

(12) United States Patent
Adams et al.

(10) Patent No.: US 8,012,482 B2
(45) Date of Patent: *Sep. 6, 2011

(54) HUMANIZED ANTI-TGF-BETA ANTIBODIES

(75) Inventors: Camellia W. Adams, San Jose, CA (US); Napoleone Ferrara, San Francisco, CA (US); Ellen Filvaroff, San Francisco, CA (US); Weiguang Mao, San Mateo, CA (US); Leonard G. Presta, San Francisco, CA (US); Max L. Tejada, Campbell, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/423,664

(22) Filed: Apr. 14, 2009

(65) Prior Publication Data
US 2009/0285810 A1 Nov. 19, 2009

Related U.S. Application Data

(62) Division of application No. 11/096,046, filed on Mar. 31, 2005, now Pat. No. 7,527,791.

(60) Provisional application No. 60/558,290, filed on Mar. 31, 2004.

(51) Int. Cl.
A61K 39/395 (2006.01)
A61K 39/00 (2006.01)
C07K 16/00 (2006.01)
C12P 21/08 (2006.01)

(52) U.S. Cl. .............. 424/145.1; 424/133.1; 424/134.1; 424/141.1; 424/158.1; 530/388.1; 530/388.24; 530/387.1

(58) Field of Classification Search .................. None
See application file for complete search history.

(56) References Cited

U.S. PATENT DOCUMENTS

| | | | |
|---|---|---|---|
| 4,301,144 A | 11/1981 | Iwashita et al. |
| 4,457,916 A | 7/1984 | Hayashi et al. |
| 4,496,689 A | 1/1985 | Mitra |
| 4,640,835 A | 2/1987 | Shimizu et al. |
| 4,670,417 A | 6/1987 | Iwasaki et al. |
| 4,676,980 A | 6/1987 | Segal et al. |
| 4,774,322 A | 9/1988 | Seyedin |
| 4,791,192 A | 12/1988 | Nakagawa et al. |
| 4,806,523 A | 2/1989 | Bentz |
| 4,816,567 A | 3/1989 | Cabilly et al. |
| 4,843,063 A | 6/1989 | Seyedin |
| 4,848,063 A | 7/1989 | Niske |
| 4,886,747 A | 12/1989 | Derynck et al. |
| 4,933,294 A | 6/1990 | Waterfield et al. |
| 4,975,278 A | 12/1990 | Senter et al. |
| 5,061,786 A | 10/1991 | Burnier et al. |
| 5,120,535 A | 6/1992 | Marquardt et al. |
| 5,208,020 A | 5/1993 | Chari et al. |
| 5,262,319 A | 11/1993 | Iwata et al. |
| 5,264,365 A | 11/1993 | Georgiou et al. |
| 5,264,586 A | 11/1993 | Nicolaou et al. |
| 5,268,455 A | 12/1993 | Cianciolo |
| 5,462,925 A | 10/1995 | Ogawa et al. |
| 5,500,362 A | 3/1996 | Robinson et al. |
| 5,508,192 A | 4/1996 | Georgiou et al. |
| 5,520,926 A | 5/1996 | Ferguson |
| 5,534,615 A | 7/1996 | Baker et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,714 A | 11/1996 | Dasch et al. |
| 5,571,894 A | 11/1996 | Wels et al. |
| 5,587,458 A | 12/1996 | King et al. |
| 5,616,561 A | 4/1997 | Barcellos-Hoff |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,654,270 A | 8/1997 | Ruoslahti et al. |
| 5,661,016 A | 8/1997 | Lonberg et al. |
| 5,662,904 A | 9/1997 | Ferguson et al. |
| 5,683,988 A | 11/1997 | Chung |
| 5,693,607 A | 12/1997 | Segarini et al. |
| 5,705,609 A | 1/1998 | Ruoslahti et al. |
| 5,712,374 A | 1/1998 | Knutsmann et al. |
| 5,714,586 A | 2/1998 | Kunstmann et al. |
| 5,726,149 A | 3/1998 | Ruoslahti et al. |
| 5,730,976 A | 3/1998 | Reed |
| 5,731,168 A | 3/1998 | Carter et al. |
| 5,733,743 A | 3/1998 | Johnson et al. |

(Continued)

FOREIGN PATENT DOCUMENTS

EP 0 173 484 A2 3/1986

(Continued)

OTHER PUBLICATIONS

Paul, Fundamental Immunology, 3rd Edition, 1993, pp. 292-295, under the heading Fv Structure and Diversity in Three Dimensions.*
MacCallum et al. J. Mol. Biol. (1996) 262:732-745.*
Casset et al. (2003) BBRC 307, 198-205.*
Bendig M. M. Methods: A Companion to Methods in Enzymology, 1995; 8:83-93.*
Adler et al., "Elevated Levels of Circulating Interleukin-6 and Transforming Growth Factor-beta 1 in Patients With Metastatic Prostatic Carcinoma" *J. Urol.* 161(1):182-187 (Jan. 1999).
Akhurst and Balmain, "Genetic events and the role of TGF beta in epithelial tumour progression" *J. Pathol.* 187:82-90 (1999).
Amendt et al., "Expression of a dominant negative type II TGF-beta receptor in mouse skin results in an increase in carcinoma incidence and an acceleration of carcinoma development" *Oncogene* 17:25-34 (1998).

(Continued)

Primary Examiner — Shulamith H Shafer
(74) *Attorney, Agent, or Firm* — Gates & Cooper LLP

(57) ABSTRACT

Humanized anti-TGF-beta antibodies are provided, as well as methods for their preparation and use, including methods for treating TGF-beta disorders, for example, cancer. Also provided are articles of manufacture designed for various uses that contain the humanized antibodies.

26 Claims, 35 Drawing Sheets

U.S. PATENT DOCUMENTS

| | | |
|---|---|---|
| 5,750,373 A | 5/1998 | Garrard et al. |
| 5,772,995 A | 6/1998 | Fakhrai |
| 5,772,998 A | 6/1998 | Dash et al. |
| 5,773,001 A | 6/1998 | Hamann et al. |
| 5,780,436 A | 7/1998 | Bhatnagar et al. |
| 5,783,185 A | 7/1998 | Dasch et al. |
| 5,801,231 A | 9/1998 | Derynck et al. |
| 5,807,708 A | 9/1998 | Falb et al. |
| 5,821,227 A | 10/1998 | Dennis et al. |
| 5,821,234 A | 10/1998 | Dzau |
| 5,821,337 A | 10/1998 | Carter et al. |
| 5,824,297 A | 10/1998 | Iwata et al. |
| 5,824,655 A | 10/1998 | Border |
| 5,830,847 A | 11/1998 | Letarte et al. |
| 5,834,248 A | 11/1998 | Falb |
| 5,837,234 A | 11/1998 | Gentile et al. |
| 5,837,242 A | 11/1998 | Holliger et al. |
| 5,858,657 A | 1/1999 | Winter et al. |
| 5,859,205 A | 1/1999 | Adair et al. |
| 5,869,462 A | 2/1999 | Dzau |
| 5,871,907 A | 2/1999 | Winter et al. |
| 5,872,215 A | 2/1999 | Osbourne et al. |
| 5,888,705 A | 3/1999 | Rubin et al. |
| 5,948,639 A | 9/1999 | Gimeno et al. |
| 5,958,411 A | 9/1999 | Logan et al. |
| 5,969,108 A | 10/1999 | McCafferty et al. |
| 5,972,335 A | 10/1999 | Ferguson et al. |
| 6,001,969 A | 12/1999 | Lin et al. |
| 6,010,872 A | 1/2000 | Lin et al. |
| 6,015,693 A | 1/2000 | Letarte et al. |
| 6,027,888 A | 2/2000 | Georgiou et al. |
| 6,083,715 A | 7/2000 | Georgiou et al. |
| 6,086,867 A | 7/2000 | Lin et al. |
| 6,090,383 A | 7/2000 | Dasch et al. |
| 6,140,471 A | 10/2000 | Johnson et al. |
| 6,143,359 A | 11/2000 | Rendina |
| 6,175,057 B1 | 1/2001 | Mucke et al. |
| 6,201,108 B1 | 3/2001 | Lin et al. |
| 6,235,883 B1 | 5/2001 | Jakobovits et al. |
| 6,419,928 B1 | 7/2002 | Dasch et al. |
| 6,455,757 B1 | 9/2002 | Mucke et al. |
| 6,492,497 B1 | 12/2002 | Thompson et al. |
| 6,500,920 B1 | 12/2002 | Haung |
| 6,509,318 B1 | 1/2003 | Bhatnagar et al. |
| 6,632,979 B2 | 10/2003 | Erickson et al. |
| 7,067,637 B1 * | 6/2006 | Hotten et al. ............ 530/388.23 |
| 7,494,651 B2 * | 2/2009 | Jones et al. ................ 424/145.1 |
| 2001/0046502 A1 | 11/2001 | Mokyr |
| 2002/0035736 A1 | 3/2002 | Erickson et al. |
| 2002/0051785 A1 | 5/2002 | Slamon et al. |
| 2002/0176758 A1 | 11/2002 | Sahm et al. |
| 2002/0176858 A1 | 11/2002 | Dash et al. |
| 2003/0017534 A1 | 1/2003 | Buelow et al. |
| 2003/0028905 A1 | 2/2003 | Knaus et al. |
| 2003/0039645 A1 | 2/2003 | Adair et al. |
| 2003/0039649 A1 | 2/2003 | Foote |
| 2003/0064069 A1 | 4/2003 | Thompson et al. |
| 2003/0125251 A1 | 7/2003 | Wakefield et al. |
| 2005/0049403 A1 | 3/2005 | Thompson |
| 2006/0251658 A1 | 11/2006 | Ledbetter et al. |

FOREIGN PATENT DOCUMENTS

| | | |
|---|---|---|
| EP | 0 184 187 A2 | 6/1986 |
| EP | 0 267 463 A2 | 5/1988 |
| EP | 0 268 561 A2 | 5/1988 |
| EP | 0404097 | 6/1990 |
| EP | 0 089 062 B1 | 12/1990 |
| EP | 0605522 | 9/1992 |
| EP | 0 171 496 B1 | 5/1993 |
| EP | 0 200 341 B1 | 1/1994 |
| EP | 0 239 400 B1 | 8/1994 |
| EP | 0 169 016 B1 | 10/1995 |
| EP | 0404097 B1 | 9/1996 |
| EP | 0 589 877 B1 | 11/1996 |
| EP | 0 813 875 A2 | 12/1997 |
| EP | 0 844 306 A1 | 5/1998 |
| EP | 0 874 046 A1 | 10/1998 |
| EP | 0605522 B1 | 6/1999 |
| EP | 0 585 287 B1 | 10/1999 |
| EP | 0 853 661 B1 | 3/2000 |
| EP | 0 557 418 B1 | 6/2000 |
| EP | 1 024 191 A2 | 8/2000 |
| EP | 0 945 464 B1 | 2/2001 |
| EP | 0 774 511 B1 | 1/2002 |
| EP | 0 120 694 B2 | 2/2002 |
| EP | 0 125 023 B2 | 3/2002 |
| EP | 0 669 833 B1 | 6/2002 |
| EP | 1 175 445 B1 | 7/2004 |
| EP | 0 656 941 B1 | 6/2005 |
| JP | 2126157 | 5/1990 |
| JP | 92041307 B | 7/1992 |
| JP | 95068278 B2 | 7/1995 |
| JP | 8119984 | 5/1996 |
| WO | WO 84/01106 | 3/1984 |
| WO | 86/01533 | 3/1986 |
| WO | WO 86/01533 | 3/1986 |
| WO | 88/07378 | 10/1988 |
| WO | WO 88/07378 | 10/1988 |
| WO | WO 90/00900 | 2/1990 |
| WO | WO 90/07861 | 7/1990 |
| WO | WO 91/00360 | 1/1991 |
| WO | WO 91/04748 | 4/1991 |
| WO | WO 91/05264 | 4/1991 |
| WO | WO 91/08291 | 6/1991 |
| WO | WO 91/09967 | 7/1991 |
| WO | WO 91/10727 | 7/1991 |
| WO | WO 91/15223 | 10/1991 |
| WO | WO 91/19513 | 12/1991 |
| WO | WO 92/00318 | 1/1992 |
| WO | WO 92/00330 | 1/1992 |
| WO | WO 92/00373 | 1/1992 |
| WO | WO 92/01047 | 1/1992 |
| WO | WO 92/01787 | 2/1992 |
| WO | WO 92/08480 | 5/1992 |
| WO | WO 92/17206 | 10/1992 |
| WO | WO 92/20791 | 11/1992 |
| WO | WO 92/22653 | 12/1992 |
| WO | WO 93/06213 | 4/1993 |
| WO | WO 93/08829 | 5/1993 |
| WO | WO 93/09228 | 5/1993 |
| WO | WO 93/09800 | 5/1993 |
| WO | WO 93/10808 | 6/1993 |
| WO | WO 93/11161 | 6/1993 |
| WO | WO 93/11236 | 6/1993 |
| WO | WO 93/14782 | 8/1993 |
| WO | WO 93/16185 | 8/1993 |
| WO | WO 93/17708 | 9/1993 |
| WO | WO 93/17715 | 9/1993 |
| WO | WO 93/19172 | 9/1993 |
| WO | WO 93/19769 | 10/1993 |
| WO | WO 93/19783 | 10/1993 |
| WO | WO 93/21232 | 10/1993 |
| WO | WO 93/21945 | 11/1993 |
| WO | WO 94/04690 | 3/1994 |
| WO | WO 94/09812 | 5/1994 |
| WO | WO 94/09815 | 5/1994 |
| WO | WO 94/10187 | 5/1994 |
| WO | WO 94/11026 | 5/1994 |
| WO | WO 94/13804 | 6/1994 |
| WO | WO 94/18991 | 9/1994 |
| WO | WO 94/25588 | 11/1994 |
| WO | WO 95/10610 | 4/1995 |
| WO | WO 95/13827 | 5/1995 |
| WO | WO 95/19987 | 7/1995 |
| WO | WO 96/16673 | 6/1996 |
| WO | WO 96/32478 | 10/1996 |
| WO | WO 97/00691 | 1/1997 |
| WO | WO 97/13844 | 4/1997 |
| WO | WO 97/31020 | 8/1997 |
| WO | WO 97/38729 | 10/1997 |
| WO | WO 97/40848 | 11/1997 |
| WO | 98/03663 | 1/1998 |
| WO | WO 98/02463 | 1/1998 |
| WO | 98/07735 | 2/1998 |
| WO | WO 98/07735 | 2/1998 |
| WO | WO 98/07849 | 2/1998 |

| WO | WO 98/08529 | 3/1998 |
| --- | --- | --- |
| WO | WO 98/17304 | 4/1998 |
| WO | WO 89/07452 | 8/1998 |
| WO | WO 98/45467 | 10/1998 |
| WO | WO 98/45479 | 10/1998 |
| WO | WO 98/48024 | 10/1998 |
| WO | WO 98/53068 | 11/1998 |
| WO | WO 98/53830 | 12/1998 |
| WO | WO 98/55512 | 12/1998 |
| WO | WO 98/56913 | 12/1998 |
| WO | WO 98/03663 | 8/1999 |
| WO | WO 99/50296 | 10/1999 |
| WO | WO 00/00641 | 1/2000 |
| WO | 00/13705 | 3/2000 |
| WO | WO 00/13705 | 5/2000 |
| WO | WO 00/34337 A | 6/2000 |
| WO | WO 00/34788 | 6/2000 |
| WO | WO 00/40227 | 7/2000 |
| WO | WO 00/43499 | 7/2000 |
| WO | WO 00/66631 | 11/2000 |
| WO | WO 01/24813 A1 | 4/2001 |
| WO | WO 01/57061 A1 | 8/2001 |
| WO | WO 01/66140 A1 | 9/2001 |
| WO | 03/015505 | 2/2003 |
| WO | WO 03/015505 A2 | 2/2003 |
| WO | 2004/065417 | 8/2004 |
| WO | WO 2004/065417 A2 | 8/2004 |
| WO | WO 2005/050200 A | 6/2005 |

OTHER PUBLICATIONS

Antoni and Mariani, "An interactive computer program for the determination of the binding constants of monoclonal antibodies by non-linear regression analysis of radioimmunoassay data" *J Immunol Methods* 83(1):63-68 (Oct. 24, 1985).

Arie et al., "Chaperone Function of FkpA, A Heat Shock Prolyl Isomerase, in the Periplasm of *Escherichia coli*" *Molecular Microbiology* 39(1):199-210 (2001).

Arteaga et al., "Anti-transforming growth factor (TGF)-beta antibodies inhibit breast cancer cell tumorigenicity and increase mouse spleen natural killer cell activity" *J. Clin. Invest.* 92:2569-2576 (Dec. 1993).

Aslakson and Millere, "Selective events in the metastatic process defined by analysis of the sequential dissemination of subpopulations of a mouse mammary tumor" *Cancer Research* 52:1399-1405 (Mar. 1992).

Assoian et al., "Type β Transforming Growth Factor in Human Platelets: Release during Platelet Degranulation and Action on Vascular Smooth Muscle Cells" *Journal of Cell Biology* 102:1217-1223 (Apr. 1986).

Barbas et al., "High-affinity self-reactive human antibodies by design and selection: targeting the integrin ligand binding site" *Proc Natl Acad Sci U S A* 90(21):10003-10007 (Nov. 1, 1993).

Barbas III et al., "In Vitro Evolution of a Neutralizing Human Antibody to Human Immunodeficiency Virus Type 1 to Enhance Affinity and Broaden Strain Cross-Reactivity" *Proc. Natl. Acad. Sci. USA* 91(9):3809-3813 (Apr. 1994).

Barcellos-Hoff and Ewan, "Transforming growth factor-beta and breast cancer: Mammary gland development" *Breast Canc. Res.* 2(2):92-99 (2000).

Barcellos-Hoff et al., "Transforming growth factor-beta activation in irradiated murine mammary gland" *J. Clin. Invest.* 93:892-899 (Feb. 1994).

Bellone et al., "Differential expression of transforming growth factors-beta1, -beta2 and -beta3 in human colon carcinoma" *Eur. J. Canc.* 37:224-233 (2001).

Benjamin et al., "Selective ablation of immature blood vessels in established human tumors follows vascular endothelial growth factor withdrawal" *J Clin Invest.* 103(2):159-165 (Jan. 1999).

Bird et al., "Single-Chain Antigen-Binding Proteins" *Science* 242:423-426 (Oct. 1988).

Boerner et al., "Production of Antigen-Specific Human Monoclonal Antibodies From In Vitro-Primed Human Splenocytes" *The Journal of Immunology* 147(1):86-95 (Jul. 1991).

Boivin et al., "Gastric lesions in transforming growth factor beta-1 heterozygous mice" *Laboratory Investigation* 74(2):513-518 (Feb. 1996).

Border et al., "Natural inhibitor of transforming growth factor-beta protects against scarring in experimental kidney disease" *Nature* 360:361-364 (Nov. 1992).

Border et al., "Suppression of experimental glomerulonephritis by antiserum against transforming growth factor beta 1" *Nature* 346:371-374 (Jul. 1990).

Border et al., "Transforming growth factor beta in diabetic nephropathy" 12(4):309-339 (Dec. 1996).

Bothmann and Pluckthun, "The Periplasmic *Escherichia coli* Peptidylprolyl cis,trans-Isomerase FkpA." *J. Bio. Chem.* 275(22):17100-17105 (Jun. 2000).

Bottinger et al., "The recombinant proregion of transforming growth factor beta 1 (Latency-associated peptide) inhibits active transforming growth factor beta 1 in transgenic mice" *Proc. Natl. Acad. Sci. USA* 93:5877-5582 (Jun. 1996).

Bottinger et al., "Transgenic mice overexpressing a dominant-negative mutant type II transforming growth factor beta receptor show enhanced tumorigenesis in the mammary gland and lung in response to the carcinogen 7,12-dimethylbenz-(a)-anthracene" *Cancer Research* 57:5564 (Dec. 1997).

Branton and Kopp, "TGF-beta and fibrosis" *Microbes Infec.* 1:1349-1365 (1999).

Brennan et al., "Preparation of bispecific antibodies by chemical recombination of monoclonal immunoglobulin $G_1$ fragments" *Science* 229:81-89 (Jul. 1985).

Brunner, "Site-directed mutagenesis of cysteine residues in the pro region if the transforming growth factor beta 1 precursor. Expression and characterization of mutant proteins" *Journal of Biological Chemistry* 264(23):13660-13664 (Aug. 1989).

Capel et al., "Heterogeneity of Human IgG Fc Receptors." *Immunomethods.* 4:25-34 (1994).

Capon et al., "Designing CD4 Immunoadhesins for AIDS Therapy" *Nature* 337(9):525-531 (Feb. 1989).

Caron et al., "Engineered Humanized Dimeric Forms of IgG are More Effective Antibodies" *Journal of Experimental Medicine* 176:1191-1195 (Oct. 1992).

Carswell et al., "An Endotoxin-induced Serum Factor That Causes Necrosis of Tumors" *Proc. Natl. Acad. Sci. USA* 72(9):3666-3670 (1975).

Carter et al., "High Level *Escherichia coli* Expression and Production of a Bivalent Humanized Antibody Fragment" *Bio/Technology.* 10(2):163-167 (Feb. 1992).

Carter et al., "Humanization of an Anti-p185$^{HER2}$ Antibody For Human Cancer Therapy" *Proc. Natl. Acad. Sci. USA* 89:4285-4289 (May 1992).

Chari et al., "Immunoconjugates Containing Novel Maytansinoids: Promising Anticancer Drugs." *Cancer Research* 52:127-131 (Jan. 1992).

Cheifetz et al., "The Transforming Growth Factor-β System, a Complex Pattern of Cross-Reactive Ligands and Receptors" *Cell* 48:409-415 (Feb. 13, 1987).

Chen and Wahl, "Manipulation of TGF-beta to control autoimmune and chronic inflammatory diseases" *Microbes Infect.* 1:1367-1380 (1999).

Chen et al., "Chaperone Activity of DsbC" *J. Bio. Chem.* 274(28):19601-19605 (Jul. 1999).

Chothia and Lesk, "Canonical Structures for the Hypervariable Regions of Immunoglobulins" *J. Mol. Biol* 196:901-917 (1987).

Clackson et al., "Making Antibody Fragments Using Phage Display Libraries" *Nature* 352(15):624-628 (Aug. 1991)

Clynes et al., "Fc Receptors Are Required in Passive and Active Immunity to Melanoma." *Proc. Natl. Acad. Sci. USA* 95(2):652-656 (1998).

Cole et al., "The EBV-Hybridoma Technique and Its Application to Human Lung Cancer" *Monoclonal Antibodies and Cancer Therapy*, New York:Alan R. Liss, Inc. pp. 77-96 (1985).

"Companies—CAT and Genzyme to develop scleroderma drug" *Scrip*, PJB Publications Ltd 2000 vol. 2580:14 (Oct. 4, 2000).

Connor et al., "Correlation of fibrosis and transforming growth factor-beta type 2 levels in the eye" *J Clin Invest.* 83(5):1661-1666 (May 1989).

Cox et al., "A directory of human germ-line V kappa segments reveals a strong bias in their usage" *European Journal of Immunology* 24:827-836 (1994).

Crown J. et al, "Taxoid Therapy of Breast Cancer" *Onkologie* 22(suppl 2):29-30 (1999).

Czarniecki et al., "Transforming growth factor-beta 1 modulates the expression of class II histocompatibility antigens on human cells" *J Immunol.* 140(12):4217-4223 (Jun. 15, 1988).

Daeron, M., "Fc Receptor Biology" *Annual Review of Immunology* 15:203-234 (1997).

Dalal et al., "Immunocytochemical localization of secreted transforming growth factor-beta 1 to the advancing edges of primary tumors and to lymph node metastases of human mammary carcinoma" *Am. J. Pathol.* 143:381-389 (Aug. 1993).

Dang et al., "SLE-like autoantibodies and Sjogren's syndrome-like lymphoproliferation in TGF-beta knockout mice" *J. Immunol.* 155:3205-3212 (1995).

Danielpour et al., "Differential Inhibition of TGF-β1 and TGF-β2 Activity by α2-Macroglobulin" *J. Cell Biochem.* 13B:84 (1989).

Danielpour et al., "Immunodetection and Quantitation of the Two Forms of Transforming Growth Factor-Beta (TGF-β1 and TGF-β2) Secreted by Cells in Culture" *J. Cellular Physiology* 138:79-86 (1989).

Danielpour et al., "Sandwich enzyme-linked immunosorbent assays (SELISAs) quantitate and distinguish two forms of transforming growth factor-beta (TGF-beta 1 and TGF-beta 2) in complex biological fluids" *Growth Factors* 2(1):61-71 (1989).

Darland et al., "Blood vessel maturation: vascular development comes of age" *J. Clin Invest.* 103(2):157-158 (Jan. 1999).

Dasch et al., "Monoclonal Antibodies Recognizing Transforming Growth Factor-β" *J. Immunol.* 142(5):1536-1541 (Mar. 1989).

Davies et al., "Endogenous TGF-beta 1 inhibits the growth and metastatic dissemination of rat oral carcinoma cell lines but enhances local bone resorption" *J. Oral. Pathol. Med.* 29:232-240 (2000).

de Haas et al., "Fcγ Receptors of Phagocytes." *J. of Laboratory Clinical Medicine.* 126:330-341 (1995).

de Martin et al., "Complementary DNA for human glioblastoma-derived T cell suppressor factor, a novel member of the transforming growth factor-β gene family" *EMBO Journal* 6(12):3673-3677 (1987).

Derynck et al., "A New Type of Transforming Growth Factor-β, TGF-β3" *EMBO Journal* 7(12):3737-3743 (1988).

Derynck et al., "Human Transforming Growth Factor-β Complementary DNA Sequence and Expression in Normal and Transformed Cells" *Nature* 316:701-705 (Aug. 1985).

Derynck et al., "Intron-exon structure of the human transforming growth factor-β precursor gene" *Nucleic Acids Research* 15(7):3188-3189 (1987).

Derynck et al., "Sequence of the porcine transforming growth factor type B gene family" *Nucl. Acids Res.* 15(7):3187 (1987).

Derynck et al., "Synthesis of messenger RNAs for transforming growth factors alpha and beta and the epidermal growth factor receptor by human tumors" *Cancer Research* 47(3):707-712 (Feb. 1, 1987).

Derynck et al., "TGF-beta signaling in tumor suppression and cancer progression" *Nat. Genet.* 29(2):117-129 (Oct. 2001).

Derynck et al., "The murine transforming growth factor-β precursor" *Journal of Biological Chemistry* 261(10):4377-4379 (1986).

Dickson et al., "Defective haematopoiesis and vasculogenesis in transforming growth factor-beta 1 knock out mice" *Development* 121(6):1845-1854 (1995).

Diebold et al., "Early-onset multifocal inflammation in the transforming growth factor beta 1-null mouse is lymphocyte mediated" *Proc Natl Acad Sci U S A* 92(26):12215-12219 (Dec. 19, 1995).

Dunker and Krieglstein, , "Targeted mutations of transforming growth factor-beta genes reveal important roles in mouse development and adult homeostasis" *European Journal of Biochemistry* 267:6982-6988 (2000).

Eastham et al., "Transforming growth factor-beta 1: comparative immunohistochemical localization in human primary and metastatic prostate cancer" *Laboratory Investigation* 73(5):628-635 (1995).

Elder et al., "Transforming Growth Factors-beta 1 and beta 2 in Serum and Urine from Patients with Bladder Carcinoma" *J. Urol.* 156:953-957 (Sep. 1996).

Ellingsworth et al., "Antibodies to the N-Terminal Portion of Cartilage-Inducing Factor A and Transforming Growth Factor Beta. Immunohistochemical Localization and Association with Differentiating Cells" *Journal of Biological Chemistry* 261(26):12362-12367 (Sep. 15, 1986).

Ellingsworth et al., "Transforming Growth Factor-βs are Equipotent Growth Inhibitors Interleukin-1-Induced Thymocyte Proliferation" *Cellular Immunology* 114(1):41-54 (Jun. 1988).

Engle et al., "Transforming growth factor beta 1 suppresses nonmetastatic colon cancer at an early stage of tumorgenesis" *Cancer Research* 59:3379-3386 (Jul. 15, 1999).

Erlebacher et al., "Increased expression of TGF-beta 2 in osteoblasts results in an osteoporosis-like phenotype" *J Cell Biol.* 132(1-2):195-210 (Jan. 1996).

Espevilk et al., Transforming growth factor-beta 1 (TGF-beta 1) and recombinant human tumor necrosis factor-alpha reciprocally regulate the generation of lymphokine-activated killer cell activity. Comparison between natural porcine platelet-derived TGF-beta 1 and TGF-beta 2, and recombinant human.

Etzioni R et al., "The case for early detection" *Nat Rev Cancer* 3(4):243-252 (Apr. 2003).

Fidler, "The pathogenesis of cancer metastasis, the 'seed and soil' hypothesis revisited" *Nat Rev Cancer* 3:453-458 (Jun. 2003).

Filvaroff Ellen et al., "Inhibition of TGF-beta receptor signaling in osteoblasts leads to decreased bone remodeling and increased trabecular bone mass" *Development* 126(19):4267-4279 (Oct. 1999).

Fishwild et al., "High-Avidity Human IgGκ Monoclonal Antibodies From a Novel Strain of *Minilocus* Transgenic Mice" *Nature Biotechnology* 14(7):845-851 (Jul. 1996).

Flanders and Roberts, "TGFβ" *Cytokine Reference*, Oppenheim and Feldmann, London:Academic Press (2000).

Flanders et al., "Antibodies to Peptide Determinants in Transforming Growth Factor β and Their Applications" *Biochemistry* 27(2):739-746 (Jan. 1988).

Flanders et al., "Antibodies to transforming growth factor-beta 2 peptides: specific detection of TGF-beta 2 in immunoassays" *Growth Factors* 3(1):45-52 (1990).

Flanders et al., "Localization and actions of transforming growth factor-beta s in the embryonic nervous system" *Development* 113(1):183-191 (Sep. 1991).

Friedman et al., "High levels of transforming growth factor beta 1 correlate with disease progression in human colon cancer" *Cancer Epidemiology, Biomarkers Prev.* 4:549-554 (Jul. 1995).

Friess et al., "Enhanced expression of transforming growth factor beta isoforms in pancreatic cancer correlates with decreased survival" *Gastroenterol.* 105(6):1846-1856 (1993).

Fujisawa et al., "Inhibitory effects of transforming growth factor-beta 1 pretreatment on experimental pulmonary metastasis of MCS-1 Chinese hamster mesenchymal chondrosarcoma cells" *Journal of Experimental Medicine* 187:203-213 (1999).

Gattoni-Celli et al., "Organ-specific metastases in melanoma: experimental animal models" *Pigment Cell Res.* 6(6):381-384 (1993).

Gazzano-Santoro, "A non-radioactive complement-dependent cytotoxicity assay for anti-CD20 monoclonal antibody" *J Immunol Methods* 202(2):163-171 (Mar. 28, 1996).

Gentry et al., "The transforming growth factor beta: amplified expression and secretion of mature and precursor polypeptides in chinese hamster ovary cells" *Molecular & Cellular Biology* 7:3418-3427 (1987).

George et al., "In vivo inhibition of rat stellate cell activation by soluble transforming growth factor beta type II receptor: a potential new therapy for hepatic fibrosis" *Proc. Natl. Acad. Sci.* 96:12719-12724 (Oct. 1999).

Ghellal et al., "Prognostic significance of TGF beta 1 and TGF beta 3 in human breast carcinoma" *Anticancer Res.* 20:4413-4418 (2000).

Giri et al., "Effect of antibody to transforming growth factor beta on bleomycin induced accumulation of lung collagen in mice" *Thorax* 48(10):959-966 (Oct.).

Goding, "Use of *Staphylococcal* protein A as an immunological reagent" *J Immunol Methods* 20:241-253 (1978).

Gold, "The role for transforming growth factor-beta (TGF-beta) in human cancer" *Crti. Rev. Oncol.* 10(4):303-360 (1999).

Gorelik and Flavell, "Abrogation of TGFbeta signaling in T cells leads to spontaneous T cell differentiation and autoimmune disease" *Immunity* 12(2):171-181 (Feb. 2000).

Gorman et al., "Transient Production of Proteins Using an Adenovirus Transformed Cell Line" *DNA Prot. Eng. Tech.* 2(1):3-10 (1990).

Gorsch et al., "Immunohistochemical staining for transforming growth factor beta 1 associates with disease progression in human breast cancer" *Cancer Research* 52:6949-6952 (Dec. 15, 1992).

Gorska et al., "Transgenic Mice Expressing a Dominant-Negative Type II TGFbeta Receptor in Mammary Epithelia Spontaneously Develop Ductal Carcinoma in Situ" *Proc. Am. Assoc. Canc. Res.* (Abstract #2270) 42:422 (Mar. 2001).

Gourdeau et al., "Antivascular and antitumor evaluation of 2-amino-4-(3-bromo-4,5-dimethoxy-phenyl)-3-cyano-4H-chromenes, a novel series of anticancer agents" *Mol Cancer Ther.* 3(11):1375-1384 (Nov. 2004).

Graham et al., "Characteristics of a Human Cell Line Transformed by DNA from Human Adenovirus Type 5" *J. Gen Virol.* 36:59-72 (1977).

Grande, "Role of transforming growth factor-beta in tissue injury and repair" *Proc. Soc. Exp. Biol. Med.* (Minireview (44066)) 214(1):27-40 (1997).

Greenwood et al., "The Preparation of I-131-Labelled Human Growth Hormone of High Specific Radioactivity" *Biochemical Journal* 89:114 (Oct. 1963).

Gridley et al., "Pilot evaluation of cytokine levels in patients undergoing radiotherapy for brain tumor" *Canc. Detect. Prev.* 22(1):20-29 (1998).

Griffiths et al., "Human anti-self antibodies with high specificity from phage display libraries" *EMBO Journal* 12:725-734 (1993).

Griffiths et al., "Isolation of High Affinity Human Antibodies Directly From Large Synthetic Repertoires" *EMBO Journal* 13:3245-3260 (1994).

Grimm et al., "TGF-beta inhibits the in vitro induction of lymphokine-activated killing activity" *Cancer Immunol Immunother.* 27(1):53-58 (1988).

Gruber et al., "Efficient Tumor Cell Lysis Mediated by a Bispecific Single Chain Antibody Expressed in *Escherichia coli*" *Journal of Immunology* 152:5368-5374 (1994).

Guise, "Molecular mechanisms of osteolytic bone metastases" *Cancer (Supplement)* 88(12):2892-2898 (Jun. 15, 2000).

Guyer et al., "Immunoglobulin Binding by Mouse Intestinal Epithelial Cell Receptors." *J. Immunol.* 117(2):587-593 (1976).

Han et al., "Favorable treatment outcome with neutralizing anti-transforming growth factor beta antibodies in experimental diabetic kidney disease" *Perit Dial Int.* 19(Suppl 2):S234-237 (1999).

Hanks et al., "Amino acid sequence of the BSC-1 cell growth inhibitor (polyergin deduced from the nucleotide sequence of the cDNA" *Proc. Natl. Acad. Sci. USA* 85:79-82 (1988).

Hara et al., "Overproduction of Penicillin-Binding Protein 7 Suppresses Thermosensitive Growth Defect at Low Osmolarity Due to an spr Mutation of *Escherichia coli*" *Micro. Drug Resistance* 2(1):63-72 (1996).

Harlow et al., "Chapter 6: Developing the Screening Method and Chapter 14: Types of Immunoassays" *Antibodies, A Laboratory Manual*, Cold Spring Harbor Laboratory pp. 174-195 and 555-612 (1988).

Hasegawa et al., "Transforming growth factor-beta 1 level correlates with angiogenesis, tumor progression, and prognosis in patients with nonsmall cell lung carcinoma" *Cancer* 91(5):964-971 (Mar. 2001).

Hawkins et al., "Selection of Phage Antibodies by Binding Affinity Mimicking Affinity Maturation" *J. Mol. Biol.* 226:889-896 (1992).

Henry, "Special Delivery: Alternative methods for delivering drugs improve performance, convenience, and patient compliance" *C&EN.* pp. 49-65 (2000).

Heppner et al., "Nontransgenic models of breast cancer" *Breast Cancer Res.* 2(5):331-334 (2000).

Hinman et al., "Preparation and Characterization of Monoclonal Antibodies conjugates of the Calicheamicins: A Novel and Potent Family of Antitumor Antibodies" *Cancer Research* 53:3336-3342 (Jul. 15, 1993).

Hino et al., "Effects of type beta transforming growth factors on haematopoietic progenitor cells" *Br J Haematol.* 70(2):143-147 (Oct. 7, 1988).

Hiraga Toru et al., "Effects of oral UFT combined with or without zoledronic acid on bone metastasis in the 4T1/luc mouse breast cancer" *Int. J. Cancer* 106(6):973-979 (Oct. 2003).

Hoefer and Anderer, "Anti-(transforming growth factor beta) antibodies with predefined specificity inhibit metastasis of highly tumorigenic human xenotransplants in nu/nu mice" *Canc. Immunol. Immunother.* 41:302-308 (1995).

Hoffman, "In vivo imaging of metastatic cancer with fluorescent proteins" *Cell Death and Differentiation* 9:786-789 (2002).

Hollinger et al., ""Diabodies": Small Bivalent and Bispecific Antibody Fragments" *Proc. Natl. Acad. Sci. USA* 90:6444-6448 (Jul. 1993).

Huston et al., "Protein Engineering of Antibody Binding Sites: Recovery of Specific Activity in an Anti-Digoxin Single-Chain Fv Analogue Produced in *Escherichia coli*" *Proc. Natl. Acad. Sci. USA* 85:5879-5883 (Aug. 1988).

Isaka et al., "Gene therapy by transforming growth factor-beta receptor-IgG Fc chimera suppressed extracellular matrix accumulation in experimental glomerulonephritis" *Kidney International* 55:465-475 (1999).

Ivanovic et al., "Elevated plasma levels of TGF-beta 1 in patients with invasive prostate cancer" *Nat. Med.* 1:282-284 (Apr. 1995).

Jackson et al., "In vitro antibody maturation. Improvement of a high affinity, neutralizing antibody against IL-1 beta" *J. Immunol.* 154(7):3310-3319 (1995).

Jakowlew et al., "Complementary Deoxyribonucleic Acid Cloning of a Messenger Ribonucleic Acid Encoding Tranforming Growth Factor-β4 from Chicken Embryo Chondrocytes" *Molecular Endocrinology* 2:1186-1195 (1988).

Jakowlew et al., "Complementary Deoxyribonucleic Acid Cloning of a Novel Transforming Growth Factor-β Messenger Ribonucleic Acid from Chick Embryo Chondrocytes" *Molecular Endocrinology* 2(8):747-755 (1988).

Jampel et al., "Transforming growth factor-beta in human aqueous humor" *Curr Eye Res.* 9(10):963-969 (Oct. 1990).

Joly et al., "Overexpression of *Escherichia coli* Oxidoreductases Increases Recombinant Insulin-Like Growth Gactor-I Accumulation" *Proc. Natl. Acad. Sci. USA* 95:2773-2777 (Mar. 1998).

Jones et al., "Replacing the Complementarity-Determining Regions in a Human Antibody with Those From a Mouse" *Nature* 321:522-525 (May 29, 1986).

Junker et al., "Transforming Growth Factor Beta 1 is Significantly Elevated in Plasma of Patients Suffering from Renal Cell Carcinoma" *Cytokine* 8(10):794-798 (Oct. 1996).

Kasid et al., "Effects of transforming growth factor-beta on human lymphokine-activated killer cell precursors. Autocrine inhibition of cellular proliferation and differentiation to immune killer cells" *J Immunol.* 141(2):690-698 (Jul. 15, 1988).

Kearney JF et al, "A new mouse myeloma cell line that has lost immunoglobulin expression but permits the construction of antibody-secreting hybrid cell lines" *J. Immunol* 123(4):1548-1550 (Oct. 1979).

Keski-Oja et al., "Immunodetection and Modulation of Cellular Growth with Antibodies against Native Transforming Growth Factor-β1" *Cancer Research* 47(24 Pt. 1):6451-6458 (Dec. 15, 1987).

Khaw et al., "Activation and suppression of fibroblast function" *Eye* 8(Pt 2):188-195 (1994).

Kim et al., "Localization of the site of the murine IgG1 molecule that is involved in binding to the murine intestinal Fc receptor" *Eur J Immunol.* 24(10):2429-24234 (Oct. 1994).

Klos Kristine et al., "Combined trastuzumab and paclitaxel treatment better inhibits ErbB-2-mediated angiogenesis in breast carcinoma through a more effective inhibition of Akt than either treatment alone" *Cancer* 98(7):1377-1385 (Oct. 1, 2003).

Kohler and Milstein., "Continuous Cultures of Fused Cells Secreting Antibody of Predefined Specificity" *Nature* 256:495-497 (Aug. 1975).

Kong et al., "Elevated plasma transforming growth factor-beta 1 levels in breast cancer patients decrease after surgical removal of the tumor" *Ann. Surg.* 222(2):155-162 (1995).

Kostelny et al., "Formation of a Bispecific Antibody by the Use of Leucine Zippers" *Journal of Immunology* 148(5):1547-1553 (Mar. 1992).

Krasagakis et al., "Elevated plasma levels of transforming growth factor (TGF)-beta1 and TGF-beta2 in patients with disseminated malignant melanoma" *Br. J. Canc.* 77:1492-1494 (1998).

Kulkarni et al., "Transforming Growth Factor 1 Null Mutation in Mice Causes Excessive Inflammatory Response and Early Death" *Proc. Natl. Acad. Sci.* 90:770-774 (Jan. 1993).

Kuppner et al., "The glioblastoma-derived T-cell suppressor factor/transforming growth factor beta 2 inhibits the generation of lymphokine-activated killer (LAK) cells" *Int J Cancer* 42(4):562-567 (Oct. 15, 1988).

kvanta, "Expression and secretion of transforming growth factor-beta in transformed and nontransformed retinal pigment epithelial cells" *Ophthalmis Res.* 26(6):361-367 (1994).

Larsson et al., "Abnormal angiogenesis but intact hematopoietic potential in TGF-beta type I receptor-deficient mice" *EMBO Journal* 20(7):1663-1673 (Apr. 2001).

Lee et al., "Beta transforming growth factors are potential regulators of B lymphopoiesis" *J Exp Med.* 166(5):1290-1299 (Nov. 1, 1987).

Lelekakis M et al., "A novel orthotopic model of breast cancer metastasis to bone" *Clinical & Experimental Metastasis* 17(2):163-170 (Mar. 1990).

Lettrio et al., "Autoimmunity Associated with TGF-1-Deficiency in Mice is Dependent on MHC Class II Antigen Expression" *J. Clin. Invest.* 98:2109-2119 (1996).

Li et al., "Angiogenesis in breast cancer: the role of transforming growth factor beta and CD105" *Microsc Res Tech.* 52(4):437-449 (Feb. 15, 2001).

Li et al., "Role of transforming growth factor 3 in lymphatic metastasis in breast cancer" *Intl. J. Canc.* 79:455-459 (1998).

Lin et al., "Progression to Malignancy in the Polyoma Middle T Oncoprotein Mouse Breast Cancer Model Provides a Reliable Model for Human Diseases" *Am. J. Pathol.* 163(5):2113-2126 (Nov. 2003).

Littlefield, J. W., "Selection of Hybrids From Matings of Fibroblasts In Vitro and Their Presumed Recombinants" *Science* 145:709-710 (Aug. 14, 1964).

Lode et al., "Targeted Therapy with a Novel Enediyene Antibiotic Calicheamicin ⊖ II Effectively Suppresses Growth and Dissemination of Liver Metastases in a Syngeneic Model of Murine Neuroblastoma" *Cancer Research* 58:2925-2928 (Jul. 15, 1998).

Logan et al., "Effects of transforming growth factor beta 1 on scar production in the injured central nervous system of the rat" 6(3):355-363 (Mar. 1994).

Lonberg and Huszar, "Human Antibodies From Transgenic Mice" *International Reviews of Immunology* 13(1):65-93 (1995).

Lonberg et al., "Antigen-Specific Human Antibodies From Mice Comprising Four Distinct Genetic Modifications" *Nature* 368(6474):856-859 (Apr. 28, 1994).

Lucas et al., "Disruption of T Cell Homeostasis in Mice Expressing a T Cell specific Dominant Negative Transforming Growth Factor II Receptor" *Journal of Experimental Medicine* 191(7):1187-1196 (Apr. 2000).

Lucas et al., "The Autocrine Production of Transforming Growth Factor-β 1 During Lymphocyte Activation: A Study with a Monoclonal Antibody-Based ELISA" *J. Immunol.* 145(5):1415-1422 (Sep. 1990).

MacCallum et al., "Changes in expression of transforming growth factor beta mRNA isoforms in patients undergoing tamoxifen therapy" *Br. J. Cancer* 74:474-478 (Feb. 1996).

Madisen et al., "Transforming Growth Factor-β2: cDNA Cloning and Sequence Analysis" *DNA* 7(1):1-8 (1988).

Maehara et al., "Role of transforming growth factor-beta 1 in invasion and metastasis in gastric carcinoma" *J. Clin. Oncolo.* 17:607-614 (Feb. 1999).

Maglione et al., "Transgenic Polyoma middle-T mice model premalignant mammary disease" *Cancer Research* 61(22):8298-8305 (Nov. 15, 2001).

Mariani et al., "Characterization of monoclonal antibodies against human chorionic somatomammotropin: competitive screening and determination of the affinity constants" *J Immunol Methods* 71(1):43-48 (Jun. 8, 1984).

Markowitz et al., "Inactivation of the type II TGF-beta receptor in colon cancer cells with microsatellite instability" *Science* 268:1336-1338 (Jun. 1995).

Marks et al., "By-Passing Immunization: Building High Affinity Human Antibodies by Chain Shuffling" *Bio/Technology* 10:779-783 (Jul. 1992).

Marks et al., "By-Passing Immunization: Human Antibodies From V-gene Libraries Displayed on Phage" *J. Mol. Biol.* 222:581-597 (1991).

Marquardt et al., "Complete amino acid sequence of human transforming growth factor type β 2" *Journal of Biological Chemistry* 262:12127-12131 (1987).

Massague et al., "TGFbeta signaling in growth control, cancer, and heritable disorders" *Cell* 103(2):295-309 (Oct. 2000).

Massey, R.J., "Catalytic antibodies catching on" *Nature* 328:457-458 (Jul. 1987).

McEarchern et al., "Invasion and metastasis of a mammary tumor involves TGF-signaling" *Int. J. Canc.* 91:76-82 (2001).

McMahon et al., "Differential effects of transforming growth factor-beta on proliferation of normal and malignant rat liver epithelial cells in culture" *Cancer Research* 46(9):4665-4671 (Sep. 1986).

Milstein et al., "Hybrid hybridomas and their use in immunohistochemistry" *Nature* 305:537-539 (Oct. 1983).

Miyajima et al., "Antibody to transforming growth factor-beta ameliorates tubular apoptosis in unilateral ureteral obstruction" *Kidney International* 58(6):2301-2313 (Dec. 2000).

Morimoto et al., "Single-step purification of F(ab')$^2$ fragments of mouse monoclonal antibodies (immunoglobulins G1) by hydrophobic interaction high performance liquid chromatography using TSKgel Phenyl-5PW" *Journal of Biochemical and Biophysical Methods* 24:107-117 (1992).

Morrison et al., "Chimeric Human Antibody Molecules: Mouse Antigen-Binding Domains with Human Constant Region Domains" *Proc. Natl. Acad. Sci. USA* 81:6851-6855 (Nov. 1984).

Morrison, "Success in Specification" *Nature* 368(6474):812-813 (Apr. 28, 1994).

Mule et al., "Transforming growth factor-beta inhibits the in vitro generation of lymphokine-activated killer cells and cytotoxic T cells" *Cancer Immunol Immunother.* 26(2):95-100 (1988).

Mundy G. R., "Cancer and Bone" *Calcified Tissue International* 64(1 suppl):s31 (1999).

Mundy G.R . et al, "Mechanisms of bone metastasis" *Cancer* 80(8 Suppl):1546-1556 (Oct. 15, 1997).

Munger et al., "Latent Transforming Growth Factor-Beta: Structural Features" *Kidney International* 51(5):1376-1382 (1997).

Munson and Rodbard, "Ligand: A Versatile Computerized Approach for Characterization of Ligand-Binding Systems" *Analytical Biochemistry* 107:220-239 (1980).

Muraoka et al., "Increased malignancy of Neu-induced mammary tumors overexpressing active transforming growth factor beta1" *MCB* 23(23):8691-8703 (Dec. 2003).

Muraoka RS et al., "Blockade of TGF-beta inhibits mammary tumor cell viability, migration, and metastases" *JCI* 109(12):1551-1559 (2002).

Muraoka-Cook, "Conditional overexpression of active transforming growth factor beta1 in vivo accelerates metastases of transgenic mammary tumors" *Cancer Research* 64(24): 9002-9011 (Dec. 2004).

Nakane and Kawaoi, "Peroxidase-labeled antibody. A new method of conjugation" *J. Histochem. and Cytochem.* 22(12):1084-1091 (Aug. 1974).

Neuberger et al., "Recombinant Antibodies Possessing Novel Effector Functions" *Nature* 312:604-608 (Dec. 13, 1984).

Neuberger, M., "Generating High-Avidity Human Mabs in Mice" *Nature Biotechnology* 14(7):826 (Jul. 1996).

Nissim et al., "Antibody fragments from a 'single pot' phage display library as immunochemical reagents" *EMBO Journal* 13(3):692-698 (1994).

Nossal, "Immunologic tolerance: collaboration between antigen and lymphokines" *Science* 245(4914):147-153 (Jul. 14, 1989).

O'Connor McCourt, "Analysis of the interaction between two TGF-beta-binding proteins and three TGF-beta isoforms using surface plasmon resonance" *Ann. N.Y. Acad. Sci.* 766:300-302 (Sep. 1995).

Oft et al., "TGFbeta signaling is necessary for carcinoma cell invasiveness and metastasis" *Curr. Biol.* 8(23):1243-1252 (Oct. 1998).

Oi and Herzenberg, "Immunoglobulin-producing Hybrid Cell Lines" *Selected Methods in Cellular Immunology*, B. Mishel and S. Schiigi, San Francisco, CA:W.J. Freeman Co., pp. 351-372 (1980).

Oshima et al., "TGF-beta receptor type II deficiency results in defects of yolk sac hematopoiesis and vasculogenesis" *Dev Biol.* 179(1):297-302 (Oct. 10, 1996).

Pena et al., "Effects of TGF-beta and TGF-beta neutralizing antibodies on fibroblast-induced collagen gel contraction: implications for proliferative vitreoretinopathy" *Invest Opthalmol Vis Sci.* 35(6):2804-2808 (May 1994).

Petit-Koskas, "Inhibition of the proliferative response of human B lymphocytes to B cell growth factor by transforming growth factor-beta" *Eur J Immunol.* 18(1):111-1116 (Jan. 1988).

Pfeffer et al., "Transforming growth factor beta 2 is the predominant isoforms in the neural retina, retinal pigment epithelium-choroid and vitreous of the monkey eye" *Exp Eye Res.* 59(3):323-333 (Sep. 1994).

Picon et al., "A subset of metastatic human colon cancers expresses elevated levels of transforming growth factor beta1" *Cancer Epidemiol Biomarkers Prev.* 7:497-504 (Jun. 1998).

Pircher et al., "Beta-transforming growth factor is stored in human blood platelets as a latent high molecular weight complex" *Biochem Biophys Res Commun.* 136(1):30-37 (Apr. 14, 1986).

Pluckthun., "Antibodies From *Escherichia coli*." *The Pharmacology of Monoclonal Antibodies: Handbook of Experimental Pharmacology.*, Rosenberg and Moore, eds., Berlin-Springer-Verlag, Chapter 11, vol. 113:269-315 (1994).

Potter et al., "Growth of primary plasmacytomas in the mineral oil-conditioned peritoneal environment" *J Natl Cancer Inst.* 49(1):305-308 (Jul. 1972).

Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).

Presta et al., "Humanization of an Antibody Directed Against IgE" *J. Immunol.* 151(5):2623-2632 (Sep. 1, 1993).

Presta, L., "Antibody Engineering" *Curr. Op. Struct. Biol.* 2:593-596 (1992).

Proba et al., "Antibody scFv Fragments Without Disulfide Bonds Made by Molecular Evolution" *J. Mol. Biol.* 275:245-253 (1998).

Proba et al., "Functional Antibody Single-Chain Fragments From the Cytoplasm of *Escherichia coli*: Influence of Thioredoxin Reductase (TrxB)" *Gene* 159:203-207 (1995).

Pulaski and Ostrand-Rosenberg, "Reduction of established spontaneous mammary carcinoma metastases following immunotherapy with major histocompatibility complex class II and B7.1 cell-based tumor vaccines" *Cancer Research* 58:1486-1493 (Apr. 1998).

Pulaski et al., "Cooperativity of *Staphylococcal aureus* enterotoxin B superantigen, major histocompatibility complex class II, and CD80 for immunotherapy of advanced spontaneous metastases in a clinically relevant postoperative mouse breast cancer model" *Cancer Research* 60:2710-2715 (May 2000).

Ramm and Pluckthun, "The Periplasmic *Escherichia coli* Peptidylprolyl cis,trans Isomerase FkpA" *J. Bio. Chem.* 275(22):17106-17113 (Jun. 2000).

Ranges et al., "Inhibition of cytotoxic T cell development by transforming growth factor beta and reversal by recombinant tumor necrosis factor alpha" *J Exp Med.* 166(4):991 (Oct. 1, 1987).

Ravetch and Kinet, "Fc Receptors" *Annu. Rev. Immunol.* 9:457-492 (1991).

Riechmann et al., "Reshaping Human Antibodies for Therapy" *Nature* 332:323-327 (Mar. 24, 1988).

Riggins et al., "Frequency of Smad gene mutations in human cancers" *Cancer Research* 57:2578-2580 (Jul. 1997).

Roberts and Sporn, "The Transforming Growth Factor-βs" *Peptide Growth Factors and Their Receptors I*, Springer-Verlag, Chapter 8, pp. 419-472 (1990).

Roberts and Wakefield, "The two faces of transforming growth factor beta in carcinogenesis" *Proc. Natl. Acad. Sci. USA* 100(15):8621-8623 (Jul. 2003).

Roberts et al., "Mesoderm induction in *Xenopus laevis* distinguishes between the various TGF-beta isoforms" *Growth Factors* 3(4):277-286 (1990).

Roberts et al., "Transforming Growth Factor Type β: Rapid Induction of Fibrosis and Angiogenesis In Vivo and Stimulation of Collagen Formation In Vitro" *Proc. Natl. Acad. Sci. USA* 83(12):4167-4171 (Jun. 1986).

Roberts et al., "Transforming growth factor-beta: possible roles in carcinogenesis" *Br J Cancer* 57(6):594-600 (Jun. 1988).

Roberts, "Molecular and cell biology of TGF-beta" *Miner Electrolyte and Metab.* 24:111-119 (1998).

Rosa et al., "Mesoderm induction in amphibians: the role of TGF-beta 2-like factors" *Science* 239(4841 Pt 1):783-785 (Feb. 12, 1988).

Ruzek et al., "Minimal effects on immune parameters following chronic anti-TGF-beta monoclonal antibody administration to normal mice" *Immunopharm. and Immunotox.* 25(2):235-237 (2003).

Saito et al., "An elevated serum level of transforming growth factor-beta 1 (TGF-beta 1) significantly correlated with lymph node metastasis and poor prognosis in patients with gastric carcinoma" *Anticancer Res.* 20:4489-4493 (2000).

Samuel et al., "Autocrine induction of tumor protease production and invasion by a metallothionein-regulated TGF-beta 1 (Ser223, 225)" *EMBO Journal* 11:1599-1605 (1992).

Schable and Zachau, "The variable genes of the human immunoglobulin kappa locus" *Biol. Chem. Hoppe-Seyler* 374:1001-1022 (Nov. 1993).

Schier et al., "Identification of functional and structural amino-acid residues by parsimonious mutagenesis" *Gene* 169:147-155 (1996).

Schlunegger and Grutter, "An unusual feature revealed by the crystal structure of 2.2 A resolution of human transforming growth factor-β2" *Nature* 358:430-434 (Jul. 30, 1992).

Schwarz et al., "Aberrant TGF-beta production and regulation in metastatic malignancy" *Growth Factors* 3:115-127 (1990).

Searle, Tim, "Trends in Antibody Reseaerch:The Monoclonal Elite" *Bioventure-View*1510:14 (Oct. 1, 2000).

Seyedin et al., "Cartilage-inducing Factor-A: Apparent Identity to Transforming Growth Factor-β" *J. Biological Chem.* 261(13):5693-5695 (1986).

Seyedin et al., "Cartilage-inducing Factor-B Is a Unique Protein Structurally and Functionally Related to Tranforming Growth Factor-β" *J. Biological Chem.* 262(5):1946-1949 (1987).

Shah et al., "Control of scarring in adult wounds by neutralising antibody to transforming growth factor beta" *Lancet* 339(8787):213-214 (Jan. 25, 1992).

Shah et al., "Neutralisation of TGF-beta 1 and TGF-beta 2 or exogenous addition of TGF-beta 3 to cutaneous rat wounds reduces scarring" *J Cell Sci.* 108(Pt 3):985-1002 (Mar. 1995).

Shah et al., "Neutralising antibody to TGF-beta 1,2 reduces cutaneous scarring in adult rodents" *J Cell Sci.* 107(Pt 5):1137-1157 (May 1994).

Shah et al., "Suppression of tumor metastasis by blockade of transforming growth factor beta signaling in bone marrow cells through a retroviral-mediated gene therapy in mice" *Cancer Research* 62(24):7135-7138 (Dec. 15, 2002).

Shalaby et al., "Development of Humanized Bispecific Antibodies Reactive with Cytotoxic Lymphocytes and Tumor Cells Overexpressing the HER2 Protooncogene" *Journal of Experimental Medicine* 175:217-225 (Jan. 1, 1992).

Sharma and Ziyadeh, "Hyperglycemia and diabetic kidney disease. The case for transforming growth factor-β as a key mediator" *Diabetes* 44(10):1139-1146 (Oct. 1995).

Sharples et al., "Cloning and Sequence Analysis of Simian Transforming Growth Factor-β cDNA" *DNA* 6(3):239-244 (1987).

Sheen-Chen et al., "Serum levels of transforming growth factor beta1 in patients with breast cancer" *Arch. Surg.* 136:937-940 (Aug. 2001).

Sheets et al., "Efficient construction of a large nonimmune phage antibody library: the production of high-affinity human single-chain antibodies to protein antigens" *Proc. Natl. Acad. Sci. USA* 95(11):6157-6162 (May 1998).

Shirai et al., "Elevated levels of plasma transforming growth factor-beta in patients with hepatocellular carcinoma" *Jpn. J. Cancer Res.* 83:676-679 (Jul. 1992).

Shopes, "A Genetically Engineered Human IgG Mutant With Enhanced Cytolytic Activity" *Journal of Immunology* 148(9):2918-2922 (May 1992).

Shull et al., "Targeted disruption of the mouse transforming growth factor-beta 1 gene results in multifocal inflammatory disease" *Nature* 359:693-699 (Oct. 1992).

Sias et al., "ELISA for Quantitation of the Extracellular Domain of p185HER2 in Biological Fluids." *Journal of Immunological Methods* 132(1):73-80 (1990).

Siegel et al., "Transforming growth factor beta signaling impairs Neu-induced mammary tumorigenesis while promoting pulmonary metastasis" *Proc Natl Acad Sci U S A.* 100(14):8403-8405 (Jul. 8, 2003).

Sims et al., "A Humanized CD18 Antibody Can Block Function Without Cell Destruction" *The Journal of Immunology* 151(4):2296-2308 (Aug. 1993).

Sing et al., "Transforming growth factor beta selectively inhibits normal and leukemic human bone marrow cell growth in vitro" *Blood* 72(5):1504-1511 (Nov. 1988).

Singer et al., "Cutaneous wound healing" *N Engl J Med.* 341(10):738-746 (Sep. 2, 1999).

Smith et al., "Soluble transforming growth factor-beta type II receptor inhibits negative remodeling, fibroblast transdifferentiation, and intimal lesion formation but not endothelial growth" *Circ. Res.* 84:1212-1222 (1999).

Spearman et al., "Antisense oligodeoxyribonucleotide inhibition of TGF-beta 1 gene expression and alterations in the growth and malignant properties of mouse fibrosarcoma cells" *Gene* 149:25-29 (1994).

Sporn et al., "Peptide growth factors are multifunctional" *Nature* 332:217-219 (1988).

Sporn et al., "Some Recent Advances in the Chemistry and Biology of Transforming Growth Factor-Beta" *Journal of Cell Biology* 105:1039-1045 (Sep. 1987).

Sporn et al., "Transforming Growth Factor-β: Biological Function and Chemical Structure" *Science* 233:532-534 (Aug. 1, 1986).

Stearns et al., "Role of interleukin 10 and transforming growth factor beta1 in the angiogenesis and metastasis of human prostate primary tumor lines from orthotopic implants in severe combined immunodeficiency mice" *Clin Cancer Res.* 5:711-720 (Mar. 1999).

Steiner and Barrack, "Transforming growth factor-beta 1 overproduction in prostate cancer: effects on growth in vivo and in vitro" *Molecular Endocrinology* 6(1):15-25 (1992).

Stenvers et al., "Heart and liver defects and reduced transforming growth factor beta2 sensitivity in transforming growth factor beta type III receptor-deficient embryos" *Mol Cell Biol.* 23(12):4371-4385 (Jun. 2003).

Stravodimos et al., "Immunohistochemical expression of transforming growth factor beta 1 and nm-23 H1 antioncogene in prostate cancer: divergent correlation with clinicopathological parameters" *Anticancer Res.* 20:3823-3828 (2000).

Strochein et al., "Negative feedback regulation of TGF-beta signaling by the SnoN oncoprotein" *Science* 286:771-774 (Oct. 1999).

Suresh et al., "Bispecific Monoclonal Antibodies from Hybrid Hybridomas" *Methods in Enzymology* 121:210-228 (1986).

Takanami et al., "Roles of the transforming growth factor beta 1 and its type I and II receptors in the development of a pulmonary adenocarcinoma: results of an immunohistochemical study" *J. Surg. Oncol.* 64(4):262-267 (1997).

Tang et al., "Transforming growth factor-beta1 is a new form of tumor suppressor with true haploid insufficiency" *Nat. Med.* 4(7):802-807 (Jul. 1998).

Tempest et al., "Human antibodies specific for human TGF-Beta derived from phage display libraries" *Immunotechnology* ((Abstracts)) 2:306 (1996).

ten Dijke et al., "Identification of Another Member of the Transforming Growth Factor Type β Gene Family" *Proc. Natl. Acad. Sci. USA* 85:4715-4719 (1988).

Traunecker et al., "Bispecific Single Chain Molecules (Janusins) Target Cytotoxic Lymphocytes on HIV Infected Cells" *EMBO Journal* 10(12):3655-3659 (1991).

Travers et al., "Growth factor expression in normal, benign, and malignant breast tissue" *BMJ* 296(6637):1621-1624 (Jun. 1988).

Tsushima et al., "High levels of transforming growth factor beta 1 in patients with colorectal cancer: Association with disease progression" *Gastroenterology* 110:375-382 (1996).

Turco et al., "Overexpression of transforming growth factor beta-type II receptor reduces tumorigenicity and metastatic potential of K-ras-transformed thyroid cells" *Int. J. Cancer* 80:85-91 (1999).

Tutt et al., "Trispecific F(ab')3 derivatives that use cooperative signaling via the TCR/CD3 complex and CD2 to activate and redirect resting cytotoxic T cells" *J. Immunol.* 147(1):60-69 (Jul. 1991).

Ueki et al., "Potentiation of metastatic capacity by transforming growth factor-beta 1 gene transfection" *Jpn. J. Cancer Res.* 84:589-593 (Jun. 1993).

Ueno et al., "A soluble transforming growth factor beta receptor expressed in muscle prevents liver fibrogenesis and dysfunction in rats" *Hum. Gene. Ther.* 11:33-42 (Jan. 2000).

Vaughan et al., "Human Antibodies With Sub-nanomolar Affinities Isolated From a Large Non-immunized Phage Display Library" *Nature Biotechnology* 14:309-314 (Mar. 1996).

Verhoeyen et al., "Reshaping Human Antibodies: Grafting an Antilysozyme Activity" *Science* 239:1534-1536 (Mar. 25, 1988).

Vilchis-Landeros et al., "Recombinant soluble betaglycan is a potent and isoform-selective transforming growth factor-beta neutralizing agent" *Biochemical Journal* 355:215-222 (2001).

Vitetta et al., "Redesigning Nature's Poisons to Create Anti-Tumor Reagents" *Science* 238:1098-1104 (1987).

Vogel, "A new blocker for the TGF-beta pathway" *Science* 286:665 (Oct. 1999).

Wahl et al., "Reversal of acute and chronic synovial inflammation by anti-transforming growth factor beta" *J Exp Med.* 177(1):225-230 (Jan. 1, 1993).

Wakefield et al., "Distribution and Modulation of the Cellular Receptor for Transforming Growth Factor-Beta" *Journal of Cell Biology* 105:965-975 (1987).

Wakefield et al., "Recombinant TGF-beta 1 is synthesized as a two-component latent complex that shares some structural features with the native platelet latent TGF-beta 1 complex" *Growth Factors* 1(3):203-218 (1989).

Walker and Dearing, "Transforming growth factor beta 1 in ductal carcinomas in situ and invasive carcinomas of the breast" *Eur. J. Canc.* 28:641-644 (1992).

Wang et al., "Reduction of bleomycin induced lung fibrosis by transforming growth factor beta soluble receptor in hamsters" *Thorax* 54:805-812 (1999).

Welch et al., "Transforming Growth Factor beta Stimulates Mammary Adenocarcinoma Cell Invasion and Metastatic Potential" *Proc. Natl. Acad. Sci.* 87:7678-7682 (Oct. 1990).

Werther et al., "Humanization of an Anti-Lymphocyte Function-Associated Antigen (LFA)-1 Monoclonal Antibody and Reengineering of the Humanized Antibody for Binding to Rhesus LFA-1" *J. of Immunology* 157:4986-4995 (1996).

Wilkstrom et al., "Transforming growth factor beta 1 is associated with angiogenesis, metastasis, and poor clinical outcome in prostate cancer" *Prostate* 37:19-29 (1998).

Wojtowicz-Praga et al., "Modulation of B16 melanoma growth and metastasis by anti-transforming growth factor beta antibody and interleukin-2" *J. Immunotherapy* 19(3):169-175 (1996).

Wolf et al., "Antibodies against transforming growth factor-beta 1 suppress intimal hyperplasia in a rat model" *J Clin Invest.* 93(3):1172-1178 (Mar. 1994).

Wolff et al., "Monoclonal antibody homodimers: enhanced antitumor activity in nude mice" *Cancer Research* 53(11):2560-2565 (Jun. 1993).

Wrana, "TGF-beta receptors and signalling mechanisms" *Miner. Electrolyte Metab.* 24:120-130 (1998).

Wrann et al., "T cell suppressor factor from human glioblastoma cells is a 12.5-kd protein closely related to transforming growth factor-beta" *EMBO Journal* 6(6):1633-1666 (Jun. 1987).

Wu RS et al., "Comparative analysis of IFN-gamma B7.1 and antisense TGF-beta gene transfer on the tumorgenicity of a poorly immunogenic metastatic mammary carcinoma" *Cancer Immunol. Immunother.* 50(5):229-240 (Jul. 2001).

Wunderlich et al., "Increased transforming growth factor beta 1 plasma level in patients with renal cell carcinoma: a tumor-specific marker?" *Urol. Int.* 60:205-207 (1998).

Xu et al., "Elevated serum levels of transforming growth factor beta 1 in Epstein-Barr virus-associated nasopharyngeal carcinoma patients" *Int. J. Cancer* 84:396-399 (1999).

Yang et al., "Lifetime exposure to a soluble TGF-beta antagonist protects mice against metastasis without adverse side effects" *JCI* 109(12):1607-1615 (Jun. 2002).

Yang et al., "Tolerization of anti-Galalphal-3Gal natural antibody-forming B cells by induction of mixed chimerism" *J. Exp. Med.* 187(8):1335-1342 (Apr. 1998).

Yelton et al., "Affinity Maturation of the BR96 Anti-Carcinoma Antibody by Codon-Based Mutagenesis" *The Journal of Immunology* 155:1994-2004 (1995).

Yin et al., "TGF-beta signaling blockade inhibits PTHrP secretion by breast cancer cells and bone metastases development" *J. Clin. Invest.* 103(2):197-206 (Jan. 1999).

Yingling et al., "Development of TGF-beta signalling inhibitors for cancer therapy" *Nat Rev Drug Discov.* 3(12):1011-1022 (Dec. 2004).

Yoneda Toshiyuki et al., "Actions of bisphosphonate on bone metastasis in animal models of breast carcinoma" *Cancer Supplement* 88(12):2979-2988 (Jun. 15, 2000).

Zapata et al., "Engineering Linear F(ab')$_2$ Fragments for Efficient Production in *Escherichia coli* and Enhanced Antiproliferative Activity" *Protein Engineering* 8(10):1057-1062 (1995).

Zheng et al., "Recombinant soluble transforming growth factor beta type II receptor ameliorates radiation enteropathy in mice" *Gastroenterology* 119:1286-1296 (Nov. 2000).

Zhou S. et al., "Targeted deletion of Smad4 shows it is required for transforming growth factor beta and activin signaling in colorectal cancer cells" *Proc. Natl. Acad. Sci. USA* 95(5):2412-2416 (Mar. 1998).

Zhu et al., "Smad3 Mutant Mice Develop Metastatic Colorectal Cancer" *Cell* 94(6):703-714 (Sep. 18, 1998).

Ziyadeh et al., "Long-term prevention of renal insufficiency, excess matrix gene expression, and glomerular mesangial matrix expansion by treatment with monoclonal antitransforming growth factor-beta antibody in db/db diabetic mice" *Proc Natl Acad Sci U S A* 97(14):8015-8020 (Jul. 5, 2000).

Zola, H., "Using Monoclonal Antibodies: Soluble Antigens" *Monoclonal Antibodies: A Manual of Techniques*, CRC Press, Chapter 6, pp. 147-158 (1987).

Zuber et al., "Transforming growth factor-beta 2 down-regulates HLA-DR antigen expression on human malignant glioma cells" *Eur J Immunol.* 18(10):1623-1626 (Oct. 18, 1988).

\* cited by examiner

FIG. 1A

Variable Light

```
              10            20           30              40
                                         CDR-L1
2G7      DIMMTQSPSSLAVSAGEKVTMSCKSSQSVLYSSNQKNYLAWYQQKPGQS
             *       ** * **  ** **
huxTGFB  DIQMTQSPSSLSASVGDRVTITCRASQSVLYSSNQKNYLAWYQQKPGKA
                                ********
huKI     DIQMTQSPSSLSASVGDRVTITCRASQSIS------NYLAWYQQKPGKA
huCDR                           RASQGIS------SYLA 50           60           70           80
           CDR-L2
2G7      PKLLIYWASTRESGVPDRFTGSGSGTDFTLTISSVQAEDLAVYYC
               *    *                    * *    *   *
huxTGFB  PKLLIYWASTRESGVPSRFSGSGSGTDFTLTISSLQPEDFATYYC
               *  **
huKI     PKLLIYAASSLESGVPSRFSGSGSGTDFTLTISSLQPEDFATYYC
huCDR          YASSLQS 90          100
           CDR-L3
2G7      HQYL-SSDTFGGGTKLEIKRTVA
              *    *
huxTGFB  HQYL-SSDTFGQGTKVEIKRTVA
         *    *****
huKI     QQYNSLPWTFGQGTKVEIKRT
huCDR    QQYNSYPYT
```

FIG. 1B

Variable Heavy

```
                    10        20        30        40
                                        CDR-H1
2G7       QVxLxQSGAELVRPGTSVKVSCKASGYAFTNYLIEWVKQRPGQGLEWIG
            *  *  **   **  *  *  ***    *              *  *   *    *
huxTGFB   EVQLVESGGGLVQPGGSLRLSCAASGYAFTNYLIEWVRQAPGKGLEWVG
                                   **  ** ***                           *
huIII     EVQLVESGGGLVQPGGSLRLSCAASGFTFSSYAMSWVRQAPGKGLEWVA
huCDR                              GFTFSSYAMH 50    a     60        70        80  abc       90
                   CDR-H2
2G7       VNNPGSGGSNYNEKFKGKATLTADKSSSTAYMQLSSLTSDDSAVYFCAR
                                *   **   *  ** *  *  **   *** *     *
huxTGFB   VNNPGSGGSNYNEKFKGRATISADNSKNTLYLQMNSLRAEDTAVYYCAR
          *****  ***  ****       *       *
huIII     VISGDGGSTYYADSVKGRFTISRDNSKNTLYLQMNSLRAEDTAVYYCAR 100       110
              CDR-H3
2G7H      SGGFYFDYWGQGTTQSPSPQPKRRAH
                **  ******
huxTGFB   SGGFYFDYWGQGTLVTVSSASTKGPS
               
huIII     GRGxSFDYWGQGTLVTVSS
```

FIG. 2

Humanized (V5) 2G7 CDRs

CDR L1  [RASQSVLYSSNQKNYLA]

5'-AGAGCCAGTCAGAGCGTGCTGTATAGTTCGAATCAGAAGAACTACCTGGCC-3'

CDR L2  [WASTRES]

5'-TGGGCTAGTACTCGCGAGTCT-3'

CDR L3  [HQYL-SSDT]

5'-CACCAGTATCTGAGCTCTGACACA-3'

CDR H1  [GYAFTNYLIE]

5'-GGCTACGCATTCACCAACTATCTGATCGAG-3'

CDR H2  [VNNPGSGGSNYNEKFKG]

5'-GTTAACAATCCTGGATCCGGAGGCTCCAACTATAACGAGAAGTTCAAGGGG-3'

CDR H3  [SGGFYFDY]

5'-TCCGGAGGCTTCTACTTCGACTAC-3'

For the murine precursor, the CDRs are the same as in the humanized version except for L1 which is here:.

CDR L1  [KSSQSVLYSSNQKNYLA]

5'AAGTCCAGTCAAAGTGTTTTATACAGTTCAAATCAGAAGAACTACTTGGCC-3'

FIG. 3

```
:::::::::::::::
p1.xTGFb.709.LandH.IgG1.RK
:::::::::::::::
< Mon Apr  2 11:49:24 2001
< /tmp_mnt/home/oz/vqa/Mac/adamscam/ss.xTGFb.709.IgG1.LandH.RK (2676
bases)
```

DIQMTQSPSSLSASVGDRVTITCRASQSVLYSSNQKNYLAWYQQKPGKAPKLLIYWASTR
ESGVPSRFSGSGSGTDFTLTISSLQPEDFATYYCHQYLSSDTFGQGTKVEIKRTVAAPSV
FIFPPPSDEQLKSGTASVVCLLNNFYPREAKVQWKVDNALQSGNSQESVTEQDSKDSTYSL
SSTLTLSKADYEKHKVYACEVTHQGLSSPVTKSFNRGECQEVQLVESGGGLVQPGGSLRL
SCAASGYAFTNYLIEWVRQAPGKGLEWIGVNNPGSGGSNYNEKFKGRFTISADNSKNTLY
LQMNSLRAEDTAVYYCARSGGFYFDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKS
LSLSPGK

```
<666 residues, 1 stop; molecular weight: 72869.74
:::::::::::::::
p1.xTGFb.H2-N1.V5L.RK.theo
:::::::::::::::
< Tue May 22 20:20:57 2001
< /tmp_mnt/home/oz/vqa/Mac/adamscam/ss.xTGFb.H2-N1.V5L.RK.theo (2518
bases)
```

DIQMTQSPSSLSASVGDRVTITCRASQSVLYSSNQKNYLAWYQQKPGKAPKLLIYWASTR
ESGVPSRFSGSGSGTDFTLTISSLQPEDFATYYCHQYLSSDTFGQGTKVEIKRTVAAPSV
FIFPPPSDEQLKSGTASVVCLLNNFYPREAKVQWKVDNALQSGNSQESVTEQDSKDSTYSL
SSTLTLSKADYEKHKVYACEVTHQGLSSPVTKSFNRGECQEVQLVESGGGLVQPGGSLRL
SCAASGYAFTNYLIEWVRQAPGKGLEWVGVINPGSGGSNYNEKFKGRATISADNSKNTLY
LQMNSLRAEDTAVYYCARSGGFYFDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKS
LSLSPGKQVRRPOSRPAEAWPWPNLFIAAYNGYK

```
<692 residues, 3 stop; molecular weight: 75854.20
:::::::::::::::
p1.xTGFb.V11.LandH.IgG1.RK
:::::::::::::::
< Fri Mar 30 11:33:04 2001
< /tmp_mnt/home/oz/vqa/Mac/adamscam/ss.xTGFb.V11.LandH.IgG1.RK (2639
bases)
```

DIQMTQSPSSLSASVGDRVTITCRASQSVLYSSNQKNYLAWYQQKPGKAPKLLIYWASTR
ESGVPSRFSGSGSGTDFTLTISSLQPEDFATYYCHQYLSSDTFGQGTKVEIKRTVAAPSV
FIFPPPSDEQLKSGTASVVCLLNNFYPREAKVQWKVDNALQSGNSQESVTEQDSKDSTYSL
SSTLTLSKADYEKHKVYACEVTHQGLSSPVTKSFNRGECEVQLVESGGGLVQPGGSLRLS
CAASGYAFTNYLIEWVRQAPGKGLEWIGVNNPGSGGSNYNEKFKGRATISADNSKNTLYL
QMNSLRAEDTAVYYCARSGGFYFDYWGQGTLVTVSSASTKGPSVFPLAPSSKSTSGGTAA
LGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSL
SLSPGK

<666 residues, 0 stop; molecular weight: 72775.63

FIG. 3 (cont.)

```
::::::::::::::::
p1.xTGFb.V5.LandH.IgG1.RK
::::::::::::::::
< Mon Mar 12 16:08:26 2001
< /tmp_mnt/home/oz/vqa/Mac/adamscam/ss.xTGFb.V5.LightandHeavy.RKthe
(3261 bases)
```

DIQMTQSPSSLSASVGDRVTITCRASQSVLYSSNQKNYLAWYQQKPGKAPKLLIYWASTR
ESGVPSRFSGSGSGTDFTLTISSLQPEDFATYYCHQYLSSDTFGQGTKVEIKRTVAAPSV
FIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGECOEVQLVESGGGLVQPGGSLRL
SCAASGYAFTNYLIEWVRQAPGKGLEWVGVNNPGSGGSNYNEKFKGRATISADNSKNTLY
LQMNSLRAEDTAVYYCARSGGFYFDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEGLHNHYTQKS
LSLSPGK

```
<666 residues, 1 stop; molecular weight: 72765.59
::::::::::::::::
p1.xTGFb.chim.LandH.IgG1.RK
::::::::::::::::
< Mon Mar 12 16:34:44 2001
< /tmp_mnt/home/oz/vqa/Mac/adamscam/ss.xTGFbchim.LandH.RKthe (2751
bases)
```

DIMMTQSPSSLAVSAGEKVTMSCKSSQSVLYSSNQKNYLAWYQQKPGQSPKLLIYWASTR
ESGVPDRFTGSGSGTDFTLTISSVQAEDLAVYYCHQYLSSDTFGGGTKLEIKRTVAAPSV
FIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGECOEVQLQQSGAELVRPGTSVKV
SCKASGYAFTNYLIEWVKQRPGQGLEWIGVNNPGSGGSNYNEKFKGKATLTADKSSSTAY
MQLSSLTSDDSAVYFCARSGGFYFDYWGQGTSVTVSSAKTTGPSVFPLAPSSKSTSGGTA
ALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKS
LSLSPGK

```
<666 residues, 1 stop; molecular weight: 72695.56
::::::::::::::::
p1.xTGFb.g1L2.V5H.RK.theo
::::::::::::::::
< Wed May 23 18:16:21 2001
< /tmp_mnt/home/oz/vqa/Mac/adamscam/ss.xTGFb.g1L2.V5H.RK.theo (2678
bases)
```

DIQMTQSPSSLSASVGDRVTITCRASQSVLYSSNQKNYLAWYQQKPGKAPKLLIYYASSL
QSGVPSRFSGSGSGTDFTLTISSLQPEDFATYYCHQYLSSDTFGQGTKVEIKRTVAAPSV
FIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGECOEVQLVESGGGLVQPGGSLRL
SCAASGYAFTNYLIEWVRQAPGKGLEWVGVNNPGSGGSNYNEKFKGRATISADNSKNTLY
LQMNSLRAEDTAVYYCARSGGFYFDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEGLHNHYTQKS
LSLSPGK

FIG. 4

```
>xTGFb_709_Heavy_Ig_nosig [1341 bases]
GAAGTTCAGCTGGTGGAGTCTGGCGGTGGCCTGGTGCAGCCAGGGGGCTCACTCCGTTTG
TCCTGTGCAGCTTCTGGCTACGCATTCACCAACTATCTGATCGAGTGGGTCCGTCAGGCC
CCGGGTAAGGGCCTCGAGTGGATCGGTGTAAACAATCCTGGATCCGGAGGCTCCAACTAT
AACGAGAAGTTCAAGGGCCGTTTCACTATAAGTGCAGACAATTCGAAAAACACATTATAC
CTGCAGATGAACAGCCTGCGTGCTGAGGACACTGCCGTCTATTATTGTGCTCGATCCGGA
GGCTTCTACTTCGACTACTGGGGTCAAGGAACCCTGGTCACCGTCTCCTCAGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACTGTGCCCTCTAGCAGCTTGGGCACCCAGACCTACATCTGC
AACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAG
TGCAAGGTCTCCAACAAAGCCTCCCAGCCCCCATCGAGAAAACCATCTCCAAAGCCAAA
GGGCAGCCCCGAGAACCACAGGTGTACACCCTGCCCCCATCCGGGAAGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAA
>xTGFb_709_Heavy_Ig_sig [1398 bases]
ATGGGATGGTCATGTATCATCCTTTTTCTAGTAGCAACTGCAACTGGAGTACATTCAGAA
GTTCAGCTGGTGGAGTCTGGCGGTGGCCTGGTGCAGCCAGGGGGCTCACTCCGTTTGTCC
TGTGCAGCTTCTGGCTACGCATTCACCAACTATCTGATCGAGTGGGTCCGTCAGGCCCCG
GGTAAGGGCCTCGAGTGGATCGGTGTAAACAATCCTGGATCCGGAGGCTCCAACTATAAC
GAGAAGTTCAAGGGCCGTTTCACTATAAGTGCAGACAATTCGAAAAACACATTATACCTG
CAGATGAACAGCCTGCGTGCTGAGGACACTGCCGTCTATTATTGTGCTCGATCCGGAGGC
TTCTACTTCGACTACTGGGGTCAAGGAACCCTGGTCACCGTCTCCTCAGCCTCCACCAAG
GGCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAGGC
GCCCTGACCAGCGGCGTGCACACCTTCCCGGCTGTCCTACAGTCCTCAGGACTCTACTCC
CTCAGCAGCGTGGTGACTGTGCCCTCTAGCAGCTTGGGCACCCAGACCTACATCTGCAAC
GTGAATCACAAGCCCAGCAACACCAAGGTGGACAAGAAAGTTGAGCCCAAATCTTGTGAC
AAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGAAGAGATGACCAAGAAC
CAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTC
TCCCTGTCTCCGGGTAAA
>xTGFb_H2-NI_Heavy_Ig_nosig [1341 bases]
GAAGTTCAGCTGGTGGAGTCTGGCGGTGGCCTGGTGCAGCCAGGGGGCTCACTCCGTTTG
TCCTGTGCAGCTTCTGGCTACGCATTCACCAACTATCTGATCGAGTGGGTCCGTCAGGCC
CCGGGTAAGGGCCTCGAGTGGGTTGGTGTTATCAATCCTGGATCCGGAGGCTCCAACTAT
AACGAGAAGTTCAAGGGGCGCGCCACTATCAGTGCAGACAATTCGAAAAACACATTATAC
CTGCAGATGAACAGCCTGCGTGCTGAGGACACTGCCGTCTATTATTGTGCTCGATCCGGA
GGCTTCTACTTCGACTACTGGGGTCAAGGAACCCTGGTCACCGTCTCCTCAGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACTGTGCCCTCTAGCAGCTTGGGCACCCAGACCTACATCTGC
AACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGTAC
CGGGTGGTCAGCGTCCTCACCGTCCTGCACCAGGACTGGCTGAATGGCAAGGAGTACAAG
```

FIG. 4 (cont.)

```
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAAGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAA
>xTGFb_H2-NI_Heavy_Ig_sig [1400 bases]
ATGGGATGGTCATGTATCATCCTTTTTCTAGTAGCAACTGCAACTGGAGTACATTCAGAA
GTTCAGCTGGTGGAGTCTGGCGGTGGCCTGGTGCAGCCAGGGGGCTCACTCCGTTTGTCC
TGTGCAGCTTCTGGCTACGCATTCACCAACTATCTGATCGAGTGGGTCCGTCAGGCCCCG
GGTAAGGGCCTCGAGTGGGTTGGTGTTATCAATCCTGGATCCGGAGGCTCCAACTATAAC
GAGAAGTTCAAGGGGCGCGCCACTATCAGTGCAGACAATTCGAAAAACACATTATACCTG
CAGATGAACAGCCTGCGTGCTGAGGACACTGCCGTCTATTATTGTGCTCGATCCGGAGGC
TTCTACTTCGACTACTGGGGTCAAGGAACCCTGGTCACCGTCTCCTCAGCCTCCACCAAG
GGCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAGGC
GCCCTGACCAGCGGCGTGCACACCTTCCCGGCTGTCCTACAGTCCTCAGGACTCTACTCC
CTCAGCAGCGTGGTGACTGTGCCCTCTAGCAGCTTGGGCACCCAGACCTACATCTGCAAC
GTGAATCACAAGCCCAGCAACACCAAGGTGGACAAGAAAGTTGAGCCCAAATCTTGTGAC
AAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGCACGTACCGG
GTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGAAGAGATGACCAAGAAC
CAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTC
TCCCTGTCTCCGGGTAAATG
>xTGFb_V11_Heavy_Ig_nosig [1341 bases]
GAAGTTCAGCTGGTGGAGTCTGGCGGTGGCCTGGTGCAGCCAGGGGGCTCACTCCGTTTG
TCCTGTGCAGCTTCTGGCTACGCATTCACCAACTATCTGATCGAGTGGGTCCGTCAGGCC
CCGGGTAAGGGCCTCGAGTGGATCGGTGTAAACAATCCTGGATCCGGAGGCTCCAACTAT
AACGAGAAGTTCAAGGGGCGCGCCACTATCAGTGCAGACAATTCGAAAAACACATTATAC
CTGCAGATGAACAGCCTGCGTGCTGAGGACACTGCCGTCTATTATTGTGCTCGATCCGGA
GGCTTCTACTTCGACTACTGGGGTCAAGGAACCCTGGTCACCGTCTCCTCAGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACTGTGCCCTCTAGCAGCTTGGGCACCCAGACCTACATCTGC
AACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAAGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAA
>xTGFb_V11_Heavy_Ig_sig [1398 bases]
ATGGGATGGTCATGTATCATCCTTTTTCTAGTAGCAACTGCAACTGGAGTACATTCAGAA
GTTCAGCTGGTGGAGTCTGGCGGTGGCCTGGTGCAGCCAGGGGGCTCACTCCGTTTGTCC
TGTGCAGCTTCTGGCTACGCATTCACCAACTATCTGATCGAGTGGGTCCGTCAGGCCCCG
GGTAAGGGCCTCGAGTGGATCGGTGTAAACAATCCTGGATCCGGAGGCTCCAACTATAAC
GAGAAGTTCAAGGGGCGCGCCACTATCAGTGCAGACAATTCGAAAAACACATTATACCTG
CAGATGAACAGCCTGCGTGCTGAGGACACTGCCGTCTATTATTGTGCTCGATCCGGAGGC
TTCTACTTCGACTACTGGGGTCAAGGAACCCTGGTCACCGTCTCCTCAGCCTCCACCAAG
GGCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAGGC
```

FIG. 4 (cont.)

GCCCTGACCAGCGGCGTGCACACCTTCCCGGCTGTCCTACAGTCCTCAGGACTCTACTCC
CTCAGCAGCGTGGTGACTGTGCCCTCTAGCAGCTTGGGCACCCAGACCTACATCTGCAAC
GTGAATCACAAGCCCAGCAACACCAAGGTGGACAAGAAAGTTGAGCCCAAATCTTGTGAC
AAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGAAGAGATGACCAAGAAC
CAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTC
TCCCTGTCTCCGGGTAAA
>xTGFb_V5_Heavy_Ig_nosig [1341 bases]
GAAGTTCAGCTGGTGGAGTCTGGCGGTGGCCTGGTGCAGCCAGGGGGCTCACTCCGTTTG
TCCTGTGCAGCTTCTGGCTACGCATTCACCAACTATCTGATCGAGTGGGTCCGTCAGGCC
CCGGGTAAGGGCCTCGAGTGGGTTGGTGTTAACAATCCTGGATCCGGAGGCTCCAACTAT
AACGAGAAGTTCAAGGGGCGCGCCACTATCAGTGCAGACAATTCGAAAAACACATTATAC
CTGCAGATGAACAGCCTGCGTGCTGAGGACACTGCCGTCTATTATTGTGCTCGATCCGGA
GGCTTCTACTTCGACTACTGGGGTCAAGGAACCCTGGTCACCGTCTCCTCAGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACTGTGCCCTCTAGCAGCTTGGGCACCCAGACCTACATCTGC
AACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAAGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGGTCTGCACAACCACTACACGCAGAAGAGC
CTCTCCCTGTCTCCGGGTAAA
>xTGFb_V5_Heavy_Ig_sig [1398 bases]
ATGGGATGGTCATGTATCATCCTTTTTCTAGTAGCAACTGCAACTGGAGTACATTCAGAA
GTTCAGCTGGTGGAGTCTGGCGGTGGCCTGGTGCAGCCAGGGGGCTCACTCCGTTTGTCC
TGTGCAGCTTCTGGCTACGCATTCACCAACTATCTGATCGAGTGGGTCCGTCAGGCCCCG
GGTAAGGGCCTCGAGTGGGTTGGTGTTAACAATCCTGGATCCGGAGGCTCCAACTATAAC
GAGAAGTTCAAGGGGCGCGCCACTATCAGTGCAGACAATTCGAAAAACACATTATACCTG
CAGATGAACAGCCTGCGTGCTGAGGACACTGCCGTCTATTATTGTGCTCGATCCGGAGGC
TTCTACTTCGACTACTGGGGTCAAGGAACCCTGGTCACCGTCTCCTCAGCCTCCACCAAG
GGCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAGGC
GCCCTGACCAGCGGCGTGCACACCTTCCCGGCTGTCCTACAGTCCTCAGGACTCTACTCC
CTCAGCAGCGTGGTGACTGTGCCCTCTAGCAGCTTGGGCACCCAGACCTACATCTGCAAC
GTGAATCACAAGCCCAGCAACACCAAGGTGGACAAGAAAGTTGAGCCCAAATCTTGTGAC
AAAACTCACACATGCCCACCGTGCCCAGCACCTGAACTCCTGGGGGACCGTCAGTCTTC
CTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGAAGAGATGACCAAGAAC
CAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAAC
GTCTTCTCATGCTCCGTGATGCATGAGGGTCTGCACAACCACTACACGCAGAAGAGCCTC
TCCCTGTCTCCGGGTAAA

FIG. 4 (cont.)

>xTGFb_V5_Light_nosig [657 bases]
GATATCCAGATGACCCAGTCCCCGAGCTCCCTGTCCGCCTCTGTGGGCGATAGGGTCACC
ATCACCTGCAGAGCCAGTCAGAGCGTGCTGTATAGTTCGAATCAGAAGAACTACCTGGCC
TGGTATCAACAGAAACCAGGAAAAGCTCCGAAACTACTGATTTACTGGGCTAGTACTCGC
GAGTCTGGAGTCCCTTCTCGCTTCTCTGGATCCGGTTCTGGGACGGATTTCACTCTGACC
ATCAGCAGTCTGCAGCCAGAAGACTTCGCAACTTATTACTGTCACCAGTATCTGAGCTCT
GACACATTTGGACAGGGTACCAAGGTGGAGATCAAACGAACTGTGGCTGCACCATCTGTC
TTCATCTTCCCGCCATCTGATGAGCAGTTGAAATCTGGAACTGCTTCTGTTGTGTGCCTG
CTGAATAACTTCTATCCCAGAGAGGCCAAAGTACAGTGGAAGGTGGATAACGCCCTCCAA
TCGGGTAACTCCCAGGAGAGTGTCACAGAGCAGGACAGCAAGGACAGCACCTACAGCCTC
AGCAGCACCCTGACGCTGAGCAAAGCAGACTACGAGAAACACAAAGTCTACGCCTGCGAA
GTCACCCATCAGGGCCTGAGCTCGCCCGTCACAAAGAGCTTCAACAGGGGAGAGTGT
>xTGFb_V5_Light_sig [714 bases]
ATGGGATGGTCATGTATCATCCTTTTTCTAGTAGCAACTGCAACTGGAGTACATTCAGAT
ATCCAGATGACCCAGTCCCCGAGCTCCCTGTCCGCCTCTGTGGGCGATAGGGTCACCATC
ACCTGCAGAGCCAGTCAGAGCGTGCTGTATAGTTCGAATCAGAAGAACTACCTGGCCTGG
TATCAACAGAAACCAGGAAAAGCTCCGAAACTACTGATTTACTGGGCTAGTACTCGCGAG
TCTGGAGTCCCTTCTCGCTTCTCTGGATCCGGTTCTGGGACGGATTTCACTCTGACCATC
AGCAGTCTGCAGCCAGAAGACTTCGCAACTTATTACTGTCACCAGTATCTGAGCTCTGAC
ACATTTGGACAGGGTACCAAGGTGGAGATCAAACGAACTGTGGCTGCACCATCTGTCTTC
ATCTTCCCGCCATCTGATGAGCAGTTGAAATCTGGAACTGCTTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGT
>xTGFb_g1L2_Light_nosig [657 bases]
GATATCCAGATGACCCAGTCCCCGAGCTCCCTGTCCGCCTCTGTGGGCGATAGGGTCACC
ATCACCTGCAGAGCCAGTCAGAGCGTGCTGTATAGTTCGAATCAGAAGAACTACCTGGCC
TGGTATCAACAGAAACCAGGAAAAGCTCCGAAACTACTGATTTACTATGCTAGCAGTCTC
CAGTCTGGAGTCCCTTCTCGCTTCTCTGGATCCGGTTCTGGGACGGATTTCACTCTGACC
ATCAGCAGTCTGCAGCCAGAAGACTTCGCAACTTATTACTGTCACCAGTATCTGAGCTCT
GACACATTTGGACAGGGTACCAAGGTGGAGATCAAACGAACTGTGGCTGCACCATCTGTC
TTCATCTTCCCGCCATCTGATGAGCAGTTGAAATCTGGAACTGCTTCTGTTGTGTGCCTG
CTGAATAACTTCTATCCCAGAGAGGCCAAAGTACAGTGGAAGGTGGATAACGCCCTCCAA
TCGGGTAACTCCCAGGAGAGTGTCACAGAGCAGGACAGCAAGGACAGCACCTACAGCCTC
AGCAGCACCCTGACGCTGAGCAAAGCAGACTACGAGAAACACAAAGTCTACGCCTGCGAA
GTCACCCATCAGGGCCTGAGCTCGCCCGTCACAAAGAGCTTCAACAGGGGAGAGTGT
>xTGFb_g1L2_Light_sig [714 bases]
ATGGGATGGTCATGTATCATCCTTTTTCTAGTAGCAACTGCAACTGGAGTACATTCAGAT
ATCCAGATGACCCAGTCCCCGAGCTCCCTGTCCGCCTCTGTGGGCGATAGGGTCACCATC
ACCTGCAGAGCCAGTCAGAGCGTGCTGTATAGTTCGAATCAGAAGAACTACCTGGCCTGG
TATCAACAGAAACCAGGAAAAGCTCCGAAACTACTGATTTACTATGCTAGCAGTCTCCAG
TCTGGAGTCCCTTCTCGCTTCTCTGGATCCGGTTCTGGGACGGATTTCACTCTGACCATC
AGCAGTCTGCAGCCAGAAGACTTCGCAACTTATTACTGTCACCAGTATCTGAGCTCTGAC
ACATTTGGACAGGGTACCAAGGTGGAGATCAAACGAACTGTGGCTGCACCATCTGTCTTC
ATCTTCCCGCCATCTGATGAGCAGTTGAAATCTGGAACTGCTTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGT

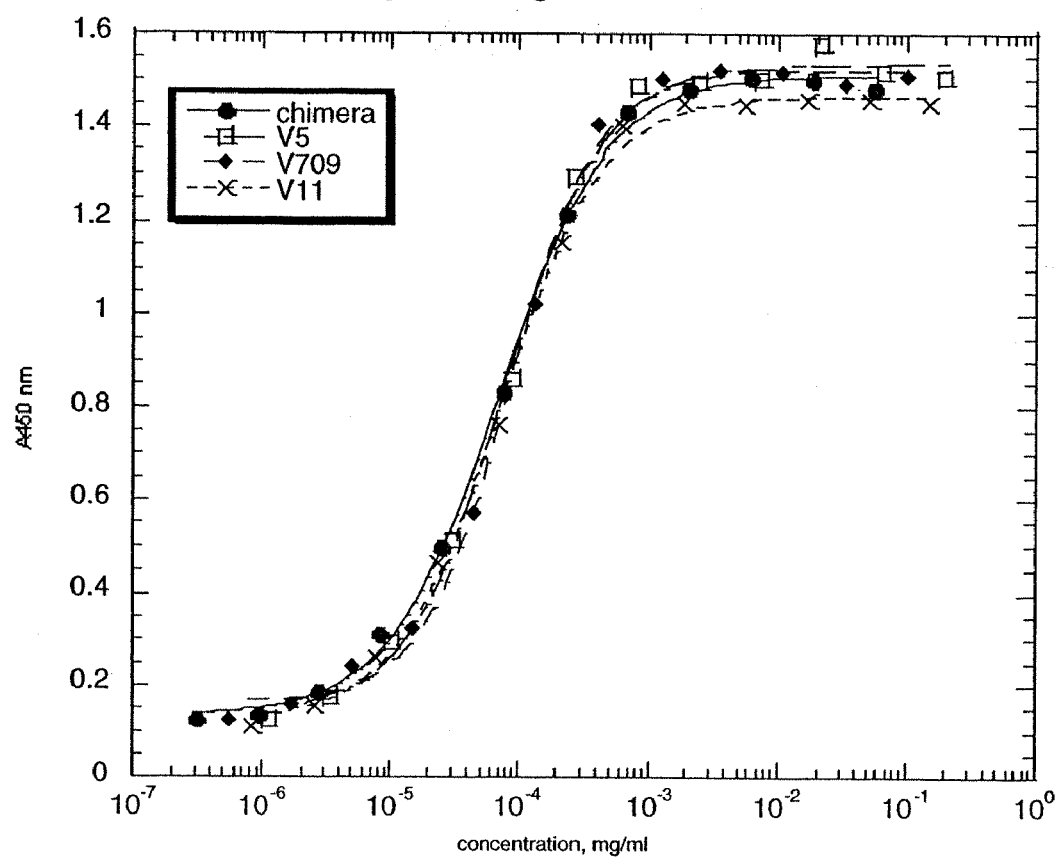

FIG. 6

TTCGAGCTCGCCCGACATTGATTATTGACTAGTTATTAATAGTAATCAATTACGGGGTCA
TTAGTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATAGTA
ACGCCAATAGGGACTTTCCATTGACGTCAATGGGTGGAGTATTTACGGTAAACTGCCCAC
TTGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCAG
TACATCTACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGACGTCAAT
GGGAGTTTGTTTTGGCACCAAAATCAACGGGACTTTCCAAAATGTCGTAACAACTCCGCC
CCATTGACGCAAATGGGCGGTAGGCGTGTACGGTGGGAGGTCTATATAAGCAGAGCTCGT
TTAGTGAACCGTCAGATCGCCTGGAGACGCCATCCACGCTGTTTTGACCTCCATAGAAGA
CACCGGGACCGATCCAGCCTCCGCGGCCGGGAACGGTGCATTGGAACGCGGATTCCCCGT
GCCAAGAGTGACGTAAGTACCGCCTATAGAGTCTATAGGCCCACCCCCTTGGCTTCGTTA
GAACGCGGCTACAATTAATACATAACCTTATGTATCATACACATACGATTTAGGTGACAC
TATAGAATAACATCCACTTTGCCTTTCTCTCCACAGGTGTCCACTCCCAGGTCCAACTGC
ACCTCGGTTCTATCGATTGAATTCCACCATGGGATGGTCATGTATCATCCTTTTTCTAGT
AGCAACTGCAACTGGAGTACATTCAGATATCCAGATGACCCAGTCCCCGAGCTCCCTGTC
CGCCTCTGTGGGCGATAGGGTCACCATCACCTGCCGTGCCAGTCAGGACATCCGTAATTA
TTTGAACTGGTATCAACAGAAACCAGGAAAAGCTCCGAAACTACTGATTTACTATACCTC
CCGCCTGGAGTCTGGAGTCCCTTCTCGCTTCTCTGGTTCTGGTTCTGGGACGGATTACAC
TCTGACCATCAGTAGTCTGCAACCGGAGGACTTCGCAACTTATTACTGTCAGCAAGGTAA
TACTCTGCCGTGGACGTTCGGACAGGGCACCAAGGTGGAGATCAAACGAACTGTGGCTGC
ACCATCTGTCTTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACAGCAC
CTACAGCCTCAGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCTTCAACAGGGG
AGAGTGTTAAGCTTGGCCGCCATGGCCCAACTTGTTTATTGCAGCTTATAATGGTTACAA
ATAAAGCAATAGCATCACAAATTTCACAAATAAAGCATTTTTTTCACTGCATTCTAGTTG
TGGTTTGTCCAAACTCATCAATGTATCTTATCATGTCTGGATCGATCGGGAATTAATTCG
GCGCAGCACCATGGCCTGAAATAACCTCTGAAAGAGGAACTTGGTTAGGTACCTTCTGAG
GCGGAAAGAACCAGCTGTGGAATGTGTGTCAGTTAGGGTGTGGAAAGTCCCCAGGCTCCC
CAGCAGGCAGAAGTATGCAAAGCATGCATCTCAATTAGTCAGCAACCAGGTGTGGAAAGT
CCCCAGGCTCCCCAGCAGGCAGAAGTATGCAAAGCATGCATCTCAATTAGTCAGCAACCA
TAGTCCCGCCCCTAACTCCGCCCATCCCGCCCCTAACTCCGCCCAGTTCCGCCCATTCTC
CGCCCCATGGCTGACTAATTTTTTTTATTTATGCAGAGGCCGAGGCCGCCTCGGCCTCTG
AGCTATTCCAGAAGTAGTGAGGAGGCTTTTTTGGAGGCCTAGGCTTTTGCAAAAAGCTGT
TAACAGCTTGGCACTGGCCGTCGTTTTACAACGTCGTGACTGGGAAAACCCTGGCGTTAC
CCAACTTAATCGCCTTGCAGCACATCCCCCCTTCGCCAGCTGGCGTAATAGCGAAGAGGC
CCGCACCGATCGCCCTTCCCAACAGTTGCGTAGCCTGAATGGCGAATGGCGCCTGATGCG
GTATTTTCTCCTTACGCATCTGTGCGGTATTTCACACCGCATACGTCAAAGCAACCATAG
TACGCGCCCTGTAGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGCTCCCTTTAGGGTTCCGATTT
AGTGCTTTACGGCACCTCGACCCCAAAAAACTTGATTTGGGTGATGGTTCACGTAGTGGG
CCATCGCCCTGATAGACGGTTTTTCGCCCTTTGACGTTGGAGTCCACGTTCTTTAATAGT
GGACTCTTGTTCCAAACTGGAACAACACTCAACCCTATCTCGGGCTATTCTTTTGATTTA
TAAGGGATTTTGCCGATTTCGGCCTATTGGTTAAAAAATGAGCTGATTTAACAAAAATTT
AACGCGAATTTTAACAAAATATTAACGTTTACAATTTTATGGTGCACTCTCAGTACAATC
TGCTCTGATGCCGCATAGTTAAGCCAACTCCGCTATCGCTACGTGACTGGGTCATGGCTG
CGCCCCGACACCCGCCAACACCCGCTGACGCGCCCTGACGGGCTTGTCTGCTCCCGGCAT

FIG. 6 (cont)

```
CCGCTTACAGACAAGCTGTGACCGTCTCCGGGAGCTGCATGTGTCAGAGGTTTTCACCGT
CATCACCGAAACGCGCGAGGCAGTATTCTTGAAGACGAAAGGGCCTCGTGATACGCCTAT
TTTTATAGGTTAATGTCATGATAATAATGGTTTCTTAGACGTCAGGTGGCACTTTTCGGG
GAAATGTGCGCGGAACCCCTATTTGTTTATTTTTCTAAATACATTCAAATATGTATCCGC
TCATGAGACAATAACCCTGATAAATGCTTCAATAATATTGAAAAGGAAGAGTATGAGTA
TTCAACATTTCCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTGATG
ACGCCGGGCAAGAGCAACTCGGTCGCCGCATACACTATTCTCAGAATGACTTGGTTGAGT
ACTCACCAGTCACAGAAAGCATCTTACGGATGGCATGACAGTAAGAGAATTATGCAGTG
CTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCAGCAG
CAATGGCAACAACGTTGCGCAAACTATTAACTGGCGAACTACTTACTCTAGCTTCCCGGC
AACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAAC
TTCATTTTTAATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTG
GCTTCAGCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAA
CGACCTACACCGAACTGAGATACCTACAGCGTGAGCATTGAGAAAGCGCCACGCTTCCCG
AAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCT
GACTTGAGCGTCGATTTTTGTGATGCTCGTCAGGGGGCGGAGCCTATGGAAAAACGCCA
GCAACGCGGCCTTTTTACGGTTCCTGGCCTTTTGCTGGCCTTTTGCTCACATGTTCTTTC
CTGCGTTATCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCC
CAATACGCAAACCGCCTCTCCCCGCGCGTTGGCCGATTCATTAATCCAGCTGGCACGACA
GGTTTCCCGACTGGAAAGCGGGCAGTGAGCGCAACGCAATTAATGTGAGTTACCTCACTC
ATTAGGCACCCCAGGCTTTACACTTTATGCTTCCGGCTCGTATGTTGTGTGGAATTGTGA
GCGGATAACAATTTCACACAGGAAACAGCTATGACCATGATTACGAATTAA
```

FIG. 7

ATTCGAGCTCGCCCGACATTGATTATTGACTAGTTATTAATAGTAATCAATTACGGGGTC
ATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGT
AACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTGGCA
GTACATCTACGTATTAGTCATCGCTATTACCATGGTGATGCGGTTTTGGCAGTACATCAA
TGGGCGTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCG
TTTAGTGAACCGTCAGATCGCCTGGAGACGCCATCCACGCTGTTTTGACCTCCATAGAAG
ACACCGGGACCGATCCAGCCTCCGCGGCCGGGAACGGTGCATTGGAACGCGGATTCCCCG
TGCCAAGAGTGACGTAAGTACCGCCTATAGAGTCTATAGGCCCACCCCCTTGGCTTCGTT
AGAACGCGGCTACAATTAATACATAACCTTATGTATCATACACATACGATTTAGGTGACA
CTATAGAATAACATCCACTTTGCCTTTCTCTCCACAGGTGTCCACTCCCAGGTCCAACTG
CACCTCGGTTCTATCGATTGAATTCCACCATGGGATGGTCATGTATCATCCTTTTTCTAG
TAGCAACTGCAACTGGAGTACATTCAGAAGTTCAGCTGGTGGAGTCTGGCGGTGGCCTGG
TGCAGCCAGGGGGCTCACTCCGTTTGTCCTGTGCAGCTTCTGGCTACTCCTTTACCGGCT
ACACTATGAACTGGGTGCGTCAGGCCCCAGGTAAGGGCCTGGAATGGGTTGCACTGATTA
ATCCTTATAAAGGTGTTACTACCTATGCCGATAGCGTCAAGGGCCGTTTCACTATAAGCG
TAGATAAATCCAAAAACACAGCCTACCTGCAAATGAACAGCCTGCGTGCTGAGGACACTG
CCGTCTATTATTGTGCTAGAAGCGGATACTACGGCGATAGCGACTGGTATTTTGACGTCT
GGGGTCAAGGAACCCTGGTCACCGTCTCCTCGGCCTCCACCAAGGGCCCATCGGTCTTCC
CCCTGGCACCCTCCTCCAAGAGCACCTCTGGGGGCACAGCGGCCCTGGGCTGCCTGGTCA
AGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGA
CTGTGCCCTCTAGCAGCTTGGGCACCCAGACCTACATCTGCAACGTGAATCACAAGCCCA
GCAACACCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCCAAAAC
CCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATG
CCAAGACAAAGCCGCGGGAGGAGCAGTACAACAGCACGTACCGTGTGGTCAGCGTCCTCA
CCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCCCCGAGAACCAC
AGGTGTACACCCTGCCCCCATCCCGGGAAGAGATGACCAAGAACCAGGTCAGCCTGACCT
GCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCT
ACAGCAAGCTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTCTCCGGGTA
AATGAGTGCGACGGCCCTAGAGTCGACCTGCAGAAGCTTGGCCGCCATGGCCCAACTTGT
TTATTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCATG
TCTGGATCGATCGGGAATTAATTCGGCGCAGCACCATGGCCTGAAATAACCTCTGAAAGA
GGAACTTGGTTAGGTACCTTCTGAGGCGGAAAGAACCATCTGTGGAATGTGTGTCAGTTA
GGGTGTGGAAAGTCCCCAGGCTCCCCAGCAGGCAGAAGTATGCAAAGCATGCATCTCAAT
TAGTCAGCAACCAGGTGTGGAAAGTCCCCAGGCTCCCCAGCAGGCAGAAGTATGCAAAGC
ATGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTTATTTATGCA
GAGGCCGAGGCCGCCTCGGCCTCTGAGCTATTCCAGAAGTAGTGAGGAGGCTTTTTTGGA
GGCCTAGGCTTTTGCAAAAAGCTGTTAACAGCTTGGCACTGGCCGTCGTTTTACAACGTC
GTGACTGGGAAAACCCTGGCGTTACCCAACTTAATCGCCTTGCAGCACATCCCCCCTTCG

FIG 7 (cont)

CCAGTTGGCGTAATAGCGAAGAGGCCCGCACCGATCGCCCTTCCCAACAGTTGCGTAGCC
TGAATGGCGAATGGCGCCTGATGCGGTATTTTCTCCTTACGCATCTGTGCGGTATTTCAC
ACCGCATACGTCAAAGCAACCATAGTACGCGCCCTGTAGCGGCGCATTAAGCGCGGCGGG
TGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGA
TTTGGGTGATGGTTCACGTAGTGGGCCATCGCCCTGATAGACGGTTTTTCGCCCTTTGAC
GTTGGAGTCCACGTTCTTTAATAGTGGACTCTTGTTCCAAACTGGAACAACACTCAACCC
TATCTCGGGCTATTCTTTTGATTTATAAGGGATTTTGCCGATTTCGGCCTATTGGTTAAA
AAATGAGCTGATTTAACAAAAATTTAACGCGAATTTTAACAAAATATTAACGTTTACAAT
TTTATGGTGCACTCTCAGTACAATCTGCTCTGATGCCGCATAGTTAAGCCAACTCCGCTA
TCGCTACGTGACTGGGTCATGGCTGCGCCCGACACCCGCCAACACCCGCTGACGCGCCC
TGACGGGCTTGTCTGCTCCCGGCATCCGCTTACAGACAAGCTGTGACCGTCTCCGGGAGC
TGCATGTGTCAGAGGTTTTCACCGTCATCACCGAAACGCGCGAGGCAGTATTCTTGAAGA
CGAAAGGGCCTCGTGATACGCCTATTTTTATAGGTTAATGTCATGATAATAATGGTTTCT
TAGACGTCAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCAATAA
TATTGAAAAAGGAAGAGTATGAGTATTCAACATTTCCGTGTCGCCCTTATTCCCTTTTTT
GCGGCATTTTGCCTTCCTGTTTTTGCTCACCCAGAAACGCTGGTGAAAGTAAAAGATGCT
GAAGATCAGTTGGGTGCACGAGTGGGTTACATCGAACTGGATCTCAACAGCGGTAAGATC
CTTGAGAGTTTTCGCCCCGAAGAACGTTTTCCAATGATGAGCACTTTTAAAGTTCTGCTA
TGTGGCGCGGTATTATCCCGTGATGACGCCGGGCAAGAGCAACTCGGTCGCCGCATACAC
TATTCTCAGAATGACTTGGTTGAGTACTCACCAGTCACAGAAAAGCATCTTACGGATGGC
ATGACAGTAAGAGAATTATGCAGTGCTGCCATAACCATGAGTGATAACACTGCGGCCAAC
TTACTTCTGACAACGATCGGAGGACCGAAGGAGCTAACCGCTTTTTTGCACAACATGGGG
GATCATGTAACTCGCCTTGATCGTTGGGAACCGGAGCTGAATGAAGCCATACCAAACGAC
GAGCGTGACACCACGATGCCAGCAGCAATGGCAACAACGTTGCGCAAACTATTAACTGGC
GAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGA
GCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATC
CTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTT
CTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAGCGTGAG
CATTGAGAAAGCGCCACGCTTCCCGAAGGGAGAAAGGCGGACAGGTATCCGGTAAGCGGC
AGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGC
TGGCCTTTTGCTCACATGTTCTTTCCTGCGTTATCCCCTGATTCTGTGGATAACCGTATT
ACCGCCTTTGAGTGAGCTGATACCGCTCGCCGCAGCCGAACGACCGAGCGCAGCGAGTCA
GTGAGCGAGGAAGCGGAAGAGCGCCCAATACGCAAACCGCCTCTCCCCGCGCGTTGGCCG
ATTCATTAATCCAACTGGCACGACAGGTTTCCCGACTGGAAAGCGGGCAGTGAGCGCAAC
GCAATTAATGTGAGTTACCTCACTCATTAGGCACCCCAGGCTTTACACTTTATGCTTCCG
GCTCGTATGTTGTGTGGAATTGTGAGCGGATAACAATTTCACACAGGAAACAGCTATGAC
CATGATTACGAATTA

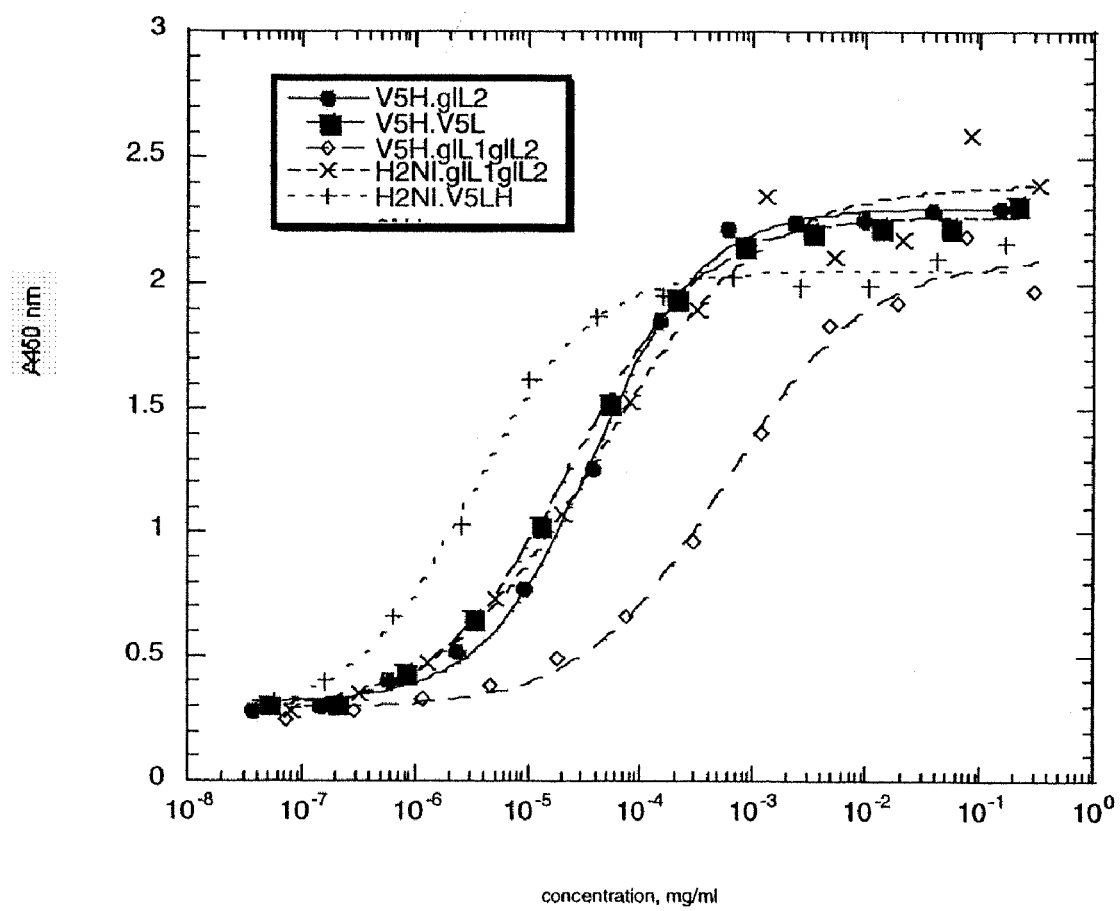

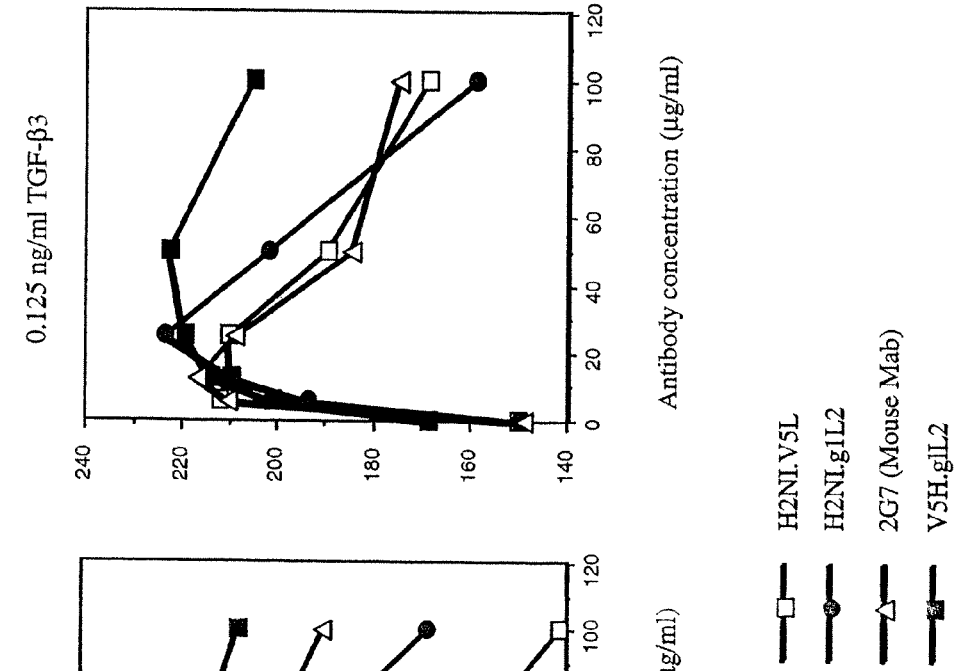
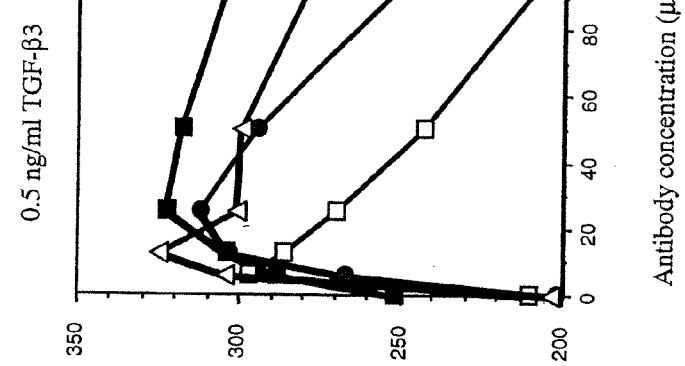
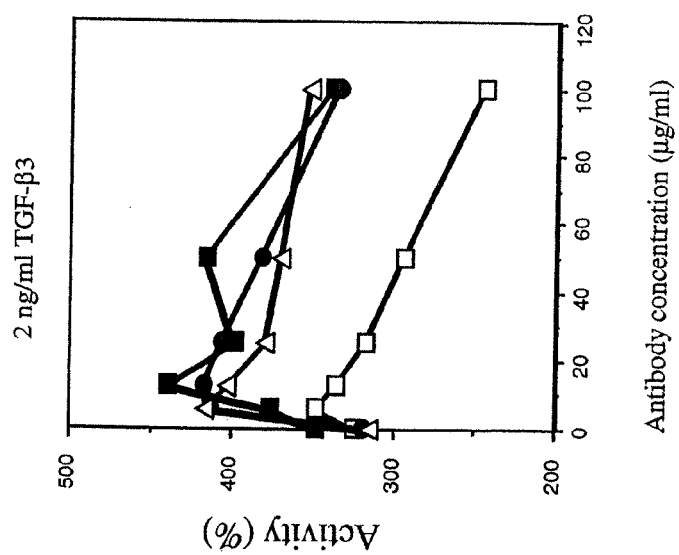

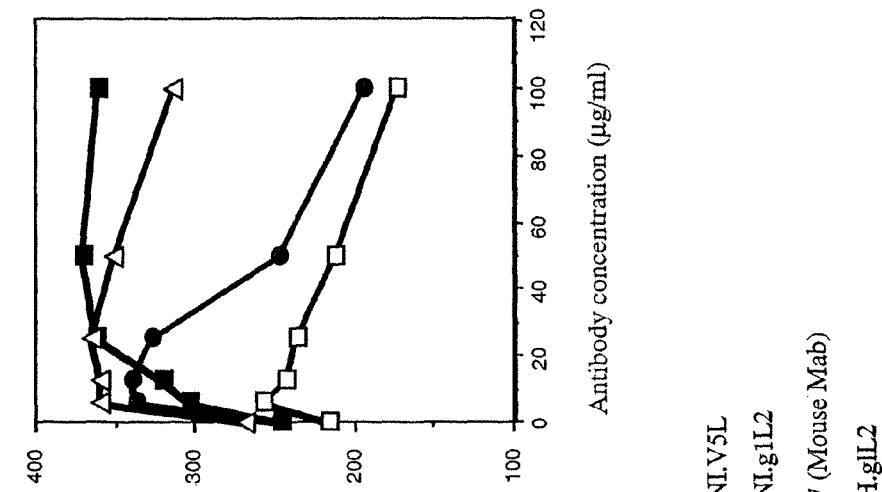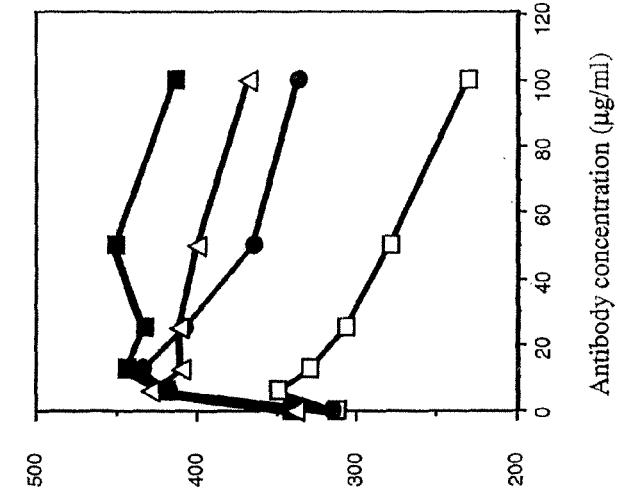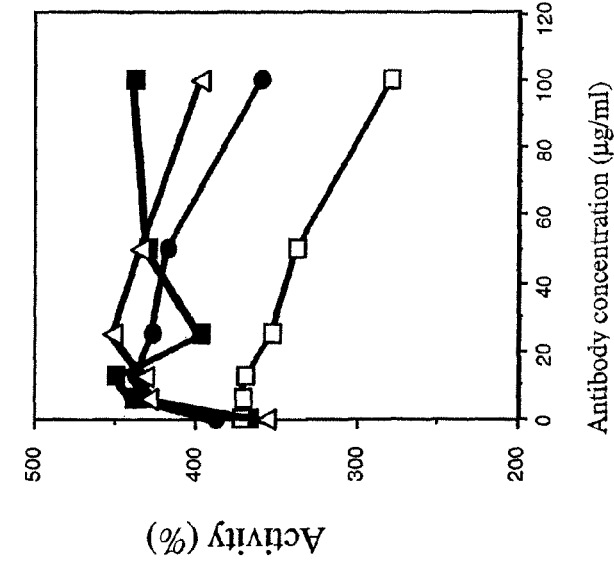
Neutralization of TGF-β2
FIG. 11A — 2 ng/ml TGF-β2
FIG. 11B — 0.5 ng/ml TGF-β2
FIG. 11C — 0.125 ng/ml TGF-β2
—□— H2NI.V5L
—●— H2NI.gIL2
—△— 2G7 (Mouse Mab)
—■— V5H.gIL2
Activity expressed relative to 100 (no TGF-β, no antibody)

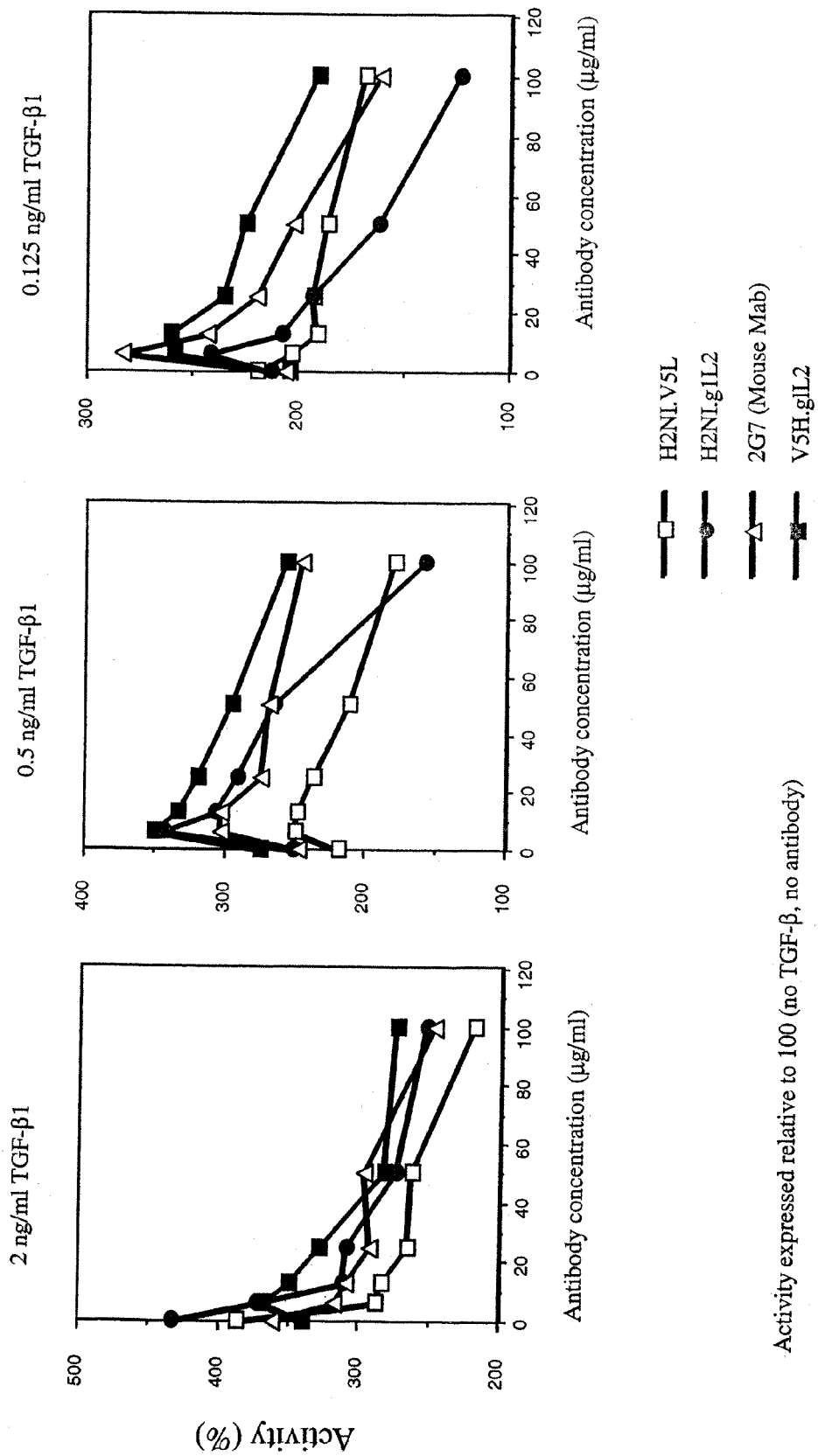

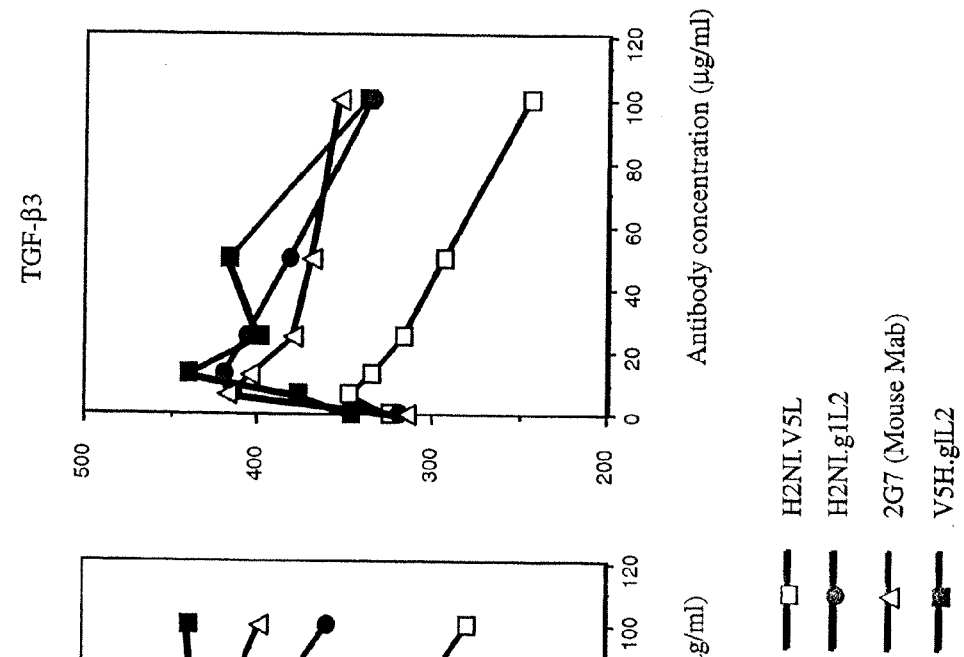
Neutralization of 2 ng/ml TGF-β
FIG. 13A  TGF-β1
FIG. 13B  TGF-β2
FIG. 13C  TGF-β3
— ■— H2NI.V5L
—□— H2NI.gIL2
—△— 2G7 (Mouse Mab)
—●— V5H.gIL2
Activity expressed relative to 100 (no TGF-β, no antibody)

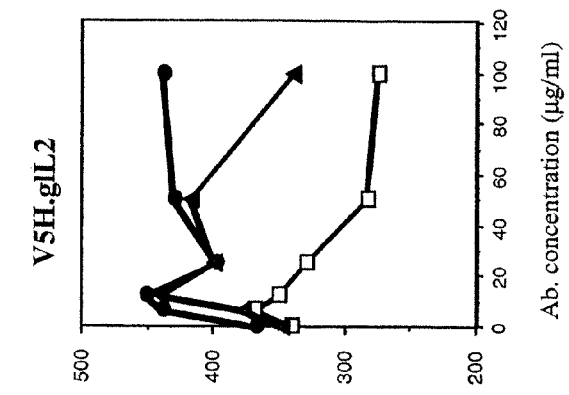
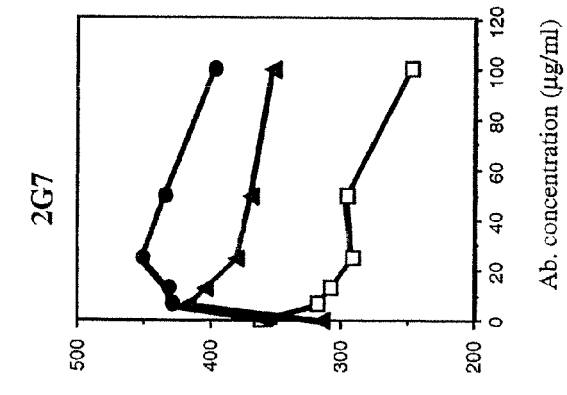
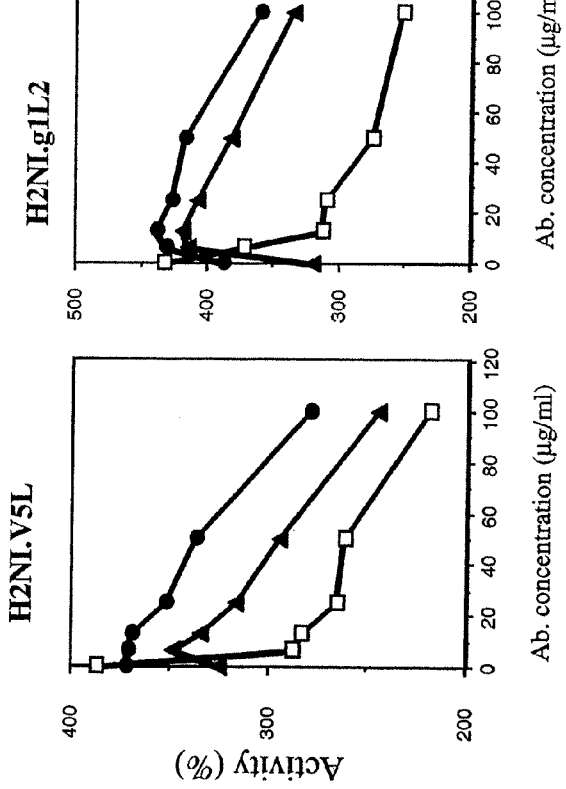
Neutralization of the three TGF-β isoforms by the different antibodies

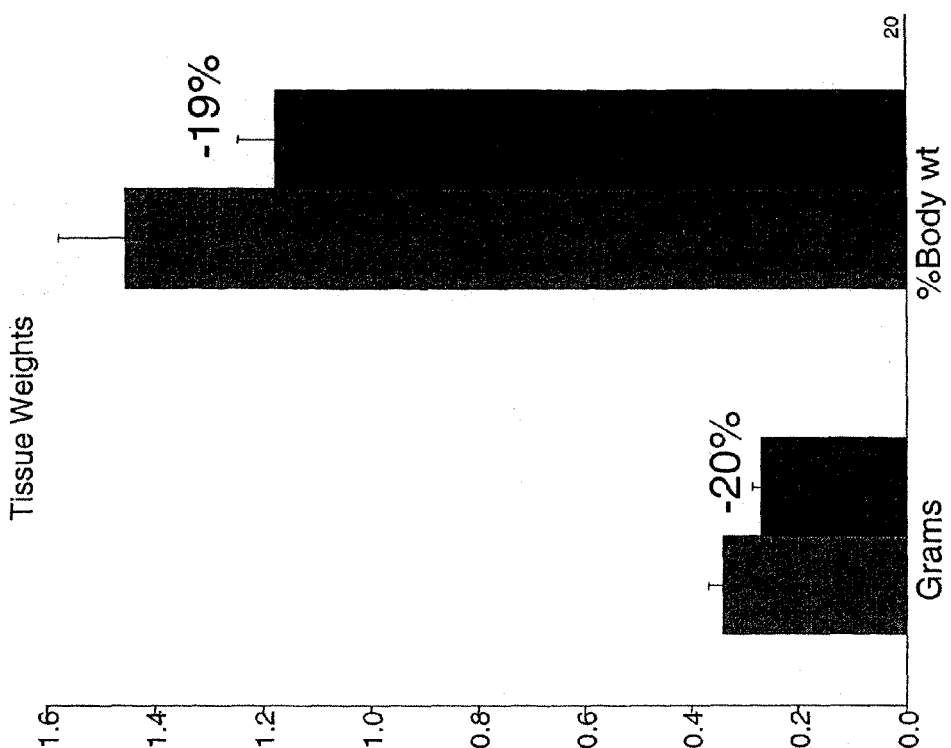
FIG. 16B Tissue Weights
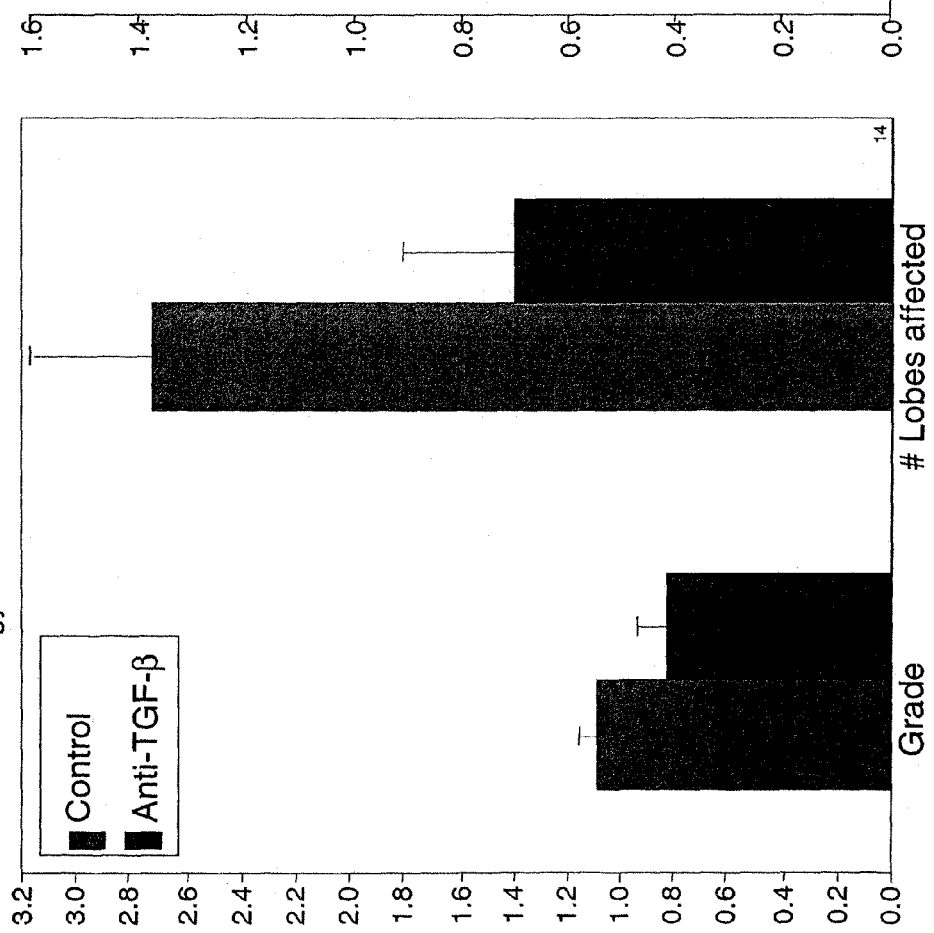
FIG. 16A Histology scores

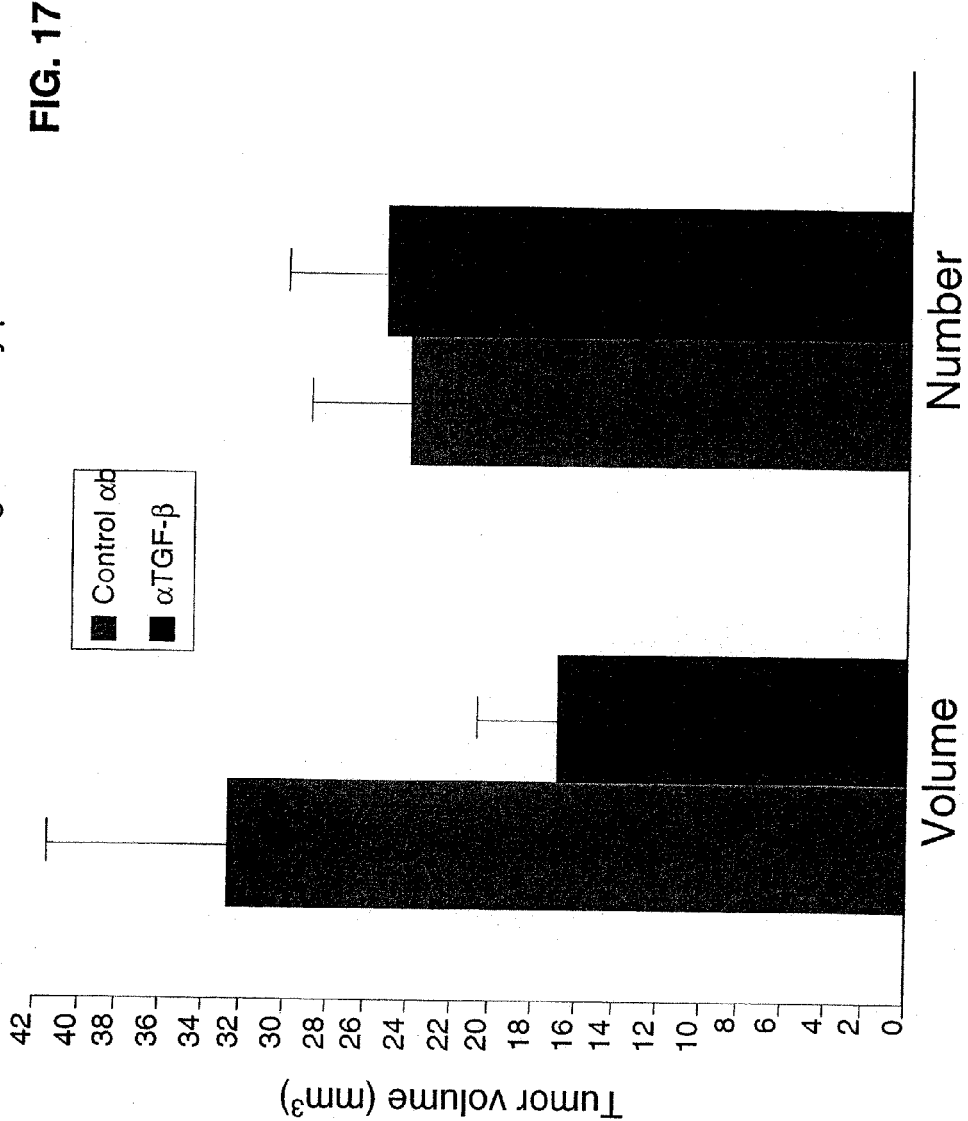

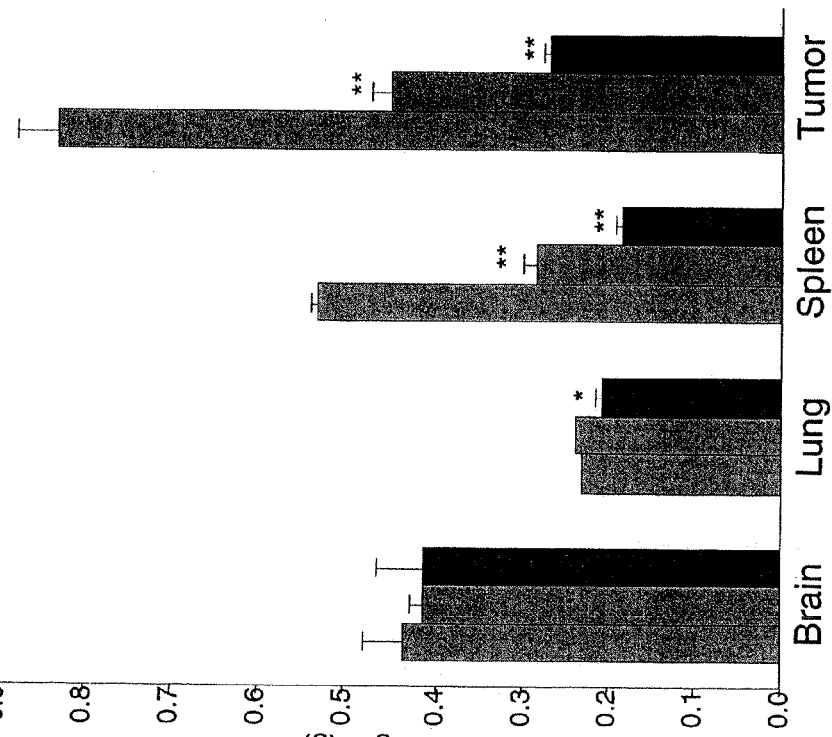
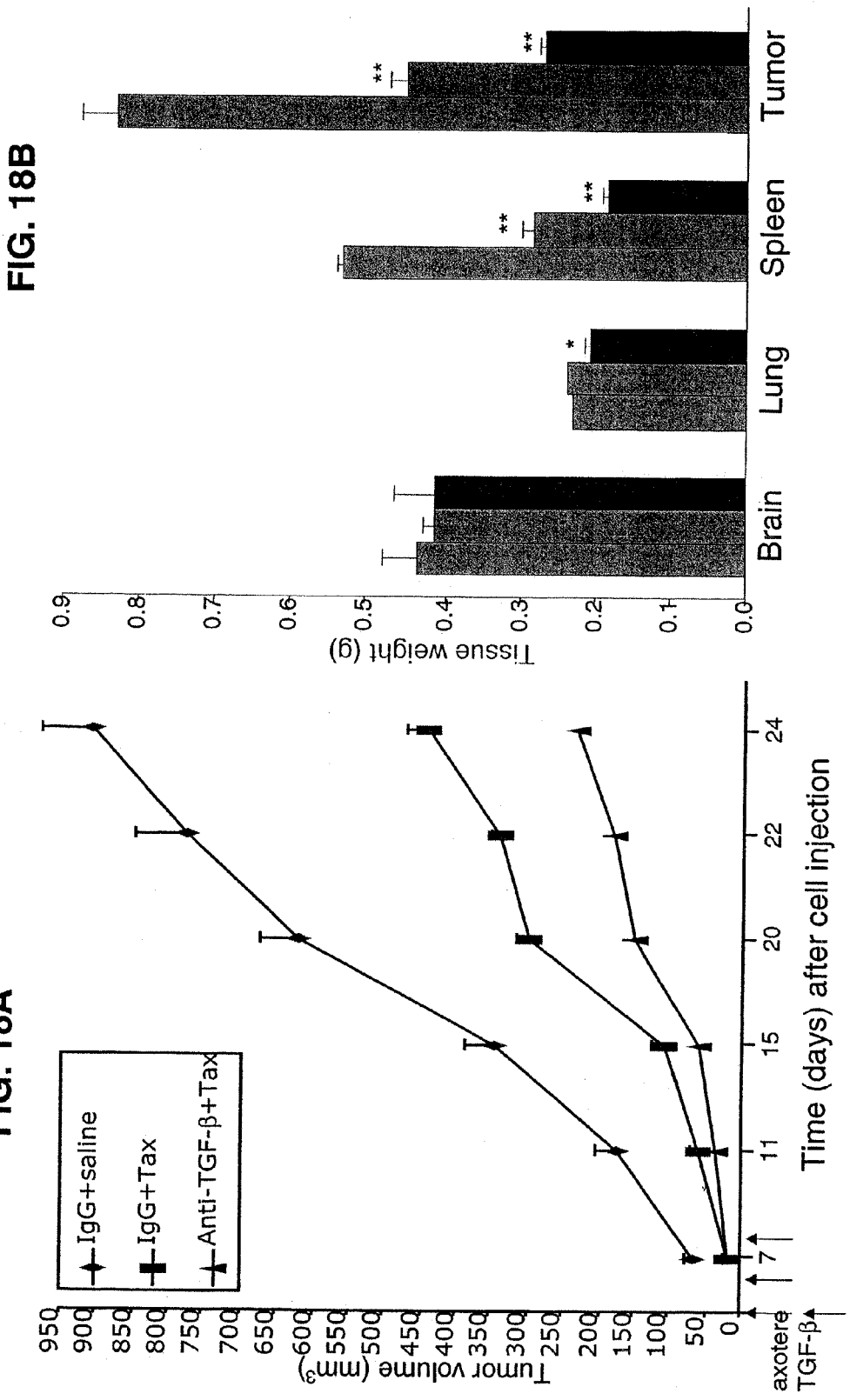

Effect of anti-TGF-β on PymT tumors

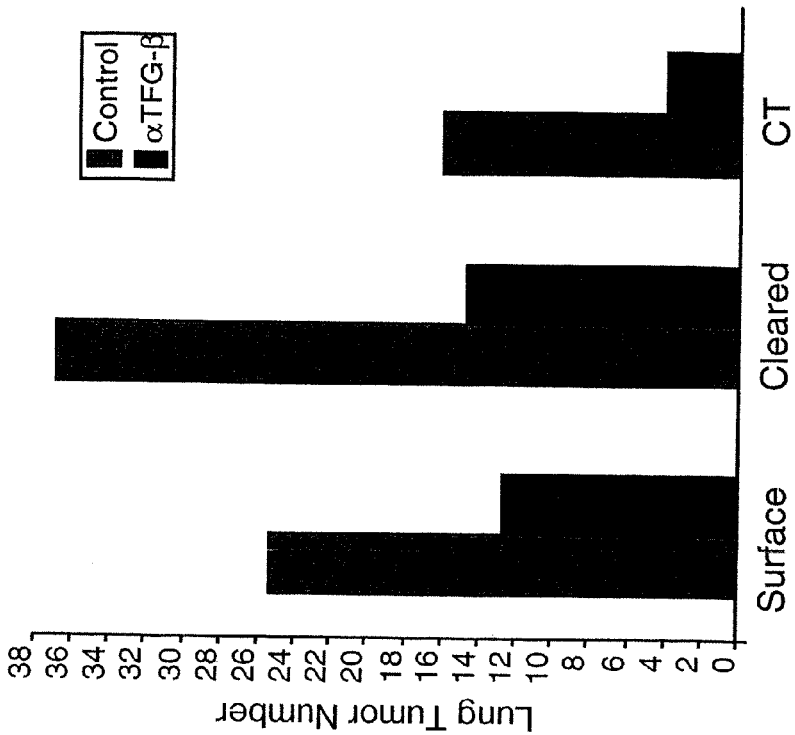
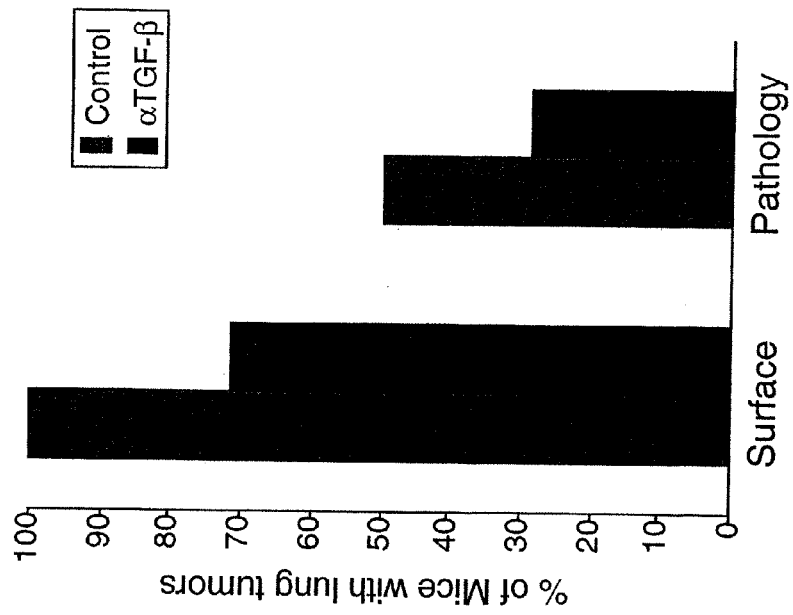
FIG. 21A Lung Tumor Incidence
FIG. 21B Lung Tumor Number
Mouse melanoma

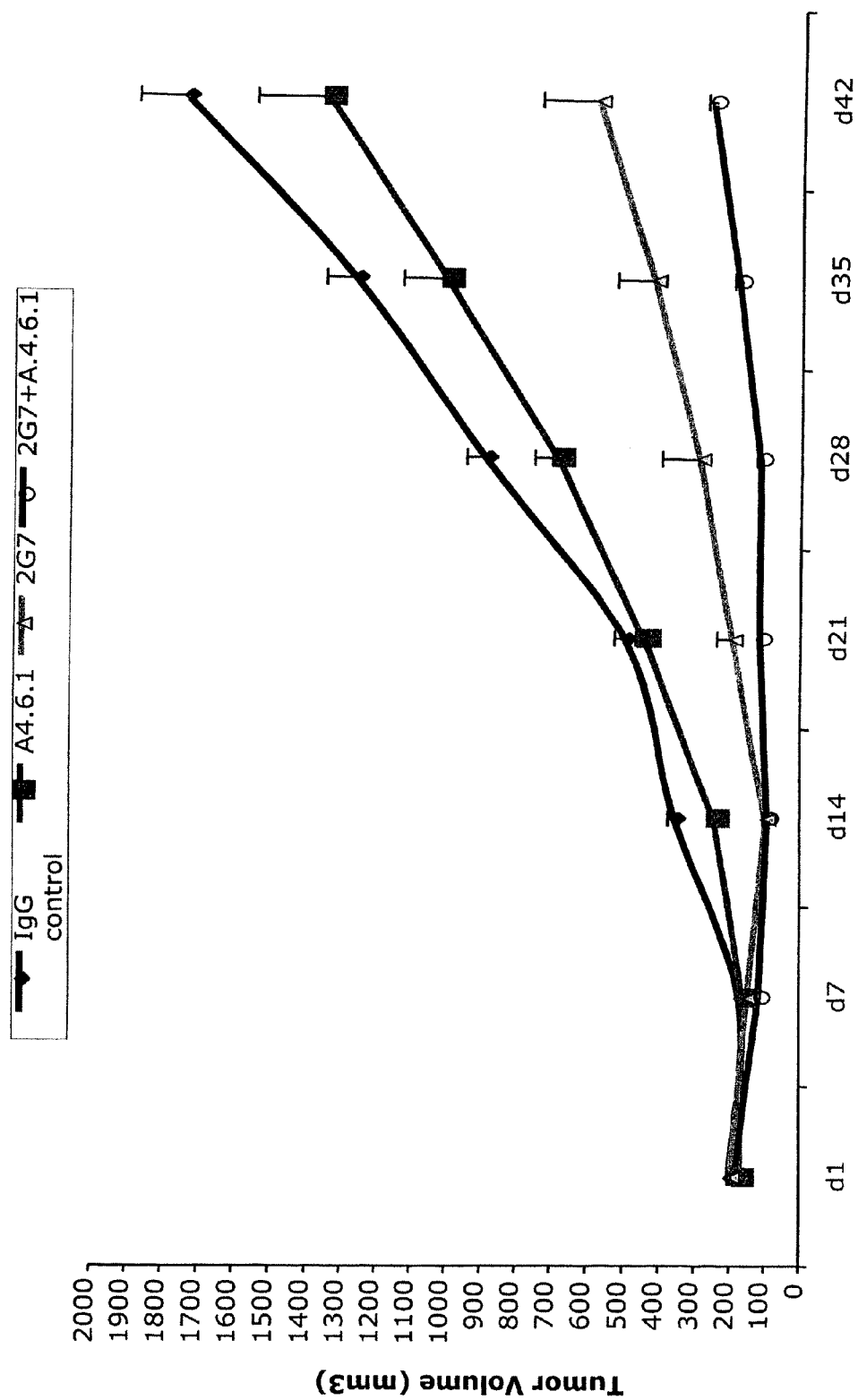

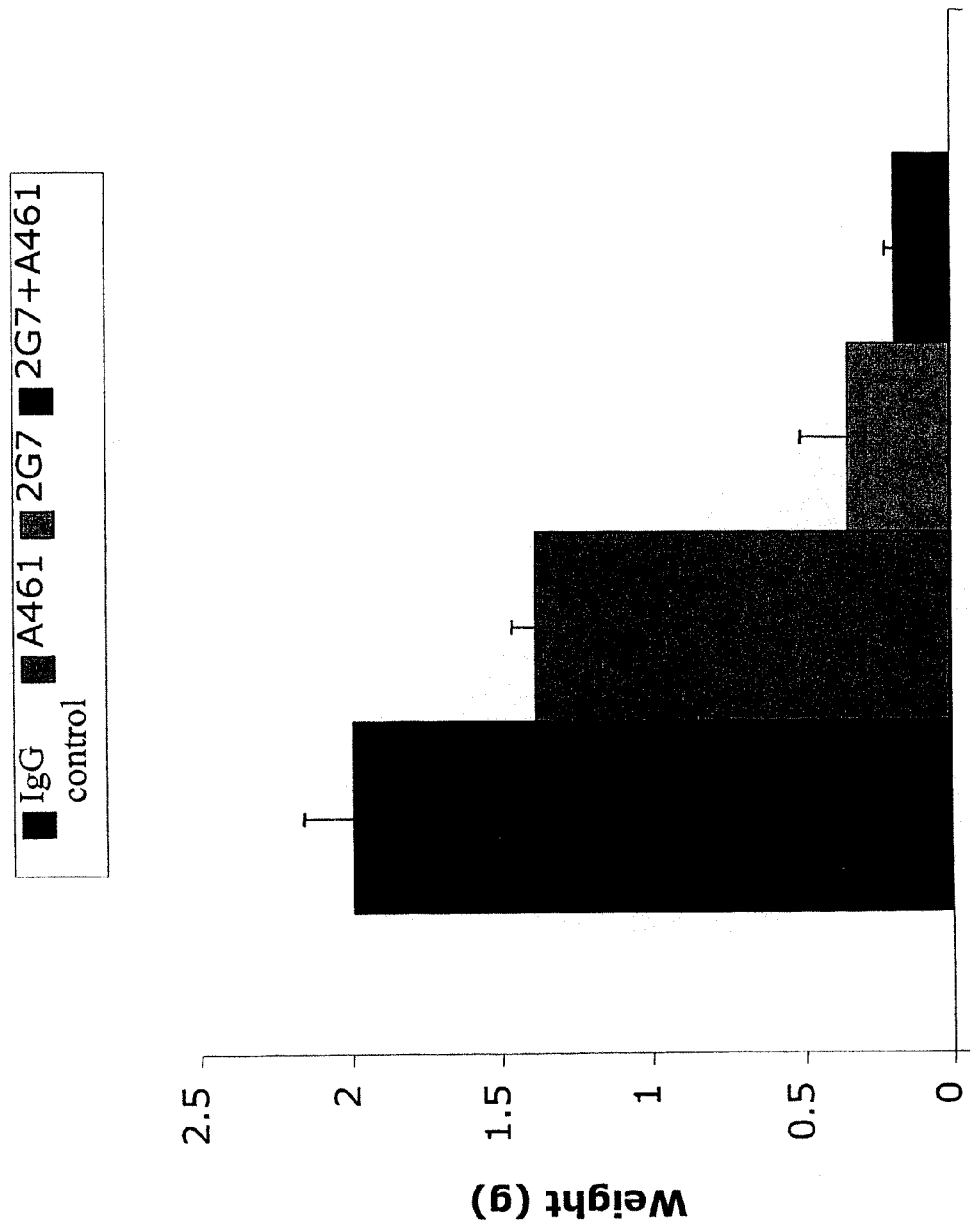

HUMANIZED ANTI-TGF-BETA ANTIBODIES

RELATED APPLICATIONS

This application claims priority under 35 U.S.C. §120 to U.S. patent application Ser. No. 11/096,046, filed Mar. 31, 2005, now U.S. Pat. No. 7,527,791, which claims priority under 35 U.S.C. §119 to U.S. Provisional Application No. 60/558,290 filed Mar. 31, 2004, the contents of each of which are incorporated herein by reference.

FIELD OF THE INVENTION

The present invention concerns humanized anti-TGF-beta antibodies and methods for preparing same and using same in methods for treating TGF-beta-related disorders. The antibodies are useful, for example, in immunoaffinity purifications, immunoassays, in vivo imaging, radioreceptor assays, and treatments where it is desired to antagonize TGF-beta activity, particularly TGF-beta1 activity.

BACKGROUND OF THE INVENTION

Transforming growth factor-beta (TGF-beta) is a multifunctional cytokine originally named for its ability to transform normal fibroblasts to cells capable of anchorage-independent growth. The TGF-betas, produced primarily by hematopoietic and tumor cells, can regulate, i.e., stimulate or inhibit, the growth and differentiation of cells from a variety of both normal and neoplastic tissue origins (Sporn et al., *Science*, 233: 532 (1986)) and stimulate the formation and elaboration of various stromal elements. For a general review of TGF-beta and its actions, see Sporn et al., *J. Cell Biol.*, 105: 1039-1045 (1987) and Sporn and Roberts, *Nature*, 332: 217-219 (1988).

They are known to be involved in many proliferative and non-proliferative cellular processes such as cell proliferation and differentiation, embryonic development, extracellular matrix formation, bone development, wound healing, hematopoiesis, and immune and inflammatory responses. Pircher et al, *Biochem. Biophys. Res. Commun.*, 136: 30-37 (1986); Wakefield et al., *Growth Factors*, 1: 203-218 (1989); Roberts and Sporn, pp 419-472 in *Handbook of Experimental Pharmacology* eds M. B. Sporn & A. B. Roberts (Springer, Heidelberg, 1990); Massague et al., *Annual Rev. Cell Biol.*, 6: 597-646 (1990); Singer and Clark, *New Eng. J. Med.*, 341: 738-745 (1999). Also, TGF-beta is used in the treatment and prevention of diseases of the intestinal mucosa. WO 2001/24813.

Of particular interest from an immunological viewpoint are the potent immunosuppressive activities of TGF-beta, which include lymphokine-activated killer (LAK) and cytotoxic T lymphocyte (CTL) inhibition (Ranges et al., *J. Exp. Med.*, 166: 991 (1987), Espevik et al., *J. Immunol.*, 140: 2312 (1988), Grimm et al., *Cancer Immunol. Immunother.*, 27: 53 (1988), Kasid et al., *J. Immunol.*, 141: 690 (1988), Mule et al., *Cancer Immunol. Immunother.*, 26: 95 (1988)), depressed B cell lymphopoiesis and kappa light-chain expression (Lee et al., *J. Exp. Med.*, 166: 1290 (1987)), negative regulation of hematopoiesis (Hino et al., *Br. J. Haematol.*, 70: 143 (1988), Sing et al., *Blood*, 72: 1504 (1988)), down-regulation of HLA-DR expression on tumor cells (Czarniecki et al., *J. Immunol.*, 140: 4217 (1988), Zuber et al., *Eur. J. Immunol.*, 18: 1623 (1988)), and inhibition of the proliferation of antigen-activated B lymphocytes in response to B-cell growth factor (Petit-Koskas et al., *Eur. J. Immunol.*, 18: 111 (1988)). The observation that many human tumors (deMartin et al., *EMBO J.*, 6: 3673 (1987), Kuppner et al., *Int. J. Cancer*, 42: 562 (1988)) and many tumor cell lines (Derynck et al., *Cancer Res.*, 47: 707 (1987), Roberts et al., *Br. J. Cancer*, 57: 594 (1988)) produce TGF-beta suggests a possible mechanism for those tumors to evade normal immunological surveillance. This negative immunomodulation, coupled with the observations that certain transformed cell lines have lost the ability to respond to TGF-beta in an autocrine fashion (Wakefield et al., *J. Cell Biol.*, 105: 965 (1987), McMahon et al., *Cancer Res.*, 46: 4665 (1986)), and that TGF-beta stimulates stroma formation, and decreases immune surveillance of the tumor, suggests attractive models for neoplasm deregulation and proliferation (Roberts et al., *Br. J. Cancer*, supra).

In addition, U.S. Pat. Nos. 5,824,297 and 5,262,319 disclose a method for inhibiting cytotoxic poisoning of normal cells by administering thereto a TGF-beta such as TGF-beta3.

There are at least five forms of TGF-beta currently identified, TGF-beta1, TGF-beta2, TGF-beta3, TGF-beta4, and TGF-beta5. Suitable methods are known for purifying this family of TGF-betas from various species such as human, mouse, green monkey, pig, bovine, chick, and frog, and from various body sources such as bone, platelets, or placenta, for producing it in recombinant cell culture, and for determining its activity. See, for example, Derynck et al., *Nature*, 316: 701-705 (1985); European Pat. Pub. Nos. 200,341 published Dec. 10, 1986, 169,016 published Jan. 22, 1986, 268,561 published May 25, 1988, and 267,463 published May 18, 1988; U.S. Pat. No. 4,774,322; Cheifetz et al, *Cell*, 48: 409-415 (1987); Jakowlew et al., *Molecular Endocrin.*, 2: 747-755 (1988); Dijke et al., *Proc. Natl. Acad. Sci. (U.S.A.)*, 85: 4715-4719 (1988); Derynck et al., *J. Biol. Chem.*, 261: 4377-4379 (1986); Sharples et al., *DNA*, 6: 239-244 (1987); Derynck et al., *Nucl. Acids. Res.*, 15: 3188-3189 (1987); Derynck et al., *Nucl. Acids. Res.*, 15: 3187 (1987); Derynck et al., *EMBO J.*, 7: 3737-3743 (1988)); Seyedin et al., *J. Biol. Chem.*, 261: 5693-5695 (1986); Madisen et al., *DNA*, 7: 1-8 (1988); and Hanks et al., *Proc. Natl. Acad. Sci. (U.S.A.)*, 85: 79-82 (1988), the entire contents of these publications being expressly incorporated by reference.

The activated form of TGF-beta1 is a homodimer formed by dimerization of the carboxy-terminal 112 amino acids of a 390-amino-acid precursor (Derynck et al., *Nature*, supra). TGF-beta2 has a precursor form of 414 amino acids and is also processed to a homodimer from the carboxy-terminal 112 amino acids that shares approximately 70% homology with the active form of TGF-beta1 (Marquardt et al., *J. Biol. Chem.*, 262: 12127 (1987)). TGF-beta2 has been purified from porcine platelets (Seyedin et al., *J. Biol. Chem.*, 262: 1946-1949 (1987)) and human glioblastoma cells (Wrann et al., *EMBO J.*, 6: 1633 (1987)), and recombinant human TGF-beta2 has been cloned (deMartin et al., supra). Recombinant TGF-beta1 has been cloned (Derynck et al., *Nature*, supra) and expressed in Chinese hamster ovary cells (Gentry et al., *Mol. Cell. Biol.*, 7: 3418-3427 (1987)). See U.S. Pat. Nos. 4,774,322; 4,843,063; and 4,848,063 regarding CIF-A and CIF-B, now recognized as TGF-beta1 and 2, respectively. Ellingsworth et al., *J. Biol. Chem.*, 261: 12362-12367 (1986). Even though there are 14 amino acid differences in the first 36 amino acid residues of the two forms (TGF-beta1 and TGF-beta2), their biological activities are similar. Cheifetz et al., *Cell*, 48: 409-415 (1987); Seyedin et al., *J. Biol. Chem.*, 262: supra.

TGF-beta3, TGF-beta4, and TGF-beta5, which are the most recently discovered forms of TGF-beta, were identified by screening cDNA libraries. None of these three putative proteins has been isolated from natural sources, although Northern blots demonstrate expression of the corresponding mRNAs. Human and porcine TGF-beta3 have been cloned and are described as homodimers and expressed in Chinese hamster ovary cells (Derynck et al., *EMBO J.*, 7: 3737-3743 (1988), ten Dijke et al., *Proc. Natl. Acad. Sci. USA*, 85: 4715 (1988); U.S. Pat. No. 4,886,747). See also WO 1992/00318 regarding TGF-beta3 proteins and antibodies thereto. TGF-beta1 differs from TGF-beta2 by 27 mainly conservative changes and from TGF-beta3 by 22 mainly conservative changes. These differences have been related to the 3-D structure. Schlunegger and Grutter, *Nature*, 358: 430-434 (1992).

TGF-beta4 and TGF-beta5 were cloned from a chicken chondrocyte cDNA library (Jakowlew et al., *Molec. Endocrinol.*, 2: 1186-1195 (1988)) and from a frog oocyte cDNA library, respectively. The frog oocyte cDNA library can be screened using a probe derived from one or more sequences of another type of TGF-beta. TGF-beta4 mRNA is detectable in chick embryo chondrocytes, but is far less abundant than TGF-beta3 mRNA in developing embryos or in chick embryo fibroblasts. TGF-beta5 mRNA is expressed in frog embryos beyond the neurula state and in *Xenopus* tadpole (XTC) cells.

The recombinant production of TGF-beta1, TGF-beta2, and TGF-beta3 is described in U.S. Pat. Nos. 5,061,786; 5,268,455 and 5,801,231. See also U.S. Pat. No. 5,120,535 on a TGF-beta2 used for treating hormonally responsive carcinoma and for production of antibodies. The heterodimer of TGF-beta1 and TGF-beta2, called TGF-beta1.2, has been identified and its uses demonstrated, as disclosed in U.S. Pat. Nos. 4,931,548 and 5,304,541, the latter also disclosing an antibody thereto. WO 1990/00900, filed 20 Jul. 1989, discloses treatment of inflammatory disorders with homodimeric TGF-beta1 and -beta2, and the heterodimer TGF-beta1.2. U.S. Pat. No. 5,462,925 discloses a heterodimer of TGF-beta2 and TGF-beta3. U.S. Pat. No. 5,780, 436 discloses small peptide mimics of TGF-beta.

Increased levels of TGF-beta activity are involved in a large number of pathologic conditions, including, but not limited to, the following: (i) fibrosis, scarring, and adhesion during wound healing; (ii) fibrotic diseases of the lungs, liver, and kidneys; (iii) atherosclerosis and arteriosclerosis; (iv) certain types of cancer including cancer of the prostate, neuroendocrine tumors of the digestive system, cancer of the cervix, glioblastomas, and gastric cancer; (v) angiopathy, vasculopathy, nephropathy; (vi) systemic sclerosis; (vii) viral infection such as hepatitis C and HIV; and (viii) immunological and inflammatory disorders and deficiencies such as rheumatoid arthritis. The modulation of immune and inflammatory responses by TGF-betas includes: (i) inhibition of proliferation of all T-cell subsets; (ii) inhibitory effects on proliferation and function of B lymphocytes; (iii) down-regulation of natural-killer cell activity and the T-cell response; (iv) regulation of cytokine production by immune cells; (v) regulation of macrophage function; and (vi) leukocyte recruitment and activation.

As to cancer specifically, members of the TGF-beta family are known to have a number of biological activities related to tumorigenesis (including angiogenesis) and metastasis. TGF-beta inhibits the proliferation of many cell types including capillary endothelial cells and smooth muscle cells. TGF-beta downregulates integrin expression (alpha1beta1, alpha2beta1, and alphavbeta3 involved in endothelial cell migration). Integrins are involved in the migration of all cells, including metastatic ones. TGF-beta downregulates matrix metalloproteinase expression needed for both angiogenesis and metastasis. TGF-beta induces plasminogen activator inhibitor, which inhibits a proteinase cascade needed for angiogenesis and metastasis. TGF-beta induces normal cells to inhibit transformed cells. See, e.g., Yingling et al., *Nature Reviews*, 3 (12): 1011-1022 (2004), which discloses that deregulation of TGF-beta has been implicated in the pathogenesis of a variety of diseases, including cancer and fibrosis, and presents the rationale for evaluating TGF-beta signaling inhibitors as cancer therapeutics, biomarkers/diagnostics, the structures of small-molecule inhibitors that are in development, and the targeted drug discovery model that is being applied to their development. Early detection of cancer is very important (Ruth et al., *Nature Reviews Cancer*, 3: 243-252 (2003)), and the pathogenesis of cancer metastasis is being studied. Fidler, *Nature Reviews Cancer*, 3: 453-458 (2003).

TGF-beta has emerged to be a major modulator of angiogenesis by regulating endothelial cell proliferation, migration, extracellular matrix (ECM) metabolism, and the expression of adhesion molecules. It is a potent growth inhibitor of normal mammary epithelial cells and a number of breast cancer cell lines. TGF-beta appears to exert pleiotropic effects in the oncogenesis of breast cancers in a contextual manner, i.e., it suppresses tumorigenesis at an early stage by direct inhibition of angiogenesis and tumor cell growth. However, over-production of TGF beta by an advanced tumor may accelerate disease progression through indirect stimulation of angiogenesis and immune suppression. The cell membrane antigen CD105 (endoglin) binds TGF beta1 and TGF beta3 and is preferentially expressed in angiogenic vascular endothelial cells. The reduction of CD105 levels in HUVEC leads to in vitro angiogenesis inhibition and massive cell mortality in the presence of TGF-beta1. CD105 null mice die in utero with impaired vasculature, indicating the pivotal role of CD105 in vascular development. Li et al., *Microsc. Res. Tech.*, 52:437-449 (2001). Abnormal angiogenesis but intact hematopoietic potential has been observed in TGF-beta type I receptor-deficient mice. Larsson et al., *EMBO J.*, 20 (7): 1663-1673 (2001). Further, TGF-beta receptor type II deficiency resulted in defects of yolk sac hematopoiesis and vasculogenesis. Oshima et al., *Developmental Biology*, 179 (1): 297-302 (1996). Also, heart and liver defects and reduced transforming growth factor beta 2 sensitivity were observed in TGF-beta type III receptor-deficient embryos. Stenvers et al., *Mol. Cell. Biol.*, 23 (12): 4371-4385 (2003). Further, targeted disruption of the mouse TGF-beta1 gene resulted in multifocal inflammatory disease. Shull et al., *Nature*, 359 (6397): 693-699 (1992). Early-onset multifocal inflammation in the TGF-beta1-null mouse was found to be lymphocyte mediated. Diebold et al., *Proc. Natl. Acad. Sci.* (*USA*), 92 (26): 12215-12219 (1995).

The most important non-proliferative function of TGF-betas is in enhancing the formation of extracellular matrices. Although this is achieved primarily through the increased transcription of both collagen and fibronectin, the inhibition of the proteases from degrading the matrix also contributes to its stability. Degradation of the extracellular matrix is inhibited by the decrease in the secretion of the proteases themselves and the simultaneous increase in the levels of protease inhibitors.

WO 1984/001106 describes TGF-beta1 and its use for the promotion of cell proliferation and tissue repair, wound healing, and treatment of traumata. U.S. Pat. No. 4,806,523 discloses that TGF-beta1 and TGF-beta2 both possess anti-inflammatory activity and are inhibitors of mitogen-stimulated T-cell proliferation and B-cell activation. It also reports that TGF-beta is localized in centers of hematopoiesis and lymphopoiesis and that TGF-beta may, therefore, be useful for treating indications associated with malfunction or dysfunction of hematopoiesis or lymphopoiesis.

TGF-beta2 has been shown to be the predominant isoform of TGF-beta in the neural retina, retinal pigment epithelium-choroid and vitreous of the human eye (Pfeffer et al. *Exp. Eye Res.*, 59: 323-333 (1994)) and found in human aqueous humour in specimens from eyes undergoing cataract extraction with intraocular lens implantation. Jampel et al., *Current Eye Research*, 9: 963-969 (1990). Non-transformed human retinal pigment epithelial cells predominantly secrete TGF-beta2. Kvanta, *Ophthalmic Res.*, 26: 361-367 (1994).

Other diseases that have potential for treatment with antibodies against TGF-beta include adult respiratory distress syndrome, cirrhosis of the liver, post-myocardial infarction, post-angioplasty restenosis, keloid scars, and scleroderma. The increased level of expression of TGF-beta2 in osteoporosis (Erlenbacher et al. *J. Cell Biol.*, 132: 195-210 (1996)) means that this is a disease potentially treatable by antibodies directed against TGF-beta2.

Because of the involvement of TGF-beta in a large number of serious pathological conditions, there is considerable interest in developing inhibitors of TGF-beta. Many of the proposals for TGF-beta inhibitors have involved antibodies.

It is a demanding task to isolate an antibody fragment specific for TGF-beta of the same species. Animals do not normally produce antibodies to self-antigens, a phenomenon called tolerance (Nossal, *Science*, 245: 147-153 (1989). In general, vaccination with a self-antigen does not result in production of circulating antibodies. It is therefore difficult to raise human antibodies to human self-antigens. There are also, in addition, ethical problems in vaccinating humans. In relation to the raising of non-human antibodies specific for TGF-beta, there are a number of problems. TGF-beta is an immunosuppressive molecule and further, there is strong conservation of sequence between human and mouse TGF-beta molecules. Mouse and human TGF-beta1 only differ by one amino acid residue, an alanine (human)-to-serine (mouse) change at a buried residue. Derynck et al., *J. Biol. Chem.*, 261: 4377-4379 (1986). Mouse and human TGF-beta2 only differ at three residues; residue 59 (T mouse, S human); residue 60 (K mouse, R human), and residue 94 (N mouse; K human). This makes it difficult to raise antibodies in mice against human TGF-beta. Further, any antibodies raised may only be directed against a restricted set of epitopes.

Monoclonal antibodies against TGF-beta have been produced by immunizing chickens and immortalizing B cells, used for, e.g. diagnosis and passive treatment of disease as described in U.S. Pat. No. 6,143,559.

Polyclonal antibodies binding to human TGF-beta1 and human TGF-beta2 against both neutralizing and non-neutralizing epitopes have been raised in rabbits (Danielpour et al., *Growth Factors*, 2: 61-71 (1989); Roberts et al. *Growth Factors*, 3: 277-286 (1990)), chickens (R&D Systems, Minneapolis) and turkeys (Danielpour et al., *J. Cell Physiol.*, 138: 79-86 (1989); Danielpour and Sporn, *J. Cell Biochem.*, 13B: 84 (1989)).

Peptides representing partial or complete TGF-beta sequences have also been used as immunogens to raise neutralizing polyclonal antisera in rabbits. Ellingsworth et al., *J. Biol. Chem.*, 261: 12362 (1986); Ellingsworth et al., *Cell. Immunol.*, 114: 41 (1988); Border et al. *Nature*, 346: 371-374 (1990); Flanders, *Biochemistry* 27: 739-746 (1988); Flanders et al., *Growth Factors*, 3: 45-52 (1990); Flanders et al., *Development*, 113: 183-191 (1991). In addition, there have been limited reports of isolation of mouse monoclonal antibodies against TGF-beta. Following immunization with bovine TGF-beta2 (identical to human TGF-beta2), three non-neutralizing monoclonal antibodies were isolated that are specific for TGF-beta2 and one neutralizing antibody that is specific for TGF-beta1 and TGF-beta2. Dasch et al., *J. Immunol.*, 142: 1536-1541 (1989). In another report, following immunization with human TGF-beta1, neutralizing antibodies were isolated that were either specific for TGF-beta1 or cross-reacted with TGF-beta1, TGF-beta2 and TGF-beta3. Lucas et al., *J. Immunol.*, 145: 1415-1422 (1990). Polyclonal antisera to human and porcine TGF-beta (Keski-Oja et al., *Cancer Res.*, 47: 6451-6458 (1987)) and to porcine TGF-beta2 (Rosa et al., *Science*, 239: 783-785 (1988)) have been shown to neutralize the biological activity of TGF-beta1 and TGF-beta2, respectively. Rabbit anti-TGF-beta serum is described in Roberts et al., *Proc. Natl. Acad. Sci. USA*, 83: 4167-4171 (1986). In addition, RIAs against TGF-beta1 using rabbit antiserum have been established to quantitate the released protein during platelet aggregation. Assoian and Sporn, *J. Cell Biol.*, 102: 12178-1223 (1986).

A neutralizing mouse monoclonal antibody that binds both TGF-beta2 and TGF-beta3 isoforms is available commercially from Genzyme Diagnostics. A mouse monoclonal antibody directed against human TGF-beta1 is available from R&D Systems. This antibody only weakly neutralizes TGF-beta1 in a neutralization assay. Neutralizing mouse monoclonal antibodies have also been generated from mice immunized with human TGF-beta1 peptides comprising amino acid positions 48 to 60 (antibody reactive with TGF-beta1, TGF-beta2 and TGF-beta3) and amino acid positions 86 to 101 (antibody specific for TGF-beta1). Hoefer and Anderer, *Cancer Immunol. Immunother.*, 41: 302-308 (1995).

Phage antibody technology (WO 1992/01047; WO 1993/19172; WO 1992/20791; WO 1993/06213; and WO 1993/11236) offers the ability to isolate directly human antibodies against human TGF-beta. The isolation of anti-self antibodies from antibody segment repertoires displayed on phage has been described. Griffiths et al., *EMBO J.*, 12: 725-734 (1993); Nissim et al. *EMBO J.*, 13: 692-698 (1994); Griffiths et al. 13: 3245-3260 (1994); Barbas et al., *Proc. Natl. Acad. Sci. USA*, 90: 10003-10007 (1993); and WO 1993/11236. In addition, Tempest et al., *Immunotechnology*, 2: 306 (1996) describes human antibodies specific for human TGF-beta derived from phage display libraries.

WO 1997/13844 discloses the isolation of human antibodies specific for human TGF-beta1 and human antibodies specific for human TGF-beta2. It describes antibodies with the 31G9 VH domain and variants of the domain, more specifically, the antibody CS37 that comprises the 31G9 VH domain together with the CS37 VL and variants of this domain, including antibodies that: (i) compete in ELISA with CS37 for binding to TGF-beta 1, (ii) bind TGF-beta 1 preferentially with respect to TGF-beta 3, and (iii) neutralize TGF-beta1.

U.S. Pat. No. 6,492,497 is based on identification of antibodies that are related to CS37, but that have unexpectedly advantageous properties with respect to binding and neutralization of TGF-beta1. They do not bind to, or neutralize, TGF-beta2 or TGF-beta3. The epitope for these antibodies lies in the C-terminal region of TGF-beta1 (residues 83-112) and includes the loop consisting of residues 92-98 of TGF-beta1, also known as finger 2, a region that has been identified as interacting with the receptor for TGF-beta.

A monoclonal antibody against human TGF-beta-1 that is highly specific and can be used for tumor diagnosis and for affinity chromatography is disclosed by JP 95068278 B2 published Jul. 26, 1995.

Use of TGF-beta and its antagonists for modulating blood pressure, and for treating hypertension and hypotension, respectively, is disclosed in WO 1991/19513.

WO 1991/15223 discloses a purified respiratory burst suppression factor that may be incubated with turkey anti-TGF-beta antibody that specifically binds TGF-beta1. The antibody completely neutralized the activity of TGF-beta1 on activated macrophages, but had no effect on the activity of the respiratory burst suppression factor on the macrophages.

Suppressing TGF-beta activity and extracellular matrix accumulation in diagnosis and treatment of fibrotic diseases such as glomerulonephritis by contact with an ECM-producing activity suppressor, such as anti-TGF-beta antibody, is disclosed in WO 1991/04748 and WO 1993/10808. Antibodies against a linear peptide from TGF-beta, and cells producing the antibodies are also disclosed.

U.S. Pat. No. 5,888,705 discloses a method of inducing the proliferation of human adult pancreatic cells or the differentiation thereof by contacting primary cultures of such cells with hepatocyte growth factor alone or in combination with anti-TGF-beta antibodies.

WO 2001/66140 discloses the use of TGF-beta antagonists such as antibodies to treat or prevent loss of renal function.

WO 2000/40227 discloses methods for treating conditions associated with the accumulation of excess extracellular matrix using agents that inhibit TGF-beta such as antibodies.

Antibodies to TGF-beta are disclosed as ameliorating tubular apoptosis in unilateral ureteral obstruction, in Miyajima et al., *Kidney International,* 58: 2301-2313 (2000).

Long-term prevention of renal insufficiency, excess matrix gene expression, and glomerular mesangial matrix expansion by treatment with monoclonal anti-TGF-beta antibody in db/db diabetic mice is disclosed in Ziyadeh et al., *Proc. Natl. Acad. Sci. USA,* 97 (14): 8015-8020 (2000).

Favorable treatment outcome with neutralizing anti-TGF-beta antibodies in experimental diabetic kidney disease is disclosed in Han and Ziyadeh, *Peritoneal dialysis international,* 19 Suppl 2: S234-237 (1999). TGF-beta was found to be a key mediator in hyperglycemia and diabetic kidney disease. Sharma and Ziyadeh, *Diabetes* 44 (10) p 1139-46 (1995). Use of TGF-beta in diabetic nephropathy is disclosed in Border et al., *Diabetes Metab. Rev.,* 12/4: 309-339 (1996).

U.S. Pat. No. 5,662,904 describes a composition for use in treating wounds to inhibit scar tissue formation. An exemplary such composition has growth-factor-neutralizing antibody, such as antibodies to TGF-beta1, TGF-beta2, and PDGF.

U.S. Pat. No. 5,972,335 discloses compositions comprising at least two antibodies for use in promoting wound healing of fibrotic disorders, where the first antibody is specific for a single epitope on TGF beta1 and the second antibody is specific for a single epitope on TGF beta2.

U.S. Pat. No. 5,958,411 discloses methods for treating a CNS pathology by administering neutralizing anti-TGF-beta antibodies.

U.S. Pat. No. 5,616,561 describes a method for treating tissue damage caused by radiation using a TGF-beta antagonist such as antibodies.

U.S. Pat. No. 6,500,920 discloses a peptide of 10-25 amino acids comprising amino acids 49-58 of a TGF-beta2, wherein the peptide is capable of inhibiting specific binding of a TGF-beta to a TGF-beta receptor on a cell.

U.S. Pat. Appln. No. 2002/0176858 and U.S. Pat. Nos. 5,693,607; 6,419,928; 6,090,383; 5,783,185; 5,772,998; and 5,571,714, as well as EP 489,062; 557,418; and 669,833, as well as WO 1992/08480; 1994/09815; and 1994/18991 disclose monoclonal antibodies to TGF-beta, including ones that neutralize the activity of TGF-beta1 and TGF-beta2, and their use in therapeutic applications for treating indications where there is an overproduction of TGF-beta (e.g., acute liver injury, interstitial lung fibrosis, liver cirrhosis, chronic hepatic fibrosis, and fibrotic skin disorders such as scleroderma) and for diagnosing or treating malignancies (e.g., sarcomas and melanomas) and metastatic cancers.

New antibodies for treating disorders associated with TGF-beta3, e.g., osteoporosis, AIDS, cancer, etc., are disclosed in WO 1992/00330 and U.S. Pat. No. 5,262,319. Such antibodies bind to human TGF-beta3 and exhibit no cross-reactivity with TGF-beta1 and beta2.

U.S. Pat. No. 6,509,318 discloses a family of small peptides found to be inhibitory to TGF-beta activity for uses such as scar tissue inhibition during wound healing.

Use of a compound (e.g. an antibody) that can inhibit the biological activity of TGF-beta on pre-damaged neurons for treating cerebral disorders, e.g. cerebral ischemia, is disclosed in WO 2000/13705.

A monoclonal antibody recognizing all three isoforms of TGF-beta that can inhibit the biological activity of TGF-beta on pre-damaged neurons, useful for treating cerebral disorders, is disclosed in WO 2000/54804. Such antibody was used to neutralize endogenous TGF-beta during the main period of ontogenetic cell death of ciliary ganglia (CG) and dorsal root ganglia (DRG) as well as spinal motoneurons in chick embryos.

Diagnosing and predicting the likelihood of development of tamoxifen-sensitive or tamoxifen-resistant breast cancer using an antibody specific to angiogenic factors or receptors, such as an antibody specific to TGF-beta3, is disclosed in WO 2000/34788.

EP 945464 B1 discloses specific binding members for human TGF-beta, that is, specific binding members comprising human antibody-antigen binding domains specific for human TGF-beta that bind specifically isoforms TGF-beta2 and TGF-beta1, or both, preferentially compared with TGF-beta3. Specific binding members may be isolated and utilized in the treatment of disease, particularly fibrotic disease and also immune/inflammatory diseases.

Antibodies against TGF-beta have been shown to be effective in the treatment of glomerulonephritis (Border et al., *Diabetes Metab. Rev.,* supra); neural scarring (Logan et al., *Eur. J. Neurosci.,* 6: 355-363 (1994); WO 1993/19783); dermal scarring (Shah et al., *Lancet,* 339: 213-214 (1992); Shah et al., *J. Cell Science,* 107: 1137-1157 (1994); Shah et al., *J. Cell Science,* 985-1002 (1995); WO1992/17206); lung fibrosis (Giri et al., *Thorax,* 48: 959-966 (1993)); arterial injury (Wolf et al., *J. Clin. Invest.,* 93: 1172-1178 (1994)); and rheumatoid arthritis (Wahl et al., *J. Exp. Medicine,* 177: 225-230 (1993)). It has been suggested that TGF-beta3 acts antagonistically to TGF-beta1 and TGF-beta2 in dermal scarring (Shah et al., 1995 supra).

Arteaga et al., *J. Clin. Invest.,* 92: 2569-2576 (1993) discloses that anti-TGF-beta antibodies inhibit breast cancer cell tumorigenicity and increase mouse spleen natural killer cell activity.

Anti-fibrotic agents for wound healing and treatment of fibrotic disorders, including anti-TGF-betas, are described in WO 1993/19769.

Specific sequences of anti-TGF-beta2 are described in EP 853,661B1.

Other applications where antibodies against TGF-beta have shown promise of therapeutic efficacy include the use of antibodies against TGF-beta for the treatment of eye diseases involving ocular fibrosis, including proliferative retinopathy (Pena et al., *Invest. Opthalmology. Vis. Sci.,* 35: 2804-2808 (1994)), prevention of cataracts (WO 1995/13827), retinal detachment, and post glaucoma drainage surgery (Khaw et al., *Eye,* 8: 188-195 (1994)). Connor et al., *J. Clin. Invest.,* 83: 1661-1666 (1989) showed that much higher levels of TGF-beta2 were present in vitreous aspirates from patients with intraocular fibrosis associated with proliferative retinopathy compared with patients with uncomplicated retinal detachment without ocular fibrosis and that the biological activity of this TGF-beta2 could be neutralized with antibodies directed against TGF-beta2.

The use of antibodies against TGF-beta for the treatment of diseases has been the subject of patent applications for fibrotic disease (WO 1991/04748); macrophage-deficiency diseases (WO 1993/14782); macrophage pathogen infections (WO 1993/17708; U.S. Pat. No. 5,730,976); and vascular disorders (WO 1993/21945).

A TGF-beta antibody-treated stem cell composition capable of survival for 14 days in vitro or ex vivo, and rapid in vivo hematopoietic system repopulation are described in WO 2000/43499.

Scrip 2580 p 14, Oct. 4, 2000 reported that Cambridge Antibody Technology (CAT) and Genzyme were working together to develop human monoclonal antibodies against TGF-beta. CAT has two fully human TGF-beta antibodies, CAT-152 and CAT-192, and Genzyme has 1D11, a murine pan-specific monoclonal antibody that neutralizes TGF-beta1, TGF-beta2 and TGF-beta3 and is being evaluated as a potential therapeutic for diffuse scleroderma. CAT was to develop a human analogue of 1D11 using its phage display technology. Several other clinical indications for anti-TGF-beta treatment, including ophthalmic indications, post-surgical scarring, fibrosis of major organs, such as the lungs, kidneys and liver, and certain cancers, will also be considered as well as treatment of malignant brain tumors by inhibiting the growth of TGF-beta2. CAT-152 (anti-TGF-beta2) is in Phase II trials to prevent post-operative scarring in patients undergoing surgery for glaucoma, and CAT-192 (anti-TGF-beta1) has completed Phase I trials. See also "Trends in Antibody Research: The Monoclonal Elite" by Tim Searle, *Bioventure-View* 1510 p 14, Oct. 1, 2000.

A method for quantifying TGF-beta using anti-TGF-beta antibody is disclosed in WO 1995/19987. A new assay for determining active TGF-beta in a sample using eukaryotic cells that contain a TGF-beta-responsive expression vector is described in WO 2000/00641. This assay includes one for determining the levels of TGF-beta isoforms in a sample, wherein cryosections are pre-incubated with anti-TGF-beta isoform neutralizing antibodies. TGF-beta immunoassays using TGF-beta antibodies are described, for example, in JP 2126157 and JP 92041307 B published Jul. 7, 1992.

Darland and D'Amore, *J. Clin. Invest.*, 103: 157-158 (1999) discloses that vessel development proceeds from a stage of growth-factor dependence where loss of a survival factor leads to apoptosis. Vessel stabilization is marked by investment with mural cells, local activation of TGF-beta, and basement membrane production. It poses several questions regarding what is the role of growth factors in the adult vascular, including VEGF and TGF-beta. Benjamin et al., *J. Clin. Invest.*, 103: 159-165 (1999) discloses selective ablation of immature blood vessels in established human tumors follows VEGF withdrawal.

Methods of making chimeric and humanized antibodies are described in, and other references in this area include, for example, U.S. Pat. No. 6,235,883 on fully human monoclonal antibodies against human epidermal growth factor receptor; EP 184187 on a mouse-human chimeric antibody; EP 844, 306 on a method of making antibodies recombinantly using phage technology; U.S. Pat. No. 5,859,205 on preparing CDR-grafted antibodies, preferably humanized antibodies, having non-human donor and human acceptor frameworks, EP 120,694; EP 125,023; EP 171,496; EP 173,494; EP 239, 400; WO 1989/07452; WO 1990/07861; and WO 1986/01533 on humanization techniques; U.S. Application No. 2003/0039649 on superhumanized antibodies; U.S. Application No. 2003/0039645 on humanized antibodies with specificity for human TNF-alpha; EP 239,400 on recombinant antibodies and their production; WO 1991/09967 on humanized antibodies; WO 1992/01047 on antibody production; WO 1992/22653 on methods for making humanized antibodies; WO 1993/11161 on multivalent antigen-binding proteins; WO 1994/13804 on multivalent antigen-binding proteins; WO 2000/66631 on specific binding members for TGF-beta; and Henry "Special Delivery: Alternative methods for delivering drugs improve performance, convenience, and patient compliance." *C & EN*, p. 49-65 (2000). See also U.S. Pat. Nos. 6,140,471 and 5,969,108 and 5,872,215 and 5,871, 907 and 5,858,657 and 5,837,242 and 5,733,743; EP 1,024, 191; EP 774,511; WO 1997/13844; EP 656,941 and 605,522 and WO 1994/13804; EP 589,877; EP 585,287; WO 1993/ 19172; EP 540,586; WO 1993/06213; WO 1992/20791; WO 1992/01787; and WO 1992/01047. Further, WO 2004/ 065417 discloses various alterations to antibodies and antigen-binding fragments to improve yield. See also US 20050049403.

There is a need to control TGF-beta molecules to prevent their deleterious effects in diseases such as those set forth above. There is also a need to provide monoclonal antibodies of high affinity that bind to TGF-beta specifically and that neutralize TGF-beta activity so as to act as a TGF-beta antagonist. The apparent loss of TGF-beta regulation by neoplastic cells coupled with the suppression of immune function and the TGF-beta-induced stroma formation makes potential intervention with TGF-beta antagonists an attractive option for cancer therapy. In addition, TGF-beta antibodies are useful in diagnostic assays and immunoaffinity purification.

SUMMARY OF THE INVENTION

In a first aspect, the present invention provides a humanized antibody that binds a TGF-beta comprising a variable heavy ($V_H$) domain that comprises non-human hypervariable region residues incorporated into a human $V_H$ domain, said variable domain comprising a framework region (FR) substitution in SEQ ID NO:6 at a position selected from the group consisting of 48, 49, 68, 70, 72, 74, and 79, utilizing the numbering system set forth in Kabat et al., *Sequences of Proteins of Immunological Interest*, 5th Ed. Public Health Service, National Institutes of Health, Bethesda, Md. (1991). The antibody includes an intact IgG1 antibody or antibody fragment such as a Fab.

Preferably, the humanized antibody comprises FR substitutions at positions 49, 68, and 72, wherein more preferably at position 49 the alanine is changed to a glycine, at position 68 the phenylalanine is changed to an alanine, and at position 72 the arginine is changed to an alanine.

In another preferred embodiment, the humanized antibody comprises FR substitutions at positions 48, 49, and 72, wherein more preferably at position 48 the valine is changed to an isoleucine, at position 49 the alanine is changed to a glycine, and at position 72 the arginine is changed to an alanine.

Also preferably, the humanized antibody comprises FR substitutions at positions 49, 70, and 72, wherein more preferably at position 49 the alanine is changed to a glycine, at position 70 the isoleucine is changed to a leucine, and at position 72 the arginine is changed to an alanine. In another aspect, an additional FR substitution is at position 74, more preferably wherein at position 74, the asparagine is changed to a lysine.

In yet another preferred embodiment, the humanized antibody comprises FR substitutions at positions 49, 72, and 74, wherein more preferably at position 49 the alanine is changed to a glycine, at position 72 the arginine is changed to an alanine, and at position 74, the asparagine is changed to a lysine.

In still yet another preferred embodiment, the humanized antibody comprises FR substitutions at positions 49, 72, and 79, wherein more preferably at position 49 the alanine is changed to a glycine, at position 72 the arginine is changed to an alanine, and at position 79 the leucine is changed to an alanine.

In another preferred embodiment, any of the antibodies above comprises variable light ($V_L$) domain complementarity-determining-region (CDR) residues RASQSVLYSSN-QKNYLA (SEQ ID NO: 18); WASTRES (SEQ ID NO: 19); and HQYLSSDT (SEQ ID NO:20), or comprises $V_L$ domain CDR residues wherein the first CDR (CDR L1) is reverted to the sequence of human germline kappa locus L8/L9: RASQGISSYLA (SEQ ID NO:7) and/or the second CDR (CDR L2) is reverted to the sequence of human germline kappa locus L8/L9/L14/L15: YASSLQS (SEQ ID NO:8). In another preferred embodiment, any of the antibodies above comprises $V_H$ domain complementarity-determining-region (CDR) residues GYAFTNYLIE (SEQ ID NO:21), VNNPGSGGSNYNEKFKG (SEQ ID NO:22), or VIN-PGSGGSNYNEKFKG (SEQ ID NO: 43); and SGGFYFDY (SEQ ID NO: 23).

Also, the invention provides any of the antibodies above conjugated with a cytotoxic agent, or not so conjugated. In addition, the invention provides a composition comprising such antibodies and a carrier.

In a further embodiment, the invention provides an isolated nucleic acid encoding the humanized antibody, a vector comprising such nucleic acid, and a host cell comprising such nucleic acid.

Additionally, the invention provides a process of producing a humanized antibody comprising culturing the host cell comprising the nucleic acid encoding the antibody so that the nucleic acid is expressed and the antibody produced, and preferably recovered from the host cell culture, more preferably from the host cell culture medium. Also, the host cell may be co-transfected with a vector comprising nucleic acid encoding the variable heavy domain and with a vector comprising nucleic acid encoding the variable light domain.

In yet another embodiment, the invention provides a method of treating a TGF-beta disorder in a mammal, preferably a primate, and more preferably a human, comprising administering to the mammal an effective amount of the humanized antibody. This may further comprise administering to the mammal an effective amount of a therapeutic agent other than the humanized antibody, such as a chemotherapeutic, anti-angiogenic, or cytotoxic agent, or a cytokine.

In still another embodiment, the invention provides a method for detecting a TGF-beta in a body sample that comprises contacting the humanized antibody with the body sample and determining whether antibody binding to the TGF-beta has occurred.

The invention also provides an article of manufacture comprising a container containing the humanized antibody and instructions directing a user to treat a TGF-beta disorder in a mammal, preferably a human, with the antibody. This article may also comprise a container containing a therapeutic agent other than the humanized antibody, wherein the instructions direct the user to treat the disorder with the antibody in combination with the agent.

In another embodiment, this invention provides a method of treating cancer in a mammal comprising administering to the mammal an effective amount of a TGF-beta antibody and an antibody that binds to vascular endothelial growth factor. Preferably, the mammal is human. In another embodiment, the TGF-beta antibody binds to any one or more of the following: TGF-beta1, TGF-beta2, and TGF-beta3. In a further embodiment, the antibody binds to TGF-beta1, or to both TGF-beta1 and TGF-beta2.

BRIEF DESCRIPTION OF THE DRAWINGS

FIGS. 1A and 1B depict alignments of the amino acid sequences of the variable light ($V_L$) (FIG. 1A) and variable heavy ($V_H$) (FIG. 1B) domains of murine monoclonal antibody 2G7 (SEQ ID NOS: 1 and 2, respectively); $V_L$ and $V_H$ domains of humanized huxTGFB version (V5H.V5L) (SEQ ID NOS: 3 and 4, respectively), and human $V_L$ and $V_H$ consensus frameworks (hum κ1, light kappa subgroup I; humIII, heavy subgroup III) (SEQ ID NOS: 5 and 6, respectively). Asterisks identify differences between humanized huxTGFB and murine monoclonal antibody 2G7 or between humanized huxTGFB and the human consensus framework regions. Complementarity Determining Regions (CDRs) are underlined, and the CDRs of the actual human germ line sequence are below the consensus framework regions for comparison (SEQ ID NOS: 7-10).

FIG. 2 shows the DNA sequences (SEQ ID NOS: 11-17) encoding the various CDR regions (SEQ ID NOS: 18-24).

FIG. 3 shows the amino acid sequences of 709.1 and H.IgG1 (SEQ ID NO:25); of H2NI.V5L (SEQ ID NO:26), of V11H.V11L (SEQ ID NO:27), of V5H.V5L (SEQ ID NO:28), of chimL.chimH (SEQ ID NO:29), and of V5H.g1L2 (SEQ ID NO:30).

FIG. 4 shows the nucleic acid sequences without and with signal sequences encoding the sequences of FIG. 3 (SEQ ID NOS:31-42).

FIG. 5 shows the binding curves of 2G7 IgG variant humanized antibodies to TGF-beta.

FIG. 6 shows the sequence of the plasmid pDR1 (SEQ ID NO:44; 5391 bp) for expression of immunoglobulin light chains as described in Example 2. pDR1 contains sequences encoding an irrelevant antibody, i.e., the light chain of a humanized anti-CD3 antibody (Shalaby et al., *J. Exp. Med.*, 175: 217-225 (1992)), the start and stop codons for which are indicated in bold and underlined.

FIG. 7 shows the sequence of plasmid pDR2 (SEQ ID NO:45; 6135 bp) for expression of immunoglobulin heavy chains as described in Example 2. pDR2 contains sequences encoding an irrelevant antibody, i.e., the heavy chain of a humanized anti-CD3 antibody (Shalaby et al., supra), the start and stop codons for which are indicated in bold and underlined.

FIG. 8 shows the binding curves of 2G7 germ-line revertant humanized antibodies to TGF-beta.

FIGS. 10A-10C show neutralization of TGF-beta3 in three different concentrations, respectively, in a 3T3 fibroblast proliferation assay by three humanized antibodies against TGF-beta (H2NI.V5L, H2NI.g1L2, and V5H.g1L2) and 2G7 murine antibody.

FIGS. 11A-11C show neutralization of TGF-beta2 in three different concentrations, respectively, in a 3T3 fibroblast proliferation assay by the four antibodies shown in FIG. 10.

FIGS. 12A-12C show neutralization of TGF-beta 1 in three different concentrations, respectively, in a 3T3 fibroblast proliferation assay by the four antibodies shown in FIG. 10.

FIGS. 13A-13C show neutralization of 2 ng/ml TGFbeta1, beta2, and beta3, respectively, in a 3T3 fibroblast proliferation assay by the four antibodies shown in FIG. 10.

FIGS. 14A-14D show neutralization of the three TGF-beta isoforms in a 3T3 fibroblast proliferation assay by humanized antibody H2NI.V5L (FIG. 14A), humanized antibody H2NI.g1L2 (FIG. 14B), 2G7 murine antibody (FIG. 14C), and humanized antibody V5H.g1L2 (FIG. 14D).

FIG. 15A show in vitro production of TGF-beta1 by normal epithelial cells (EpC) (C57) and by tumor EpC (4T1 model). FIG. 15B shows the effect of anti-TGF-beta antibody 2G7 in vivo on the serum TGF-beta1 levels in the tumor EpC versus IgG control antibody (isotype-matched IgG, which is an anti-ragweed antibody) in normal and tumor EpC. This same IgG control is used for the remaining figures, and in FIG. 28 an IgG control is used that may or may not be the same.

FIGS. 16A and 16B show the effect of anti-TGF-beta antibody 2G7 on secondary lung tumors versus IgG control. FIG. 16A shows histology scores with grade and number of lobes affected for both IgG control antibody and TGF-beta antibody 2G7, and FIG. 16B shows tissue weights in grams and percentage body weight for the same control and TGF-beta antibody 2G7.

FIG. 17 shows the effect of anti-TGF-beta antibody 2G7 on quantification of lung tumors by uCT versus IgG control, both by tumor volume and tumor number.

FIGS. 18A and 18B show the effect of anti-TGF-beta antibody 2G7 and chemotherapy in the 4T1 breast cancer model versus IgG control. FIG. 18A shows tumor volume as a function of time after cell injection for IgG with saline control, IgG and docetaxel (TAXOTERE®) control, and anti-TGF-beta 2G7 and docetaxel (TAXOTERE®). FIG. 18B shows tissue weight for brain, lung, spleen, and tumor for the two controls (IgG with and without TAXOTERE® docetaxel) and the anti-TGF-beta with docetaxel (TAXOTERE®).

FIG. 20A shows tumor volume as a function of days of tumor growth for the TGF-beta antibody and an IgG control, and FIG. 20B shows tumor weight for the TGF-beta antibody and IgG control.

FIGS. 21A and 21B show a mouse melanoma model B16 and the effect of TGF-beta antibody 2G7 versus IgG control. FIG. 21A shows the percentage of mice with lung tumors for surface and pathology for the control and TGF-beta antibody, and FIG. 21B shows the lung tumor number for surface, cleared, and CT for the control and TGF-beta antibody.

FIG. 27 shows the effect of the TGF-beta antibody 2G7, the murine monoclonal anti-VEGF antibody A461, and a combination of the two antibodies on tumor volume in a human lung cell Calu-6 mouse xenograft versus the IgG control over a period of time up to day 42. Treatment with the various agents is started at day 2.

FIG. 28 shows final tumor weights for the Calu-6 experiment in FIG. 27 for the three types of antibody treatments and an IgG control.

DETAILED DESCRIPTION OF THE PREFERRED EMBODIMENTS

I. Definitions

Figure 9:
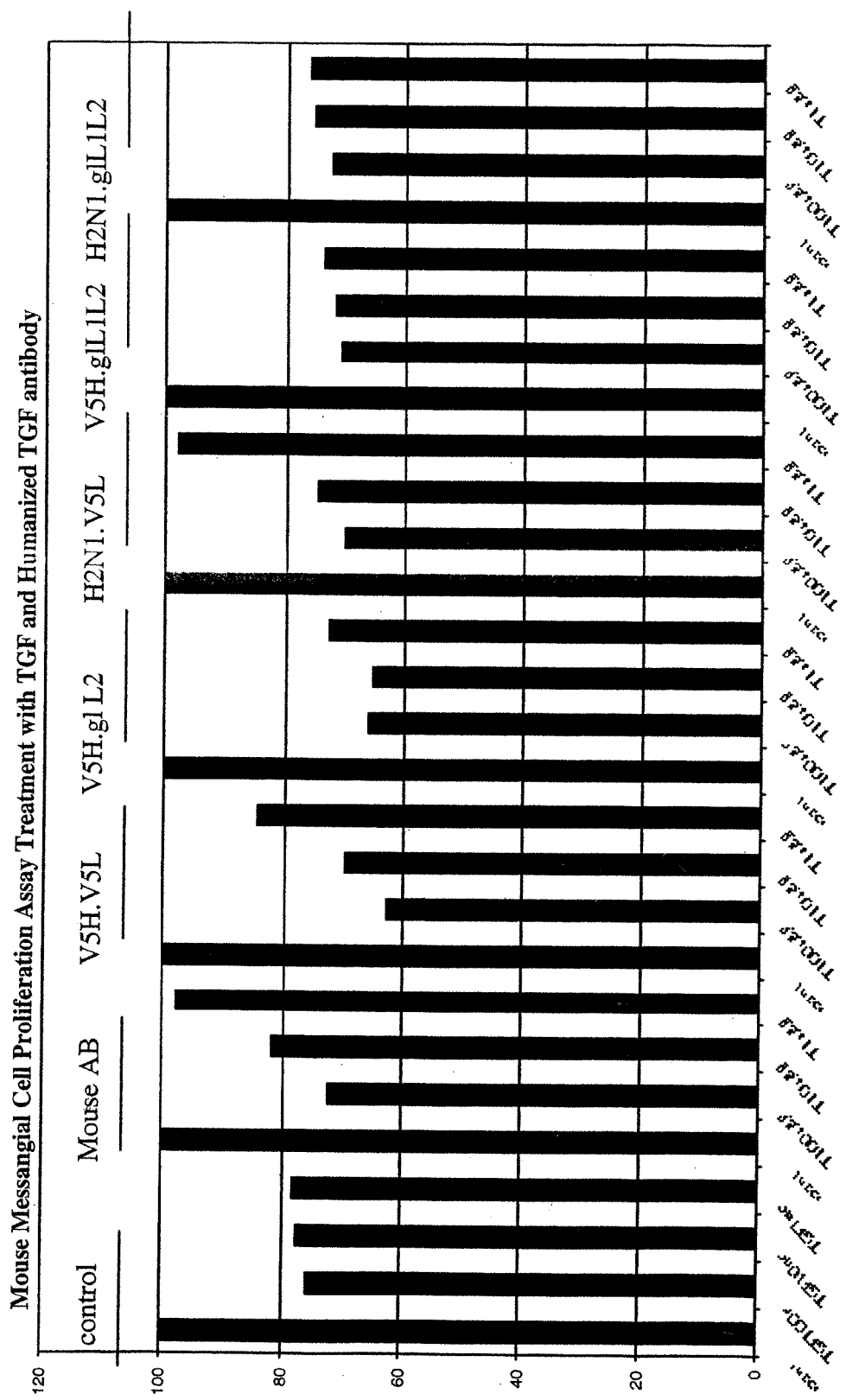
FIG. 9 shows the blocking results of a mouse mesangial cell proliferation assay of TGF-beta1 antibody 2G7 and several humanized TGF-beta variant antibodies.

The terms "TGF-beta" and "transforming growth factor-beta" are used interchangeably herein and refer to the family of molecules described hereinabove that have either the full-length, native amino acid sequence of any of the TGF-betas from humans, including the latent forms and associated or unassociated complex of precursor and mature TGF-beta ("latent TGF-beta"). Reference to such TGF-beta herein will be understood to be a reference to any one of the currently identified forms, including TGF-beta1, TGF-beta2, TGF-beta3, TGF-beta4, and TGF-beta5 and latent versions thereof, as well as to human TGF-beta species identified in the future, including polypeptides derived from the sequence of any known TGF-beta and being at least about 75%, preferably at least about 80%, more preferably at least about 85%, still more preferably at least about 90%, and even more preferably at least about 95% homologous with the sequence. The specific terms "TGF-beta1," "TGF-beta2," and "TGF-beta3", as well as "TGF-beta4" and "TGF-beta5," refer to the TGF-betas defined in the literature, e.g., Derynck et al., *Nature*, supra, Seyedin et al., *J. Biol. Chem.*, 262, supra, and deMartin et al., supra. The term "TGF-beta" refers to the gene encoding human TGF-beta. Preferred TGF-beta is native-sequence human TGF-beta.

Members of the TGF-beta family are defined as those that have nine cysteine residues in the mature portion of the molecule, share at least 65% homology with other known TGF-beta sequences in the mature region, and may compete for the same receptor. In addition, they all appear to be encoded as a larger precursor that shares a region of high homology near the N-terminus and shows conservation of three cysteine residues in the portion of the precursor that will later be removed by processing. Moreover, the TGF-betas appear to have a processing site with four or five amino acids.

A "native-sequence" polypeptide is one that has the same amino acid sequence as a polypeptide (e.g., TGF-beta1) derived from nature. Such native-sequence polypeptides can be isolated from nature or can be produced by recombinant or synthetic means. Thus, a native-sequence polypeptide can have the amino acid sequence of naturally occurring human polypeptide, murine polypeptide, or polypeptide from any other mammalian species.

The term "amino acid sequence variant" refers to polypeptides having amino acid sequences that differ to some extent from a native-sequence polypeptide. Ordinarily, amino acid sequence variants will possess at least about 70% homology with the native-sequence polypeptide or portion thereof that is being compared with the variant, and preferably, they will be at least about 80%, more preferably at least about 90%, and still more preferably at least about 95% homologous with such native-sequence polypeptide or portion. The amino acid sequence variants possess substitutions, deletions, and/or insertions at certain positions within the native amino acid sequence.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352: 624-628 (1991) and Marks et al., *J. Mol. Biol.*, 222: 581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable-domain antigen-binding sequences derived from a non-human primate (e.g. Old World Monkey, Ape etc) and human constant-region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one that comprises an antigen-binding variable region as well as a light-chain constant domain ($C_L$) and heavy-chain constant domains, $C_H1$, $C_H2$ and $C_H3$. The constant domains may be native-sequence constant domains (e.g. human native-sequence constant domains) or amino acid sequence variants thereof. Preferably, the intact antibody has one or more effector functions.

Antibody "effector functions" refer to those biological activities attributable to the Fc region (a native-sequence Fc region or amino acid sequence variant Fc region) of an antibody. Examples of antibody effector functions include C1q binding; complement-dependent cytotoxicity; Fc receptor binding; antibody-dependent cell-mediated cytotoxicity (ADCC); phagocytosis; down-regulation of cell-surface receptors (e.g. B-cell receptor; BCR); etc.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and µ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol*, 9: 457-92 (1991). To assess ADCC activity of a molecule of interest, an in vitro ADCC assay, such as that described in U.S. Pat. No. 5,500,362 or 5,821,337, may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci.* (*USA*), 95:652-656 (1998).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils, with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daëron, *Annu. Rev. Immunol.* 15: 203-234 (1997)). FcRs are reviewed in Ravetch and Kinet, *Annu. Rev. Immunol.*, 9: 457-492 (1991); Capel et al., *Immunomethods*, 4: 25-34 (1994); and de Haas et al., *J. Lab. Clin. Med.*, 126: 330-41 (1995). Other FcRs, including those to be identified in the future, are encompassed by the term "FcR" herein. The term also includes the neonatal receptor, FcRn, which is responsible for the transfer of maternal IgGs to the fetus. Guyer et al., *J. Immunol.*, 117: 587 (1976) and Kim et al., *J. Immunol.*, 24: 249 (1994).

"Complement-dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light-chain and the heavy-chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., supra). The constant domains are not involved directly in binding an antibody to an antigen, but exhibit various effector functions, such as participation of the antibody in antibody-dependent cellular cytotoxicity (ADCC).

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al, supra) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, *J. Mol. Biol.*, 196: 901-917 (1987)). "Framework Region" or "FR" residues are those variable-domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy-chain and one light-chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy-chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains. "Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994). Anti-TGF-beta antibody scFv fragments are described in WO 1993/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 1993/11161; and Hollinger et al., *Proc. Natl. Acad. Sci. USA*, 90: 6444-6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody.

These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature*, 321: 522-525 (1986); Riechmann et al., *Nature*, 332: 323-329 (1988); and Presta, *Curr. Op. Struct. Biol.*, 2: 593-596 (1992).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "that binds" an antigen of interest, e.g. TGF-beta antigen, is one capable of binding that antigen with sufficient affinity such that the antibody is useful as a therapeutic agent in targeting a cell expressing the antigen. Where the antibody is one that binds TGF-beta, it will usually preferentially bind TGF-beta as opposed to other members of the TGF-beta superfamily, and may be one that does not significantly cross-react with other proteins of such family such as BMPs, activin, etc. In such embodiments, the extent of binding of the antibody to these non-TGF-beta proteins will be less than 10% as determined by fluorescence-activated cell sorting (FACS) analysis or radioimmunoprecipitation (RIA).

An antibody having a "biological characteristic" of a designated antibody, such as the monoclonal antibody designated 2G7, is one that possesses one or more of the biological characteristics of that antibody that distinguish it from other antibodies that bind to the same antigen (e.g. TGF-beta). For example, an antibody with a biological characteristic of 2G7 may block activation of a TGF-beta, and/or bind the same epitope in the extracellular domain of TGF-beta as that bound by 2G7.

Unless indicated otherwise, the expression "monoclonal antibody 2G7" refers to an antibody that has antigen-binding residues of, or derived from, the murine 2G7 antibody of the Examples below. For example, the monoclonal antibody 2G7 may be murine monoclonal antibody 2G7 or a variant thereof, such as humanized antibody 2G7, possessing antigen-binding amino acid residues of murine monoclonal antibody 2G7. Examples of humanized 2G7 antibodies are provided in Example 2 below. Unless indicated otherwise, the expression "rhuMAb 2G7" when used herein refers to an antibody comprising the variable light ($V_L$) and variable heavy ($V_H$) sequences of SEQ ID NOS:1 and 2, respectively, fused to human light and heavy IgG1 (non-A allotype) constant-region sequences optionally expressed by a Chinese Hamster Ovary (CHO) cell.

A "growth-inhibitory agent" when used herein refers to a compound or composition that inhibits growth of a cell, especially a TGF-beta-expressing cancer cell either in vitro or in vivo. Thus, the growth-inhibitory agent may be one that significantly reduces the percentage of TGF-beta-expressing cells in S phase. Examples of growth-inhibitory agents include agents that block cell-cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA-alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth-inhibitory" antibodies are those that bind to TGF-beta and inhibit the growth of cancer cells overexpressing TGF-beta. Preferred growth-inhibitory anti-TGF-beta antibodies inhibit growth of SK-BR-3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SK-BR-3 cells to the antibody (see U.S. Pat. No. 5,677,171 issued Oct. 14, 1997). The SK-BR-3 cell growth-inhibition assay is described in more detail in that patent.

An antibody that "induces cell death" is one that causes a viable cell to become nonviable. The cell is generally one that expresses the TGF-beta receptor, especially where the cell overexpresses the TGF-beta receptor. Preferably, the cell is a cancer cell, e.g. a breast, ovarian, stomach, endometrial, salivary gland, lung, kidney, colon, thyroid, pancreatic or bladder cell. In vitro, the cell may be a SK-BR-3, BT474, Calu 3, MDA-MB-453, MDA-MB-361 or SKOV3 cell. Cell death in vitro may be determined in the absence of complement and immune effector cells to distinguish cell death induced by antibody-dependent cell-mediated cytotoxicity (ADCC) or complement-dependent cytotoxicity (CDC). Thus, the assay for cell death may be performed using heat-inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al., *Cytotechnology*, 17:1-11 (1995)) or 7AAD can be assessed relative to untreated cells. Preferred cell-death-inducing antibodies are those that induce PI uptake in the PI uptake assay in BT474 cells (see below).

An antibody that "induces apoptosis" is one that induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one that overexpresses the TGF-beta receptor. Preferably, the cell is a tumor cell, e.g., a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2- to 50-fold, preferably about 5- to 50-fold, and most preferably about 10- to 50-fold, induction of annexin binding relative to untreated cells in an annexin-binding assay using BT474 cells (see below). Sometimes the pro-apoptotic antibody will be one that further blocks TGF-beta binding (e.g. 2G7 antibody); i.e. the antibody shares a biological characteristic with an antibody to TGF-beta. In other situations, the antibody is one that does not significantly block TGF-beta. Further, the antibody may be one that, while inducing apoptosis, does not induce a large reduction in the percent of cells in S phase (e.g. one that only induces about 0-10% reduction in the percent of these cells relative to control).

The "epitope 2G7" is the region in the extracellular domain of TGF-beta to which the antibody 2G7 (ATCC HB10240) binds. To screen for antibodies that bind to the 2G7 epitope, a routine cross-blocking assay, such as that described in *Antibodies, A Laboratory Manual*, Cold Spring Harbor Laboratory, Ed Harlow and David Lane (1988), can be performed.

A "TGF-beta antibody" refers to an antibody that binds to any of the isoforms of TGF-beta, preferably binding to either TGF-beta1, TGF-beta2, or TGF-beta3, or to any combination thereof, more preferably at least TGF-beta1, or at least TGF-beta2, and most preferably TGF-beta1, or TGF-beta1 together with TGF-beta2. Optionally, the antibody may bind to at least TGF-beta3.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder.

"Mammal" for purposes of treatment refers to any animal classified as a mammal, including humans, domestic and farm animals, and zoo, sports, or pet animals, such as dogs, horses, cats, cows, etc. Preferably, the mammal is a primate, such as a monkey, ape, or human, for example, and most preferably a human.

"TGF-beta disorders" or "TGF-beta-related disorders" refers to any disorder, disease, or condition that would benefit from treatment with the anti-TGF-beta antibody. This includes chronic and acute disorders or diseases including those pathological conditions that predispose the mammal to the disorder in question. Disorders to be treated herein include diseases characterized by accumulation of extracellular matrix, diseases caused by circulating TGF-beta or TGF-beta activated at a local site, conditions caused by suppression of the immune system due to endogenous TGF-beta production, acute immune deficiencies resulting from severe injuries, burns, and illnesses such as viral or bacterial infections, multi-organ systemic illnesses due to TGF-beta production or overproduction, and TGF-beta-producing tumors. Non-limiting specific examples include neuronal, glial, astrocytal, hypothalamic and other glandular, macrophagal, epithelial, stromal and blastocoelic disorders, fibrosis, scarring, tissue damage such as caused by radiation, and adhesion during wound healing, fibrotic skin disorders such as scleroderma, CNS pathology scar tissue, dermal scarring, keloid scarring, and neural scarring, fibrotic diseases of the peritoneal cavity, lungs, liver, and kidneys such as chronic hepatic fibrosis, acute liver injury, interstitial lung and renal fibrosis, and liver cirrhosis, cystic fibrosis, vascular disorders, e.g., cardiac fibrosis, arterial injury such as atherosclerosis and arteriosclerosis, benign and malignant tumors, certain leukemias not inhibited by TGF-beta, and malignancies (e.g., sarcomas, carcinomas, and melanomas), including prostate, fibrotic, ovarian, malignant melanoma, breast, lung, colon, rectal, colorectal, or cervical cancer and metastatic cancer, as well as neuroendocrine tumors of the digestive system and glioblastomas, angiopathy, vasculopathy, nephropathy, systemic sclerosis, infections such as macrophage pathogen infections and viral infections such as hepatitis C and HIV, immunological, angiogenic, and inflammatory disorders and deficiencies such as rheumatoid arthritis, an ocular disorder, especially those involving ocular fibrosis, including proliferative retinopathy, retinal detachment and post-glaucoma drainage surgery such as neural retina, retinal pigment epithelium-choroid and vitreous of the human eye, and cataracts, osteoporosis, adult respiratory distress syndrome, post-myocardial infarction, post-angioplasty restenosis, glomerulonephritis, a diabetes-related condition such as hyperglycemia, diabetes, diabetic kidney disease, diabetic nephropathy, diabetic neuropathy or retinopathy, and macrophage-deficiency diseases.

Preferably, the disorder is fibrosis, an arterial injury, an infection, rheumatoid arthritis, diabetes or a diabetic condition, or a malignancy, such as cancer that expresses TGF-beta, more preferably wherein the cancer is characterized by excessive activation of TGF-beta. Such cancer may overexpress TGF-beta, or alternatively not be characterized by overexpression of TGF-beta.

The term "effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary-gland carcinoma, kidney or renal cancer, prostate cancer, vulval cancer, thyroid cancer, hepatic carcinoma, carcinoma, penile carcinoma, as well as head and neck cancer.

A "TGF-beta-expressing cancer" is one that produces sufficient levels of TGF-beta at the surface of cells thereof, such that an anti-TGF-beta antibody can bind thereto and have a therapeutic effect with respect to the cancer.

A cancer "characterized by excessive activation" of a TGF-beta receptor is one in which the extent of TGF-beta receptor activation in cancer cells significantly exceeds the level of activation of that receptor in non-cancerous cells of the same tissue type. Such excessive activation may result from overexpression of the TGF-beta receptor and/or greater than normal levels of a TGF-beta ligand available for activating the TGF-beta receptor in the cancer cells. Such excessive activation may cause and/or be caused by the malignant state of a cancer cell. In some embodiments, the cancer will be subjected to a diagnostic or prognostic assay to determine whether amplification and/or overexpression of a TGF-beta receptor is occurring that results in such excessive activation of the TGF-beta receptor. Alternatively, or additionally, the cancer may be subjected to a diagnostic or prognostic assay to determine whether amplification and/or overexpression of a TGF-beta ligand is occurring in the cancer that attributes to excessive activation of the receptor. In a subset of such cancers, excessive activation of the receptor may result from an autocrine-stimulatory pathway.

In an "autocrine"-stimulatory pathway, self-stimulation occurs by virtue of the cancer cell producing both a TGF-beta ligand and its cognate TGF-beta receptor. For example, the cancer may express or overexpress TGF-beta receptor and also express or overexpress a TGF-beta ligand (e.g. TGF-beta1).

A cancer that "overexpresses" a TGF-beta receptor is one that has significantly higher levels of a TGF-beta receptor, at the cell surface thereof, compared to a non-cancerous cell of the same tissue type. Such overexpression may be caused by gene amplification or by increased transcription or translation. TGF-beta receptor overexpression may be determined in a diagnostic or prognostic assay by evaluating increased levels of the TGF-beta protein present on the surface of a cell (e.g. via an immunohistochemistry assay; IHC). Alternatively, or additionally, one may measure levels of TGF-beta-encoding nucleic acid in the cell, e.g. via fluorescent in situ hybridization (FISH; see WO 1998/45479 published October, 1998), southern blotting, or polymerase chain reaction (PCR) techniques, such as real-time quantitative PCR (RT-PCR). One may also study TGF-beta receptor overexpression by measuring shed antigen (e.g., TGF-beta extracellular domain) in a biological fluid such as serum (see, e.g., U.S. Pat. No. 4,933,294 issued Jun. 12, 1990; WO 1991/05264 published Apr. 18, 1991; U.S. Pat. No. 5,401,638 issued Mar. 28, 1995; and Sias et al. *J. Immunol. Methods,* 132: 73-80 (1990)). Aside from the above assays, various in vivo assays are available to the skilled practitioner. For example, one may expose cells within the body of the patient to an antibody that is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer that is "not characterized by overexpression of the TGF-beta receptor" is one that, in a diagnostic assay, does not express higher than normal levels of TGF-beta receptor compared to a non-cancerous cell of the same tissue type.

A cancer that "overexpresses" a TGF-beta ligand is one that produces significantly higher levels of that ligand compared to a non-cancerous cell of the same tissue type. Such overexpression may be caused by gene amplification or by increased transcription or translation. Overexpression of the TGF-beta ligand may be determined diagnostically by evaluating levels of the ligand (or nucleic acid encoding it) in the patient, e.g. in a tumor biopsy or by various diagnostic assays such as the IHC, FISH, southern blotting, PCR, or in vivo assays described above.

A "hormone-independent" cancer is one in which proliferation thereof is not dependent on the presence of a hormone that binds to a receptor expressed by cells in the cancer. Such cancers do not undergo clinical regression upon administration of pharmacological or surgical strategies that reduce the hormone concentration in or near the tumor. Examples of hormone-independent cancers include androgen-independent prostate cancer, estrogen-independent breast cancer, endometrial cancer, and ovarian cancer. Such cancers may begin as hormone-dependent tumors and progress from a hormone-sensitive stage to a hormone-refractory tumor following anti-hormonal therapy.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), and toxins such as small-molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK® krestin; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes (or taxoids), e.g. paclitaxel (TAXOL®, Bristol-Myers Squibb Oncology, Princeton, N.J.) and docetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP- 16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Ralf and H-Ras; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies that bind to EGFR include MAb 579 (ATCC CRL HB 8506), MAb 455 (ATCC CRL HB8507), MAb 225 (ATCC CRL 8508), MAb 528 (ATCC CRL 8509) (see U.S. Pat. No. 4,943,533, Mendelsohn et al.) and variants thereof, such as chimerized 225 (C225) and reshaped human 225 (H225) (see, WO 1996/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR (see WO 1998/50433, Abgenix). The anti-EGFR antibody may be conjugated with a cyotoxic agent, thus generating an immunoconjugate (see, e.g., EP 659,439, Merck Patent GmbH). Examples of small molecules that bind to EGFR include ZD1839 (Astra Zeneca), CP-358774 (OSI/Pfizer), and AG1478.

A "therapeutic agent other than the humanized antibody" refers to any agent that is effective in treating a TGF-beta disorder other than the antibodies herein, and include those types listed below.

An "anti-angiogenic agent" refers to a compound that blocks, or interferes with, to some degree, the development of blood vessels. The anti-angiogenic factor may be, e.g., a small molecule or antibody that binds a growth factor or growth factor receptor involved in promoting angiogenesis. Examples include antagonists to vascular endothelial growth factor (VEGF), such as antibodies that specifically bind VEGF, e.g., AVASTIN®. "Antibodies that bind to VEGF" include chimeric, human and humanized antibodies as well as fragments, and also include antibodies that block or neutralize VEGF or block VEGF binding to one or more VEGF receptors, preferably both receptors.

The expression "regulators of immune function in a mammal" refers to cytokines and growth factors that regulate a mammal's immune function, including interleukins, tumor necrosis factor, lymphotoxin, epidermal growth factor, platelet-derived growth factor, TGF-α, macrophage-migration-inhibitory factor, macrophage-activation factor, fibroblast growth factor, macrophage-activating factors, interferons, and colony-stimulating factors. These regulators may be derived from natural sources, formed by leukocytes, synthesized by chemical methods if appropriate, or prepared recombinantly. Preferred are IL-1, IL-2, IL-6, and IFN-II.

The term "cytokine" is a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle-stimulating hormone (FSH), thyroid-stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; insulin-like growth factor-I and -II; erythropoietin (EPO); osteoinductive factors; interferons such as interferon-α, -β, and -γ; colony-stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native-sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine, and other 5-fluorouridine prodrugs that can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids, and/or surfactant that is useful for delivery of a drug (such as the anti-TGF-beta antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications, and/or warnings concerning the use of such therapeutic products.

A "cardioprotectant" is a compound or composition that prevents or reduces myocardial dysfunction (i.e. cardiomyopathy and/or congestive heart failure) associated with administration of a drug, such as an anthracycline antibiotic and/or an anti-TGF-beta antibody, to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al., *The Annals of Pharmacotherapy*, 28: 1063-1072 (1994)); a lipid-lowering agent and/or anti-oxidant such as probucol (Singal et al., *J. Mol. Cell Cardiol.*, 27: 1055-1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino)propylphosphorothioic acid (WR-151327), see Green et al., *Cancer Research*, 54: 738-741 (1994); digoxin (Bristow, M. R. In: Bristow M R, ed. *Drug-Induced Heart Disease* (New York: Elsevier 191-215 (1980)); beta-blockers such as metoprolol (Hjalmarson et al., *Drugs*, 47:Suppl 4:31-9 (1994); and Shaddy et al., *Am. Heart J.*, 129: 197-199 (1995)); vitamin E; ascorbic acid (vitamin C); free-radical scavengers such as oleanolic acid, ursolic acid, and N-acetylcysteine (NAC); spin-trapping compounds such as alpha-phenyl-tert-butyl nitrone (PBN) (Paracchini et al., *Anticancer Res.*, 13: 1607-1612 (1993)); selenoorganic compounds such as P251 (Elbesen); and the like.

An "isolated" nucleic acid molecule is a nucleic acid molecule that is identified and separated from at least one contaminant nucleic acid molecule with which it is ordinarily associated in the natural source of the antibody-encoding nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome-binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "body sample" refers to any liquid or biological sample that contains or may contain the TGF-beta to be detected. The sample includes fluids such as human or animal body fluids, e.g., blood, serum, urine, amniotic fluid, tissue extracts, cerebrospinal fluid, and the like. The samples may require special treatment such as extraction before being analyzed, depending on the tendency of the components contained therein toward lability, aggregation, or absorption by the storage container.

II. Production of Humanized Anti-TGF-Beta Antibodies

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321: 522-525 (1986); Riechmann et al., *Nature*, 332: 323-327 (1988); Verhoeyen et al., *Science*, 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Another method for making humanized antibodies is described in U.S. Patent Publication 2003/0017534 published Jan. 23, 2003, wherein humanized antibodies and antibody preparations are produced from transgenic non-human animals. The non-human animals are genetically engineered to contain one or more humanized immunoglobulin loci that are capable of undergoing gene rearrangement and gene conversion in the transgenic non-human animals to produce diversified humanized immunoglobulins.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151: 2296 (1993); Chothia et al., *J. Mol. Biol.*, 196: 901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151: 2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Example 2 below describes production of exemplary humanized anti-TGF-beta antibodies that bind TGF-beta. The humanized antibody herein comprises non-human hypervariable region residues incorporated into a human variable heavy domain and further comprises a framework region (FR) substitution at a position selected from the group consisting of 48, 49, 68, 70, 72, 74 and 79, utilizing the variable domain numbering system set forth in Kabat et al., supra. In one embodiment, the humanized antibody comprises FR substitutions at two or more of positions 48, 49, 68, 70, 72, 74, and 79; and in other embodiments, at three or four or more of such positions. In preferred embodiments, the antibody comprises FR substitutions at positions 49, 68 and 72, or positions 48, 49 and 72, or positions 49, 70, and 72 or positions 49, 70, 72, and 74, or positions 49, 72, and 74, or positions 49, 72, and 79. It is preferred that there are fewer rather than more framework substitutions to minimize immunogenicity, but efficacy is also a very important consideration. The amino acids actually substituted are those that are preferably conserved so as not to change the immunogenicity or efficacy. At position 48, the change is preferably from valine to isoleucine, at position 49, the change is preferably from alanine to glycine, at position 68, the change is preferably phenylalanine to alanine, at position 70, the change is preferably phenylalanine to alanine, at position 72, the change is preferably arginine to alanine, at position 74, the change is preferably asparagine to lysine, and at position 79, the change is preferably leucine to alanine.

An exemplary humanized antibody of interest herein comprises variable heavy-domain complementarity-determining residues GYAFTNYLIE (SEQ ID NO:21); VNNPGSGGSNYNEKFKG (SEQ ID NO:22) or VIN-PGSGGSNYNEKFKG (SEQ ID NO:43); and/or SGGFY-FDY (SEQ ID NO:23), optionally comprising amino acid modifications of those CDR residues, e.g. where the modifications essentially maintain or improve affinity of the antibody. For example, the antibody variant of interest may have from about one to about seven or about five amino acid substitutions in the above variable heavy-domain CDR sequences. Such antibody variants may be prepared by affinity maturation, e.g., as described below. Preferably, the residues are two or more of GYAFTNYLIE (SEQ ID NO:21); VNNPGSGGSNYNEKFKG (SEQ ID NO:22) or VIN-PGSGGSNYNEKFKG (SEQ ID NO:43), most preferably all three; and/or SGGFYFDY (SEQ ID NO:23). The most preferred humanized antibody comprises the variable heavy-domain amino acid sequence in SEQ ID NO:4 or the one with GYAFTNYLIE (SEQ ID NO:21); VINPGSGGSNYNEK-FKG (SEQ ID NO:43); and SGGFYFDY (SEQ ID NO: 23).

The humanized antibody may comprise variable light-domain complementarity-determining residues RASQSV-LYSSNQKNYLA (SEQ ID NO:18) or RASQGISSYLA (SEQ ID NO:7); WASTRES (SEQ ID NO:19) or YASSLQS (SEQ ID NO:8); and/or HQYLSSDT (SEQ ID NO:20), e.g. in addition to those variable heavy-domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light-domain CDR sequences. Such antibody variants may be prepared by affinity maturation, e.g., as described below. Preferably, the residues are two or more of RASQSVLYSS-NQKNYLA (SEQ ID NO:18); WASTRES (SEQ ID NO:19); and/or HQYLSSDT (SEQ ID NO:20), most preferably all three. The most preferred humanized antibody comprises the variable light-domain amino acid sequence in SEQ ID NO:3.

The present application also contemplates affinity-matured antibodies that bind TGF-beta. The parent antibody may be a human antibody or a humanized antibody, e.g., one comprising the variable light and/or heavy sequences of SEQ ID NOS:3 and 4, respectively (i.e. Version 5). The affinity-matured antibody preferably binds to TGF-beta with an affinity superior to that of murine 2G7 or variant 5 (e.g. from about two- or about four-fold, to about 100-fold or about 1000-fold improved affinity, e.g. as assessed using a TGF-beta-extracellular domain (ECD) ELISA).

Various forms of the humanized antibody or affinity-matured antibody are contemplated. For example, the humanized antibody or affinity-matured antibody may be an antibody fragment, such as a Fab, that is optionally conjugated with one or more cytotoxic agent(s) in order to generate an immunoconjugate. Alternatively, the humanized antibody or affinity-matured antibody may be an intact antibody, such as an intact IgG1 antibody.

Various techniques have been developed for the production of antibody fragments of humanized antibodies. Traditionally, these fragments were derived via proteolytic digestion of intact antibodies (see, e.g., Morimoto et al., *Journal of Biochemical and Biophysical Methods,* 24:107-117 (1992); and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology,* 10: 163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv). See WO 1993/16185; U.S. Pat. No. 5,571,894; and U.S. Pat. No. 5,587,458. The antibody fragment may also be a "linear antibody", e.g., as described in U.S. Pat. No. 5,641,870, for example. Such linear antibody fragments may be monospecific or bispecific.

Bispecific antibodies are antibodies that have binding specificities for at least two different epitopes. Exemplary bispecific antibodies may bind to two different epitopes of the TGF-beta protein. Other such antibodies may combine a TGF-beta binding site with binding site(s) for HER-2, EGFR, ErbB, ErbB3, and/or ErbB4. Alternatively, an anti-TGF-beta arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the TGF-beta-expressing cell. Bispecific antibodies may also be used to localize cytotoxic agents to cells that express TGF-beta. These antibodies possess a TGF-beta-binding arm and an arm that binds the cytotoxic agent (e.g. saporin, anti-interferon-α, vinca alkaloid, ricin A chain, methotrexate, or radioactive isotope hapten). Bispecific antibodies can be prepared as full-length antibodies or antibody fragments (e.g. F(ab')$_2$ bispecific antibodies).

WO 1996/16673 describes a bispecific anti-TGF-beta/anti-FcγRIII antibody and U.S. Pat. No. 5,837,234 discloses a bispecific anti-TGF-beta/anti-FcγRI antibody. A bispecific anti-TGF-beta/Fcα antibody is shown in WO 1998/02463. U.S. Pat. No. 5,821,337 teaches a bispecific anti-TGF-beta/anti-CD3 antibody.

Methods for making bispecific antibodies are known in the art. Traditional production of full-length bispecific antibodies is based on the coexpression of two immunoglobulin heavy-chain-light-chain pairs, where the two chains have different specificities (Millstein et al., *Nature*, 305: 537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 1993/08829, and in Traunecker et al., *EMBO J.*, 10: 3655-3659 (1991).

According to a different approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding, present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy-chain-light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 1994/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 1991/00360, WO 1992/200373, and EP 03089). Heteroconjugate antibodies may be made using any convenient cross-linking methods. Suitable cross-linking agents are well known in the art, and are disclosed, for example, in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the TGF-beta receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.*, 147: 60 (1991).

One may assess the growth-inhibitory effects of the antibody by assessing, for example, its ability to neutralize, antagonize, or inhibit a TGF-beta activity, e.g., substantially preventing at least one of the undesirable growth-inhibitory, immunosuppressive, stroma-forming (the stromal elements including inflammatory cells, endothelial cells, and fibroblasts), or anchorage-independent growth-promoting activities of a mature TGF-beta, as it is defined in the literature. The antibody is thus able to block the activity of all endogenous TGF-beta produced by tumors and suppressor lymphoid cells (T cells). One way to measure such neutralization is by $^3$H-thymidine uptake inhibition of a mink lung fibroblast cell line, e.g., Mv-3D9, wherein as the concentration of the antibody is increased, the activity of the TGF-beta is steadily decreased, either linearly or non-linearly. The mink lung cell line is very sensitive to the growth-inhibitory effects of TGF-beta and is a relatively easy assay to perform. Generally, the assay is performed by incubating the cells with a mixture of a TGF-beta and the antibody in minimal essential media containing 2 mM glutamine and 5% fetal bovine serum for 18-24 hours at 37° C. in 5% $CO_2$ and then pulsing with 1 μCi of $^3$H-thymidine in 20 μl and harvesting after four hours at 37° C. Preferably, the antibody will be able to inhibit cell proliferation by TGF-beta to a greater extent than monoclonal antibody 2G7. Another way to assess growth-inhibitory effects of the antibody is to test whether it inhibits TGF-beta in a mouse mesangial cell-proliferation assay as set forth in the Examples below. The antibodies herein are also useful in a receptor-binding or radioreceptor assay in a conventional manner, as by incubating a mixture of radiolabeled TGF-beta (e.g., radioiodinated rhTGF-beta1) and the antibody with cells containing the TGF-beta receptor (e.g., mink lung fibroblast cells such as the Mv1Lu cell line, which is available from the ATCC as ATCC No. CCL-64), and determining if the antibody blocks binding of the labeled TGF-beta to the receptor.

To select for antibodies that induce cell death, loss of membrane integrity as indicated by, e.g., PI, trypan blue or 7AAD uptake may be assessed relative to control. The preferred assay is the PI uptake assay using BT474 cells. According to this assay, BT474 cells (which can be obtained from the American Type Culture Collection (Manassas, Va.)) are cultured in Dulbecco's Modified Eagle Medium (D-MEM): Ham's F-12 (50:50) supplemented with 10% heat-inactivated FBS (Hyclone) and 2 mM L-glutamine. (Thus, the assay is performed in the absence of complement and immune effector cells.) The BT474 cells are seeded at a density of $3 \times 10^6$ per dish in 100×20-mm dishes and allowed to attach overnight. The medium is then removed and replaced with fresh medium alone or medium containing 10 μg/ml of the appropriate monoclonal antibody. The cells are incubated for a 3-day time period. Following each treatment, monolayers are washed with phosphate-buffered saline (PBS) and detached by trypsinization. Cells are then centrifuged at 1200 rpm for 5 minutes at 4° C., and the pellet is resuspended in 3 ml ice cold $Ca^{2+}$ binding buffer (10 mM Hepes, pH 7.4, 140 mM NaCl, 2.5 mM $CaCl_2$) and aliquoted into 35-mm strainer-capped 12×75 tubes (1 ml per tube, 3 tubes per treatment group) for removal of cell clumps. Tubes then receive PI (10 μg/ml). Samples may be analyzed using a FACSCAN™ flow cytometer and FACSCONVERT™ CellQuest software (Becton Dickinson). Those antibodies that induce statistically significant levels of cell death as determined by PI uptake may be selected as cell-death-inducing antibodies.

In order to select for antibodies that induce apoptosis, an annexin-binding assay using BT474 cells is available. The BT474 cells are cultured and seeded in dishes as discussed in the preceding paragraph. The medium is then removed and replaced with fresh medium alone or medium containing 10 μg/ml of the monoclonal antibody. Following a three-day incubation period, monolayers are washed with PBS and detached by trypsinization. Cells are then centrifuged, resuspended in $Ca^{2+}$ binding buffer and aliquoted into tubes as discussed above for the cell-death assay. Tubes then receive labeled annexin (e.g. annexin V-FTIC) (1 μg/ml). Samples may be analyzed using a FACSCAN™ flow cytometer and FACSCONVERT™ CellQuest software (Becton Dickinson). Those antibodies that induce statistically significant levels of annexin binding relative to control are selected as apoptosis-inducing antibodies.

In addition to the annexin-binding assay, a DNA-staining assay using BT474 cells is available. In order to perform this assay, BT474 cells that have been treated with the antibody of interest as described in the preceding two paragraphs are incubated with 9 μg/ml HOECHST 33342™ fluorescence probe for 2 hr at 37° C., then analyzed on an EPICS ELITE™ flow cytometer (Coulter Corporation) using MODFIT LT™ software (Verity Software House). Antibodies that induce a change in the percentage of apoptotic cells that is 2-fold or greater (and preferably 3-fold or greater) than untreated cells (up to 100% apoptotic cells) may be selected as pro-apoptotic antibodies using this assay.

To screen for antibodies that bind to an epitope on TGF-beta bound by an antibody of interest, a routine cross-blocking assay, such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

The invention also pertains to immunoconjugates comprising an antibody conjugated to a cytotoxic agent such as a chemotherapeutic agent, toxin (e.g. a small-molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small-molecule toxins, such as a calicheamicin, a maytansine (U.S. Pat. No. 5,208,020), a trichothene, and CC1065 anti-cancer agent, are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me, which may be reduced to May-SH3 and reacted with modified antibody (Chari et al., *Cancer Research*, 52: 127-131 (1992)) to generate a maytansinoid-antibody immunoconjugate.

Another immunoconjugate of interest comprises an anti-TGF-beta antibody conjugated to one or more calicheamicin molecules. The calicheamicin family of antibiotics is capable of producing double-stranded DNA breaks at sub-picomolar concentrations. Structural analogues of calicheamicin that may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research*, 53: 3336-3342 (1993) and Lode et al. *Cancer Research*, 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 1993/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated anti-TGF-beta antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCl), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 1994/11026. The linker may be a "cleavable linker" facilitating release of the cytotoxic drug in the cell. For example, an acid-labile linker, peptidase-sensitive linker, dimethyl linker, or disulfide-containing linker (Chari et al. *Cancer Research,* 52: 127-131 (1992)) may be used.

Alternatively, a fusion protein comprising the anti-TGF-beta antibody and cytotoxic agent may be made, e.g. by recombinant techniques or peptide synthesis.

In yet another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) that is conjugated to a cytotoxic agent (e.g. a radionucleotide).

The antibodies of the present invention may also be used in ADEPT by conjugating the antibody to a prodrug-activating enzyme that converts a prodrug (e.g. a peptidyl chemotherapeutic agent, see WO 1981/01145) to an active anti-cancer drug. See, for example, WO 1988/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature,* 328:457-458 (1987)). Antibody-abzyme conjugates can be prepared as described herein for delivery of the abzyme to a tumor cell population.

The enzymes useful in this invention can be covalently bound to the anti-TGF-beta antibodies by techniques well known in the art such as the use of the heterobifunctional crosslinking reagents discussed above. Alternatively, fusion proteins comprising at least the antigen-binding region of an antibody of the invention linked to at least a functionally active portion of a suitable enzyme can be constructed using recombinant DNA techniques well known in the art (see, e.g., Neuberger et al., *Nature,* 312: 604-608 (1984)).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug-delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The anti-TGF-beta antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); U.S. Pat. Nos. 4,485,045 and 4,544,545; and WO 1997/38731 published Oct. 23, 1997. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.*, 257: 286-288 (1982) via a disulfide-interchange reaction. A chemotherapeutic agent is optionally contained within the liposome. See Gabizon et al., *J. National Cancer Inst.*, 81(19): 1484 (1989).

III. Vectors, Host Cells and Recombinant Methods

The invention also provides isolated nucleic acid encoding the humanized anti-TGF-beta antibody, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription-termination sequence.

(i) Signal Sequence Component

The anti-TGF-beta antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-TGF-beta antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α-factor leader (including *Saccharomyces* and *Kluyveromyces* α-factor leaders), acid-phosphatase leader, the *C. albicans* glucoamylase leader, or the signal described in WO 1990/13646. In mammalian cell expression, mammalian signal sequences as well as viral secretory leaders, for example, the herpes simplex gD signal, are available.

The DNA for such precursor region is ligated in reading frame to DNA encoding the anti-TGF-beta antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-TGF-beta antibody-encoding nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-TGF-beta antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6-μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9: 968-975 (1991).

(iv) Promoter Component

Expression and cloning vectors usually contain a promoter that is recognized by the host organism and is operably linked to the anti-TGF-beta antibody-encoding nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-TGF-beta antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO:46) region where N may be any nucleotide. At the 3' end of most eukaryotic genes is an AATAAA (SEQ ID NO:47) sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-TGF-beta antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), heterologous mammalian promoters, e.g., the actin promoter or an immunoglobulin promoter, and heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature, 297:598-601 (1982) on expression of human β-interferon cDNA in mouse cells under the control of a thymidine kinase promoter from herpes simplex virus. Alternatively, the rous sarcoma virus long-terminal repeat can be used as the promoter.

(v) Enhancer Element Component

Transcription of a DNA encoding the anti-TGF-beta antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early-promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the anti-TGF-beta antibody-encoding sequence, but is preferably located at a site 5' from the promoter.

(vi) Transcription Termination Component

Expression vectors used in eukaryotic host cells (for example, yeast, fungi, insect, plant, animal, human, or nucleated cells from other multicellular organisms) will also contain sequences necessary for the termination of transcription and for stabilizing the mRNA. Such sequences are commonly available from the 5' end, occasionally 3' end, of untranslated regions of eukaryotic or viral DNAs or cDNAs. These regions contain nucleotide segments transcribed as polyadenylated fragments in the untranslated portion of the mRNA encoding anti-TGF-beta antibody. One useful transcription termination component is the bovine growth hormone polyadenylation region. See WO 1994/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-TGF-beta antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244, 234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-TGF-beta antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/−DHFR (CHO, Urlaub et al., *Proc. Natl. Acad. Sci. USA,* 77:4216 (1980), including DG44 (Urlaub et al., *Som. Cell and Mol. Gen.,* 12: 555-566 (1986)) and DP12 cell lines); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2).

Host cells are transformed with the above-described expression or cloning vectors for anti-TGF-beta antibody production and cultured in conventional nutrient media modified as appropriate for inducing promoters, selecting transformants, or amplifying the genes encoding the desired sequences.

(viii) Culturing the Host Cells

The host cells used to produce the anti-TGF-beta antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described, for example, in Ham et al., *Meth. Enz.* 58:44 (1979); Barnes et al., *Anal. Biochem.* 102:255 (1980); U.S. Pat. No. 4,767,704; 4,657,866; 4,927,762; 4,560,655; or 5,122,469; WO 1990/03430; WO 1987/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Anti-TGF-Beta Antibody

When using recombinant techniques, the antibody can be produced intracellularly or in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology,* 10:163-167 (1992) describes a procedure for isolating antibodies that are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an AMICON™ or MILLIPORE PELLICON™ ultrafiltration unit. A protease inhibitor such as phenylmethylsulphonyl fluoride (PMSF) may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.,* 62:1-13 (1983)). Protein G is recommended for all mouse isotypes and for human γ3 (Guss et al., *EMBO J.,* 5:15671575 (1986)). The matrix to which the affinity ligand is attached is most often agarose, but other matrices are available. Mechanically stable matrices such as controlled-pore glass or poly(styrenedivinyl)benzene allow for faster flow rates and shorter processing times than can be achieved with agarose. Where the antibody comprises a $C_H3$ domain, the BAKERBOND ABX™ resin (J. T. Baker, Phillipsburg, N.J.) is useful for purification. Other techniques for protein purification such as fractionation on an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium-sulfate precipitation are also available depending on the antibody to be recovered.

Following any preliminary purification step(s), the mixture comprising the antibody of interest and contaminants may be subjected to low-pH hydrophobic-interaction chromatography using an elution buffer at a pH between about 2.5-4.5, preferably performed at low-salt concentrations (e.g., from about 0-0.25M salt).

IV. Pharmaceutical Formulations

Therapeutic formulations of the antibodies used in accordance with the present invention are prepared for storage by mixing an antibody having the desired degree of purity with optional pharmaceutically acceptable carriers, excipients, or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized anti-TGF-beta antibody formulations are described in WO 1997/04801, expressly incorporated herein by reference.

The formulation herein may also contain more than one active compound as necessary for the particular indication being treated, preferably those with complementary activities that do not adversely affect each other. For example, it may be desirable to further provide antibodies that bind to HER-2, EGFR, TGF-beta (e.g. an antibody that binds a different epitope on TGF-beta), ErbB3, ErbB4, or vascular endothelial growth factor (VEGF) antigens in the one formulation. Alternatively, or additionally, the composition may further comprise a chemotherapeutic agent, cytotoxic agent, cytokine, growth-inhibitory agent, anti-hormonal agent, TGF-beta-targeted drug, anti-angiogenic agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug-delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Treatment with the Anti-TGF-Beta Antibodies

It is contemplated that, according to the present invention, the anti-TGF-beta antibodies may be used to treat various diseases or disorders. Exemplary conditions or disorders include benign or malignant tumors; leukemias and lymphoid malignancies; and other disorders such as neuronal, glial, astrocytal, hypothalamic, glandular, macrophagal, epithelial, stromal, blastocoelic, inflammatory, angiogenic and immunologic disorders.

Generally, the disorder to be treated is a TGF-beta disorder, most preferably cancer. Examples of cancer to be treated herein include, but are not limited to, carcinoma, blastoma, and sarcoma, and certain leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

In one embodiment, the cancer will be one that expresses (and may overexpress) a TGF-beta receptor.

Examples of cancers that may express/overexpress TGF-beta receptor(s) include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. However, the cancer to be treated by the antibody herein may be any cancer, not simply those that express or overexpress a TGF-beta receptor.

If the cancer to be treated herein may be one characterized by excessive activation of a TGF-beta receptor, such excessive activation may be attributable to overexpression or increased production of the TGF-beta receptor. In one embodiment of the invention, a diagnostic or prognostic assay will be performed to determine whether the patient's cancer is characterized by excessive activation of a TGF-beta receptor. For example, TGF-beta gene amplification and/or overexpression of a TGF-beta receptor in the cancer may be determined. Various assays for determining such amplification/overexpression are available in the art, e.g., immunohistochemistry (IHC); FISH, southern blotting, or PCR techniques.

Moreover, TGF-beta receptor overexpression or amplification may be evaluated using an in vivo diagnostic assay, e.g. by administering a molecule (such as an antibody) that binds the molecule to be detected and is tagged with a detectable label (e.g. a radioactive isotope) and externally scanning the patient for localization of the label.

Assays useful for determining if the humanized antibody herein is found to enhance the tumor-reduction activity of TNF-α in both in vivo and in vitro tests are described below:

A. Cytotoxic Assay Procedure

The L-929 assay system is a convenient in vitro assay that permits rapid measurement of the activity of the antibody herein optionally in conjunction with an appropriate regulator of immune function. Its degree of correlation with the in vivo tumor-necrosis assay of Carswell et al., *Proc. Natl. Acad. Sci. USA*, 72:3666 (1975) is at present unknown; however, as it utilizes murine tumor cells specifically, the correlation is expected to be high. The proteins tumor necrosis factor (TNF-α) and lymphotoxin (TNF-beta) give activity in this assay. The assay is similar in concept to that disclosed in U.S. Pat. No. 4,457,916, which used murine L-M cells and methylene blue staining. However, the L-929 assay has been shown to correlate (for TNF-α derived from HL-60 cells) with human tumor cell line cytotoxicity.

In the L-929 assay system herein, L-929 cells are prepared overnight as monolayers in microtiter plates. The best samples are diluted twofold across the plate, UV irradiated, and then added onto the prepared cell monolayers. The culture media in the wells are then brought to 1 µg/ml actinomycin D. The plates are allowed to incubate 18 hours at 37° C. and the plates are scored visually under the microscope. Each well is given a 25, 50, 75, or 100% mark signifying the extent of cell death in the well. One unit of TNF activity is defined as the reciprocal of the dilution at which 50% killing occurs.

B. In Vivo Assays

Preparations may also be tested for activity using the ability of the anti-TGF-beta antibody to kill or repress the growth of tumors and to protect the animal bearing the tumor from mortality. Balb/c mice are injected subcutaneously with various types of tumor cells to create a localized tumor. Tumor cell lines include MethA mouse fibrosarcoma, obtained as a cell suspension from ascites fluid, and MCF-7, a human breast carcinoma that is administered as a 1-mm$^3$ clump of cells.

For the assay, female Balb/c mice (19-22 g) are injected subcutaneously by a 26-gauge needle with either suspension containing $5\times10^5$ fibrosarcoma cells in 0.1 ml of medium or with the MCF-7 clumps. (The fibrosarcoma suspension is prepared from 8-day-old ascites fluid by cell counting and dilution with serum-free medium.) After 9-10 days, when the tumor becomes palpable, 1 µg per mouse of TNF-α is injected intravenously, and administration of the TNF-α is repeated, if desired, on subsequent days. Results are assessed by measuring tumor volume and by survival rate. The test is repeated using separate sequential injections of 1 µg per mouse of TNF-α and 10 mg/kg per mouse of antibody 4A11. The test antibody is compared against these agents for activity.

Where the cancer to be treated is hormone-independent cancer, expression of the hormone (e.g. androgen) and/or its cognate receptor in the tumor may be assessed using any of the various assays available, e.g. as described above. Alternatively, or additionally, the patient may be diagnosed as having hormone-independent cancer in that the patient no longer responds to anti-androgen therapy.

In certain embodiments, an immunoconjugate comprising the anti-TGF-beta antibody conjugated with a cytotoxic agent is administered to the patient. Preferably, the immunoconjugate and/or TGF-beta protein to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases, and DNA endonucleases.

The anti-TGF-beta antibodies or immunoconjugates are administered to a human patient in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous, intraperitoneal, or subcutaneous administration of the antibody is preferred, with subcutaneous or intraperitoneal routes being particular preferred. A preferred administration schedule is about 2-3 times per week, depending on the particular mammal being treated, the type of antibody, and other factors well known to the practitioner. However, other administration schedules are operable herein.

Other therapeutic regimens may be combined with the administration of the anti-TGF-beta antibody. The combined administration includes co-administration, using separate formulations or a single pharmaceutical formulation, and consecutive administration in either order, wherein preferably there is a time period while both (or all) active agents simultaneously exert their biological activities.

In one preferred embodiment, the patient is treated with two different anti-TGF-beta antibodies.

It may also be desirable to combine administration of the anti-TGF-beta antibody or antibodies with administration of an antibody directed against another tumor-associated antigen. The other antibody in this case may, for example, bind to an antigen such as HER-2, EGFR, ErbB3, ErbB4, vascular endothelial growth factor (VEGF), or a B-cell surface marker or antigen (an antigen expressed on the surface of a B cell that can be targeted with an antagonist that binds thereto), such as, for example, the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see The Leukocyte Antigen Facts Book, 2$^{nd}$ Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a mammal and may be expressed on both precursor B cells and mature B cells. The preferred B-cell surface markers herein are CD20 and CD22. In another aspect, the TGF-beta antibody may be combined with an anti-angiogenic agent, which acts to inhibit angiogenesis. An example is an antagonist to VEGF, such as an antibody, e.g., AVASTIN™.

In one embodiment, the treatment of the present invention involves the combined administration of an anti-TGF-beta antibody (or antibodies) and one or more regulators of immune function in a mammal, such as cytokines, as well as chemotherapeutic agents or growth-inhibitory agents, including co-administration of cocktails of different chemotherapeutic agents. Preferred chemotherapeutic agents include taxanes (such as paclitaxel and docetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry, Williams & Wilkins, Baltimore, Md. (1992).

The antibody may be combined with an anti-hormonal compound, e.g., an anti-estrogen compound such as tamoxifen or an aromatase inhibitor such as anastrozole; an anti-progesterone such as onapristone (see, EP 616 812); or an anti-androgen such as flutamide, in dosages known for such molecules. Where the cancer to be treated is hormone-independent cancer, the patient may previously have been subjected to anti-hormonal therapy and, after the cancer becomes hormone independent, the anti-TGF-beta antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. One may also co-administer a cytotoxic agent. In addition to the above therapeutic regimes, the patient may be subjected to surgical removal of cancer cells and/or radiation therapy.

The anti-TGF-beta antibodies herein may also be combined with an EGFR-targeted drug such as those discussed above in the definitions section resulting in a complementary, and potentially synergistic, therapeutic effect.

Suitable dosages for any of the above co-administered agents are those presently used and may be lowered due to the combined action (synergy) of the agent and anti-TGF-beta antibody.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs.

The preferred dosage of the antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses, of the anti-TGF-beta antibody). An initial higher loading dose, followed by one or more lower doses, may be administered. An exemplary dosing regimen comprises administering an initial loading dose of about 4 mg/kg, followed by a weekly maintenance dose of about 2 mg/kg of the anti-TGF-beta antibody. However, other dosage regimens may be useful. The progress of this therapy is easily monitored by conventional techniques and assays.

Alternatively, the antibody is suitably administered serially or in combination with radiological treatments—irradiation or introduction of radioactive substances—such as those referred to in UICC (Ed.), *Klinische Onkologie*, Springer-Verlag (1982).

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO 1996/07321 published Mar. 14, 1996 concerning the use of gene therapy to generate intracellular antibodies.

There are two major approaches to getting the nucleic acid (optionally contained in a vector) into the patient's cells, in vivo and ex vivo. For in vivo delivery the nucleic acid is injected directly into the patient, usually at the site where the antibody is required. For ex vivo treatment, the patient's cells are removed, the nucleic acid is introduced into these isolated cells, and the modified cells are administered to the patient either directly or, for example, encapsulated within porous membranes that are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, cell fusion, DEAE-dextran, the calcium-phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g. capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.*, 262:4429-4432 (1987) and Wagner et al., *Proc. Natl. Acad. Sci. USA*, 87:3410-3414 (1990). For review of the currently known gene marking and gene therapy protocols, see Anderson et al., *Science*, 256: 808-813 (1992). See also WO 1993/25673 and the references cited therein.

In one specific embodiment, cancer, such as lung cancer, melanoma, breast cancer, kidney cancer, colorectal cancer, pancreatic cancer, or prostate cancer, is treated in a mammal, preferably a human, by administering to the mammal an effective amount of a TGF-beta antibody and an antibody that binds to VEGF, optionally along with any other suitable agent as herein set forth. Preferably, the TGF-beta antibody is a monoclonal antibody, more preferably it binds to any one or more of the following: TGF-beta1, TGF-beta2, and TGF-beta3, and still more preferably binds to at least TGF-beta1, or both TGF-beta1 and TGF-beta2, and most preferably is the humanized antibody as set forth herein. In another embodiment, the antibody that binds to VEGF is a monoclonal antibody and more preferably it blocks or neutralizes VEGF and/or blocks VEGF binding to one or both of its receptors.

VI. Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example, the container may be an intravenous solution bag or a vial having a stopper pierceable by a hypodermic injection needle). At least one active agent in the composition is the humanized anti-TGF-beta antibody herein. The label or package insert indicates that the composition is used for treating the condition of choice, such as cancer. In one embodiment, the label or package insert indicates that the composition comprising the antibody can be used to treat a TGF-beta disorder, for example, to treat cancer that expresses a TGF-beta receptor. In addition, the label or package insert may indicate that the patient to be treated is one having cancer characterized by excessive activation of a TGF-beta receptor. The label or package insert may also indicate that the composition can be used to treat cancer, wherein the cancer is not characterized by overexpression of a TGF-beta receptor. In other embodiments, the package insert may indicate that the antibody or composition can be used to treat breast cancer (e.g. metastatic breast cancer); hormone-independent cancer; prostate cancer (e.g. androgen-independent prostate cancer); lung cancer (e.g. nonsmall cell lung cancer); colon, rectal or colorectal cancer; or any of the other diseases or disorders disclosed herein.

Moreover, the article of manufacture may comprise (a) a first container with a composition contained therein, wherein the composition comprises the humanized antibody herein, and (b) a second container with a composition contained therein, wherein the composition comprises a therapeutic agent other than the humanized antibody. The article of manufacture in this embodiment of the invention may further comprise a package insert indicating that the first and second compositions can be used in combination to treat a TGF-beta disorder such as cancer. Such therapeutic agent may be any of the adjunct therapies described in the preceding section (e.g., a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

VII. Non-Therapeutic Uses for the Anti-TGF-Beta Antibody

The antibodies (e.g. the humanized anti-TGF-beta antibodies) of the invention have further non-therapeutic applications.

For example, the antibodies may be used as affinity-purification agents. In this process, the antibodies are immobilized on a solid phase such as a SEPHADEX™ resin or filter paper, using methods well known in the art. The immobilized antibody is contacted with a sample containing the TGF-beta protein (or fragment thereof) to be purified, and thereafter the support is washed with a suitable solvent that will remove substantially all the material in the sample except the TGF-beta protein, which is bound to the immobilized antibody. Finally, the support is washed with another suitable solvent, such as glycine buffer, pH 5.0, that will release the TGF-beta protein from the antibody.

Anti-TGF-beta antibodies may also be useful in diagnostic assays for TGF-beta protein, e.g., detecting its expression in specific cells, tissues, or serum.

For diagnostic applications, the antibody typically will be labeled with a detectable moiety. Numerous labels are available that can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991), for example, and radioactivity can be measured using scintillation counting.

(b) Fluorescent labels such as rare-earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., "Methods for the Preparation of Enzyme-Antibody Conjugates for use in Enzyme Immunoassay," in *Methods in Enzym.* (Ed., J. Langone & H. Van Vunakis), Academic Press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin, and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-TGF-beta antibody need not be labeled, and the presence thereof can be detected using a labeled antibody that binds to the TGF-beta antibody.

The antibodies of the present invention may be employed in any known assay method, such as competitive-binding assays, direct and indirect sandwich assays, and immunoprecipitation assays. Zola, *Monoclonal Antibodies: A Manual of Techniques*, pp. 147-158 (CRC Press, Inc. 1987).

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}In$, $^{99}Tc$, $^{14}C$, $^{131}I$, $^{125}I$, $^{3}H$, $^{32}P$ or $^{35}S$) so that, for example, a tumor can be localized using immunoscintiography.

As a matter of convenience, the antibodies of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor that provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration.

The antibody herein is also useful for in vivo imaging, where the labeled antibody is administered to a host, preferably the bloodstream, and the presence and location of the labeled antibody in the host is assayed. This imaging technique is suitably used in the staging and treatment of neoplasms. The antibody is suitably labeled with any moiety that is detectable in a host, including non-radioactive indicators detectable by, e.g., nuclear magnetic resonance, or other means known in the art. Preferably, however, the label is a radiolabel, including iodine, e.g., $^{125}$I and $^{131}$I, selenium, bifunctional chelates, copper, e.g., $^{67}$Cu, technetium, e.g., $^{99}$mTc, and rhenium, e.g., $^{186}$Re and $^{188}$Re. The radioisotope is conjugated to the protein by any means, including metal-chelating compounds or lactoperoxidase, or iodogen techniques for iodination.

Murine monoclonal antibody 2G7 was deposited with the American Type Culture Collection, 10801 University Boulevard, Manassas, Va. 20110-2209, USA (ATCC) as HB10240 on Sep. 28, 1989; and murine monoclonal antibody 4A11 was deposited as ATCC HB10241 on Sep. 28, 1989.

Further details of the invention are illustrated by the following non-limiting Examples. The disclosures of all citations in the specification are expressly incorporated herein by reference.

Example 1

Production and Characterization of Monoclonal Antibodies 2G7 and 4A11

A. Assay Procedures

I. ELISA Determination

96-Well polystyrene assay plates were coated with 100 µl/well of purified TGF-beta1 at 1 µg/ml in pH 9.6 carbonate buffer for 18 hours at 4° C. Coated plates were blocked with 0.5% bovine serum albumin (BSA) in PBS (called BPBS) for one hour at 22° C., washed with 0.05% TWEEN 20™ surfactant in PBS (called PBST), and incubated with 100 µl of hybridoma supernatants for one hour at 22° C. Plates were washed with PBST, and bound antibodies were detected with a goat anti-mouse IgG conjugated with peroxidase (Tago, Burlingame, Calif.). The plates were washed with PBST, and o-phenylenediamine dihydrochloride substrate was added at 100 µl/well. The reaction was stopped after 15 minutes and the optical density at 492 nm was determined on a UVMAX™ plate reader (Molecular Devices, Palo Alto, Calif.).

II. Iodination of rTGF-Beta1

Purified TGF-beta1 was iodinated by a modified procedure using CHLORAMINE T™ n-chloro-para-toluene sulfonamide sodium salt (Greenwood et al., Biochem. J., 89: 114 (1963)). Briefly, 10 µg of purified rTGF-beta1 was labeled with 1 mCi of Na$^{125}$I on ice using three sequential additions of 20 µl of 0.1 mg/ml CHLORAMINE T™ n-chloro-para-toluene sulfonamide sodium salt separated by two-minute incubations. The reaction was stopped using sequential additions of 20 µl of 50 mM N-acetyl tyrosine, 1 M potassium iodine, followed by 200 µl of 8 M urea. The iodinated rTGF-beta1 was separated from free Na$^{125}$I by HPLC using a C18 column and a trifluoroacetic acid/acetonitrile gradient, and fractions containing the main peak were pooled and stored at −70° C. (specific activity 112 µCi/µg).

III. Antigen-Capture Radioimmunoassay

IMMULON™ 2 "REMOVAWELL"™ microtiter strips (Dynatech, Chantily, Va.) were coated with 5 µg/ml goat anti-mouse IgG (Boehringer Mannheim) in pH 9.6 carbonate for 18 hours at 4° C. The wells were washed with PBST, blocked with PBS containing 0.1% gelatin (called PBSG), washed with PBST, and incubated with hybridoma supernatants for four hours at 22° C. The wells were washed with PBST, and approximately 75,000 CPM/well of $^{125}$I-rTGF-beta1, in 100 µl of 0.1% gelatin in PBST, was added and incubated for two hours at 22° C. The plates were washed with PBST, and bound $^{125}$I-rTGF-beta1 was quantitated on a GAMMAMASTER™ counter (LKB, Sweden).

IV. Immunoprecipitation of $^{125}$I-rTGF-Beta

The specificity of anti-TGF-beta monoclonal antibodies was also evaluated by their ability to immunoprecipitate $^{125}$I-rTGF-beta1 or porcine, platelet-derived $^{125}$I-TGF-beta2 (R & D Systems, Minneapolis, Minn.; specific activity 103.4 µCi/µg). Two µg of purified monoclonal antibody was incubated with 5×10$^4$ CPM of $^{125}$I-rTGF-beta1 or $^{125}$I-TGF-beta2 for two hours at 22° C. The immunocomplexes were pelleted with protein A-SEPHAROSE™ agarose (Repligen, Cambridge, Mass.) coated with rabbit anti-mouse IgG (Boehringer Mannheim Biochemicals, Indianapolis, Ind.) and subsequently washed 3× with PBST. The complexes were dissociated from the protein A-SEPHAROSE™ agarose with reducing sample buffer, electrophoresed into 12% SDS-polyacrylamide gel (SDS-PAGE), and exposed to autoradiography.

V. Affinity Determination of TGF-Beta Monoclonal Antibodies

The solid-phase radioimmunoassay procedure described by Mariani et al., J. Immunol. Methods, 71: 43 (1984) was used to determine the affinities of the TGF-beta-specific monoclonal antibodies. Briefly, purified anti-TGF-beta monoclonal antibodies were coated on IMMULON™ 2 "REMOVAWELL"™ microtiter strips in pH 9.6 carbonate buffer for 18 hours at 4° C. The wells were washed and blocked as described above. 40,000 CPM/well of either $^{125}$I-rTGF-beta1 or porcine $^{125}$I-TGF-beta2 (R & D Systems), in 50 µl PBSG, was added to 2-fold serial dilutions of non-labeled rTGF-beta1 or porcine TGF-beta2 ranging from 2500 to 9.7 ng/well, in 50 µl PBSG. The resulting mixture was incubated for 18 hours at 4° C. The wells were washed and counted as described above and the affinity constants determined by Scatchard analysis (Munson and Pollard, Anal. Biochem., 107: 220 (1980)), which yields similar results as the non-linear regression analysis of Antoni and Mariani, J. Immunol. Meth., 83: 61 (1985).

VI. Purification of Monoclonal Antibodies from Ascites Fluid

Parental hybridoma cultures secreting antibody that was positive in the above assays were cloned by limiting dilution and grown in ascites fluid in Balb/c mice (Potter et al., JNCI, 49: 305 (1972)) primed with PRISTANE™ primer. The monoclonal antibodies were purified from ascites fluid over protein A-SEPHAROSE™ agarose and eluted in 0.1 M acetic acid, 0.5 M NaCl, pH 2.4, using established procedures (Goding, *J. Immunol. Methods*, 20: 241 (1978)) and stored sterile in PBS at 4° C.

VII. Monoclonal Antibody Neutralization of In Vitro TGF-Beta Specific Activity

The in vitro TGF-beta assay used the mink lung fibroblast cell line, Mv-3D9 (subcloned from Mv1Lu, which is available from the American Type Culture Collection, Manassas, Va., as ATCC No. CCL-64). Briefly, purified anti-TGF-beta monoclonal antibodies and controls were incubated with either rTGF-beta1, native porcine TGF-beta2 (R & D Systems), or rTGF-beta3 (Derynck et al., *Nature*, supra) at a final concentration of 1000-2000 pg/ml for 18 hours at 4° C. Fifty µl of these mixtures were added to 96-well microtiter plates followed by $1 \times 10^4$ Mv-3D9 cells, in 50 µl of minimal essential media containing 2 mM glutamine and 5% fetal bovine serum, and incubated for 18-24 hours at 37° C. in 5% $CO_2$. The wells were pulsed with 1 µCi of $^3$H-thymidine in 20 µl and harvested after four hours at 37° C. and counted in a scintillation counter. The percent inhibition of $^3$H-thymidine uptake for each dilution of TGF-beta standard was used to calculate the TGF-beta activity in pg/ml of the negative control monoclonal antibody and TGF-beta-specific-monoclonal-antibody-treated samples.

VIII. Isotyping of Monoclonal Antibodies

Isotyping of TGF-beta1-reactive monoclonal antibodies was performed using the PANDEX™ fluorescence screen machine technology. Rat-anti-mouse-IgG-antisera-coated polystyrene particles were used to bind the monoclonal antibody from culture supernatant dispensed into PANDEX™ 96-well assay plates. The plates were washed and FITC-conjugated-rat-monoclonal-anti-mouse-isotype-specific reagents (Becton Dickinson Monoclonal Center) added. The bound fluorescence was quantitated by the PANDEX™ fluorescence screen machine technology.

IX. Epitope Analysis

Purified anti-rTGF-beta1 monoclonal antibodies were coupled to horseradish peroxidase (HRP) by the method of Nakane and Kawaoi, *J. Histochem. Cytochem.*, 22: 1084 (1974). rTGF-beta1-coated plates were incubated with 50 µg/ml of purified anti-rTGF-beta1 or negative control in PBS for two hours at 22° C. A predetermined dilution of the anti-rTGF-beta monoclonal antibody-HRP conjugate was then added to the plates and incubated for one hour at 22° C. The plates were washed and substrate was added and reactivity quantitated as described above. The percent blocking of the heterologous anti-rTGF-beta1 monoclonal antibodies was compared to the autologous, positive blocking control.

X. Immunoblot Analysis

One µg/lane of rTGF-beta1 was electrophoresed in 12% SDS-PAGE using non-reducing sample buffer to determine the reactivities of the various monoclonal antibodies with the dimer forms of rTGF-beta1. The peptides were transblotted onto nitrocellulose paper and probed with the appropriate monoclonal antibody conjugated with HRP. Bound antibody was visualized using the insoluble substrate 4-chloro-1-naphthol (Kirkegaard and Perry, Gathersburg, Md.). The reaction was stopped after 15 minutes by exhaustive washing with distilled water and the immunoblots were dried and photographed.

B. Production of Anti-TGF-Beta1- and Anti-TGF-Beta2-Specific Monoclonal Antibodies In the initial immunization protocols, Balb/c mice were immunized with rTGF-beta1 (produced and purified as described by Derynck et al., *Nature*, supra) by subcutaneous and intraperitoneal routes using a variety of immunogen preparations, doses, and schedules and using both complete and incomplete Freund's adjuvant. The immunization schedules were continued for up to 11 weeks. Several mice responded with measurable but low anti-rTGF-beta1 titers and two of these mice were sacrificed and their spleens used for fusions. From 1152 parental cultures only 84 positive anti-TGF-beta supernatants were detected. Ten of these hybridomas were cloned and resulted in monoclonal antibodies of low affinity that could not be used for assay development or purification.

As an alternative strategy, a group of ten Balb/c female mice (Charles River Breeding Laboratories, Wilmington, Mass.) were injected with 5 µg/dose of purified TGF-beta1 in 100-µl DETOX™ adjuvant (RIBI ImmunoChem Res. Inc., Hamilton, Mont.) in the hind foot pads on days 0, 3, 7, 10, and 14. On day 17 the animals were sacrificed, their draining inguinal and popliteal lymph nodes were removed, and the lymphocytes were dissociated from the node stroma using stainless-steel mesh. The lymphocyte suspensions from all ten mice were pooled and fused with the mouse myeloma line X63-Ag8.653 (Kearney et al., *J. Immunol.*, 123: 1548 (1979)) using 50% polyethylene glycol 4000 by an established procedure (Oi and Herzenberg, in *Selected Methods in Cellular Immunology*, B. Mishel and S. Schiigi, eds. (W.J. Freeman Co., San Francisco, Calif., 1980), p. 351). The fused cells were plated into a total of 1344 96-well microtiter plates at a density of $2 \times 10^5$ cells/well followed by HAT selection (Littlefield, J. W., *Science*, 145: 709 (1964)) on day 1 post-fusion.

1190 of the wells were reactive with immobilized recombinant TGF-beta1 in the ELISA test. Eighteen of these cultures remained stable when expanded and cell lines were cryopreserved. These parental cultures were isotyped and assayed for their ability to capture $^{125}$I-rTGF-beta1 and to neutralize in vitro TGF-beta1 activity. From the 18 parental cultures that were assayed for neutralization of rTGF-beta1 and subsequently isotyped, two were of the IgG1 kappa isotype; the remainder were of the IgG2b kappa isotype. Only the monoclonal antibodies belonging to the IgG1 subclass were found to demonstrate rTGF-beta1 inhibitory (neutralization) activity in vitro. Three stable hybridomas were selected that secreted high-affinity anti-TGF-beta monoclonal antibodies. The characterization of these antibodies is detailed further below.

C. Immunoprecipitation of Radioiodinated TGF-Beta

Immunoprecipitation experiments were performed to determine the ability of the three monoclonal antibodies to recognize and precipitate TGF-beta1 in solution. The autoradiograph showed that the anti-TGF-beta monoclonal antibodies 2G7, 4A11, and 12H5 immunoprecipitated equivalent amounts of $^{125}$I-rTGF-beta1, whereas the control monoclonal antibody 6G12 was negative. The immunoprecipitated bands had an apparent molecular weight of approximately 14.5 kD. A competitive inhibition assay was used to determine the affinity of interaction between TGF-beta1 and each of the monoclonal antibodies. Monoclonal antibodies 2G7 and 4A11 had equally higher affinities, which were $1.2 \times 10^8$ l/mole.

Immunoprecipitation experiments were also performed to determine the ability of the monoclonal antibodies selected to recognize and precipitate TGF-beta2 in solution. The autoradiograph showed that, in contrast to rTGF-beta1, only antibody 2G7 immunoprecipitated $^{125}$I-TGF-beta2 to any measurable degree. Comparison of 4A11 and 12H5 to the negative control reveals little specific precipitation. These results were surprising in that cross-blocking experiments revealed that 4A11 and 2G7 were able to inhibit the binding of one another to human rTGF-beta1. See Table 1.

TABLE 1

| Binding Monoclonal Antibody | Percent Crossblocking of Mabs to TGF-beta1 Blocking Monoclonal Antibody | | | |
|---|---|---|---|---|
| | 2G7 | 4A11 | 12H5 | 456* |
| 2G7 | 100 | 74 | 32 | 1.9 |
| 4A11 | 96 | 100 | 19 | 1.5 |
| 12H5 | 28 | 12 | 100 | 3.4 |

*Mab 456 is a control antibody that reacts with CD4.

Taken together, the data indicate that the epitopes recognized by these two monoclonal antibodies are distinct but are either in close proximity or somehow affect the binding of one another from a distance. From both the immunoprecipitation and cross-blocking experiments, 12H5 appears to be a distinct epitope, although some blocking was observed. This conclusion is also supported by the neutralization data below.

D. Immunoblot Analysis with rTGF-Beta1

Since the active form of TGF-beta is a homodimer, immunoblots were performed to determine whether the monoclonal antibodies recognized this form. The antibodies 2G7, 4A11 and 12H5 all reacted in an indirect immunoblot with the TGF-beta1 dimer (non-reduced) form. 2G7 gave a much stronger band than either 4A11 or 12H5. As in the immunoprecipitation experiment, control antibody 6G12 was negative. This pattern of reactivity was also observed in a direct Western blot with HRP conjugates of these monoclonal antibodies.

In summary, the protocol employing foot-pad immunizations coupled with fusions of the draining lymph nodes was performed after multiple unsuccessful attempts at breaking tolerance to rTGF-beta1 using a variety of immunization procedures and dosing schedules in Balb/c and C3H mice with complete and incomplete Freund's adjuvant. In general, this procedure was found useful to generate a rapid response with very high affinity to these weak immunogens, in contrast to the experience of Dasch et al., supra, who generated a TGF-beta1- and TGF-beta2-neutralizing monoclonal antibody using purified bovine bone-derived TGF-beta2 in Freund's adjuvant as immunogen in Balb/c mice.

All three monoclonal antibodies bound to rTGF-beta1 in the immunoblot, ELISA, cross-blocking, and immunoprecipitation assays. Two of the anti-rTGF-beta antibodies neutralized rTGF-beta1 activity in vitro, while only one of the two neutralized both TGF-beta2 and TGF-beta3 activity in the mink lung fibroblast cell assay. The TGF-beta1-neutralizing antibodies also blocked radioiodinated rTGF-beta1 binding in a radioreceptor assay, indicating that the in vitro neutralization of rTGF-beta1 activity may be due to receptor blocking.

Example 2

Humanized 2G7 Antibodies

The variable domains of murine monoclonal antibody 2G7 were first cloned into a vector that allows production of a mouse/human chimeric Fab fragment. Total RNA was isolated from the hybridoma cells using a STRAGENE™ RNA extraction kit following manufacturer's protocols. The variable domains were amplified by RT-PCR, gel purified, and inserted into a derivative of a pUC119-based plasmid containing a human kappa constant domain and human $C_H1$ domain as previously described (Carter et al., Proc. Natl. Acad. Sci. (USA), 89: 4285 (1992) and U.S. Pat. No. 5,821, 337). The resultant plasmid was transformed into E. coli strain 16C9 for expression of the Fab fragment. Growth of cultures, induction of protein expression, and purification of Fab fragment were as previously described (Werther et al., J. Immunol., 157: 4986-4995 (1996); Presta et al., Cancer Research, 57: 4593-4599 (1997)).

DNA sequencing of the chimeric clone allowed identification of the CDR residues (Kabat et al., supra). Using oligonucleotide site-directed mutagenesis, all six of these CDR regions were introduced into a complete human framework ($V_L$ kappa subgroup I and $V_H$ subgroup III) contained on plasmid VX4 as previously described (Presta et al., Cancer Research, 57: 4593-4599 (1997)). Protein from the resultant "CDR-swap" was expressed and purified as above. Binding studies were performed to compare the two versions. Briefly, a NUNC MAXISORP™ plate was coated with 1 microgram per ml of TGF-beta extracellular domain (ECD; produced as described in WO 1990/14357) in 50 mM of carbonate buffer, pH 9.6, overnight at 4° C., and then blocked with ELISA diluent (0.5% BSA, 0.05% POLYSORBATE™ 20 non-ionic surfactant, PBS) at room temperature for 1 hour. Serial dilutions of samples in ELISA diluent were incubated on the plates for 2 hours. After washing, bound Fab fragment was detected with biotinylated murine anti-human kappa antibody (ICN 634771) followed by streptavidin-conjugated horseradish peroxidase (Sigma) and using 3,3',5,5'-tetramethyl benzidine (Kirkegaard & Perry Laboratories, Gaithersburg, Md.) as substrate. Absorbance was read at 450 nm. Binding of the CDR-swap Fab was significantly reduced compared to binding of the chimeric Fab fragment.

To restore binding of the humanized Fab, mutants were constructed using DNA from the CDR-swap as template. Using a computer-generated model, these mutations were designed to change human framework region residues to their murine counterparts at positions where the change might affect CDR conformations or the antibody-antigen interface. Mutants are shown in Table 2. (Note that all amino-acid numbering is expressed as in Kabat et al., supra.) For sequences, see FIGS. 1-4.

TABLE 2

Designation of Humanized 2G7 FR Mutations

| Mutant no. | Framework region (FR) substitutions as compared to human anti-TGF-beta consensus sequence (SEQ ID NO: 6) |
|---|---|
| Version 3 | ArgH72Ala |
| Version 4 | ArgH72Ala, AlaH49Gly, |
| Version 5 | ArgH72Ala, AlaH49Gly, PheH68Ala |
| Version 6 | ArgH72Ala, AlaH49Gly, LeuH79Ala |
| Version 709 | ArgH72Ala, AlaH49Gly, ValH48Ile |
| Version 710 | ArgH72Ala, AlaH49Gly, IleH70Leu |
| Version 11 | ArgH72Ala, AlaH49Gly, AsnH74Lys |
| Version 712 | ArgH72Ala, AlaH49Gly, IleH70Leu, AsnH74Lys |

Versions 3 and 4 were used as intermediates to obtain the humanized Fab versions bearing later numbers. Version 5, with the changes AlaH49Gly, PheH68Ala, and ArgH72Ala, appears to have binding restored to that of the original chimeric 2G7 Fab fragment, as do Versions 709 and 11 (FIG. 5). Versions 710 and 712 are expected to have similar binding to the chimeric fragment, but version 712 has an additional framework mutation that might not be desirable due to the possibility of increased immunogenicity. Additional FR or CDR residues, such as L3, L24, L54, and/or H35, may be modified (e.g. substituted as follows: GlnL3Met, ArgL24Lys, ArgL54Leu, GluH35Ser). Substitutions that might be desirable to enhance stability are the substitution of leucine or isoleucine for methionine to decrease oxidation, or the change of asparagines in the CDRs to other residues to decrease the possibility of de-amidation. Alternatively, or additionally, the humanized antibody may be affinity matured (see above) to further improve or refine its affinity and/or other biological activities.

Plasmids for expression of full-length IgG's were constructed by subcloning the VL and VH domains of chimeric 2G7 Fab as well as humanized Fab versions 5, 709, and 11 into previously described pRK vectors for mammalian cell expression (Gorman et al., *DNA Prot. Eng. Tech.*, 2:3-10 (1990)). Briefly, each Fab construct was digested with EcoRV and BlpI to excise a VL fragment, which was cloned into the EcoRV/BlpI sites of plasmid pDR1 (see FIG. 6) for expression of the complete light chain (VL-CL domains). Additionally, each Fab construct was digested with PvuII and ApaI to excise a VH fragment, which was cloned into the PvuII/ApaI sites of plasmid pDR2 (see FIG. 7) for expression of the complete heavy chain (VH-CH1-CH2-CH3 domains).

For each IgG variant, transient transfections were performed by co-transfecting a light-chain-expressing plasmid and a heavy-chain-expressing plasmid into an adenovirus-transformed human embryonic kidney cell line, 293 (Graham et al., *J. Gen. Virol.*, 36:59-74 (1977)). Briefly, 293 cells were split on the day prior to transfection, and plated in serum-containing medium. On the following day, a calcium phosphate precipitate was prepared from double-stranded DNA of the light and heavy chains, along with pADVANTAGE™ vector DNA (Promega, Madison, Wis.), and added dropwise to the plates. Cells were incubated overnight at 37° C., then washed with PBS and cultured in serum-free medium for 4 days at which time conditioned medium was harvested. Antibodies were purified from culture supernatants using protein A-SEPHAROSE CL-4B™ agarose, then buffer-exchanged into 10 mM sodium succinate, 140 mM NaCl, pH 6.0, and concentrated using a CENTRICON-10™ microconcentrator (Amicon). Protein concentrations were determined by measuring absorbance at 280 nm or by quantitative amino-acid analysis.

Additional modifications to hu2G7 Version 5 IgG were made in order to clarify which CDRs contributed to binding, which CDRs could be reverted to the sequence of human germline kappa loci without loss of activity, or for stabilization of the antibody. These are named as shown in Table 3, and the amino acid differences between version 5 and these versions are given.

TABLE 3

Designation of Humanized 2G7 CDR Mutations

| Mutant no. Version 5 (V5H.V5L) | CDR substitutions as compared to human anti-TGF-beta version 5. |
|---|---|
| H2N1.V5L | Same as Version 5 except Asn51 is changed to Ile in the CDR H2 |
| V5H.g1L2 | Same as Version 5 except the CDR L2 is reverted to the sequence of human germline kappa locus L8/L9/L14/L15: YASSLQS (SEQ ID NO: 8) |
| V5H.g1L1g1L2 | Same as Version 5 except the CDR L1 is reverted to the sequence of human germline kappa locus L8/L9: RASQGISSYLA (SEQ ID NO: 7) and CDR L2 is reverted to the sequence of human germline kappa locus L8/L9/L14/L15: YASSLQS (SEQ ID NO: 8) |
| H2NI.g1L1g1L2 | Same as Version 5 except the CDR L1 is reverted to the sequence of human germline kappa locus L8/L9: RASQGISSYLA (SEQ ID NO: 7) and CDR L2 is reverted to the sequence of |

TABLE 3-continued

Designation of Humanized 2G7 CDR Mutations

| Mutant no. Version 5 (V5H.V5L) | CDR substitutions as compared to human anti-TGF-beta version 5. |
|---|---|
| | human germline kappa locus L8/L9/L14/L15: YASSLQS (SEQ ID NO: 8), and Asn51 is changed to Ile in CDR H2. |

The name for the germline sequence used for CDR L1 is L8/L9, as set forth in FIG. 4 of Cox et al., *Eur. J. Immunol.*, 24: 827-836 (1994) and in FIG. 2e of Schable and Zachau, *Biol. Chem. Hoppe-Seyler*, 374: 1001-1022 (1993). For CDRL2, the germline sequence is named L8/L9/L14/L15 (see Cox et al, supra, and Schable and Zachau, supra).

Reversions to the sequence of human germline (gl) kappa locus were made in all the CDR's, but only the germline revertants set forth above showed binding (see FIG. 8). It can be seen from this figure that V5H.g1L2, with CDR L2 reverted to the sequence of the human germline kappa locus, still binds to TGF-beta as well as V5H.V5L. The two versions V5H.g1L1g1L2 and H2NI.g1L1g1L2, as well as H2NI.V5L, did not bind as well as the chimera.

A mouse mesangial cell-proliferation assay was used to test a control antibody and several humanized antibodies (V5H.V5L, V5H.g1L2, H2NI.V5L, V5H.g1L1g1L2, and H2N1.g1L1g1L2). The protocol is as follows:

On day 1: Mouse mesangial cells were plated on a 96-well plate in Media (a 3:1 mixture of Dulbecco's modified Eagle's medium and Ham's F12 medium-95%-fetal bovine serum-5%-supplemented with 14 mM HEPES buffer) and grown overnight.

On day 2: TGF-beta with three different concentrations (100 ng, 10 ng and 1 ng) and five different types of humanized TGF antibody (20 :g/ml) were diluted in serum-free Media and added to the cells. A mouse TGF antibody was used as a control (2G7).

On day 4: After 48 hours incubation, 20 μl of reaction buffer (CELLTITER 96 AQUEOUS ONE SOLUTION REAGENT™ buffer (Promega Inc. Cat number G3580)) was added to each well of the plate and allowed to incubate for 2 hours. The absorbance (OD) was measured at 490 nm.

H2NI.V5L (20 μg/ml) completely blocked cell inhibition induced by TGF-beta at 1 ng/ml level, which is the same result as using the chimeric mouse control (see FIG. 9). Version 5 (V5H.V5L) also blocked cell inhibition similarly to the control.

Various humanized antibodies were tested for their activity in neutralizing various TGF-betas versus 2G7 using the 3T3 cell line from fibroblasts of disaggregated Swiss mouse embryos stimulated with one of three TGF-betas in vitro and then their proliferation was measured as activity. The results are shown in FIGS. 10-14. These figures indicate that the humanized antibody H2NI.V5L was quite superior in blocking activity to the control 2G7 antibody. The other humanized antibodies tested, H2NI.g1L2 (CDR L2 reverted to the sequence of the human germline kappa locus) and V5H.g1L2 (CDR L2 reverted to the sequence of the human germline kappa locus), showed comparable inhibitory activity, with V5H.g1L2 being the least effective for all of TGF-beta1 through -beta3.

In summary, humanized antibodies V5H.V5L, V5H.g1L2, H2NI.V5L, H2NI.g1L2, and Versions 709, 710, and 711 are the most preferred humanized versions since they bind TGF-beta comparably as the chimeric antibody (chimH.chimL;

2G7 Fab fragment) and/or neutralize TGF-beta or block cell inhibition induced by TGF-betas in vitro and have the fewest framework changes of all the humanized antibodies tested, which would minimize the risk of an immune response in patients. In addition, H2NI.V5L is a particularly preferred antibody, as it appears to be superior in neutralization activity of all three TGF-beta isoforms (TGF-beta 1,2,3) and might have improved stability due to the changes in the CDR H2. Further, those humanized antibodies herein that exhibit improved ability to block activity of all three TGF-beta ligands in vitro compared to the mouse monoclonal antibody 2G7 are expected to work better than 2G7 in the various indications below by virtue of their superior ability to inhibit pan-TGF-beta-induced effects, as shown in the assay for TGF-beta-induced fibroblast proliferation (FIGS. 10-14).

Example 3

Therapy of Relapsed or Refractory Prostate Cancer

The antibody herein is a full-length, humanized monoclonal antibody (produced in CHO cells) directed against TGF-beta. It is indicated as a single agent for treatment of hormone-refractory (androgen-independent) prostate cancer patients. Primary endpoints for efficacy include overall survival compared to best available care (Mitoxantrone/Prednisone), when used as a single agent, and safety. Secondary efficacy endpoints include: time-to-disease progression, response rate, quality of life, pain and/or duration of response. The antibody is administered intravenously (IV) weekly or every three weeks at 2 or 4 mg/kg, respectively, until disease progression. The antibody is supplied as a multi-dose liquid formulation (20-mL fill at a concentration of 20 mg/mL or higher concentration).

The antibody is also indicated in combination with chemotherapy for treatment of hormone-refractory (androgen-independent) prostate cancer patients. Primary endpoints for efficacy include overall survival compared to chemotherapy, and safety. Secondary efficacy endpoints include: time-to-disease progression, response rate, quality of life, pain and/or duration of response. The antibody is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

Examples of drugs that can be combined with the humanized anti-TGF-beta antibody to treat prostate cancer (e.g. androgen-independent prostate cancer) include a farnesyl transferase inhibitor; an anti-angiogenic agent (e.g. an anti-VEGF antibody); an EGFR-targeted drug (e.g. C225 or ZD1839); HERCEPTIN® anti-HER-2 antibody, or an anti-ErbB antibody that induces apoptosis such as 7C2 or 7F3, including humanized or affinity-matured variants thereof; 2C4 or humanized 2C4; another anti-TGF-beta antibody (e.g. a monoclonal TGF-beta antibody); a cytokine (e.g. IL-2, IL-12, G-CSF or GM-CSF); an anti-androgen (such as flutamide or cyproterone acetate); leuprolide; suramin; a chemotherapeutic agent such as vinblastine, estramustine, mitoxantrone, liarozole (a retinoic acid metabolism-blocking agent), cyclophosphamide, anthracycline antibiotics such as doxorubicin, a taxane (e.g. paclitaxel or docetaxel), or methotrexate, or any combination of the above, such as vinblastine/estramustine or cyclophosphamide/doxorubicin/methotrexate; prednisone; hydrocortizone; or combinations thereof. Standard doses for these various drugs can be administered, e.g. 40 mg/m²/wk docetaxel (TAXOTERE®); 6 (AUC) carboplatin; and 200 mg/m² paclitaxel (TAXOL®).

Since TGF-beta has also been implicated in prostate cancer (Shah et al., *Cancer Research,* 62: 7135-7138 (2002)), the antibody can be tested in prostate cancer models (e.g., TRAMP transgenic mice as well as transplanted PC-3 cells) with an expectation of success.

Example 4

Therapy of Breast Cancer

The antibody herein is indicated as a single agent for treatment of breast cancer patients, especially but not limited to metastatic patients. Primary endpoints for efficacy include response rate and safety. Secondary efficacy endpoints include: overall survival, time-to-disease progression, quality of life, and/or duration of response. The humanized antibody herein is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

The humanized antibody herein is also indicated in combination with chemotherapy for treatment of breast cancer patients. Primary endpoints for efficacy include overall survival compared to chemotherapy alone, and safety. Secondary efficacy endpoints include: time-to-disease progression, response rate, quality of life, and/or duration of response. The humanized antibody is administered intravenously (IV) weekly or every three weeks at 2 or 4 mg/kg, respectively, until disease progression. The antibody is supplied as a multi-dose liquid formulation (20-mL fill at a concentration of 20 mg/mL or higher concentration).

Examples of drugs that can be combined with the humanized anti-TGF-beta antibody herein to treat breast cancer (e.g. metastatic breast cancer that is not characterized by TGF-beta overexpression) include chemotherapeutic agents such as anthracycline antibiotics (e.g. doxorubicin), cyclophosphomide, a taxane (e.g. paclitaxel or docetaxel), navelbine, xeloda, mitomycin C, a platinum compound, oxaliplatin, gemcitabine, or combinations of two or more of these such as doxorubicin/cyclophosphomide; HERCEPTIN® anti-HER-2 antibody, or an anti-ErbB antibody that induces apoptosis such as 7C2 or 7F3, including humanized or affinity-matured variants thereof; 2C4 or humanized 2C4; another anti-TGF-beta antibody (e.g. a monoclonal TGF-beta antibody); an anti-estrogen (e.g. tamoxifen); an aromatase inhibitor (e.g. anastrozole); a farnesyl transferase inhibitor; an anti-angiogenic agent (e.g. an anti-VEGF antibody); an EGFR-targeted drug (e.g. C225 or ZD1839); a cytokine (e.g. IL-2, IL-12, G-CSF or GM-CSF); or combinations of the above. Standard dosages for such additional drugs may be used.

The humanized antibody herein is additionally indicated in combination with HERCEPTIN® anti-HER-2 antibody or rhuMAb 2C4 for treatment of breast cancer patients, especially those with metastasis. Primary endpoints for efficacy include response rate, and safety. Secondary efficacy endpoints include: time-to-disease progression, overall survival compared to HERCEPTIN® anti-HER-2 antibody or rhuMAb 2C4 alone, quality of life, and/or duration of response. RhuMAb 2C4 is administered intravenously (IV) weekly or every three weeks at 2 or 4 mg/kg, respectively, until disease progression. The antibody rhuMAb 2C4 is supplied as a multi-dose liquid formulation (20 mL fill at a concentration of 20 mg/mL or higher concentration). HERCEPTIN® anti-HER-2 antibody is administered IV as an initial loading dose of 4 mg/kg followed by a weekly maintenance dose of 2 mg/kg. HERCEPTIN® anti-HER-2 antibody is supplied as a lyophilized powder. Each vial of HERCEPTIN® anti-HER-2 antibody contains 440 mg HERCEPTIN® anti-HER-2 antibody, 9.9 mg L-histidine HCl, 6.4 mg L-histidine, 400 mg α-α-trehalose dihydrate, and 1.8 mg POLYSORBATE 20™ surfactant. Reconstitution with 20 mL of Bacteriostatic Water for Injection (BWFI), containing 1.1% benzyl alcohol as a preservative, yields 21 mL of a multi-dose solution containing 21 mg/mL HERCEPTIN® anti-HER-2 antibody, at a pH of approximately 6.0.

Using the murine antibody 2G7 in the 4T1 epithelial cells from a spontaneous mouse mammary tumor model of breast cancer, cells ($1.5 \times 10^5$) were injected into the mammary fat of mice (day 0). In this model, a palpable primary tumor appears by one week; secondary metastases appear in the lungs by week 2, in the liver by week 3, and in the bone between weeks 4 and 5. Tissues are harvested at week 5. The 2G7 antibody and two control IgG antibodies were injected intraperitoneally into mice at 25 mg/kg 3×/week and serum TGF-beta production by the 4T1 cells was measured in the tissue culture media (or blood for the in vivo studies) by a commercial ELISA from R&D systems.

Figures 15A, 15B:
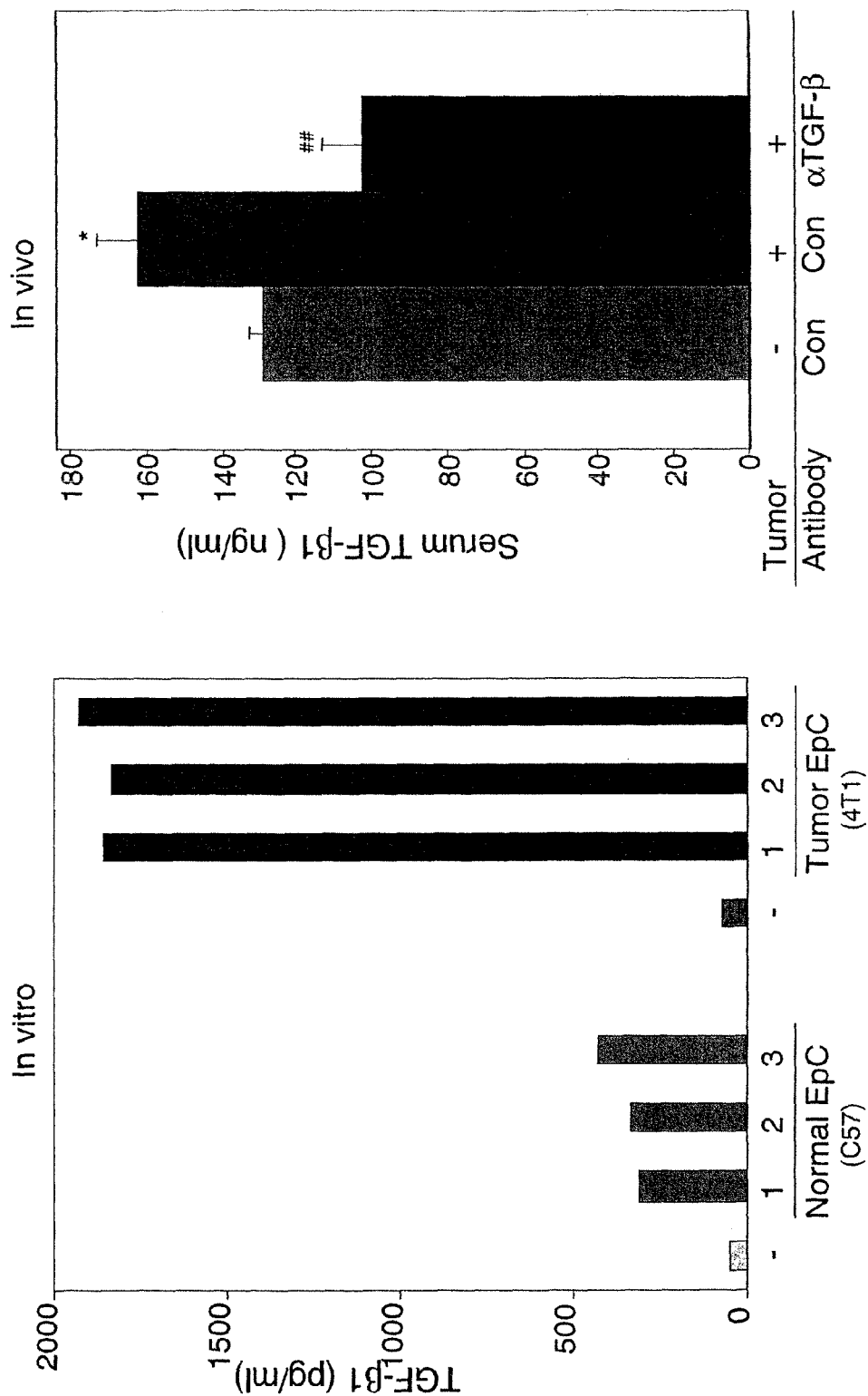
FIGS. 15A and 15B show ELISA results of production and inhibition of TGF-beta by normal and tumor epithelial cells.

FIG. 15A shows TGF-beta production by the 4T1 cells and normal mouse epithelial cells C57 as a control by ELISA in vitro. FIG. 15B shows the effect on serum TGF-beta production by 4T1 cells in vivo of the 2G7 antibody in mice with tumors (+anti-TGFbeta) versus mice without tumors (−Con) treated with control (Con) antibodies (isotype-matched IgG, which is an anti-ragweed antibody), and versus mice with tumors (+Con) treated with control antibodies. These results show that the 4T1 epithelial tumor cells produced more TGF-beta than the control C57 epithelial cells in vitro (FIG. 15A), and that the 2G7 antibody herein decreased the amount of free TGF-beta in the circulation relative to mice with tumors treated with control antibodies (FIG. 15B).

Serum levels of free TGF-beta were reduced in mice treated with the anti-TGF-beta antibody 2G7, consistent with previous results that anti-TGF-beta antibodies may alter the availability of TGF-beta in vivo (Wojtowicz-Praga et al., *Immunother Emphasis Tumor Immunol.*, 19(3):169-75 (1996). Erratum in: *J Immunother Emphasis Tumor Immunol*, 19(5):386 (1996), Verma U M (corrected to Verma U N)). In addition, the antibody used herein (2G7) did not interfere in ELISA assays as evidenced by the fact that ELISA readings were not affected by the addition of 2G7 to control plasma at dilutions of 1:10, 1:100, and 1:1000 as compared with vehicle. Ziyadeh et al., *Proc. Natl. Acad. Sci. USA*, 97: 8015-20 (2000).

FIG. 16A shows the histology scores and FIG. 16B shows the tissue weights for secondary lung tumors produced by the tumor cell model used for FIG. 15 with the anti-ragweed IgG control and anti-TGF-beta 2G7 as given to the mice per the description for FIG. 15, indicating that anti-TGF-beta lowered the grade, the number of lobes affected, the tissue weight in grams, and the lung weights as a percentage of body weight versus the control. Secondary lung tumors were detected by ex vivo computed tomography scanning.

FIG. 17 shows the quantification of lung tumors of the above mouse model by uCT, indicating tumor volume and number, with anti-TGF-beta 2G7 showing lower tumor volume than the IgG control, with both 2G7 and the control given to the mice per the description for FIG. 15 (i.e., 25 mg/kg 3×/week intraperitoneally).

FIG. 18A shows the tumor volume in the above mouse model as a function of time in days after cell injection using 25 mg/kg 3×/week intraperitoneally of the IgG control with saline or with taxol, and 25 mg/kg 3×/week intraperitoneally of anti-TGF-beta 2G7 with taxol, indicating that the latter was most effective in reducing tumor volume. FIG. 18B shows that the anti-TGF-beta antibody 2G7 with chemotherapy reduced tissue weight—lung, spleen, and tumors—over both the IgG/saline control and the IgG/chemotherapy controls.

Figure 19:
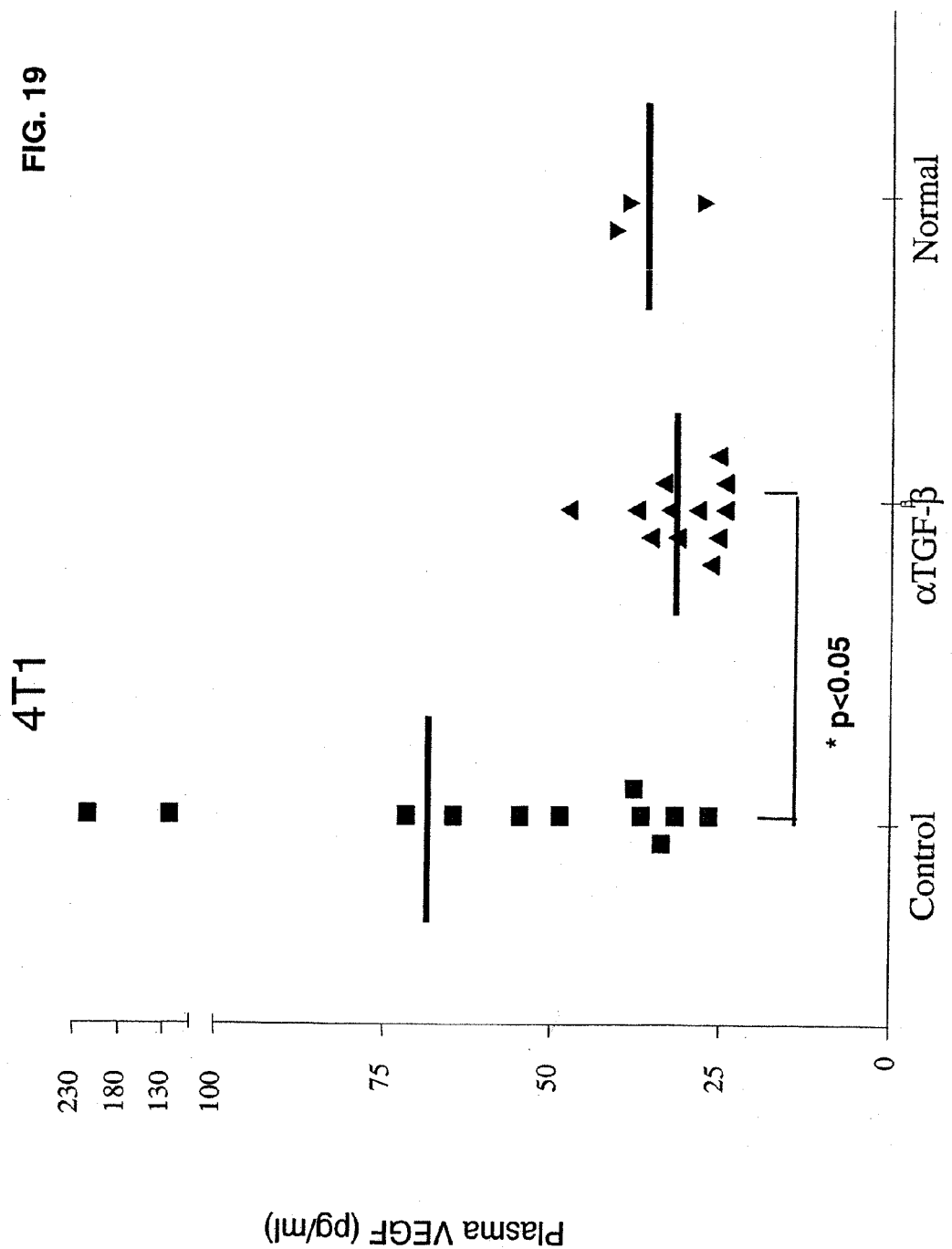
FIG. 19 shows plasma VEGF levels (pg/ml) in mice without tumors (Normal), or in mice with 4T1 mammary tumors treated with either control IgG (control) or anti-TGF-beta (2G7).

Further, the 2G7 antibody decreased systemic levels of vascular endothelial growth factor (VEGF) versus the IgG control in this mouse model. FIG. 19 shows plasma VEGF levels (pg/ml) in mice without tumors (Normal), or in mice with 4T1 mammary tumors treated with either control IgG (control) or anti-TGF-beta 2G7 (aTGF-b) (25 kg/kg 3×/week intraperitoneally for control and anti-TGF-beta). Each point represents an individual mouse. The bar indicates the mean for the group.

In summary, in the breast cancer model of epithelial cells derived from spontaneous mammary tumors in Balb C mice (4T1) being injected into mammary fat pads of syngeneic mice, the 2G7 antibody was found to decrease circulating levels of free TGF-beta1 and systemic VEGF levels and have a small but significant transitory ability to decrease primary tumor growth versus controls. Early treatment with 2G7 decreased secondary lung tumors.

Further, early treatment with the 2G7 antibodies overcame much of the breast tumor-induced bone destruction occurring in this model, using the same scanning as for lungs. See Table 4. In this Table, trabecular number refers to the number of trabeculae (the small spicules of bone which extend into the marrow cavity), and trabecular thickness refers to the average thickness of these trabeculae. Both of these parameters indicate quantity of bone and are determined using micro-computed tomography and an algorithm to quantitate various bone parameters (Table 4).

TABLE 4

Measurement of Bone Regeneration

| | Trabecular Number | Trabecular Thickness | Bone volume (BV)/total volume | Bone Surface/ BV | Mineral Density |
|---|---|---|---|---|---|
| 2G7 without primary tumor | −2.8% | Not assessed | −4.8% | Not assessed | Not assessed |
| With primary tumor | −7.2% | −22.5% | −28.3% | +28.6% | −15.9% |
| 2G7 with primary tumor | +6.5% | +7.2% | +14.3% | −6.6% | +6.3% |

Note, that percentages refer to:
1) relative to normal mice (i.e. without tumors) for the "2G7 without primary tumor" and "with primary tumor" samples.
2) relative to mice with tumors treated with IgG control antibodies for the "2G7 with primary tumor" sample.

Figure 20B:
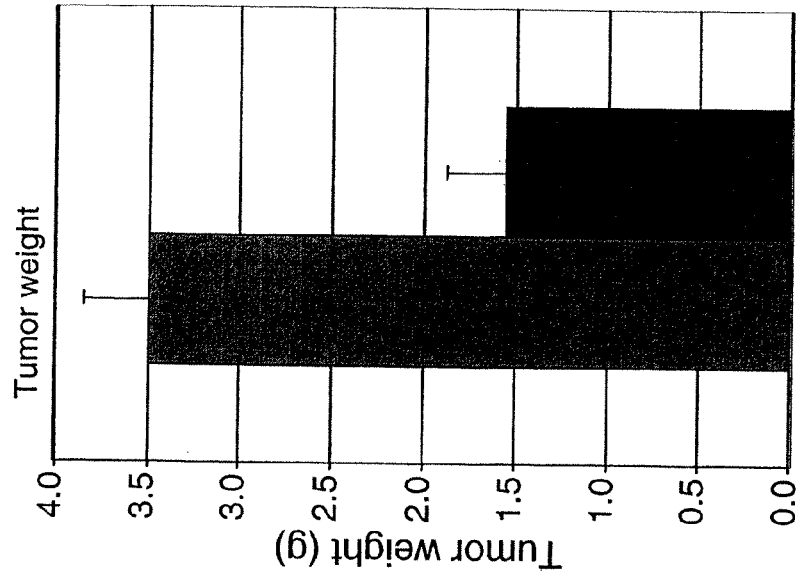
FIGS. 20A and 20B show the effect of TGF-beta antibody 2G7 in a different breast cancer model PymT.
Figure 20A:
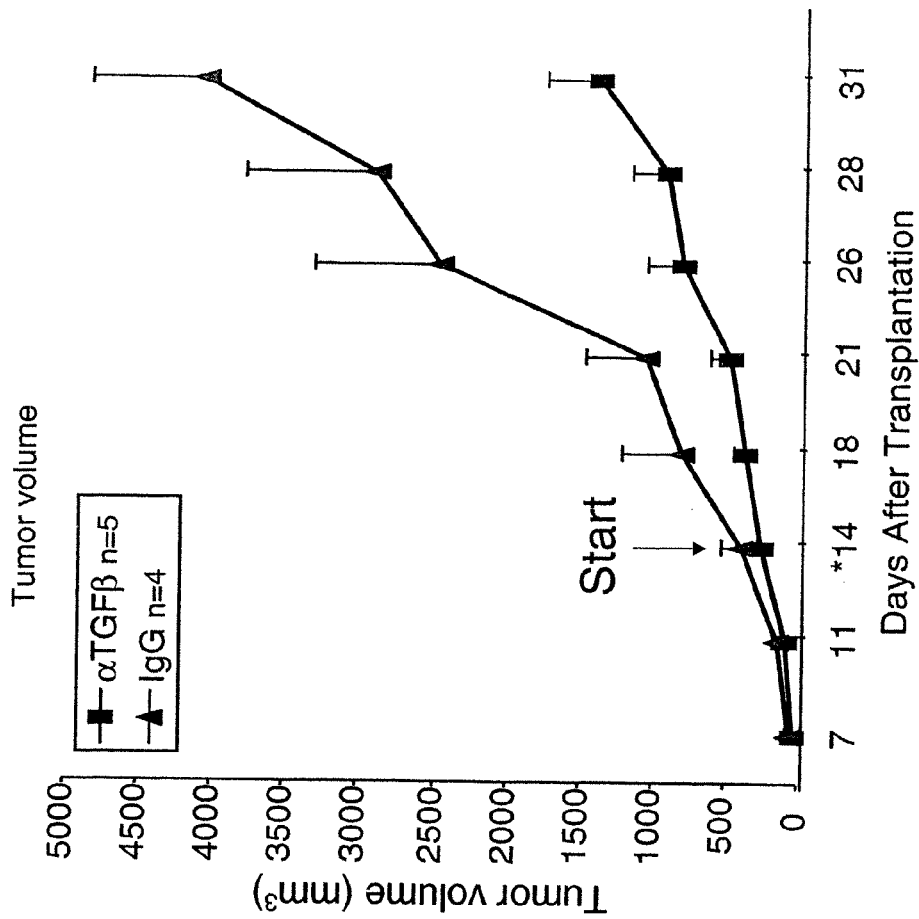

The antibody 2G7 was also tested in a breast cancer model (PymT), as described in Maglione et al., Transgenic Polyoma middle-T mice model premalignant mammary disease, *Cancer Res.*, 61(22):8298-305 (2001) and Lin et al., Progression to malignancy in the polyoma middle T oncoprotein mouse breast cancer model provides a reliable model for human diseases, *Am J Pathol.*, 163(5):2113-26 (2003). Both antibodies (IgG control (anti-ragweed antibody) and anti-TGF-beta 2G7) were dosed the same: 25 mg/kg 3×/week intraperitoneally. FIG. 20A shows the effect of anti-TGF-beta 2G7 versus the IgG control on tumor volume as a function of days of tumor growth in the PymT model, indicating that the 2G7 antibody reduced tumor volume over time versus the IgG control. FIG. 20B shows that tumor weight was also reduced with the TGF-beta antibody 2G7 versus the IgG control. It was also found that there are decreased VEGF levels in PyMT tumors relative to Her2 tumors.

In view of these data, it is expected that the humanized versions of the 2G7 antibodies herein will act similarly to 2G7 in terms of tumor growth and metastasis.

Unlike the 4T1 epithelial cells, Her+ epithelial cells did not synthesize high levels of TGF-beta in vitro, were growth inhibited by TGF-beta in vitro (Siegel et al., Transforming growth factor beta signaling impairs Neu-induced mammary tumorigenesis while promoting pulmonary metastasis. *Proc Natl Acad Sci USA,* 100(14):8430-5 (2003)), and were not growth inhibited by anti-TGF-beta treatment in vivo. Furthermore, VEGF levels were increased in this model when anti-TGF-beta antibody 2G7 was given versus an IgG control.

Staining of three of the breast tumor models (4T1, PyMt and Her2) for basement membrane (collagen IV), endothelial cells (CD31), or vessel-supporting cells called pericytes (SMA or NG2) revealed differences in these model systems in terms of these three components. These components, without being limited to any one theory, may be predictive with regards to sensitivity of tumors to anti-TGF-beta treatment.

Given the proposed bi-functional nature of the role of TGF-beta in cancer, use of a diagnostic to determine how/if the patient will respond may prove to be useful in the application of TGF-beta inhibitory strategies for the treatment of cancer. For example, For example, determining whether or not a given patient's cancer cells remain sensitive to the growth-inhibitory effects of TGF-beta may be important.

Without being limited to any one theory, below is a list of potential diagnostic markers to select patients/tumors most likely to respond to anti-TGF-beta treatment, which list is not limiting:

1) Expression of one or more of the three TGF-beta isoforms, TGF-beta1, -2, and/or -3, especially those with higher expression levels, with a particular focus on TGF-beta1.
   a. This would cover a number of different types of cancer, including, but not limited to: breast, pancreas, prostate, kidney, lung, and skin (melanoma). It was found that there was significant overexpression in these tumor types of TGF-beta1 in comparison to matched normal tissue samples of the same tissue type.
   b. Her2-negative breast cancers as opposed to Her2-positive breast cancers, as the former may respond better to antibody treatment as indicated by higher expression of TGF-beta1. In this regard, it was found that there was significant overexpression in these tumor types of TGF-beta1 in comparison to matched normal tissue samples of the same tissue type.
2) As a corollary to #1, tumor cell production, independent of whether TGF-beta is also made in the stroma/environment.
3) Mutation in, and decreased expression of, one or more TGF-beta receptors, especially, but not limited to, TGF-beta1 RI or TGF-betaRII (type-IIR).
4) Mutations or changes in the levels or localization of molecules in the TGF-beta signaling pathway, including, but not limited to: SMADs/phosphoSMADs, c-myc, CDC25A, p15INK4B, p21WAF1/CiP1, and p27K1P1.
5) Alterations in other signaling pathways known to impact TGF-b activity, including, but not limited to: FoxG1, Jagged/Notch, CDK2, and CDK4, and especially Her2/neu, Estrogen Receptor levels, Ras activity, phosphatidylinositol 3-kinase (PI3K), AKT and MAPK activity, as well as p53 status.

In addition to the above-listed diagnostic markers to determine which tumors to treat, several markers may be used to evaluate (within the tumor and/or in the periphery) biological activity of anti-TGF-beta antibodies in patients before and after treatment, including, but not limited to:

1) TGF-beta levels, in the tumor or in the circulation (as shown by FIG. 15B as well as by immunohistochemistry (IHC) data showing TGF-beta1 protein expression in stained tissue sections of tumor xenografts Colo205 and Calu6 tumors, HPAC tumors, and a human tumor sample of ductal breast adenocarcinoma).
2) VEGF levels, in the tumor or in the circulation (as shown by FIG. 19, and also by the data showing that VEGF levels are increased in the Her2-positive model when 2G7 is provided versus the control).
3) Levels of molecules such as the SMADs/phosphoSMADs within the TGF-b signaling pathway, in the tumor and/or in peripheral cells such as blood mononuclear cells (BMCs).
4) Indicators of immune cell function, especially NK, T-cell, and macrophage activity.

Example 5

Therapy of Lung Cancer

The humanized antibody herein is indicated as a single agent for treatment of stage IIIb or IV non-small cell lung cancer (NSCLC). Primary endpoints for efficacy include response rate, and safety. Secondary efficacy endpoints include: overall survival, time-to-disease progression, quality of life, and/or duration of response. The humanized antibody is administered intravenously (IV) weekly or every three weeks at 2 or 4 mg/kg, respectively, until disease progression. The antibody is supplied as a multi-dose liquid formulation (20-mL fill at a concentration of 20 mg/mL or higher concentration).

The humanized antibody is also indicated in combination with chemotherapy for treatment of metastatic non-small cell lung cancer patients. Primary endpoints for efficacy include overall survival compared to standard therapy, and safety. Secondary efficacy endpoints include: time-to-disease progression, response rate, quality of life and/or duration of response. The humanized antibody is administered intravenously (IV) weekly or every three weeks at 2 or 4 mg/kg, respectively, until disease progression. The antibody is supplied as a multi-dose liquid formulation (20-mL fill at a concentration of 20 mg/mL or higher concentration).

Examples of additional drugs that can be combined with the antibody herein to treat lung cancer include chemotherapeutic agents such as carboplatin, a taxane (e.g. paclitaxel or docetaxel), gemcitabine, navelbine, cisplatin, oxaliplatin, or combinations of any of these such as carboplatin/docetaxel; HERCEPTIN® anti-HER-2 antibody, or an anti-ErbB antibody that induces apoptosis such as 7C2 or 7F3, including humanized or affinity-matured variants thereof; 2C4 or humanized 2C4; another anti-TGF-beta antibody (e.g. a monoclonal TGF-beta antibody); a farnesyl transferase inhibitor; an anti-angiogenic agent (e.g. an anti-VEGF antibody); an EGFR-targeted drug (e.g. C225 or ZD1839); a cytokine (e.g. IL-2, IL-12, G-CSF or GM-CSF); or combinations of the above.

Example 6

Therapy of Colorectal Cancer

The humanized antibody herein is indicated as a single agent for treatment of metastatic colorectal cancer. Primary endpoints for efficacy include response rate and safety. Secondary efficacy endpoints include: overall survival, time-to-disease progression, quality of life, and/or duration of response. The humanized antibody is administered intravenously (IV) weekly or every three weeks at 2 or 4 mg/kg, respectively, until disease progression. The antibody is supplied as a multi-dose liquid formulation (20-mL fill at a concentration of 20 mg/mL or higher concentration).

The humanized antibody is also indicated in combination with chemotherapy for treatment of metastatic colorectal cancer patients. Primary endpoints for efficacy include overall survival compared to standard therapy, and safety. Secondary efficacy endpoints include: time-to-disease progression, response rate, quality of life, and/or duration of response. The humanized antibody is administered intravenously (IV) weekly or every three weeks at 2 or 4 mg/kg, respectively, until disease progression. The antibody is supplied as a multi-dose liquid formulation (20-mL fill at a concentration of 20 mg/mL or higher concentration).

Examples of chemotherapeutic agents used to treat colorectal cancer that can be combined with the humanized antibody that binds TGF-beta include 5-fluorouracil (5-FU), leucovorin (LV), CPT-11, levamisole, or combinations of any two or more of these, e.g., 5-FU/LV/CPT-11. Standard dosages of such chemotherapeutic agents can be administered. Other drugs that may be combined with the anti-TGF-beta antibody to treat colorectal cancer include a farnesyl transferase inhibitor; an anti-angiogenic agent (e.g. an anti-VEGF antibody); an EGFR-targeted drug (e.g. C225 or ZD1839); a cytokine (e.g. IL-2, IL-12, G-CSF or GM-CSF); HERCEPTIN® anti-HER-2 antibody, or an anti-ErbB antibody that induces apoptosis such as 7C2 or 7F3, including humanized or affinity-matured variants thereof; 2C4 or humanized 2C4; another anti-TGF-beta antibody (e.g. a monoclonal TGF-beta antibody); or combinations of the above.

Given the possible role of TGF-beta in colon cancer, the antibody can be tested in colon cancer models (e.g., HT29 and HCT116) and expected to work.

Example 7

Therapy of Melanoma

Figure 22:
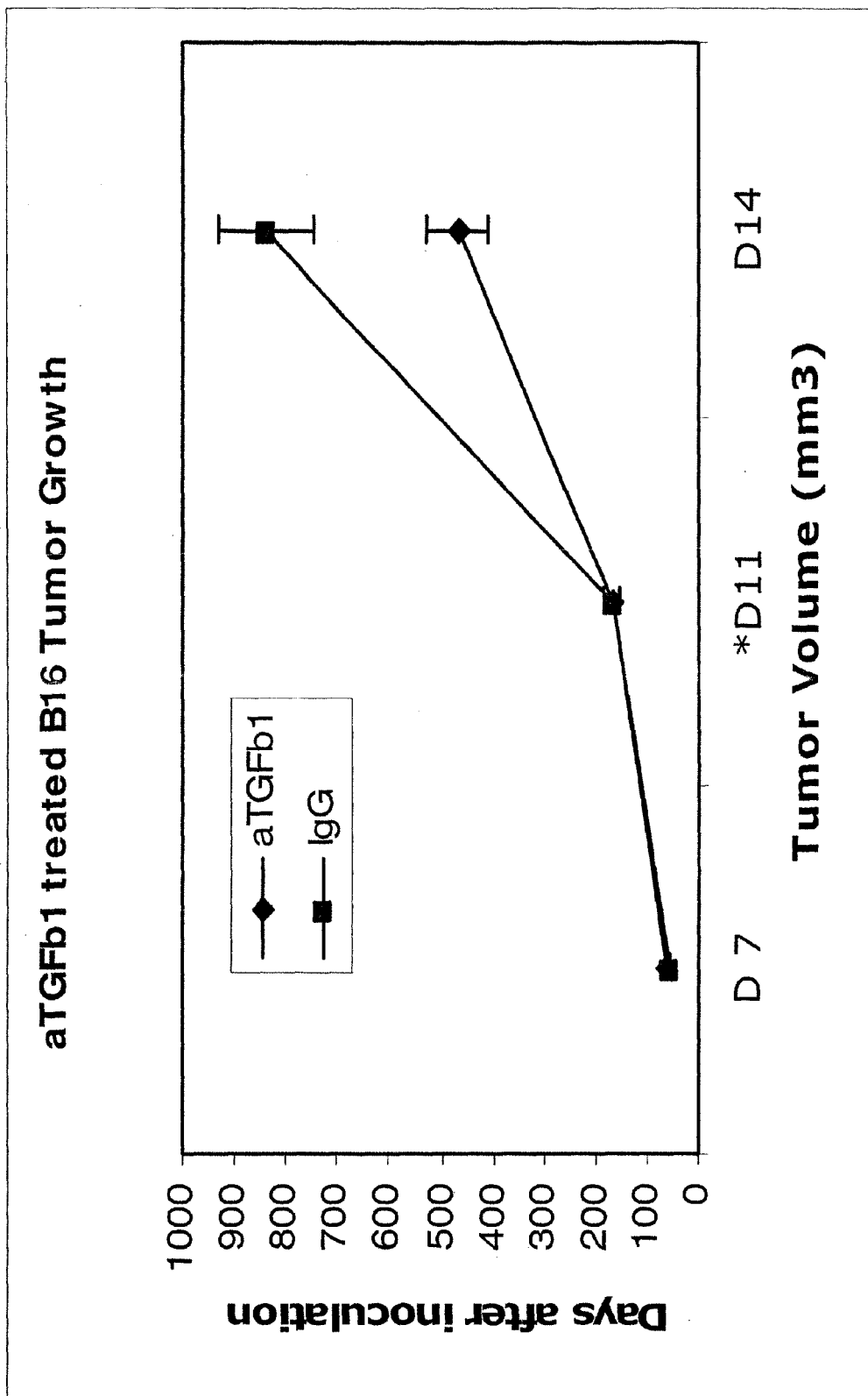
FIG. 22 shows the effect of the TGF-beta antibody 2G7 on B16 tumor growth (volume) over 14 days after inoculation versus the control IgG.
Figure 23:
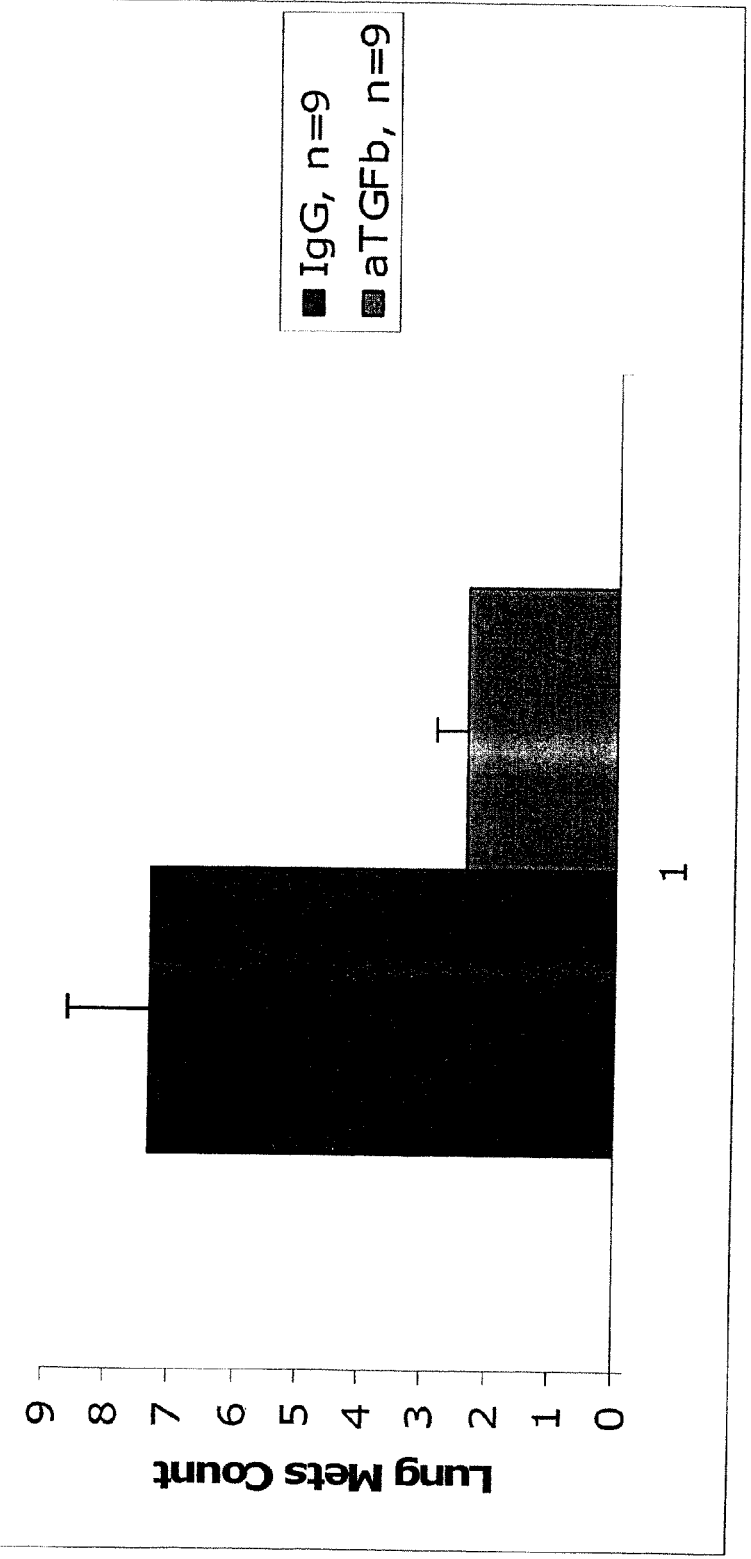
FIG. 23 shows the effect of the TGF-beta antibody 2G7 on B16 (E6) visible lung metastasis count versus the IgG control
Figure 24:
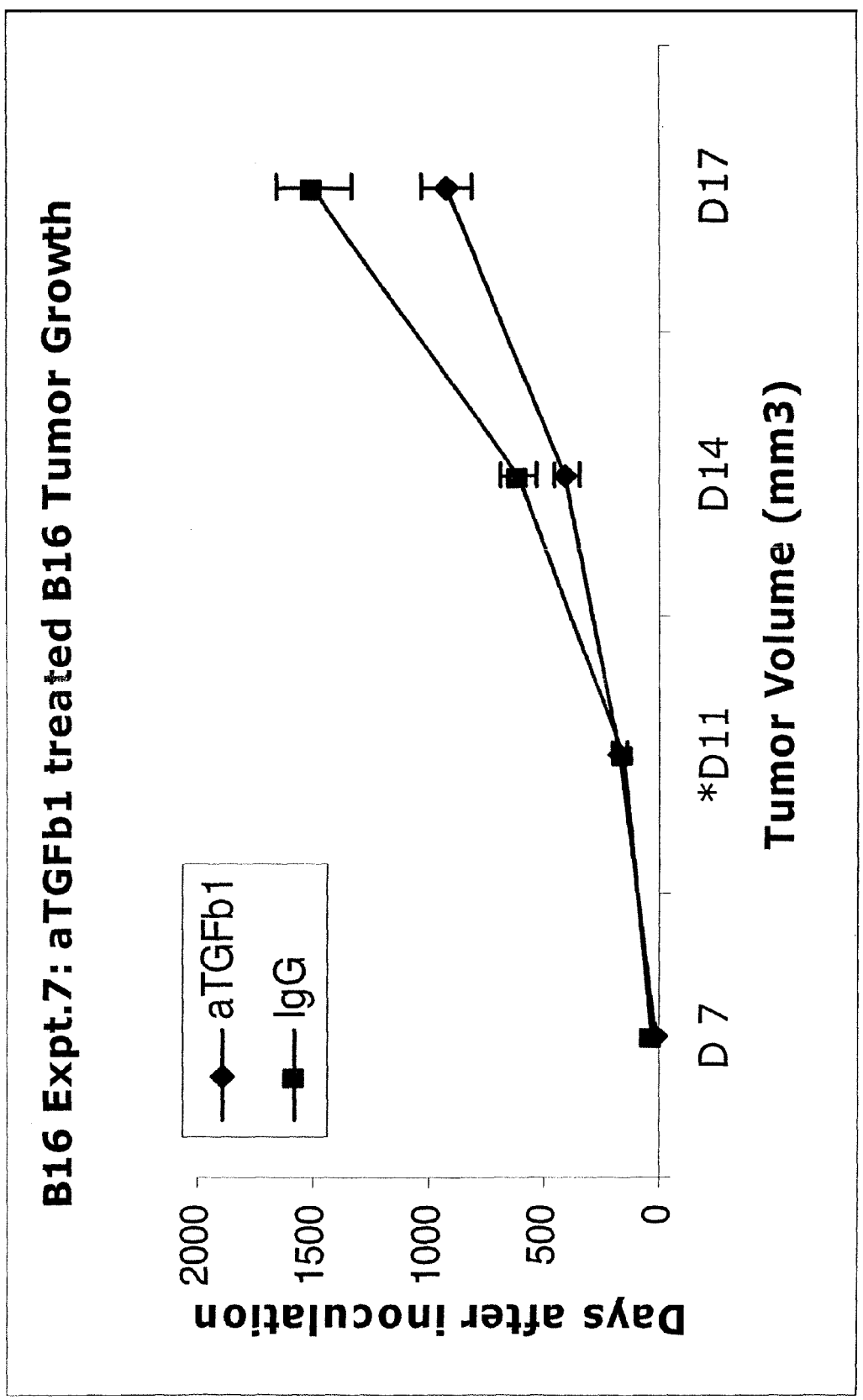
FIG. 24 shows the effect of the TGF-beta antibody 2G7 on B16 tumor growth (volume) over 17 days after inoculation versus the IgG control.
Figure 25:
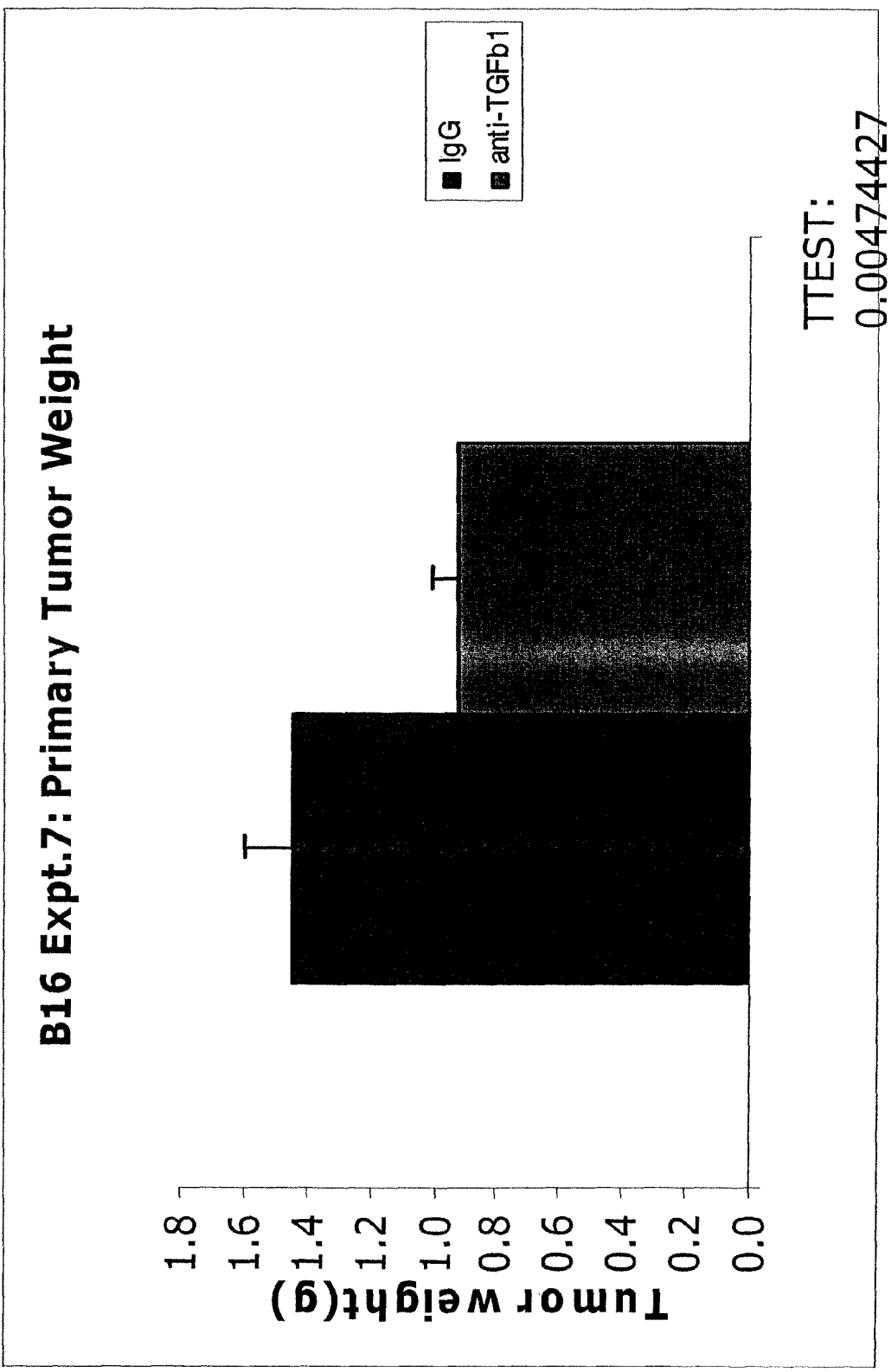
FIG. 25 shows the effect of the TGF-beta antibody 2G7 on B16 primary tumor weight versus the IgG control.
Figure 26:
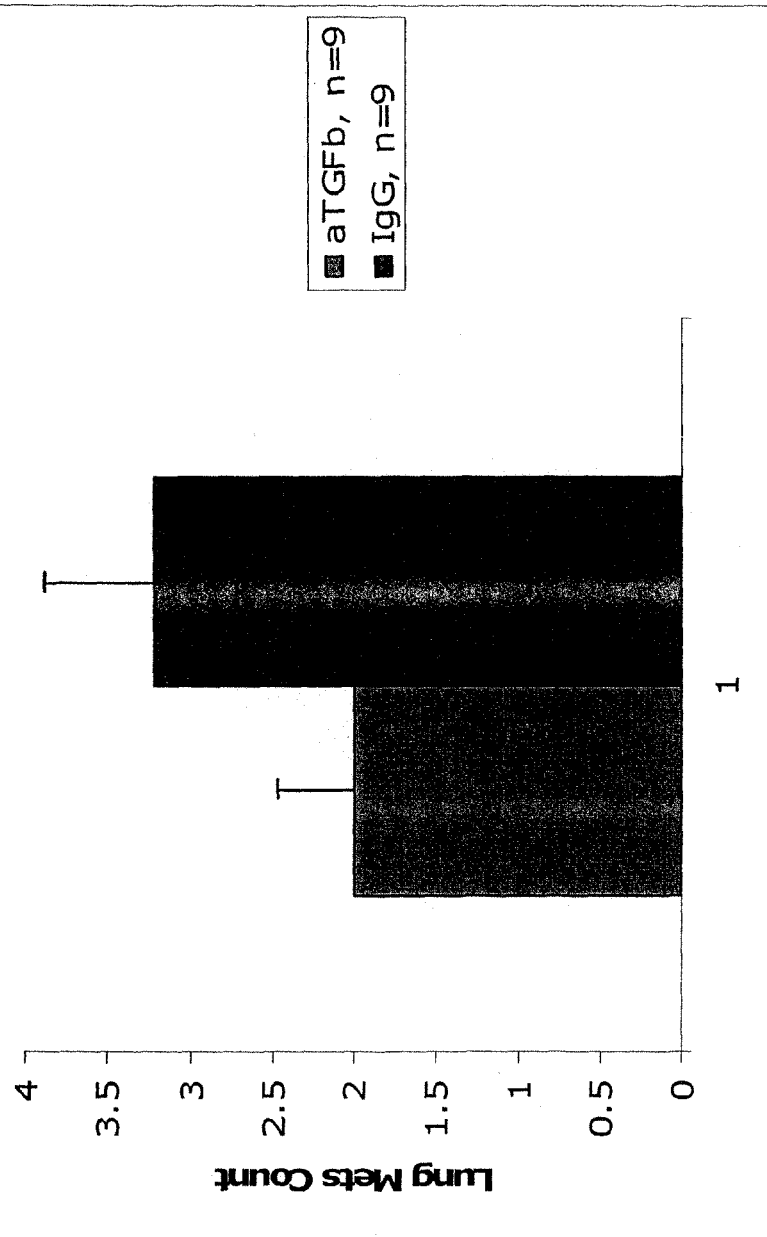
FIG. 26 shows the effect of the TGF-beta antibody 2G7 on B16 (E7) visible lung metastasis count versus the IgG control.

The results with monoclonal antibody 2G7 in this Example suggest that the humanized antibodies herein would be useful for treatment of malignant melanoma. The murine anti-TGF-beta1 antibody 2G7 was tested in animal models of melanoma. Specifically, in syngeneic C57black6 mice injected subcutaneously with mouse melanoma cells (B16F10 or B16B16), treatment with anti-TGF-beta (2G7) at 25 mg/kg 3×/week intraperitoneally decreased primary tumor size relative to treatment with the isotype-matched IgG control (anti-ragweed antibody) (at 25 mg/kg 3×/week intraperitoneally) (FIGS. 22, 24, and 25). In this B16 model, anti-TGF-beta 2G7 treatment also reduced the percentage of mice with lung tumors (i.e. lung tumor incidence) (FIG. 21A) and lung tumor number (FIG. 21B) relative to the control, for each method of tumor quantification, i.e. surface counting ("surface"), histological examination ("pathology"), quantifying all visible tumors after making the tissue transparent ("cleared") or through use of microcomputed tomography ("CT"). See also FIGS. 23 and 26).

Calu-6 (human non-small cell lung carcinoma) tumor cells (American Type Culture Collection (ATCC), Manassas, Va.) were found to produce TGF-beta in vitro. Calu-6 CM cells induced VEGF and SMA expression in fibroblasts in vitro, an effect which was inhibited by treatment with the murine anti-TGF-beta 2G7 antibody. These results suggest, without being limited to any one theory, that TGF-beta may be involved in activation of stromal cells in the tumor environment. Xenotransplants of these cells were made into nude mice (see, e.g., Gourdeau et al., *Mol Cancer Ther.*, 3:1375-1384 (2004)) and the tumor volume was tested after treatment with the control IgG2b antibody used in the B16 experiment above (at 25 mg/kg 3×/week intraperitoneally), along an anti-VEGF antibody (A461) (at 5 mg/kg 3×/week intraperitoneally), murine anti-TGF-beta antibody 2G7 (at 25 mg/kg 3×/week intraperitoneally), and the combination of 2G7 and A461 (dosing as above). The tumor volume and tumor weight results, shown in FIGS. 27 and 28, respectively, indicate that the combination of 2G7 and the anti-VEGF antibody was the most superior treatment, followed by the 2G7 antibody. The results show that the two antibodies (anti-TGF-beta and anti-VEGF) are additive and/or synergize with one another.

Based on these data, it is expected that the humanized antibodies herein will also reduce primary and secondary tumors involved in malignant melanoma. Specifically, the humanized antibody H2NI.V5L may be tested in two models in which efficacy was shown with the murine antibody 2G7:

1) mouse melanoma cells (B16) into syngeneic mice and
2) Calu-6 (human NSCLC) tumor cells as xenotransplants into nude mice.

In the B16 model, cells are implanted subcutaneously into mice. In both models treatment with various anti-TGF-beta antibodies including H2NI.V5L (25 mg/kg 3×/week) or control antibodies (25 mg/kg 3×/week) starts when a palpable tumor is present. Tumors are measured 2-3× per week.

Prior to testing any antibodies, the ability of H2NI.V5L to inhibit TGF-beta-induced fibroblast (NIH3T3) cell growth is ascertained.

If the mouse Fc part of H2NI.V5L is not required for activity in mice, then it is expected that H2NI.V5L will have the same activity as, or better activity than, the original mouse monoclonal 2G7 in mice. If the mouse Fc part of the antibody is required for activity in mice, then H2NI.V5L is not expected to be as effective as the original mouse monoclonal 2G7 in the mouse studies. However, H2NI.V5L (and the other humanized antibodies as claimed herein) are expected to remain effective in humans, since the human Fc will be active therein.

Example 8

Pharmacokinetics of 2G7 Antibody in Normal and Tumor-Bearing Mice

The purpose herein is to evaluate the pharmacokinetic (PK) characteristics of the murine anti-TGF-beta 2G7 in normal v. tumor-bearing mice.

Study Design:

The animal model was Balb/c mice bearing 4T1-cell-induced mammary tumors. The dosing was a single 43 mg/kg dose in four groups:
Grp 1: Non-tumor bearing mice IV
Grp 2: Tumor bearing mice IV
Grp 3: Tumor bearing mice IP
Grp 4: Tumor bearing mice SC
N=3 mice per group per timepoint. Each mouse bled 3 times.

Serum was collected for the murine anti-TGF-beta ELISA at 5, 15, 30, 60 min; 3, 6, 24 hours; 3, 7, 10 14, 21 days.

Results:

The results show that the elimination profile of murine anti-TGF-beta appears faster in tumor-bearing mice than normal mice. Further, there is greater than 95% bioavailability of the antibody following both the IP and SC routes of administration. The half-life was 2-3 days in the tumor-bearing mice.

Thus, the PK profile for the 2G7 antibody appears to be acceptable. In the normal mouse, the half life of the antibody was four days, which is within the range of that observed for other antibodies and fusion proteins in normal mice. In the tumor-bearing mice, the antibody clearance was about 2-fold faster, which is not likely a factor at this dose level. The bioavailability of greater than 95% indicates that IP or SC administration is an appropriate route for therapies. The 2-3 day half-life supports a 2-3× weekly dosing regimen.

What is claimed is:

1. A humanized antibody that binds a TGF-beta1, TGF-beta2 or TGF-beta3 protein, the humanized antibody comprising:

a variable heavy ($V_H$) domain that comprises the non-human hypervariable region residues of SEQ ID NO: 21, SEQ ID NO: 22 and SEQ ID NO: 23 incorporated into a human $V_H$ domain, said variable domain further comprising a framework region (FR) comprising the framework residues of SEQ ID NO:6 and comprising one or more FR substitutions in SEQ ID NO:6 at a position selected from the group consisting of 48, 49, 68, and 72; and a variable light ($V_L$) domain chain that comprises complementarity-determining-region (CDR) residues RASQSVLYSSNQKNYLA (SEQ ID NO:18) or RASQGISSYLA (SEQ ID NO:7); WASTRES (SEQ ID NO:19) or YASSLQS (SEQ ID NO:8); and HQYLSSDT (SEQ ID NO:20).

2. The humanized antibody of claim 1 comprising FR substitutions at positions 49, 68, and 72.

3. The humanized antibody of claim 2 wherein at position 49 the alanine is changed to a glycine, at position 68 the phenylalanine is changed to an alanine, and at position 72 the arginine is changed to an alanine.

4. The humanized antibody of claim 1 comprising FR substitutions at positions 48, 49, and 72.

5. The humanized antibody of claim 4 wherein at position 48 the valine is changed to an isoleucine, at position 49 the alanine is changed to a glycine, and at position 72 the arginine is changed to an alanine.

6. The humanized antibody of claim 1 comprising FR substitutions at positions 49, 70, and 72.

7. The humanized antibody of claim 6 wherein at position 49 the alanine is changed to a glycine, at position 70 the isoleucine is changed to a leucine, and at position 72 the arginine is changed to an alanine.

8. The humanized antibody of claim 6 wherein an additional FR substitution is at position 74.

9. The humanized antibody of claim 8 wherein at position 74 the asparagine is changed to a lysine.

10. The humanized antibody of claim 1 comprising FR substitutions at positions 49, 72, and 74.

11. The humanized antibody of claim 10 wherein at position 49 the alanine is changed to a glycine, at position 72 the arginine is changed to an alanine, and at position 74 the asparagine is changed to a lysine.

12. The humanized antibody of claim 1 comprising FR substitutions at positions 49, 72, and 79.

13. The humanized antibody of claim 12 wherein at position 49 the alanine is changed to a glycine, at position 72 the arginine is changed to an alanine, and at position 79 the leucine is changed to an alanine.

14. The humanized antibody of claim 1 comprising variable light ($V_L$) domain complementarity-determining-region (CDR) residues RASQSVLYSSNQKNYLA (SEQ ID NO:18); WASTRES (SEQ ID NO:19); and HQYLSSDT (SEQ ID NO:20).

15. The humanized antibody of claim 1 comprising the $V_L$ domain amino acid sequence in SEQ ID NO:3.

16. The humanized antibody of claim 1 comprising the $V_H$ domain amino acid sequence in SEQ ID NO:4.

17. The humanized antibody of claim 1 that is an intact IgG1 antibody.

18. The humanized antibody of claim 1 that is an antibody fragment.

19. The humanized antibody of claim 18 that is a Fab fragment.

20. The humanized antibody of claim 1 that is not conjugated with a cytotoxic agent.

21. The humanized antibody of claim 1 that is conjugated with a cytotoxic agent.

22. A composition comprising the humanized antibody of claim 1 and a carrier.

23. An article of manufacture comprising a container containing the humanized antibody of claim 1 and instructions directing a user to treat a TGF-beta disorder in a mammal with the antibody in an effective amount, wherein the TGF-beta disorder is a colo-rectal cancer, a melanoma or a cancer of the breast, prostate or lung.

24. The article of claim 23 additionally comprising a container containing a therapeutic agent other than the humanized antibody, wherein the instructions direct the user to treat the disorder with the antibody in combination with the agent in effective amounts.

25. The article of claim 23 wherein the mammal is a human.

26. The humanized antibody of claim 1, further comprising a FR substitution at positions 70, 74 or 79.

* * * * *

SEQUENCE LISTING

<160> NUMBER OF SEQ ID NOS: 47

<210> SEQ ID NO 1
<211> LENGTH: 116
<212> TYPE: PRT
<213> ORGANISM: Mus musculus

<400> SEQUENCE: 1

```
Asp Ile Met Met Thr Gln Ser Pro Ser Ser Leu Ala Val Ser Ala
 1               5                  10                  15

Gly Glu Lys Val Thr Met Ser Cys Lys Ser Ser Gln Ser Val Leu
                20                  25                  30

Tyr Ser Ser Asn Gln Lys Asn Tyr Leu Ala Trp Tyr Gln Gln Lys
                35                  40                  45

Pro Gly Gln Ser Pro Lys Leu Leu Ile Tyr Trp Ala Ser Thr Arg
                50                  55                  60

Glu Ser Gly Val Pro Asp Arg Phe Thr Gly Ser Gly Ser Gly Thr
                65                  70                  75

Asp Phe Thr Leu Thr Ile Ser Ser Val Gln Ala Glu Asp Leu Ala
                80                  85                  90

Val Tyr Tyr Cys His Gln Tyr Leu Ser Ser Asp Thr Phe Gly Gly
                95                 100                 105

Gly Thr Lys Leu Glu Ile Lys Arg Thr Val Ala
               110                 115
```

<210> SEQ ID NO 2
<211> LENGTH: 124
<212> TYPE: PRT
<213> ORGANISM: Mus musculus
<220> FEATURE:
<221> NAME/KEY: Unsure
<222> LOCATION: 3, 5
<223> OTHER INFORMATION: Unknown amino acid

<400> SEQUENCE: 2

```
Gln Val Xaa Leu Xaa Gln Ser Gly Ala Glu Leu Val Arg Pro Gly
 1               5                  10                  15

Thr Ser Val Lys Val Ser Cys Lys Ala Ser Gly Tyr Ala Phe Thr
                20                  25                  30

Asn Tyr Leu Ile Glu Trp Val Lys Gln Arg Pro Gly Gln Gly Leu
                35                  40                  45

Glu Trp Ile Gly Val Asn Asn Pro Gly Ser Gly Gly Ser Asn Tyr
                50                  55                  60

Asn Glu Lys Phe Lys Gly Lys Ala Thr Leu Thr Ala Asp Lys Ser
                65                  70                  75

Ser Ser Thr Ala Tyr Met Gln Leu Ser Ser Leu Thr Ser Asp Asp
                80                  85                  90

Ser Ala Val Tyr Phe Cys Ala Arg Ser Gly Gly Phe Tyr Phe Asp
                95                 100                 105

Tyr Trp Gly Gln Gly Thr Thr Gln Ser Pro Ser Pro Gln Pro Lys
               110                 115                 120

Arg Arg Ala His
```

<210> SEQ ID NO 3
<211> LENGTH: 116
<212> TYPE: PRT
<213> ORGANISM: Artificial sequence
<220> FEATURE:

```
<223> OTHER INFORMATION: sequence is synthesized

<400> SEQUENCE: 3

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Val Leu
                 20                  25                  30

Tyr Ser Ser Asn Gln Lys Asn Tyr Leu Ala Trp Tyr Gln Gln Lys
             35                  40                  45

Pro Gly Lys Ala Pro Lys Leu Leu Ile Tyr Trp Ala Ser Thr Arg
         50                  55                  60

Glu Ser Gly Val Pro Ser Arg Phe Ser Gly Ser Gly Ser Gly Thr
 65                  70                  75

Asp Phe Thr Leu Thr Ile Ser Ser Leu Gln Pro Glu Asp Phe Ala
                 80                  85                  90

Thr Tyr Tyr Cys His Gln Tyr Leu Ser Ser Asp Thr Phe Gly Gln
             95                 100                 105

Gly Thr Lys Val Glu Ile Lys Arg Thr Val Ala
        110                 115

<210> SEQ ID NO 4
<211> LENGTH: 124
<212> TYPE: PRT
<213> ORGANISM: Artificial sequence
<220> FEATURE:
<223> OTHER INFORMATION: sequence is synthesized

<400> SEQUENCE: 4

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ala Phe Thr
                 20                  25                  30

Asn Tyr Leu Ile Glu Trp Val Arg Gln Ala Pro Gly Lys Gly Leu
             35                  40                  45

Glu Trp Val Gly Val Asn Asn Pro Gly Ser Gly Gly Ser Asn Tyr
         50                  55                  60

Asn Glu Lys Phe Lys Gly Arg Ala Thr Ile Ser Ala Asp Asn Ser
 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Ser Gly Gly Phe Tyr Phe Asp
             95                 100                 105

Tyr Trp Gly Gln Gly Thr Leu Val Thr Val Ser Ser Ala Ser Thr
        110                 115                 120

Lys Gly Pro Ser

<210> SEQ ID NO 5
<211> LENGTH: 109
<212> TYPE: PRT
<213> ORGANISM: Artificial sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
                 20                  25                  30
```

```
Asn Tyr Leu Ala Trp Tyr Gln Gln Lys Pro Gly Lys Ala Pro Lys
                 35                  40                  45

Leu Leu Ile Tyr Ala Ala Ser Leu Glu Ser Gly Val Pro Ser
         50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

Tyr Asn Ser Leu Pro Trp Thr Phe Gly Gln Gly Thr Lys Val Glu
             95                 100                 105

Ile Lys Arg Thr

<210> SEQ ID NO 6
<211> LENGTH: 117
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 102
<223> OTHER INFORMATION: Unknown amino acid

<400> SEQUENCE: 6

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
             20                  25                  30

Ser Tyr Ala Met Ser Trp Val Arg Gln Ala Pro Gly Lys Gly Leu
             35                  40                  45

Glu Trp Val Ala Val Ile Ser Gly Asp Gly Ser Thr Tyr Tyr
             50                  55                  60

Ala Asp Ser Val Lys Gly Arg Phe Thr Ile Ser Arg Asp Asn Ser
             65                  70                  75

Lys Asn Thr Leu Tyr Leu Gln Met Asn Ser Leu Arg Ala Glu Asp
             80                  85                  90

Thr Ala Val Tyr Tyr Cys Ala Arg Gly Arg Gly Xaa Ser Phe Asp
             95                 100                 105

Tyr Trp Gly Gln Gly Thr Leu Val Thr Val Ser Ser
            110                 115

<210> SEQ ID NO 7
<211> LENGTH: 11
<212> TYPE: PRT
<213> ORGANISM: Artificial sequence
<220> FEATURE:
<223> OTHER INFORMATION: sequence is synthesized

<400> SEQUENCE: 7

Arg Ala Ser Gln Gly Ile Ser Ser Tyr Leu Ala
 1               5                  10

<210> SEQ ID NO 8
<211> LENGTH: 7
<212> TYPE: PRT
<213> ORGANISM: Artificial sequence
<220> FEATURE:
<223> OTHER INFORMATION: sequence is synthesized

<400> SEQUENCE: 8

Tyr Ala Ser Ser Leu Gln Ser
 1               5
```

<210> SEQ ID NO 9
<211> LENGTH: 9
<212> TYPE: PRT
<213> ORGANISM: Artificial sequence
<220> FEATURE:
<223> OTHER INFORMATION: sequence is synthesized

<400> SEQUENCE: 9

Gln Gln Tyr Asn Ser Tyr Pro Tyr Thr
 1               5

<210> SEQ ID NO 10
<211> LENGTH: 10
<212> TYPE: PRT
<213> ORGANISM: Artificial sequence
<220> FEATURE:
<223> OTHER INFORMATION: sequence is synthesized

<400> SEQUENCE: 10

Gly Phe Thr Phe Ser Ser Tyr Ala Met His
 1               5                  10

<210> SEQ ID NO 11
<211> LENGTH: 51
<212> TYPE: DNA
<213> ORGANISM: Artificial sequence
<220> FEATURE:
<223> OTHER INFORMATION: sequence is synthesized

<400> SEQUENCE: 11
agagccagtc agagcgtgct gtatagttcg aatcagaaga actacctggc        50
c                                                             51

<210> SEQ ID NO 12
<211> LENGTH: 21
<212> TYPE: DNA
<213> ORGANISM: Artificial sequence
<220> FEATURE:
<223> OTHER INFORMATION: sequence is synthesized

<400> SEQUENCE: 12
tgggctagta ctcgcgagtc t                                       21

<210> SEQ ID NO 13
<211> LENGTH: 24
<212> TYPE: DNA
<213> ORGANISM: Artificial sequence
<220> FEATURE:
<223> OTHER INFORMATION: sequence is synthesized

<400> SEQUENCE: 13
caccagtatc tgagctctga caca                                    24

<210> SEQ ID NO 14
<211> LENGTH: 30
<212> TYPE: DNA
<213> ORGANISM: Artificial sequence
<220> FEATURE:
<223> OTHER INFORMATION: sequence is synthesized

<400> SEQUENCE: 14
ggctacgcat tcaccaacta tctgatcgag                              30

<210> SEQ ID NO 15
<211> LENGTH: 51

```
<212> TYPE: DNA
<213> ORGANISM: Artificial sequence
<220> FEATURE:
<223> OTHER INFORMATION: sequence is synthesized

<400> SEQUENCE: 15
gttaacaatc ctggatccgg aggctccaac tataacgaga agttcaaggg        50
g                                                             51

<210> SEQ ID NO 16
<211> LENGTH: 24
<212> TYPE: DNA
<213> ORGANISM: Artificial sequence
<220> FEATURE:
<223> OTHER INFORMATION: sequence is synthesized

<400> SEQUENCE: 16
tccggaggct tctacttcga ctac                                    24

<210> SEQ ID NO 17
<211> LENGTH: 51
<212> TYPE: DNA
<213> ORGANISM: Mus musculus

<400> SEQUENCE: 17
aagtccagtc aaagtgtttt atacagttca aatcagaaga actacttggc        50
c                                                             51

<210> SEQ ID NO 18
<211> LENGTH: 17
<212> TYPE: PRT
<213> ORGANISM: Artificial sequence
<220> FEATURE:
<223> OTHER INFORMATION: sequence is synthesized

<400> SEQUENCE: 18

Arg Ala Ser Gln Ser Val Leu Tyr Ser Ser Asn Gln Lys Asn Tyr
 1               5                  10                  15

Leu Ala

<210> SEQ ID NO 19
<211> LENGTH: 7
<212> TYPE: PRT
<213> ORGANISM: Artificial sequence
<220> FEATURE:
<223> OTHER INFORMATION: sequence is synthesized

<400> SEQUENCE: 19

Trp Ala Ser Thr Arg Glu Ser
 1               5

<210> SEQ ID NO 20
<211> LENGTH: 8
<212> TYPE: PRT
<213> ORGANISM: Artificial sequence
<220> FEATURE:
<223> OTHER INFORMATION: sequence is synthesized

<400> SEQUENCE: 20

His Gln Tyr Leu Ser Ser Asp Thr
 1               5

<210> SEQ ID NO 21
<211> LENGTH: 10
<212> TYPE: PRT
```

```
<213> ORGANISM: Artificial sequence
<220> FEATURE:
<223> OTHER INFORMATION: sequence is synthesized

<400> SEQUENCE: 21

Gly Tyr Ala Phe Thr Asn Tyr Leu Ile Glu
 1               5                  10

<210> SEQ ID NO 22
<211> LENGTH: 17
<212> TYPE: PRT
<213> ORGANISM: Artificial sequence
<220> FEATURE:
<223> OTHER INFORMATION: sequence is synthesized

<400> SEQUENCE: 22

Val Asn Asn Pro Gly Ser Gly Gly Ser Asn Tyr Asn Glu Lys Phe
 1               5                  10                  15

Lys Gly

<210> SEQ ID NO 23
<211> LENGTH: 8
<212> TYPE: PRT
<213> ORGANISM: Artificial sequence
<220> FEATURE:
<223> OTHER INFORMATION: sequence is synthesized

<400> SEQUENCE: 23

Ser Gly Gly Phe Tyr Phe Asp Tyr
 1               5

<210> SEQ ID NO 24
<211> LENGTH: 17
<212> TYPE: PRT
<213> ORGANISM: Mus musculus

<400> SEQUENCE: 24

Lys Ser Ser Gln Ser Val Leu Tyr Ser Asn Gln Lys Asn Tyr
 1               5                  10                  15

Leu Ala

<210> SEQ ID NO 25
<211> LENGTH: 667
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 220
<223> OTHER INFORMATION: Unknown amino acid

<400> SEQUENCE: 25

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Val Leu
                20                  25                  30

Tyr Ser Ser Asn Gln Lys Asn Tyr Leu Ala Trp Tyr Gln Gln Lys
                35                  40                  45

Pro Gly Lys Ala Pro Lys Leu Leu Ile Tyr Trp Ala Ser Thr Arg
                50                  55                  60

Glu Ser Gly Val Pro Ser Arg Phe Ser Gly Ser Gly Ser Gly Thr
                65                  70                  75

Asp Phe Thr Leu Thr Ile Ser Ser Leu Gln Pro Glu Asp Phe Ala
```

```
                80                  85                  90
Thr Tyr Tyr Cys His Gln Tyr Leu Ser Ser Asp Thr Phe Gly Gln
                95                 100                 105
Gly Thr Lys Val Glu Ile Lys Arg Thr Val Ala Ala Pro Ser Val
               110                 115                 120
Phe Ile Phe Pro Pro Ser Asp Glu Gln Leu Lys Ser Gly Thr Ala
               125                 130                 135
Ser Val Val Cys Leu Leu Asn Asn Phe Tyr Pro Arg Glu Ala Lys
               140                 145                 150
Val Gln Trp Lys Val Asp Asn Ala Leu Gln Ser Gly Asn Ser Gln
               155                 160                 165
Glu Ser Val Thr Glu Gln Asp Ser Lys Asp Ser Thr Tyr Ser Leu
               170                 175                 180
Ser Ser Thr Leu Thr Leu Ser Lys Ala Asp Tyr Glu Lys His Lys
               185                 190                 195
Val Tyr Ala Cys Glu Val Thr His Gln Gly Leu Ser Ser Pro Val
               200                 205                 210
Thr Lys Ser Phe Asn Arg Gly Glu Cys Xaa Glu Val Gln Leu Val
               215                 220                 225
Glu Ser Gly Gly Gly Leu Val Gln Pro Gly Gly Ser Leu Arg Leu
               230                 235                 240
Ser Cys Ala Ala Ser Gly Tyr Ala Phe Thr Asn Tyr Leu Ile Glu
               245                 250                 255
Trp Val Arg Gln Ala Pro Gly Lys Gly Leu Glu Trp Ile Gly Val
               260                 265                 270
Asn Asn Pro Gly Ser Gly Gly Ser Asn Tyr Asn Glu Lys Phe Lys
               275                 280                 285
Gly Arg Phe Thr Ile Ser Ala Asp Asn Ser Lys Asn Thr Leu Tyr
               290                 295                 300
Leu Gln Met Asn Ser Leu Arg Ala Glu Asp Thr Ala Val Tyr Tyr
               305                 310                 315
Cys Ala Arg Ser Gly Gly Phe Tyr Phe Asp Tyr Trp Gly Gln Gly
               320                 325                 330
Thr Leu Val Thr Val Ser Ser Ala Ser Thr Lys Gly Pro Ser Val
               335                 340                 345
Phe Pro Leu Ala Pro Ser Ser Lys Ser Thr Ser Gly Gly Thr Ala
               350                 355                 360
Ala Leu Gly Cys Leu Val Lys Asp Tyr Phe Pro Glu Pro Val Thr
               365                 370                 375
Val Ser Trp Asn Ser Gly Ala Leu Thr Ser Gly Val His Thr Phe
               380                 385                 390
Pro Ala Val Leu Gln Ser Ser Gly Leu Tyr Ser Leu Ser Ser Val
               395                 400                 405
Val Thr Val Pro Ser Ser Ser Leu Gly Thr Gln Thr Tyr Ile Cys
               410                 415                 420
Asn Val Asn His Lys Pro Ser Asn Thr Lys Val Asp Lys Lys Val
               425                 430                 435
Glu Pro Lys Ser Cys Asp Lys Thr His Thr Cys Pro Pro Cys Pro
               440                 445                 450
Ala Pro Glu Leu Leu Gly Gly Pro Ser Val Phe Leu Phe Pro Pro
               455                 460                 465
Lys Pro Lys Asp Thr Leu Met Ile Ser Arg Thr Pro Glu Val Thr
               470                 475                 480
```

```
Cys Val Val Val Asp Val Ser His Glu Asp Pro Glu Val Lys Phe
                485                 490                 495

Asn Trp Tyr Val Asp Gly Val Glu Val His Asn Ala Lys Thr Lys
                500                 505                 510

Pro Arg Glu Glu Gln Tyr Asn Ser Thr Tyr Arg Val Val Ser Val
                515                 520                 525

Leu Thr Val Leu His Gln Asp Trp Leu Asn Gly Lys Glu Tyr Lys
                530                 535                 540

Cys Lys Val Ser Asn Lys Ala Leu Pro Ala Pro Ile Glu Lys Thr
                545                 550                 555

Ile Ser Lys Ala Lys Gly Gln Pro Arg Glu Pro Gln Val Tyr Thr
                560                 565                 570

Leu Pro Pro Ser Arg Glu Glu Met Thr Lys Asn Gln Val Ser Leu
                575                 580                 585

Thr Cys Leu Val Lys Gly Phe Tyr Pro Ser Asp Ile Ala Val Glu
                590                 595                 600

Trp Glu Ser Asn Gly Gln Pro Glu Asn Asn Tyr Lys Thr Thr Pro
                605                 610                 615

Pro Val Leu Asp Ser Asp Gly Ser Phe Phe Leu Tyr Ser Lys Leu
                620                 625                 630

Thr Val Asp Lys Ser Arg Trp Gln Gln Gly Asn Val Phe Ser Cys
                635                 640                 645

Ser Val Met His Glu Ala Leu His Asn His Tyr Thr Gln Lys Ser
                650                 655                 660

Leu Ser Leu Ser Pro Gly Lys
                665

<210> SEQ ID NO 26
<211> LENGTH: 695
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 220, 668, 673
<223> OTHER INFORMATION: Unknown amino acid

<400> SEQUENCE: 26

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Val Leu
                 20                  25                  30

Tyr Ser Ser Asn Gln Lys Asn Tyr Leu Ala Trp Tyr Gln Gln Lys
                 35                  40                  45

Pro Gly Lys Ala Pro Lys Leu Leu Ile Tyr Trp Ala Ser Thr Arg
                 50                  55                  60

Glu Ser Gly Val Pro Ser Arg Phe Ser Gly Ser Gly Ser Gly Thr
                 65                  70                  75

Asp Phe Thr Leu Thr Ile Ser Ser Leu Gln Pro Glu Asp Phe Ala
                 80                  85                  90

Thr Tyr Tyr Cys His Gln Tyr Leu Ser Ser Asp Thr Phe Gly Gln
                 95                 100                 105

Gly Thr Lys Val Glu Ile Lys Arg Thr Val Ala Ala Pro Ser Val
                110                 115                 120

Phe Ile Phe Pro Pro Ser Asp Glu Gln Leu Lys Ser Gly Thr Ala
                125                 130                 135
```

-continued

```
Ser Val Val Cys Leu Leu Asn Asn Phe Tyr Pro Arg Glu Ala Lys
            140                 145                 150

Val Gln Trp Lys Val Asp Asn Ala Leu Gln Ser Gly Asn Ser Gln
            155                 160                 165

Glu Ser Val Thr Glu Gln Asp Ser Lys Asp Ser Thr Tyr Ser Leu
            170                 175                 180

Ser Ser Thr Leu Thr Leu Ser Lys Ala Asp Tyr Glu Lys His Lys
            185                 190                 195

Val Tyr Ala Cys Glu Val Thr His Gln Gly Leu Ser Ser Pro Val
            200                 205                 210

Thr Lys Ser Phe Asn Arg Gly Glu Cys Xaa Glu Val Gln Leu Val
            215                 220                 225

Glu Ser Gly Gly Gly Leu Val Gln Pro Gly Gly Ser Leu Arg Leu
            230                 235                 240

Ser Cys Ala Ala Ser Gly Tyr Ala Phe Thr Asn Tyr Leu Ile Glu
            245                 250                 255

Trp Val Arg Gln Ala Pro Gly Lys Gly Leu Glu Trp Val Gly Val
            260                 265                 270

Ile Asn Pro Gly Ser Gly Gly Ser Asn Tyr Asn Glu Lys Phe Lys
            275                 280                 285

Gly Arg Ala Thr Ile Ser Ala Asp Asn Ser Lys Asn Thr Leu Tyr
            290                 295                 300

Leu Gln Met Asn Ser Leu Arg Ala Glu Asp Thr Ala Val Tyr Tyr
            305                 310                 315

Cys Ala Arg Ser Gly Gly Phe Tyr Phe Asp Tyr Trp Gly Gln Gly
            320                 325                 330

Thr Leu Val Thr Val Ser Ser Ala Ser Thr Lys Gly Pro Ser Val
            335                 340                 345

Phe Pro Leu Ala Pro Ser Ser Lys Ser Thr Ser Gly Gly Thr Ala
            350                 355                 360

Ala Leu Gly Cys Leu Val Lys Asp Tyr Phe Pro Glu Pro Val Thr
            365                 370                 375

Val Ser Trp Asn Ser Gly Ala Leu Thr Ser Gly Val His Thr Phe
            380                 385                 390

Pro Ala Val Leu Gln Ser Ser Gly Leu Tyr Ser Leu Ser Ser Val
            395                 400                 405

Val Thr Val Pro Ser Ser Ser Leu Gly Thr Gln Thr Tyr Ile Cys
            410                 415                 420

Asn Val Asn His Lys Pro Ser Asn Thr Lys Val Asp Lys Lys Val
            425                 430                 435

Glu Pro Lys Ser Cys Asp Lys Thr His Thr Cys Pro Pro Cys Pro
            440                 445                 450

Ala Pro Glu Leu Leu Gly Gly Pro Ser Val Phe Leu Phe Pro Pro
            455                 460                 465

Lys Pro Lys Asp Thr Leu Met Ile Ser Arg Thr Pro Glu Val Thr
            470                 475                 480

Cys Val Val Val Asp Val Ser His Glu Asp Pro Glu Val Lys Phe
            485                 490                 495

Asn Trp Tyr Val Asp Gly Val Glu Val His Asn Ala Lys Thr Lys
            500                 505                 510

Pro Arg Glu Glu Gln Tyr Asn Ser Thr Tyr Arg Val Val Ser Val
            515                 520                 525

Leu Thr Val Leu His Gln Asp Trp Leu Asn Gly Lys Glu Tyr Lys
            530                 535                 540
```

```
Cys Lys Val Ser Asn Lys Ala Leu Pro Ala Pro Ile Glu Lys Thr
            545                 550                 555
Ile Ser Lys Ala Lys Gly Gln Pro Arg Glu Pro Gln Val Tyr Thr
            560                 565                 570
Leu Pro Pro Ser Arg Glu Glu Met Thr Lys Asn Gln Val Ser Leu
            575                 580                 585
Thr Cys Leu Val Lys Gly Phe Tyr Pro Ser Asp Ile Ala Val Glu
            590                 595                 600
Trp Glu Ser Asn Gly Gln Pro Glu Asn Asn Tyr Lys Thr Thr Pro
            605                 610                 615
Pro Val Leu Asp Ser Asp Gly Ser Phe Phe Leu Tyr Ser Lys Leu
            620                 625                 630
Thr Val Asp Lys Ser Arg Trp Gln Gln Gly Asn Val Phe Ser Cys
            635                 640                 645
Ser Val Met His Glu Ala Leu His Asn His Tyr Thr Gln Lys Ser
            650                 655                 660
Leu Ser Leu Ser Pro Gly Lys Xaa Val Arg Arg Pro Xaa Ser Arg
            665                 670                 675
Pro Ala Glu Ala Trp Pro Pro Trp Pro Asn Leu Phe Ile Ala Ala
            680                 685                 690
Tyr Asn Gly Tyr Lys
            695

<210> SEQ ID NO 27
<211> LENGTH: 666
<212> TYPE: PRT
<213> ORGANISM: Artificial sequence
<220> FEATURE:
<223> OTHER INFORMATION: sequence is synthesized

<400> SEQUENCE: 27

Asp Ile Gln Met Thr Gln Ser Pro Ser Ser Leu Ser Ala Ser Val
  1               5                  10                  15
Gly Asp Arg Val Thr Ile Thr Cys Arg Ala Ser Gln Ser Val Leu
            20                  25                  30
Tyr Ser Ser Asn Gln Lys Asn Tyr Leu Ala Trp Tyr Gln Gln Lys
            35                  40                  45
Pro Gly Lys Ala Pro Lys Leu Leu Ile Tyr Trp Ala Ser Thr Arg
            50                  55                  60
Glu Ser Gly Val Pro Ser Arg Phe Ser Gly Ser Gly Ser Gly Thr
            65                  70                  75
Asp Phe Thr Leu Thr Ile Ser Ser Leu Gln Pro Glu Asp Phe Ala
            80                  85                  90
Thr Tyr Tyr Cys His Gln Tyr Leu Ser Ser Asp Thr Phe Gly Gln
            95                  100                 105
Gly Thr Lys Val Glu Ile Lys Arg Thr Val Ala Ala Pro Ser Val
            110                 115                 120
Phe Ile Phe Pro Pro Ser Asp Glu Gln Leu Lys Ser Gly Thr Ala
            125                 130                 135
Ser Val Val Cys Leu Leu Asn Asn Phe Tyr Pro Arg Glu Ala Lys
            140                 145                 150
Val Gln Trp Lys Val Asp Asn Ala Leu Gln Ser Gly Asn Ser Gln
            155                 160                 165
Glu Ser Val Thr Glu Gln Asp Ser Lys Asp Ser Thr Tyr Ser Leu
            170                 175                 180
```

```
Ser Ser Thr Leu Thr Leu Ser Lys Ala Asp Tyr Glu Lys His Lys
            185                 190                 195

Val Tyr Ala Cys Glu Val Thr His Gln Gly Leu Ser Ser Pro Val
            200                 205                 210

Thr Lys Ser Phe Asn Arg Gly Glu Cys Glu Val Gln Leu Val Glu
            215                 220                 225

Ser Gly Gly Gly Leu Val Gln Pro Gly Ser Leu Arg Leu Ser
            230                 235                 240

Cys Ala Ala Ser Gly Tyr Ala Phe Thr Asn Tyr Leu Ile Glu Trp
            245                 250                 255

Val Arg Gln Ala Pro Gly Lys Gly Leu Glu Trp Ile Gly Val Asn
            260                 265                 270

Asn Pro Gly Ser Gly Gly Ser Asn Tyr Asn Glu Lys Phe Lys Gly
            275                 280                 285

Arg Ala Thr Ile Ser Ala Asp Asn Ser Lys Asn Thr Leu Tyr Leu
            290                 295                 300

Gln Met Asn Ser Leu Arg Ala Glu Asp Thr Ala Val Tyr Tyr Cys
            305                 310                 315

Ala Arg Ser Gly Gly Phe Tyr Phe Asp Tyr Trp Gly Gln Gly Thr
            320                 325                 330

Leu Val Thr Val Ser Ser Ala Ser Thr Lys Gly Pro Ser Val Phe
            335                 340                 345

Pro Leu Ala Pro Ser Ser Lys Ser Thr Ser Gly Gly Thr Ala Ala
            350                 355                 360

Leu Gly Cys Leu Val Lys Asp Tyr Phe Pro Glu Pro Val Thr Val
            365                 370                 375

Ser Trp Asn Ser Gly Ala Leu Thr Ser Gly Val His Thr Phe Pro
            380                 385                 390

Ala Val Leu Gln Ser Ser Gly Leu Tyr Ser Leu Ser Ser Val Val
            395                 400                 405

Thr Val Pro Ser Ser Ser Leu Gly Thr Gln Thr Tyr Ile Cys Asn
            410                 415                 420

Val Asn His Lys Pro Ser Asn Thr Lys Val Asp Lys Lys Val Glu
            425                 430                 435

Pro Lys Ser Cys Asp Lys Thr His Thr Cys Pro Pro Cys Pro Ala
            440                 445                 450

Pro Glu Leu Leu Gly Gly Pro Ser Val Phe Leu Phe Pro Pro Lys
            455                 460                 465

Pro Lys Asp Thr Leu Met Ile Ser Arg Thr Pro Glu Val Thr Cys
            470                 475                 480

Val Val Val Asp Val Ser His Glu Asp Pro Glu Val Lys Phe Asn
            485                 490                 495

Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu
            515                 520                 525

Thr Val Leu His Gln Asp Trp Leu Asn Gly Lys Glu Tyr Lys Cys
            530                 535                 540

Lys Val Ser Asn Lys Ala Leu Pro Ala Pro Ile Glu Lys Thr Ile
            545                 550                 555

Ser Lys Ala Lys Gly Gln Pro Arg Glu Pro Gln Val Tyr Thr Leu
            560                 565                 570

Pro Pro Ser Arg Glu Glu Met Thr Lys Asn Gln Val Ser Leu Thr
            575                 580                 585
```

```
Cys Leu Val Lys Gly Phe Tyr Pro Ser Asp Ile Ala Val Glu Trp
            590                 595                 600

Glu Ser Asn Gly Gln Pro Glu Asn Asn Tyr Lys Thr Thr Pro Pro
            605                 610                 615

Val Leu Asp Ser Asp Gly Ser Phe Phe Leu Tyr Ser Lys Leu Thr
            620                 625                 630

Val Asp Lys Ser Arg Trp Gln Gln Gly Asn Val Phe Ser Cys Ser
            635                 640                 645

Val Met His Glu Ala Leu His Asn His Tyr Thr Gln Lys Ser Leu
            650                 655                 660

Ser Leu Ser Pro Gly Lys
            665

<210> SEQ ID NO 28
<211> LENGTH: 667
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 220
<223> OTHER INFORMATION: Unknown amino acid

<400> SEQUENCE: 28

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Val Leu
                20                  25                  30

Tyr Ser Ser Asn Gln Lys Asn Tyr Leu Ala Trp Tyr Gln Gln Lys
             35                  40                  45

Pro Gly Lys Ala Pro Lys Leu Leu Ile Tyr Trp Ala Ser Thr Arg
         50                  55                  60

Glu Ser Gly Val Pro Ser Arg Phe Ser Gly Ser Gly Ser Gly Thr
             65                  70                  75

Asp Phe Thr Leu Thr Ile Ser Ser Leu Gln Pro Glu Asp Phe Ala
             80                  85                  90

Thr Tyr Tyr Cys His Gln Tyr Leu Ser Ser Asp Thr Phe Gly Gln
             95                 100                 105

Gly Thr Lys Val Glu Ile Lys Arg Thr Val Ala Ala Pro Ser Val
            110                 115                 120

Phe Ile Phe Pro Pro Ser Asp Glu Gln Leu Lys Ser Gly Thr Ala
            125                 130                 135

Ser Val Val Cys Leu Leu Asn Asn Phe Tyr Pro Arg Glu Ala Lys
            140                 145                 150

Val Gln Trp Lys Val Asp Asn Ala Leu Gln Ser Gly Asn Ser Gln
            155                 160                 165

Glu Ser Val Thr Glu Gln Asp Ser Lys Asp Ser Thr Tyr Ser Leu
            170                 175                 180

Ser Ser Thr Leu Thr Leu Ser Lys Ala Asp Tyr Glu Lys His Lys
            185                 190                 195

Val Tyr Ala Cys Glu Val Thr His Gln Gly Leu Ser Ser Pro Val
            200                 205                 210

Thr Lys Ser Phe Asn Arg Gly Glu Cys Xaa Glu Val Gln Leu Val
            215                 220                 225

Glu Ser Gly Gly Gly Leu Val Gln Pro Gly Gly Ser Leu Arg Leu
            230                 235                 240
```

```
Ser Cys Ala Ala Ser Gly Tyr Ala Phe Thr Asn Tyr Leu Ile Glu
            245                 250                 255

Trp Val Arg Gln Ala Pro Gly Lys Gly Leu Glu Trp Val Gly Val
            260                 265                 270

Asn Asn Pro Gly Ser Gly Gly Ser Asn Tyr Asn Glu Lys Phe Lys
            275                 280                 285

Gly Arg Ala Thr Ile Ser Ala Asp Asn Ser Lys Asn Thr Leu Tyr
            290                 295                 300

Leu Gln Met Asn Ser Leu Arg Ala Glu Asp Thr Ala Val Tyr Tyr
            305                 310                 315

Cys Ala Arg Ser Gly Gly Phe Tyr Phe Asp Tyr Trp Gly Gln Gly
            320                 325                 330

Thr Leu Val Thr Val Ser Ser Ala Ser Thr Lys Gly Pro Ser Val
            335                 340                 345

Phe Pro Leu Ala Pro Ser Ser Lys Ser Thr Ser Gly Gly Thr Ala
            350                 355                 360

Ala Leu Gly Cys Leu Val Lys Asp Tyr Phe Pro Glu Pro Val Thr
            365                 370                 375

Val Ser Trp Asn Ser Gly Ala Leu Thr Ser Gly Val His Thr Phe
            380                 385                 390

Pro Ala Val Leu Gln Ser Ser Gly Leu Tyr Ser Leu Ser Ser Val
            395                 400                 405

Val Thr Val Pro Ser Ser Ser Leu Gly Thr Gln Thr Tyr Ile Cys
            410                 415                 420

Asn Val Asn His Lys Pro Ser Asn Thr Lys Val Asp Lys Lys Val
            425                 430                 435

Glu Pro Lys Ser Cys Asp Lys Thr His Thr Cys Pro Pro Cys Pro
            440                 445                 450

Ala Pro Glu Leu Leu Gly Gly Pro Ser Val Phe Leu Phe Pro Pro
            455                 460                 465

Lys Pro Lys Asp Thr Leu Met Ile Ser Arg Thr Pro Glu Val Thr
            470                 475                 480

Cys Val Val Val Asp Val Ser His Glu Asp Pro Glu Val Lys Phe
            485                 490                 495

Asn Trp Tyr Val Asp Gly Val Glu Val His Asn Ala Lys Thr Lys
            500                 505                 510

Pro Arg Glu Glu Gln Tyr Asn Ser Thr Tyr Arg Val Val Ser Val
            515                 520                 525

Leu Thr Val Leu His Gln Asp Trp Leu Asn Gly Lys Glu Tyr Lys
            530                 535                 540

Cys Lys Val Ser Asn Lys Ala Leu Pro Ala Pro Ile Glu Lys Thr
            545                 550                 555

Ile Ser Lys Ala Lys Gly Gln Pro Arg Glu Pro Gln Val Tyr Thr
            560                 565                 570

Leu Pro Pro Ser Arg Glu Glu Met Thr Lys Asn Gln Val Ser Leu
            575                 580                 585

Thr Cys Leu Val Lys Gly Phe Tyr Pro Ser Asp Ile Ala Val Glu
            590                 595                 600

Trp Glu Ser Asn Gly Gln Pro Glu Asn Asn Tyr Lys Thr Thr Pro
            605                 610                 615

Pro Val Leu Asp Ser Asp Gly Ser Phe Phe Leu Tyr Ser Lys Leu
            620                 625                 630

Thr Val Asp Lys Ser Arg Trp Gln Gln Gly Asn Val Phe Ser Cys
```

```
                        635                 640                 645
Ser Val Met His Glu Gly Leu His Asn His Tyr Thr Gln Lys Ser
                650                 655                 660

Leu Ser Leu Ser Pro Gly Lys
            665
```

<210> SEQ ID NO 29
<211> LENGTH: 667
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 220
<223> OTHER INFORMATION: Unknown amino acid

<400> SEQUENCE: 29

```
Asp Ile Met Met Thr Gln Ser Pro Ser Leu Ala Val Ser Ala
  1               5                  10                  15

Gly Glu Lys Val Thr Met Ser Cys Lys Ser Gln Ser Val Leu
                 20                  25                  30

Tyr Ser Ser Asn Gln Lys Asn Tyr Leu Ala Trp Tyr Gln Lys
             35                  40                      45

Pro Gly Gln Ser Pro Lys Leu Leu Ile Tyr Trp Ala Ser Thr Arg
             50                      55                  60

Glu Ser Gly Val Pro Asp Arg Phe Thr Gly Ser Gly Ser Gly Thr
                 65                  70                  75

Asp Phe Thr Leu Thr Ile Ser Ser Val Gln Ala Glu Asp Leu Ala
                 80                  85                  90

Val Tyr Tyr Cys His Gln Tyr Leu Ser Ser Asp Thr Phe Gly Gly
                 95                 100                 105

Gly Thr Lys Leu Glu Ile Lys Arg Thr Val Ala Ala Pro Ser Val
                110                 115                 120

Phe Ile Phe Pro Pro Ser Asp Glu Gln Leu Lys Ser Gly Thr Ala
                125                 130                 135

Ser Val Val Cys Leu Leu Asn Asn Phe Tyr Pro Arg Glu Ala Lys
                140                 145                 150

Val Gln Trp Lys Val Asp Asn Ala Leu Gln Ser Gly Asn Ser Gln
                155                 160                 165

Glu Ser Val Thr Glu Gln Asp Ser Lys Asp Ser Thr Tyr Ser Leu
                170                 175                 180

Ser Ser Thr Leu Thr Leu Ser Lys Ala Asp Tyr Glu Lys His Lys
                185                 190                 195

Val Tyr Ala Cys Glu Val Thr His Gln Gly Leu Ser Ser Pro Val
                200                 205                 210

Thr Lys Ser Phe Asn Arg Gly Glu Cys Xaa Glu Val Gln Leu Gln
                215                 220                 225

Gln Ser Gly Ala Glu Leu Val Arg Pro Gly Thr Ser Val Lys Val
                230                 235                 240

Ser Cys Lys Ala Ser Gly Tyr Ala Phe Thr Asn Tyr Leu Ile Glu
                245                 250                 255

Trp Val Lys Gln Arg Pro Gly Gln Gly Leu Glu Trp Ile Gly Val
                260                 265                 270

Asn Asn Pro Gly Ser Gly Gly Ser Asn Tyr Asn Glu Lys Phe Lys
                275                 280                 285

Gly Lys Ala Thr Leu Thr Ala Asp Lys Ser Ser Ser Thr Ala Tyr
```

```
                        290                 295                 300
Met Gln Leu Ser Ser Leu Thr Ser Asp Asp Ser Ala Val Tyr Phe
                    305                 310                 315
Cys Ala Arg Ser Gly Gly Phe Tyr Phe Asp Tyr Trp Gly Gln Gly
                320                 325                 330
Thr Ser Val Thr Val Ser Ser Ala Lys Thr Thr Gly Pro Ser Val
            335                 340                 345
Phe Pro Leu Ala Pro Ser Ser Lys Ser Thr Ser Gly Gly Thr Ala
        350                 355                 360
Ala Leu Gly Cys Leu Val Lys Asp Tyr Phe Pro Glu Pro Val Thr
    365                 370                 375
Val Ser Trp Asn Ser Gly Ala Leu Thr Ser Gly Val His Thr Phe
380                 385                 390
Pro Ala Val Leu Gln Ser Ser Gly Leu Tyr Ser Leu Ser Ser Val
                395                 400                 405
Val Thr Val Pro Ser Ser Leu Gly Thr Gln Thr Tyr Ile Cys
            410                 415                 420
Asn Val Asn His Lys Pro Ser Asn Thr Lys Val Asp Lys Lys Val
        425                 430                 435
Glu Pro Lys Ser Cys Asp Lys Thr His Thr Cys Pro Pro Cys Pro
    440                 445                 450
Ala Pro Glu Leu Leu Gly Gly Pro Ser Val Phe Leu Phe Pro Pro
455                 460                 465
Lys Pro Lys Asp Thr Leu Met Ile Ser Arg Thr Pro Glu Val Thr
                470                 475                 480
Cys Val Val Val Asp Val Ser His Glu Asp Pro Glu Val Lys Phe
            485                 490                 495
Asn Trp Tyr Val Asp Gly Val Glu Val His Asn Ala Lys Thr Lys
        500                 505                 510
Pro Arg Glu Glu Gln Tyr Asn Ser Thr Tyr Arg Val Val Ser Val
    515                 520                 525
Leu Thr Val Leu His Gln Asp Trp Leu Asn Gly Lys Glu Tyr Lys
530                 535                 540
Cys Lys Val Ser Asn Lys Ala Leu Pro Ala Pro Ile Glu Lys Thr
                545                 550                 555
Ile Ser Lys Ala Lys Gly Gln Pro Arg Glu Pro Gln Val Tyr Thr
            560                 565                 570
Leu Pro Pro Ser Arg Glu Glu Met Thr Lys Asn Gln Val Ser Leu
        575                 580                 585
Thr Cys Leu Val Lys Gly Phe Tyr Pro Ser Asp Ile Ala Val Glu
    590                 595                 600
Trp Glu Ser Asn Gly Gln Pro Glu Asn Asn Tyr Lys Thr Thr Pro
605                 610                 615
Pro Val Leu Asp Ser Asp Gly Ser Phe Phe Leu Tyr Ser Lys Leu
                620                 625                 630
Thr Val Asp Lys Ser Arg Trp Gln Gln Gly Asn Val Phe Ser Cys
            635                 640                 645
Ser Val Met His Glu Ala Leu His Asn His Tyr Thr Gln Lys Ser
        650                 655                 660
Leu Ser Leu Ser Pro Gly Lys
    665

<210> SEQ ID NO 30
<211> LENGTH: 667
```

```
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 220
<223> OTHER INFORMATION: Unknown amino acid

<400> SEQUENCE: 30

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Val Leu
            20                  25                  30

Tyr Ser Ser Asn Gln Lys Asn Tyr Leu Ala Trp Tyr Gln Gln Lys
        35                  40                  45

Pro Gly Lys Ala Pro Lys Leu Leu Ile Tyr Tyr Ala Ser Ser Leu
    50                  55                  60

Gln Ser Gly Val Pro Ser Arg Phe Ser Gly Ser Gly Ser Gly Thr
65                  70                  75

Asp Phe Thr Leu Thr Ile Ser Ser Leu Gln Pro Glu Asp Phe Ala
            80                  85                  90

Thr Tyr Tyr Cys His Gln Tyr Leu Ser Ser Asp Thr Phe Gly Gln
        95                 100                 105

Gly Thr Lys Val Glu Ile Lys Arg Thr Val Ala Ala Pro Ser Val
   110                 115                 120

Phe Ile Phe Pro Pro Ser Asp Glu Gln Leu Lys Ser Gly Thr Ala
125                 130                 135

Ser Val Val Cys Leu Leu Asn Asn Phe Tyr Pro Arg Glu Ala Lys
            140                 145                 150

Val Gln Trp Lys Val Asp Asn Ala Leu Gln Ser Gly Asn Ser Gln
        155                 160                 165

Glu Ser Val Thr Glu Gln Asp Ser Lys Asp Ser Thr Tyr Ser Leu
    170                 175                 180

Ser Ser Thr Leu Thr Leu Ser Lys Ala Asp Tyr Glu Lys His Lys
185                 190                 195

Val Tyr Ala Cys Glu Val Thr His Gln Gly Leu Ser Ser Pro Val
            200                 205                 210

Thr Lys Ser Phe Asn Arg Gly Glu Cys Xaa Glu Val Gln Leu Val
        215                 220                 225

Glu Ser Gly Gly Gly Leu Val Gln Pro Gly Gly Ser Leu Arg Leu
    230                 235                 240

Ser Cys Ala Ala Ser Gly Tyr Ala Phe Thr Asn Tyr Leu Ile Glu
245                 250                 255

Trp Val Arg Gln Ala Pro Gly Lys Gly Leu Glu Trp Val Gly Val
            260                 265                 270

Asn Asn Pro Gly Ser Gly Gly Ser Asn Tyr Asn Glu Lys Phe Lys
        275                 280                 285

Gly Arg Ala Thr Ile Ser Ala Asp Asn Ser Lys Asn Thr Leu Tyr
    290                 295                 300

Leu Gln Met Asn Ser Leu Arg Ala Glu Asp Thr Ala Val Tyr Tyr
305                 310                 315

Cys Ala Arg Ser Gly Gly Phe Tyr Phe Asp Tyr Trp Gly Gln Gly
            320                 325                 330

Thr Leu Val Thr Val Ser Ser Ala Ser Thr Lys Gly Pro Ser Val
        335                 340                 345
```

Phe Pro Leu Ala Pro Ser Ser Lys Ser Thr Ser Gly Gly Thr Ala
                350                 355                 360

Ala Leu Gly Cys Leu Val Lys Asp Tyr Phe Pro Glu Pro Val Thr
            365                 370                 375

Val Ser Trp Asn Ser Gly Ala Leu Thr Ser Gly Val His Thr Phe
        380                 385                 390

Pro Ala Val Leu Gln Ser Ser Gly Leu Tyr Ser Leu Ser Ser Val
    395                 400                 405

Val Thr Val Pro Ser Ser Ser Leu Gly Thr Gln Thr Tyr Ile Cys
410                 415                 420

Asn Val Asn His Lys Pro Ser Asn Thr Lys Val Asp Lys Lys Val
                425                 430                 435

Glu Pro Lys Ser Cys Asp Lys Thr His Thr Cys Pro Pro Cys Pro
            440                 445                 450

Ala Pro Glu Leu Leu Gly Gly Pro Ser Val Phe Leu Phe Pro Pro
        455                 460                 465

Lys Pro Lys Asp Thr Leu Met Ile Ser Arg Thr Pro Glu Val Thr
    470                 475                 480

Cys Val Val Val Asp Val Ser His Glu Asp Pro Glu Val Lys Phe
485                 490                 495

Asn Trp Tyr Val Asp Gly Val Glu Val His Asn Ala Lys Thr Lys
                500                 505                 510

Pro Arg Glu Glu Gln Tyr Asn Ser Thr Tyr Arg Val Val Ser Val
            515                 520                 525

Leu Thr Val Leu His Gln Asp Trp Leu Asn Gly Lys Glu Tyr Lys
        530                 535                 540

Cys Lys Val Ser Asn Lys Ala Leu Pro Ala Pro Ile Glu Lys Thr
    545                 550                 555

Ile Ser Lys Ala Lys Gly Gln Pro Arg Glu Pro Gln Val Tyr Thr
560                 565                 570

Leu Pro Pro Ser Arg Glu Glu Met Thr Lys Asn Gln Val Ser Leu
                575                 580                 585

Thr Cys Leu Val Lys Gly Phe Tyr Pro Ser Asp Ile Ala Val Glu
            590                 595                 600

Trp Glu Ser Asn Gly Gln Pro Glu Asn Asn Tyr Lys Thr Thr Pro
        605                 610                 615

Pro Val Leu Asp Ser Asp Gly Ser Phe Phe Leu Tyr Ser Lys Leu
    620                 625                 630

Thr Val Asp Lys Ser Arg Trp Gln Gln Gly Asn Val Phe Ser Cys
635                 640                 645

Ser Val Met His Glu Gly Leu His Asn His Tyr Thr Gln Lys Ser
                650                 655                 660

Leu Ser Leu Ser Pro Gly Lys
                665

<210> SEQ ID NO 31
<211> LENGTH: 1341
<212> TYPE: DNA
<213> ORGANISM: Artificial sequence
<220> FEATURE:
<223> OTHER INFORMATION: sequence is synthesized

<400> SEQUENCE: 31
gaagttcagc tggtggagtc tggcggtggc ctggtgcagc cagggggctc        50
actccgtttg tcctgtgcag cttctggcta cgcattcacc aactatctga       100

```
tcgagtgggt ccgtcaggcc ccgggtaagg gcctcgagtg gatcggtgta        150
aacaatcctg gatccggagg ctccaactat aacgagaagt tcaagggccg        200
tttcactata agtgcagaca attcgaaaaa cacattatac ctgcagatga        250
acagcctgcg tgctgaggac actgccgtct attattgtgc tcgatccgga        300
ggcttctact tcgactactg gggtcaagga accctggtca ccgtctcctc        350
agcctccacc aagggcccat cggtcttccc cctggcaccc tcctccaaga        400
gcacctctgg gggcacagcg ccctgggct gcctggtcaa ggactacttc         450
cccgaaccgg tgacggtgtc gtggaactca ggcgccctga ccagcggcgt        500
gcacaccttc ccggctgtcc tacagtcctc aggactctac tccctcagca        550
gcgtggtgac tgtgccctct agcagcttgg cacccagac ctacatctgc         600 aacgtgaatc acaagcccag caacaccaag gtggacaaga agttgagcc         650 caaatcttgt gacaaaactc acacatgccc accgtgccca gcacctgaac        700
tcctgggggg accgtcagtc ttcctcttcc ccccaaaacc caaggacacc        750
ctcatgatct cccggacccc tgaggtcaca tgcgtggtgg tggacgtgag        800
ccacgaagac cctgaggtca agttcaactg gtacgtggac ggcgtggagg        850
tgcataatgc caagacaaag ccgcgggagg agcagtacaa cagcacgtac        900
cgtgtggtca gcgtcctcac cgtcctgcac caggactggc tgaatggcaa        950
ggagtacaag tgcaaggtct ccaacaaagc cctcccagcc cccatcgaga       1000
aaaccatctc caaagccaaa gggcagcccc gagaaccaca ggtgtacacc       1050
ctgcccccat cccgggaaga gatgaccaag aaccaggtca gcctgacctg       1100
cctggtcaaa ggcttctatc ccagcgacat cgccgtggag tgggagagca       1150
atgggcagcc ggagaacaac tacaagacca cgcctcccgt gctggactcc       1200
gacggctcct tcttcctcta cagcaagctc accgtggaca agagcaggtg       1250
gcagcagggg aacgtcttct catgctccgt gatgcatgag gctctgcaca       1300
accactacac gcagaagagc ctctccctgt ctccgggtaa a               1341
```

<210> SEQ ID NO 32
<211> LENGTH: 1398
<212> TYPE: DNA
<213> ORGANISM: Artificial sequence
<220> FEATURE:
<223> OTHER INFORMATION: sequence is synthesized

<400> SEQUENCE: 32

```
atgggatggt catgtatcat cctttttcta gtagcaactg caactggagt         50
acattcagaa gttcagctgg tggagtctgg cggtggcctg gtgcagccag        100
ggggctcact ccgtttgtcc tgtgcagctt ctggctacgc attcaccaac        150
tatctgatcg agtgggtccg tcaggcccg gtaagggcc tcgagtggat          200 cggtgtaaac aatcctggat ccggaggctc aactataac gagaagttca         250 agggccgttt cactataagt gcagacaatt cgaaaacac attatacctg         300 cagatgaaca gcctgcgtgc tgaggacact gccgtctatt attgtgctcg        350
atccggaggc ttctacttcg actactgggg tcaaggaacc ctggtcaccg        400
tctcctcagc ctccaccaag ggcccatcgg tcttcccct ggcaccctcc         450 tccaagagca cctctggggg cacagcggcc ctgggctgcc tggtcaagga        500
```

| | |
|---|---|
| ctacttcccc gaaccggtga cggtgtcgtg gaactcaggc gccctgacca | 550 |
| gcggcgtgca caccttcccg gctgtcctac agtcctcagg actctactcc | 600 |
| ctcagcagcg tggtgactgt gccctctagc agcttgggca cccagaccta | 650 |
| catctgcaac gtgaatcaca agcccagcaa caccaaggtg gacaagaaag | 700 |
| ttgagcccaa atcttgtgac aaaactcaca catgcccacc gtgcccagca | 750 |
| cctgaactcc tggggggacc gtcagtcttc ctcttccccc caaaacccaa | 800 |
| ggacaccctc atgatctccc ggacccctga ggtcacatgc gtggtggtgg | 850 |
| acgtgagcca cgaagaccct gaggtcaagt tcaactggta cgtggacggc | 900 |
| gtggaggtgc ataatgccaa gacaaagccg cgggaggagc agtacaacag | 950 |
| cacgtaccgt gtggtcagcg tcctcaccgt cctgcaccag gactggctga | 1000 |
| atggcaagga gtacaagtgc aaggtctcca acaaagccct cccagccccc | 1050 |
| atcgagaaaa ccatctccaa agccaaaggg cagccccgag aaccacaggt | 1100 |
| gtacaccctg cccccatccc gggaagagat gaccaagaac caggtcagcc | 1150 |
| tgacctgcct ggtcaaaggc ttctatccca gcgacatcgc cgtggagtgg | 1200 |
| gagagcaatg ggcagccgga gaacaactac aagaccacgc ctcccgtgct | 1250 |
| ggactccgac ggctccttct tcctctacag caagctcacc gtggacaaga | 1300 |
| gcaggtggca gcagggaac gtcttctcat gctccgtgat gcatgaggct | 1350 |
| ctgcacaacc actacacgca gaagagcctc tccctgtctc cgggtaaa | 1398 |

<210> SEQ ID NO 33
<211> LENGTH: 1341
<212> TYPE: DNA
<213> ORGANISM: Artificial sequence
<220> FEATURE:
<223> OTHER INFORMATION: sequence is synthesized

<400> SEQUENCE: 33

| | |
|---|---|
| gaagttcagc tggtggagtc tggcggtggc ctggtgcagc cagggggctc | 50 |
| actccgtttg tcctgtgcag cttctggcta cgcattcacc aactatctga | 100 |
| tcgagtgggt ccgtcaggcc ccgggtaagg gcctcgagtg ggttggtgtt | 150 |
| atcaatcctg gatccggagg ctccaactat aacgagaagt tcaaggggcg | 200 |
| cgccactatc agtgcagaca attcgaaaaa cacattatac ctgcagatga | 250 |
| acagcctgcg tgctgaggac actgccgtct attattgtgc tcgatccgga | 300 |
| ggcttctact tcgactactg gggtcaagga accctggtca ccgtctcctc | 350 |
| agcctccacc aagggcccat cggtcttccc cctggcaccc tcctccaaga | 400 |
| gcacctctgg gggcacagcg gccctgggct gcctggtcaa ggactacttc | 450 |
| cccgaaccgt gacggtgtc gtggaactca ggcgccctga ccagcggcgt | 500 |
| gcacaccttc ccggctgtcc tacagtcctc aggactctac tccctcagca | 550 |
| gcgtggtgac tgtgccctct agcagcttgg gcacccagac ctacatctgc | 600 |
| aacgtgaatc acaagcccag caacaccaag gtggacaaga agttgagcc | 650 |
| caaatcttgt gacaaaactc acacatgccc accgtgccca gcacctgaac | 700 |
| tcctgggggg accgtcagtc ttcctcttcc ccccaaaacc caaggacacc | 750 |
| ctcatgatct cccggacccc tgaggtcaca tgcgtggtgg tggacgtgag | 800 |
| ccacgaagac cctgaggtca agttcaactg gtacgtggac ggcgtggagg | 850 |

```
tgcataatgc caagacaaag ccgcgggagg agcagtacaa cagcacgtac        900
cgggtggtca gcgtcctcac cgtcctgcac caggactggc tgaatggcaa        950
ggagtacaag tgcaaggtct ccaacaaagc cctcccagcc cccatcgaga       1000
aaaccatctc caaagccaaa gggcagcccc gagaaccaca ggtgtacacc       1050 ctgccccat cccgggaaga gatgaccaag aaccaggtca gcctgacctg        1100
cctggtcaaa ggcttctatc ccagcgacat cgccgtggag tgggagagca       1150
atgggcagcc ggagaacaac tacaagacca cgcctcccgt gctggactcc       1200
gacggctcct tcttcctcta cagcaagctc accgtggaca gagcaggtg        1250 gcagcagggg aacgtcttct catgctccgt gatgcatgag gctctgcaca       1300
accactacac gcagaagagc ctctccctgt ctccgggtaa a                1341
```

<210> SEQ ID NO 34
<211> LENGTH: 1400
<212> TYPE: DNA
<213> ORGANISM: Artificial sequence
<220> FEATURE:
<223> OTHER INFORMATION: sequence is synthesized

<400> SEQUENCE: 34

```
atgggatggt catgtatcat cctttttcta gtagcaactg caactggagt         50
acattcagaa gttcagctgg tggagtctgg cggtggcctg gtgcagccag        100
ggggctcact ccgtttgtcc tgtgcagctt ctggctacgc attcaccaac        150
tatctgatcg agtgggtccg tcaggccccg ggtaagggcc tcgagtgggt        200
tggtgttatc aatcctggat ccggaggctc aactataac gagaagttca        250 aggggcgcgc cactatcagt gcagacaatt cgaaaaacac attatacctg        300
cagatgaaca gcctgcgtgc tgaggacact gccgtctatt attgtgctcg        350
atccggaggc ttctacttcg actactgggg tcaaggaacc ctggtcaccg        400
tctcctcagc ctccaccaag ggcccatcgg tcttccccct ggcaccctcc        450
tccaagagca cctctggggg cacagcggcc ctgggctgcc tggtcaagga        500
ctacttcccc gaaccggtga cggtgtcgtg gaactcaggc gccctgacca        550
gcggcgtgca ccttcccgc tgtcctac agtcctcagg actctactcc           600
ctcagcagcg tggtgactgt gccctctagc agcttgggca cccagaccta        650
catctgcaac gtgaatcaca agcccagcaa caccaaggtg gacaagaaag        700
ttgagcccaa atcttgtgac aaaactcaca catgcccacc gtgcccagca        750
cctgaactcc tggggggacc gtcagtcttc ctcttccccc caaaacccaa        800
ggacaccctc atgatctccc ggacccctga ggtcacatgc gtggtggtgg        850
acgtgagcca cgaagaccct gaggtcaagt tcaactggta cgtggacggc        900
gtggaggtgc ataatgccaa gacaaagccg cgggaggagc agtacaacag        950
cacgtaccgg gtggtcagcg tcctcaccgt cctgcaccag gactggctga       1000
atggcaagga gtacaagtgc aaggtctcca acaaagccct cccagccccc       1050
atcgagaaaa ccatctccaa agccaaaggg cagccccgag aaccacaggt       1100
gtacaccctg cccccatccc gggaagagat gaccaagaac caggtcagcc       1150
tgacctgcct ggtcaaaggc ttctatccca gcgacatcgc cgtggagtgg       1200
gagagcaatg ggcagccgga gaacaactac aagaccacgc ctcccgtgct       1250
```

| | |
|---|---|
| ggactccgac ggctccttct tcctctacag caagctcacc gtggacaaga | 1300 |
| gcaggtggca gcaggggaac gtcttctcat gctccgtgat gcatgaggct | 1350 |
| ctgcacaacc actacacgca agagcctc tccctgtctc cgggtaaatg | 1400 |

<210> SEQ ID NO 35
<211> LENGTH: 1341
<212> TYPE: DNA
<213> ORGANISM: Artificial sequence
<220> FEATURE:
<223> OTHER INFORMATION: sequence is synthesized

<400> SEQUENCE: 35

| | |
|---|---|
| gaagttcagc tggtggagtc tggcggtggc ctggtgcagc caggggggctc | 50 |
| actccgtttg tcctgtgcag cttctggcta cgcattcacc aactatctga | 100 |
| tcgagtgggt ccgtcaggcc ccgggtaagg gcctcgagtg gatcggtgta | 150 |
| aacaatcctg gatccggagg ctccaactat aacgagaagt tcaaggggcg | 200 |
| cgccactatc agtgcagaca attcgaaaaa cacattatac ctgcagatga | 250 |
| acagcctgcg tgctgaggac actgccgtct attattgtgc tcgatccgga | 300 |
| ggcttctact tcgactactg gggtcaagga accctggtca ccgtctcctc | 350 |
| agcctccacc aagggcccat cggtcttccc cctggcaccc tcctccaaga | 400 |
| gcacctctgg gggcacagcg gccctgggct gcctggtcaa ggactacttc | 450 |
| cccgaaccgg tgacggtgtc gtggaactca ggcgccctga ccagcggcgt | 500 |
| gcacaccttc ccggctgtcc tacagtcctc aggactctac tccctcagca | 550 |
| gcgtggtgac tgtgccctct agcagcttgg gcacccagac ctacatctgc | 600 |
| aacgtgaatc acaagcccag caacaccaag gtggacaaga agttgagcc | 650 |
| caaatcttgt gacaaaactc acacatgccc accgtgccca gcacctgaac | 700 |
| tcctgggggg accgtcagtc ttcctcttcc cccaaaaacc caaggacacc | 750 |
| ctcatgatct cccggacccc tgaggtcaca tgcgtggtgg tggacgtgag | 800 |
| ccacgaagac cctgaggtca agttcaactg gtacgtggac ggcgtggagg | 850 |
| tgcataatgc caagacaaag ccgcgggagg agcagtacaa cagcacgtac | 900 |
| cgtgtggtca gcgtcctcac cgtcctgcac caggactggc tgaatggcaa | 950 |
| ggagtacaag tgcaaggtct ccaacaaagc cctcccagcc ccatcgaga | 1000 |
| aaaccatctc caaagccaaa gggcagcccc gagaaccaca ggtgtacacc | 1050 |
| ctgcccccat cccgggaaga gatgaccaag aaccaggtca gcctgacctg | 1100 |
| cctggtcaaa ggcttctatc ccagcgacat cgccgtggag tgggagagca | 1150 |
| atgggcagcc ggagaacaac tacaagacca cgcctcccgt gctggactcc | 1200 |
| gacggctcct tcttcctcta cagcaagctc accgtggaca gagcaggtg | 1250 |
| gcagcagggg aacgtcttct catgctccgt gatgcatgag gctctgcaca | 1300 |
| accactacac gcagaagagc ctctccctgt ctccgggtaa a | 1341 |

<210> SEQ ID NO 36
<211> LENGTH: 1398
<212> TYPE: DNA
<213> ORGANISM: Artificial sequence
<220> FEATURE:
<223> OTHER INFORMATION: sequence is synthesized

<400> SEQUENCE: 36

| | |
|---|---|
| atgggatggt catgtatcat ccttttttcta gtagcaactg caactggagt | 50 |
| acattcagaa gttcagctgg tggagtctgg cggtggcctg gtgcagccag | 100 |
| ggggctcact ccgtttgtcc tgtgcagctt ctggctacgc attcaccaac | 150 |
| tatctgatcg agtgggtccg tcaggccccg ggtaagggcc tcgagtggat | 200 |
| cggtgtaaac aatcctggat ccggaggctc caactataac gagaagttca | 250 |
| aggggcgcgc cactatcagt gcagacaatt cgaaaaacac attataccctg | 300 |
| cagatgaaca gcctgcgtgc tgaggacact gccgtctatt attgtgctcg | 350 |
| atccggaggc ttctacttcg actactgggg tcaaggaacc ctggtcaccg | 400 |
| tctcctcagc ctccaccaag ggcccatcgg tcttccccct ggcaccctcc | 450 |
| tccaagagca cctctggggg cacagcggcc ctgggctgcc tggtcaagga | 500 |
| ctacttcccc gaaccggtga cggtgtcgtg gaactcaggc gccctgacca | 550 |
| gcggcgtgca ccttcccg gctgtcctac agtcctcagg actctactcc | 600 |
| ctcagcagcg tggtgactgt gccctctagc agcttgggca cccagaccta | 650 |
| catctgcaac gtgaatcaca agcccagcaa caccaaggtg gacaagaaag | 700 |
| ttgagcccaa atcttgtgac aaaactcaca catgcccacc gtgcccagca | 750 |
| cctgaactcc tggggggacc gtcagtcttc ctcttccccc caaaacccaa | 800 |
| ggacaccctc atgatctccc ggaccctga ggtcacatgc gtggtggtgg | 850 |
| acgtgagcca cgaagaccct gaggtcaagt tcaactggta cgtggacggc | 900 |
| gtggaggtgc ataatgccaa gacaaagccg cgggaggagc agtacaacag | 950 |
| cacgtaccgt gtggtcagcg tcctcaccgt cctgcaccag gactggctga | 1000 |
| atggcaagga gtacaagtgc aaggtctcca acaaagccct cccagccccc | 1050 |
| atcgagaaaa ccatctccaa agccaaaggg cagccccgag aaccacaggt | 1100 |
| gtacaccctg cccccatccc gggaagagat gaccaagaac caggtcagcc | 1150 |
| tgacctgcct ggtcaaaggc ttctatccca gcgacatcgc cgtggagtgg | 1200 |
| gagagcaatg ggcagccgga gaacaactac aagaccacgc ctcccgtgct | 1250 |
| ggactccgac ggctccttct tcctctacag caagctcacc gtggacaaga | 1300 |
| gcaggtggca gcaggggaac gtcttctcat gctccgtgat gcatgaggct | 1350 |
| ctgcacaacc actacacgca gaagagcctc tccctgtctc cgggtaaa | 1398 |

<210> SEQ ID NO 37
<211> LENGTH: 1341
<212> TYPE: DNA
<213> ORGANISM: Artificial sequence
<220> FEATURE:
<223> OTHER INFORMATION: sequence is synthesized

<400> SEQUENCE: 37

| | |
|---|---|
| gaagttcagc tggtggagtc tggcggtggc ctggtgcagc caggggggctc | 50 |
| actccgtttg tcctgtgcag cttctggcta cgcattcacc aactatctga | 100 |
| tcgagtgggt ccgtcaggcc ccgggtaagg gcctcgagtg ggttggtgtt | 150 |
| aacaatcctg gatccggagg ctccaactat aacgagaagt tcaaggggcg | 200 |
| cgccactatc agtgcagaca attcgaaaaa cacattatac ctgcagatga | 250 |
| acagcctgcg tgctgaggac actgccgtct attattgtgc tcgatccgga | 300 |
| ggcttctact tcgactactg gggtcaagga accctggtca ccgtctcctc | 350 |

| | |
|---|---|
| agcctccacc aagggcccat cggtcttccc cctggcaccc tcctccaaga | 400 |
| gcacctctgg gggcacagcg gccctgggct gcctggtcaa ggactacttc | 450 |
| cccgaaccgg tgacggtgtc gtggaactca ggcgccctga ccagcggcgt | 500 |
| gcacaccttc ccggctgtcc tacagtcctc aggactctac tccctcagca | 550 |
| gcgtggtgac tgtgccctct agcagcttgg gcacccagac ctacatctgc | 600 |
| aacgtgaatc acaagcccag caacaccaag gtggacaaga agttgagcc | 650 |
| caaatcttgt gacaaaactc acacatgccc accgtgccca gcacctgaac | 700 |
| tcctgggggg accgtcagtc ttcctcttcc ccccaaaacc caaggacacc | 750 |
| ctcatgatct cccggacccc tgaggtcaca tgcgtggtgg tggacgtgag | 800 |
| ccacgaagac cctgaggtca agttcaactg gtacgtggac ggcgtggagg | 850 |
| tgcataatgc caagacaaag ccgcgggagg agcagtacaa cagcacgtac | 900 |
| cgtgtggtca gcgtcctcac cgtcctgcac caggactggc tgaatggcaa | 950 |
| ggagtacaag tgcaaggtct ccaacaaagc cctcccagcc cccatcgaga | 1000 |
| aaaccatctc caaagccaaa gggcagcccc gagaaccaca ggtgtacacc | 1050 |
| ctgcccccat cccgggaaga gatgaccaag aaccaggtca gcctgacctg | 1100 |
| cctggtcaaa ggcttctatc ccagcgacat cgccgtggag tgggagagca | 1150 |
| atgggcagcc ggagaacaac tacaagacca cgcctcccgt gctggactcc | 1200 |
| gacggctcct tcttcctcta cagcaagctc accgtggaca agagcaggtg | 1250 |
| gcagcagggg aacgtcttct catgctccgt gatgcatgag ggtctgcaca | 1300 |
| accactacac gcagaagagc ctctccctgt ctccgggtaa a | 1341 |

<210> SEQ ID NO 38
<211> LENGTH: 1398
<212> TYPE: DNA
<213> ORGANISM: Artificial sequence
<220> FEATURE:
<223> OTHER INFORMATION: sequence is synthesized

<400> SEQUENCE: 38

| | |
|---|---|
| atgggatggt catgtatcat ccttttctcta gtagcaactg caactggagt | 50 |
| acattcagaa gttcagctgg tggagtctgg cggtggcctg gtgcagccag | 100 |
| ggggctcact ccgtttgtcc tgtgcagctt ctggctacgc attcaccaac | 150 |
| tatctgatcg agtgggtccg tcaggccccg ggtaagggcc tcgagtgggt | 200 |
| tggtgttaac aatcctggat ccggaggctc caactataac gagaagttca | 250 |
| aggggcgcgc cactatcagt gcagacaatt cgaaaaacac attatacctg | 300 |
| cagatgaaca gcctgcgtgc tgaggacact gccgtctatt attgtgctcg | 350 |
| atccggaggc ttctacttcg actactgggg tcaaggaacc ctggtcaccg | 400 |
| tctcctcagc ctccaccaag ggcccatcgg tcttcccct ggcaccctcc | 450 |
| tccaagagca cctctggggg cacagcggcc ctgggctgcc tggtcaagga | 500 |
| ctacttcccc gaaccggtga cggtgtcgtg gaactcaggc gccctgacca | 550 |
| gcggcgtgca caccttcccg gctgtcctac agtcctcagg actctactcc | 600 |
| ctcagcagcg tggtgactgt gccctctagc agcttgggca cccagaccta | 650 |
| catctgcaac gtgaatcaca agcccagcaa caccaaggtg gacaagaaag | 700 |
| ttgagcccaa atcttgtgac aaaactcaca catgcccacc gtgcccagca | 750 |

| | |
|---|---|
| cctgaactcc tgggggggacc gtcagtcttc ctcttccccc caaaacccaa | 800 |
| ggacacccctc atgatctccc ggaccccctga ggtcacatgc gtggtggtgg | 850 |
| acgtgagcca cgaagaccct gaggtcaagt tcaactggta cgtggacggc | 900 |
| gtggaggtgc ataatgccaa gacaaagccg cgggaggagc agtacaacag | 950 |
| cacgtaccgt gtggtcagcg tcctcaccgt cctgcaccag gactggctga | 1000 |
| atggcaagga gtacaagtgc aaggtctcca acaaagccct cccagccccc | 1050 |
| atcgagaaaa ccatctccaa agccaaaggg cagccccgag aaccacaggt | 1100 |
| gtacaccctg cccccatccc gggaagagat gaccaagaac caggtcagcc | 1150 |
| tgacctgcct ggtcaaaggc ttctatccca gcgacatcgc cgtggagtgg | 1200 |
| gagagcaatg ggcagccgga gaacaactac aagaccacgc ctcccgtgct | 1250 |
| ggactccgac ggctccttct tcctctacag caagctcacc gtggacaaga | 1300 |
| gcaggtggca gcaggggaac gtcttctcat gctccgtgat gcatgagggt | 1350 |
| ctgcacaacc actacacgca gaagagcctc tccctgtctc cgggtaaa | 1398 |

<210> SEQ ID NO 39
<211> LENGTH: 657
<212> TYPE: DNA
<213> ORGANISM: Artificial sequence
<220> FEATURE:
<223> OTHER INFORMATION: sequence is synthesized

<400> SEQUENCE: 39

| | |
|---|---|
| gatatccaga tgacccagtc cccgagctcc ctgtccgcct ctgtgggcga | 50 |
| tagggtcacc atcacctgca gagccagtca gagcgtgctg tatagttcga | 100 |
| atcagaagaa ctacctggcc tggtatcaac agaaaccagg aaaagctccg | 150 |
| aaactactga tttactgggc tagtactcgc gagtctggag tcccttctcg | 200 |
| cttctctgga tccggttctg ggacggattt cactctgacc atcagcagtc | 250 |
| tgcagccaga agacttcgca acttattact gtcaccagta tctgagctct | 300 |
| gacacatttg gacagggtac caaggtggag atcaaacgaa ctgtggctgc | 350 |
| accatctgtc ttcatcttcc cgccatctga tgagcagttg aaatctggaa | 400 |
| ctgcttctgt tgtgtgcctg ctgaataact tctatcccag agaggccaaa | 450 |
| gtacagtgga aggtggataa cgccctccaa tcgggtaact cccaggagag | 500 |
| tgtcacagag caggacagca aggacagcac ctacagcctc agcagcaccc | 550 |
| tgacgctgag caaagcagac tacgagaaac acaaagtcta cgcctgcgaa | 600 |
| gtcacccatc agggcctgag ctcgcccgtc acaaagagct tcaacagggg | 650 |
| agagtgt | 657 |

<210> SEQ ID NO 40
<211> LENGTH: 714
<212> TYPE: DNA
<213> ORGANISM: Artificial sequence
<220> FEATURE:
<223> OTHER INFORMATION: sequence is synthesized

<400> SEQUENCE: 40

| | |
|---|---|
| atgggatggt catgtatcat cctttttcta gtagcaactg caactggagt | 50 |
| acattcagat atccagatga cccagtcccc gagctccctg tccgcctctg | 100 |
| tgggcgatag ggtcaccatc acctgcagag ccagtcagag cgtgctgtat | 150 |

| | |
|---|---|
| agttcgaatc agaagaacta cctggcctgg tatcaacaga aaccaggaaa | 200 |
| agctccgaaa ctactgattt actgggctag tactcgcgag tctggagtcc | 250 |
| cttctcgctt ctctggatcc ggttctggga cggatttcac tctgaccatc | 300 |
| agcagtctgc agccagaaga cttcgcaact tattactgtc accagtatct | 350 |
| gagctctgac acatttggac agggtaccaa ggtggagatc aaacgaactg | 400 |
| tggctgcacc atctgtcttc atcttcccgc catctgatga gcagttgaaa | 450 |
| tctggaactg cttctgttgt gtgcctgctg aataacttct atcccagaga | 500 |
| ggccaaagta cagtggaagg tggataacgc cctccaatcg ggtaactccc | 550 |
| aggagagtgt cacagagcag gacagcaagg acagcaccta cagcctcagc | 600 |
| agcaccctga cgctgagcaa agcagactac gagaaacaca agtctacgc | 650 |
| ctgcgaagtc acccatcagg gcctgagctc gcccgtcaca aagagcttca | 700 |
| acaggggaga gtgt | 714 |

<210> SEQ ID NO 41
<211> LENGTH: 657
<212> TYPE: DNA
<213> ORGANISM: Artificial sequence
<220> FEATURE:
<223> OTHER INFORMATION: sequence is synthesized

<400> SEQUENCE: 41

| | |
|---|---|
| gatatccaga tgacccagtc cccgagctcc ctgtccgcct ctgtgggcga | 50 |
| tagggtcacc atcacctgca gagccagtca gagcgtgctg tatagttcga | 100 |
| atcagaagaa ctacctggcc tggtatcaac agaaaccagg aaaagctccg | 150 |
| aaactactga tttactatgc tagcagtctc cagtctggag tcccttctcg | 200 |
| cttctctgga tccggttctg ggacggattt cactctgacc atcagcagtc | 250 |
| tgcagccaga agacttcgca acttattact gtcaccagta tctgagctct | 300 |
| gacacatttg gacagggtac caaggtggag atcaaacgaa ctgtggctgc | 350 |
| accatctgtc ttcatcttcc cgccatctga tgagcagttg aaatctggaa | 400 |
| ctgcttctgt tgtgtgcctg ctgaataact tctatcccag agaggccaaa | 450 |
| gtacagtgga aggtggataa cgccctccaa tcgggtaact cccaggagag | 500 |
| tgtcacagag caggacagca aggacagcac ctacagcctc agcagcaccc | 550 |
| tgacgctgag caaagcagac tacgagaaac acaaagtcta cgcctgcgaa | 600 |
| gtcacccatc agggcctgag ctcgcccgtc acaaagagct caacagggg | 650 |
| agagtgt | 657 |

<210> SEQ ID NO 42
<211> LENGTH: 714
<212> TYPE: DNA
<213> ORGANISM: Artificial sequence
<220> FEATURE:
<223> OTHER INFORMATION: sequence is synthesized

<400> SEQUENCE: 42

| | |
|---|---|
| atgggatggt catgtatcat ccttttctta gtagcaactg caactggagt | 50 |
| acattcagat atccagatga cccagtcccc gagctccctg tccgcctctg | 100 |
| tgggcgatag ggtcaccatc acctgcagag ccagtcagag cgtgctgtat | 150 |
| agttcgaatc agaagaacta cctggcctgg tatcaacaga aaccaggaaa | 200 |

| | |
|---|---|
| agctccgaaa ctactgattt actatgctag cagtctccag tctggagtcc | 250 |
| cttctcgctt ctctggatcc ggttctggga cggatttcac tctgaccatc | 300 |
| agcagtctgc agccagaaga cttcgcaact tattactgtc accagtatct | 350 |
| gagctctgac acatttggac agggtaccaa ggtggagatc aaacgaactg | 400 |
| tggctgcacc atctgtcttc atcttcccgc catctgatga gcagttgaaa | 450 |
| tctggaactg cttctgttgt gtgcctgctg aataacttct atcccagaga | 500 |
| ggccaaagta cagtggaagg tggataacgc cctccaatcg ggtaactccc | 550 |
| aggagagtgt cacagagcag gacagcaagg acagcaccta cagcctcagc | 600 |
| agcaccctga cgctgagcaa agcagactac gagaaacaca agtctacgc | 650 |
| ctgcgaagtc acccatcagg gcctgagctc gcccgtcaca aagagcttca | 700 |
| acaggggaga gtgt | 714 |

<210> SEQ ID NO 43
<211> LENGTH: 17
<212> TYPE: PRT
<213> ORGANISM: Artificial sequence
<220> FEATURE:
<223> OTHER INFORMATION: sequence is synthesized

<400> SEQUENCE: 43

Val Ile Asn Pro Gly Ser Gly Gly Ser Asn Tyr Asn Glu Lys Phe
1               5                   10                  15
Lys Gly

<210> SEQ ID NO 44
<211> LENGTH: 5391
<212> TYPE: DNA
<213> ORGANISM: Artificial sequence
<220> FEATURE:
<223> OTHER INFORMATION: sequence is synthesized

<400> SEQUENCE: 44

| | |
|---|---|
| ttcgagctcg cccgacattg attattgact agttattaat agtaatcaat | 50 |
| tacggggtca ttagttcata gcccatatat ggagttccgc gttacataac | 100 |
| ttacggtaaa tggcccgcct ggctgaccgc ccaacgaccc ccgcccattg | 150 |
| acgtcaataa tgacgtatgt tcccatagta acgccaatag ggactttcca | 200 |
| ttgacgtcaa tgggtggagt atttacggta aactgcccac ttggcagtac | 250 |
| atcaagtgta tcatatgcca agtacgcccc ctattgacgt caatgacggt | 300 |
| aaatggcccg cctggcatta tgcccagtac atgaccttat gggactttcc | 350 |
| tacttggcag tacatctacg tattagtcat cgctattacc atggtgatgc | 400 |
| ggttttggca gtacatcaat gggcgtggat agcggtttga ctcacgggga | 450 |
| tttccaagtc tccaccccat tgacgtcaat gggagtttgt tttggcacca | 500 |
| aaatcaacgg gactttccaa aatgtcgtaa caactccgcc ccattgacgc | 550 |
| aaatgggcgg taggcgtgta cggtgggagg tctatataag cagagctcgt | 600 |
| ttagtgaacc gtcagatcgc ctggagacgc catccacgct gttttgacct | 650 |
| ccatagaaga caccgggacc gatccagcct ccgcggccgg gaacggtgca | 700 |
| ttggaacgcg gattccccgt gccaagagtg acgtaagtac cgcctataga | 750 |
| gtctataggc ccaccccctt ggcttcgtta gaacgcggct acaattaata | 800 |
| cataacctta tgtatcatac acatacgatt taggtgacac tatagaataa | 850 |

| | |
|---|---|
| catccacttt gcctttctct ccacaggtgt ccactcccag gtccaactgc | 900 |
| acctcggttc tatcgattga attccaccat gggatggtca tgtatcatcc | 950 |
| tttttctagt agcaactgca actggagtac attcagatat ccagatgacc | 1000 |
| cagtccccga gctccctgtc cgcctctgtg ggcgataggg tcaccatcac | 1050 |
| ctgccgtgcc agtcaggaca tccgtaatta tttgaactgg tatcaacaga | 1100 |
| aaccaggaaa agctccgaaa ctactgattt actatacctc ccgcctggag | 1150 |
| tctggagtcc cttctcgctt ctctggttct ggttctggga cggattacac | 1200 |
| tctgaccatc agtagtctgc aaccggagga cttcgcaact tattactgtc | 1250 |
| agcaaggtaa tactctgccg tggacgttcg gacagggcac caaggtggag | 1300 |
| atcaaacgaa ctgtggctgc accatctgtc ttcatcttcc cgccatctga | 1350 |
| tgagcagttg aaatctggaa ctgcctctgt tgtgtgcctg ctgaataact | 1400 |
| tctatcccag agaggccaaa gtacagtgga aggtggataa cgccctccaa | 1450 |
| tcgggtaact cccaggagag tgtcacagag caggacagca aggacagcac | 1500 |
| ctacagcctc agcagcaccc tgacgctgag caaagcagac tacgagaaac | 1550 |
| acaaagtcta cgcctgcgaa gtcacccatc agggcctgag ctcgcccgtc | 1600 |
| acaaagagct tcaacagggg agagtgttaa gcttggccgc catggcccaa | 1650 |
| cttgttattt gcagcttata atggttacaa ataaagcaat agcatcacaa | 1700 |
| atttcacaaa taaagcattt ttttcactgc attctagttg tggtttgtcc | 1750 |
| aaactcatca atgtatctta tcatgtctgg atcgatcggg aattaattcg | 1800 |
| gcgcagcacc atggcctgaa ataacctctg aaagaggaac ttggttaggt | 1850 |
| accttctgag gcggaaagaa ccagctgtgg aatgtgtgtc agttagggtg | 1900 |
| tggaaagtcc ccaggctccc cagcaggcag aagtatgcaa agcatgcatc | 1950 |
| tcaattagtc agcaaccagg tgtggaaagt ccccaggctc cccagcaggc | 2000 |
| agaagtatgc aaagcatgca tctcaattag tcagcaacca tagtcccgcc | 2050 |
| cctaactccg cccatcccgc ccctaactcc gcccagttcc gcccattctc | 2100 |
| cgccccatgg ctgactaatt ttttttattt atgcagaggc cgaggccgcc | 2150 |
| tcggcctctg agctattcca gaagtagtga ggaggctttt ttggaggcct | 2200 |
| aggcttttgc aaaaagctgt taacagcttg gcactggccg tcgttttaca | 2250 |
| acgtcgtgac tgggaaaacc ctggcgttac ccaacttaat cgccttgcag | 2300 |
| cacatccccc cttcgccagc tggcgtaata gcgaagaggc ccgcaccgat | 2350 |
| cgcccttccc aacagttgcg tagcctgaat ggcgaatggc gcctgatgcg | 2400 |
| gtattttctc cttacgcatc tgtgcggtat ttcacaccgc atacgtcaaa | 2450 |
| gcaaccatag tacgcgccct gtagcggcgc attaagcgcg gcgggtgtgg | 2500 |
| tggttacgcg cagcgtgacc gctacacttg ccagcgccct agcgcccgct | 2550 |
| cctttcgctt tcttcccttc ctttctcgcc acgttcgccg gctttccccg | 2600 |
| tcaagctcta aatcggggc tccctttagg gttccgattt agtgctttac | 2650 |
| ggcacctcga ccccaaaaaa cttgatttgg gtgatggttc acgtagtggg | 2700 |
| ccatcgccct gatagacggt ttttcgccct ttgacgttgg agtccacgtt | 2750 |
| ctttaatagt ggactcttgt tccaaactgg aacaacactc aacccatct | 2800 |
| cgggctattc ttttgattta agggatttt gccgatttc ggcctattgg | 2850 |

```
ttaaaaaatg agctgattta acaaaaattt aacgcgaatt ttaacaaaat      2900
attaacgttt acaattttat ggtgcactct cagtacaatc tgctctgatg      2950
ccgcatagtt aagccaactc cgctatcgct acgtgactgg gtcatggctg      3000
cgccccgaca cccgccaaca cccgctgacg cgccctgacg ggcttgtctg      3050
ctcccggcat ccgcttacag acaagctgtg accgtctccg ggagctgcat      3100
gtgtcagagg ttttcaccgt catcaccgaa acgcgcgagg cagtattctt      3150
gaagacgaaa gggcctcgtg atacgcctat ttttataggt taatgtcatg      3200
ataataatgg tttcttagac gtcaggtggc acttttcggg gaaatgtgcg      3250
cggaacccct atttgtttat ttttctaaat acattcaaat atgtatccgc      3300
tcatgagaca ataaccctga taaatgcttc aataatattg aaaaaggaag      3350
agtatgagta ttcaacattt ccgtgtcgcc cttattccct ttttgcggc       3400
attttgcctt cctgttttg ctcacccaga acgctggtg aaagtaaaag        3450
atgctgaaga tcagttgggt gcacgagtgg gttacatcga actggatctc      3500
aacagcggta agatccttga gagttttcgc cccgaagaac gttttccaat      3550
gatgagcact tttaaagttc tgctatgtgg cgcggtatta tcccgtgatg      3600
acgccgggca agagcaactc ggtcgccgca tacactattc tcagaatgac      3650
ttggttgagt actcaccagt cacagaaaag catcttacgg atggcatgac      3700
agtaagagaa ttatgcagtg ctgccataac catgagtgat aacactgcgg      3750
ccaacttact tctgacaacg atcggaggac cgaaggagct aaccgctttt      3800
ttgcacaaca tgggggatca tgtaactcgc cttgatcgtt gggaaccgga      3850
gctgaatgaa gccataccaa acgacgagcg tgacaccacg atgccagcag      3900
caatggcaac aacgttgcgc aaactattaa ctggcgaact acttactcta      3950
gcttcccggc aacaattaat agactggatg gaggcggata agttgcagg       4000
accacttctg cgctcggccc ttccggctgg ctggtttatt gctgataaat      4050
ctggagccgg tgagcgtggg tctcgcggta tcattgcagc actggggcca      4100
gatggtaagc cctcccgtat cgtagttatc tacacgacgg ggagtcaggc      4150
aactatggat gaacgaaata gacagatcgc tgagataggt gcctcactga      4200
ttaagcattg gtaactgtca gaccaagttt actcatatat actttagatt      4250
gatttaaaac ttcattttta atttaaaagg atctaggtga agatccttt       4300
tgataatctc atgaccaaaa tcccttaacg tgagttttcg ttccactgag      4350
cgtcagaccc cgtagaaaag atcaaaggat cttcttgaga tcctttttt       4400
ctgcgcgtaa tctgctgctt gcaaacaaaa aaaccaccgc taccagcggt      4450
ggtttgtttg ccggatcaag agctaccaac tctttttccg aaggtaactg      4500
gcttcagcag agcgcagata ccaaatactg tccttctagt gtagccgtag      4550
ttaggccacc acttcaagaa ctctgtagca ccgcctacat acctcgctct      4600
gctaatcctg ttaccagtgg ctgctgccag tggcgataag tcgtgtctta      4650
ccgggttgga ctcaagacga tagttaccgg ataaggcgca gcggtcgggc      4700
tgaacggggg gttcgtgcac acagcccagc ttggagcgaa cgacctacac      4750
cgaactgaga tacctacagc gtgagcattg agaaagcgcc acgcttcccg      4800
aagggagaaa ggcggacagg tatccggtaa gcggcagggt cggaacagga      4850
```

| | |
|---|---|
| gagcgcacga gggagcttcc aggggggaaac gcctggtatc tttatagtcc | 4900 |
| tgtcgggttt cgccacctct gacttgagcg tcgattttg tgatgctcgt | 4950 |
| cagggggggcg gagcctatgg aaaaacgcca gcaacgcggc cttttttacgg | 5000 |
| ttcctggcct tttgctggcc ttttgctcac atgttctttc ctgcgttatc | 5050 |
| ccctgattct gtggataacc gtattaccgc ctttgagtga gctgataccg | 5100 |
| ctcgccgcag ccgaacgacc gagcgcagcg agtcagtgag cgaggaagcg | 5150 |
| gaagagcgcc caatacgcaa accgcctctc ccgcgcgtt ggccgattca | 5200 |
| ttaatccagc tggcacgaca ggtttcccga ctggaaagcg ggcagtgagc | 5250 |
| gcaacgcaat taatgtgagt tacctcactc attaggcacc ccaggcttta | 5300 |
| cactttatgc ttccggctcg tatgttgtgt ggaattgtga gcggataaca | 5350 |
| atttcacaca ggaaacagct atgaccatga ttacgaatta a | 5391 |

<210> SEQ ID NO 45
<211> LENGTH: 6135
<212> TYPE: DNA
<213> ORGANISM: Artificial sequence
<220> FEATURE:
<223> OTHER INFORMATION: sequence is synthesized

<400> SEQUENCE: 45

| | |
|---|---|
| attcgagctc gcccgacatt gattattgac tagttattaa tagtaatcaa | 50 |
| ttacggggtc attagttcat agcccatata tggagttccg cgttacataa | 100 |
| cttacggtaa atggcccgcc tggctgaccg cccaacgacc cccgcccatt | 150 |
| gacgtcaata atgacgtatg ttcccatagt aacgccaata gggactttcc | 200 |
| attgacgtca atgggtggag tatttacggt aaactgccca cttggcagta | 250 |
| catcaagtgt atcatatgcc aagtacgccc cctattgacg tcaatgacgg | 300 |
| taaatggccc gcctggcatt atgcccagta catgacctta tgggactttc | 350 |
| ctacttggca gtacatctac gtattagtca tcgctattac catggtgatg | 400 |
| cggttttggc agtacatcaa tgggcgtgga tagcggtttg actcacgggg | 450 |
| atttccaagt ctccacccca ttgacgtcaa tgggagtttg ttttggcacc | 500 |
| aaaatcaacg ggactttcca aaatgtcgta acaactccgc cccattgacg | 550 |
| caaatgggcg gtaggcgtgt acggtgggag gtctatataa gcagagctcg | 600 |
| tttagtgaac cgtcagatcg cctggagacg ccatccacgc tgttttgacc | 650 |
| tccatagaag acaccgggac cgatccagcc tccgcggccg ggaacggtgc | 700 |
| attggaacgc ggattccccg tgccaagagt gacgtaagta ccgcctatag | 750 |
| agtctatagg cccacccccct tggcttcgtt agaacgcggc tacaattaat | 800 |
| acataacctt atgtatcata cacatacgat ttaggtgaca ctatagaata | 850 |
| acatccactt tgccttctc tccacaggtg tccactccca ggtccaactg | 900 |
| cacctcggtt ctatcgattg aattccacca tgggatggtc atgtatcatc | 950 |
| cttttctag tagcaactgc aactggagta cattcagaag ttcagctggt | 1000 |
| ggagtctggc ggtggcctgg tgcagccagg ggctcactc cgtttgtcct | 1050 |
| gtgcagcttc tggctactcc tttaccggct acactatgaa ctgggtgcgt | 1100 |
| caggccccag gtaagggcct ggaatgggtt gcactgatta atcctatata | 1150 |
| aggtgttact acctatgccg atagcgtcaa gggccgtttc actataagcg | 1200 |

```
tagataaatc caaaaacaca gcctacctgc aaatgaacag cctgcgtgct      1250
gaggacactg ccgtctatta ttgtgctaga agcggatact acggcgatag      1300
cgactggtat tttgacgtct ggggtcaagg aaccctggtc accgtctcct      1350
cggcctccac caagggccca tcggtcttcc ccctggcacc ctcctccaag      1400
agcacctctg ggggcacagc ggccctgggc tgcctggtca aggactactt      1450
ccccgaaccg gtgacggtgt cgtggaactc aggcgccctg accagcggcg      1500
tgcacacctt cccggctgtc ctacagtcct caggactcta ctccctcagc      1550
agcgtggtga ctgtgccctc tagcagcttg ggcacccaga cctacatctg      1600
caacgtgaat cacaagccca gcaacaccaa ggtggacaag aaagttgagc      1650
ccaaatcttg tgacaaaact cacacatgcc caccgtgccc agcacctgaa      1700
ctcctggggg gaccgtcagt cttcctcttc cccccaaaac ccaaggacac      1750
cctcatgatc tcccggaccc ctgaggtcac atgcgtggtg gtggacgtga      1800
gccacgaaga ccctgaggtc aagttcaact ggtacgtgga cggcgtggag      1850
gtgcataatg ccaagacaaa gccgcgggag gagcagtaca acagcacgta      1900
ccgtgtggtc agcgtcctca ccgtcctgca ccaggactgg ctgaatggca      1950
aggagtacaa gtgcaaggtc tccaacaaag ccctcccagc ccccatcgag      2000
aaaaccatct ccaaagccaa agggcagccc cgagaaccac aggtgtacac      2050
cctgccccca tcccgggaag agatgaccaa gaaccaggtc agcctgacct      2100
gcctggtcaa aggcttctat cccagcgaca tcgccgtgga gtgggagagc      2150
aatgggcagc cggagaacaa ctacaagacc acgcctcccg tgctggactc      2200
cgacggctcc ttcttcctct acagcaagct caccgtggac aagagcaggt      2250
ggcagcaggg gaacgtcttc tcatgctccg tgatgcatga ggctctgcac      2300
aaccactaca cgcagaagag cctctccctg tctccgggta aatgagtgcg      2350
acggccctag agtcgacctg cagaagcttg gccgccatgg cccaacttgt      2400
ttattgcagc ttataatggt tacaaataaa gcaatagcat cacaaatttc      2450
acaaataaag catttttttc actgcattct agttgtggtt tgtccaaact      2500
catcaatgta tcttatcatg tctggatcga tcgggaatta attcggcgca      2550
gcaccatggc ctgaaataac ctctgaaaga ggaacttggt taggtacctt      2600
ctgaggcgga agaaccatc tgtggaatgt gtgtcagtta gggtgtggaa      2650
agtccccagg ctccccagca ggcagaagta tgcaaagcat gcatctcaat      2700
tagtcagcaa ccaggtgtgg aaagtcccca ggctccccag caggcagaag      2750
tatgcaaagc atgcatctca attagtcagc aaccatagtc cgcccctaa      2800 ctccgcccat cccgcccta actccgccca gttccgccca ttctccgccc      2850
catggctgac taattttttt tatttatgca gaggccgagg ccgcctcggc      2900
ctctgagcta ttccagaagt agtgaggagg ctttttttgga ggcctaggct      2950 tttgcaaaaa gctgttaaca gcttggcact ggccgtcgtt ttacaacgtc      3000
gtgactggga aaaccctggc gttacccaac ttaatcgcct tgcagcacat      3050
ccccccttcg ccagttggcg taatagcgaa gaggcccgca ccgatcgccc      3100
ttcccaacag ttgcgtagcc tgaatggcga atggcgcctg atgcggtatt      3150
ttctccttac gcatctgtgc ggtatttcac accgcatacg tcaaagcaac      3200
```

```
catagtacgc gccctgtagc ggcgcattaa gcgcggcggg tgtggtggtt        3250
acgcgcagcg tgaccgctac acttgccagc gccctagcgc ccgctccttt        3300
cgctttcttc ccttcctttc tcgccacgtt cgccggcttt ccccgtcaag        3350
ctctaaatcg ggggctccct ttagggttcc gatttagtgc tttacggcac        3400
ctcgacccca aaaacttga tttggtgat ggttcacgta gtgggccatc           3450
gccctgatag acggtttttc gcccttgac gttggagtcc acgttcttta          3500
atagtggact cttgttccaa actgaacaa cactcaaccc tatctcgggc          3550
tattcttttg atttataagg gatttgccg atttcggcct attggttaaa         3600
aaatgagctg atttaacaaa aatttaacgc gaattttaac aaaatattaa        3650
cgtttacaat tttatggtgc actctcagta caatctgctc tgatgccgca        3700
tagttaagcc aactccgcta tcgctacgtg actgggtcat ggctgcgccc        3750
cgacacccgc caacacccgc tgacgcgccc tgacgggctt gtctgctccc        3800
ggcatccgct tacagacaag ctgtgaccgt ctccgggagc tgcatgtgtc        3850
agaggttttc accgtcatca ccgaaacgcg cgaggcagta ttcttgaaga        3900
cgaaagggcc tcgtgatacg cctattttta taggttaatg tcatgataat        3950
aatggtttct tagacgtcag gtggcacttt tcggggaaat gtgcgcggaa        4000
cccctatttg tttatttttc taaatacatt caaatatgta tccgctcatg        4050
agacaataac cctgataaat gcttcaataa tattgaaaaa ggaagagtat        4100
gagtattcaa catttccgtg tcgcccttat ccctttttt gcggcatttt         4150 gccttcctgt ttttgctcac ccagaaacgc tggtgaaagt aaaagatgct        4200
gaagatcagt tgggtgcacg agtgggttac atcgaactgg atctcaacag        4250
cggtaagatc cttgagagtt ttcgccccga agaacgtttt ccaatgatga        4300
gcacttttaa agttctgcta tgtggcgcgg tattatcccg tgatgacgcc        4350
gggcaagagc aactcggtcg ccgcatacac tattctcaga atgacttggt        4400
tgagtactca ccagtcacag aaaagcatct tacggatggc atgacagtaa        4450
gagaattatg cagtgctgcc ataaccatga gtgataacac tgcggccaac        4500
ttacttctga caacgatcgg aggaccgaag gagctaaccg cttttttgca        4550
caacatgggg gatcatgtaa ctcgccttga tcgttgggaa ccggagctga        4600
atgaagccat accaaacgac gagcgtgaca ccacgatgcc agcagcaatg        4650
gcaacaacgt tgcgcaaact attaactggc gaactactta ctctagcttc        4700
ccggcaacaa ttaatagact ggatggaggc ggataaagtt gcaggaccac        4750
ttctgcgctc ggcccttccg gctggctggt ttattgctga taaatctgga        4800
gccggtgagc gtgggtctcg cggtatcatt gcagcactgg ggccagatgg        4850
taagccctcc cgtatcgtag ttatctacac gacgggagt caggcaacta         4900 tggatgaacg aaatagacag atcgctgaga taggtgcctc actgattaag        4950
cattggtaac tgtcagacca agtttactca tatatacttt agattgattt        5000
aaaacttcat ttttaattta aaaggatcta ggtgaagatc cttttttgata       5050 atctcatgac caaaatccct taacgtgagt tttcgttcca ctgagcgtca        5100
gaccccgtag aaaagatcaa aggatcttct tgagatcctt ttttttctgcg       5150 cgtaatctgc tgcttgcaaa caaaaaaacc accgctacca gcggtggttt        5200
```

```
gtttgccgga tcaagagcta ccaactcttt ttccgaaggt aactggcttc        5250
agcagagcgc agataccaaa tactgtcctt ctagtgtagc cgtagttagg        5300
ccaccacttc aagaactctg tagcaccgcc tacatacctc gctctgctaa        5350
tcctgttacc agtggctgct gccagtggcg ataagtcgtg tcttaccggg        5400
ttggactcaa gacgatagtt accggataag gcgcagcggt cgggctgaac        5450 gggggggttcg tgcacacagc ccagcttgga gcgaacgacc tacaccgaac       5500
tgagatacct acagcgtgag cattgagaaa gcgccacgct ccccgaaggg        5550
agaaaggcgg acaggtatcc ggtaagcggc agggtcggaa caggagagcg        5600
cacgagggag cttccagggg gaaacgcctg gtatctttat agtcctgtcg        5650
ggtttcgcca cctctgactt gagcgtcgat ttttgtgatg ctcgtcaggg        5700
gggcggagcc tatggaaaaa cgccagcaac gcggcctttt tacggttcct        5750
ggccttttgc tggcctttg ctcacatgtt ctttcctgcg ttatcccctg         5800
attctgtgga taaccgtatt accgcctttg agtgagctga taccgctcgc        5850
cgcagccgaa cgaccgagcg cagcgagtca gtgagcgagg aagcggaaga        5900
gcgcccaata cgcaaaccgc ctctccccgc gcgttggccg attcattaat        5950
ccaactggca cgacaggttt cccgactgga aagcgggcag tgagcgcaac        6000
gcaattaatg tgagttacct cactcattag gcaccccagg ctttacactt        6050
tatgcttccg gctcgtatgt tgtgtggaat tgtgagcgga taacaatttc        6100
acacaggaaa cagctatgac catgattacg aatta                       6135

<210> SEQ ID NO 46
<211> LENGTH: 6
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 2
<223> OTHER INFORMATION: Unknown base

<400> SEQUENCE: 46 cncaat                                                          6

<210> SEQ ID NO 47
<211> LENGTH: 6
<212> TYPE: DNA
<213> ORGANISM: Artificial sequence
<220> FEATURE:
<223> OTHER INFORMATION: sequence is synthesized

<400> SEQUENCE: 47 aataaa                                                          6
```